US012540193B2

(12) United States Patent
Sonenshein et al.

(10) Patent No.: US 12,540,193 B2
(45) Date of Patent: Feb. 3, 2026

(54) ANTI-ADAM8 ANTIBODIES AND USES OF THE SAME

(71) Applicant: TRUSTEES OF TUFTS COLLEGE, Medford, MA (US)

(72) Inventors: Gail Sonenshein, Brookline, MA (US); Nora Mineva, Brighton, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 1064 days.

(21) Appl. No.: 17/615,312

(22) PCT Filed: May 29, 2020

(86) PCT No.: PCT/US2020/035280

§ 371 (c)(1),
(2) Date: Nov. 30, 2021

(87) PCT Pub. No.: WO2020/243541

PCT Pub. Date: Dec. 3, 2020

(65) Prior Publication Data

US 2022/0227882 A1 Jul. 21, 2022

Related U.S. Application Data

(60) Provisional application No. 62/855,575, filed on May 31, 2019.

(51) Int. Cl.
*C07K 16/28* (2006.01)
*A61K 39/00* (2006.01)
*G01N 33/574* (2006.01)

(52) U.S. Cl.
CPC ... *C07K 16/2896* (2013.01); *G01N 33/57484* (2013.01); *A61K 2039/505* (2013.01); *C07K 2317/24* (2013.01); *C07K 2317/33* (2013.01); *C07K 2317/34* (2013.01); *C07K 2317/73* (2013.01); *C07K 2317/76* (2013.01); *C07K 2317/92* (2013.01)

(58) Field of Classification Search
CPC .............. A61P 35/00; G01N 33/57484; C07K 2317/34; C07K 2317/76
See application file for complete search history.

(56) References Cited

U.S. PATENT DOCUMENTS

| | | | |
|---|---|---|---|
| 5,053,394 | A | 10/1991 | Ellestad et al. |
| 5,208,020 | A | 5/1993 | Chari et al. |
| 7,226,596 | B2 | 6/2007 | Bodary et al. |
| 2003/0113764 | A1 | 6/2003 | Bodary et al. |
| 2006/0275288 | A1 | 12/2006 | Grihalde et al. |
| 2008/0175842 | A1 | 7/2008 | Bodary et al. |
| 2016/0130365 | A1 | 5/2016 | Sonenshein et al. |
| 2017/0107258 | A1 | 4/2017 | Bartsch et al. |
| 2020/0062862 | A1 | 2/2020 | Sonenshein et al. |

FOREIGN PATENT DOCUMENTS

| | | |
|---|---|---|
| EP | 0338841 | 10/1989 |
| EP | 2336363 | 6/2011 |
| WO | WO 1987/004462 | 7/1987 |
| WO | WO 1989/001036 | 2/1989 |
| WO | WO 2001/009189 | 2/2001 |
| WO | WO 2005/090991 | 9/2005 |
| WO | WO 2012/088105 | 6/2012 |
| WO | WO 2014/186364 | 11/2014 |

OTHER PUBLICATIONS

Briney et al. (Commonality despite exceptional diversity in the baseline human antibody repertoire. Nature. 566:393-399) (Year: 2019).*
Mineva et al., Pharmaceutics Apr. 13, 2024; 16 (4): 536 ("Mineva").*
Extended European Search Report in European Appln. No. 20813778.6, dated Jun. 7, 2023, 16 pages.
Li et al., "Upregulation of a disintegrin and metalloprotease 8 influences tumor metastasis and prognosis in patients with osteosarcoma," *Pathology & Oncology Research*, 18:657-661, Jul. 2012.
Perez et al., "Epitope mapping of 10 monoclonal antibodies against the pig analogue of human membrane cofactor protein (MCP)," *Immunology*, 96(4):663-670, Apr. 1999.
Schlomann et al., "ADAM8 as a drug target in pancreatic cancer," *Nature Communications*, 6(6175): 16 pages, Jan. 28, 2015.
Abd El-Rehim et al., "Expression of a disintegrin and metalloprotease 8 and endostatin in human osteosarcoma: Implication in tumor progression and prognosis," *J Egypt Natl Canc Inst*, 27(1):1-9, 2015.
Adams et al., "Molecular regulation of angiogenesis and lymphangiogenesis," *Nat Rev Mol Cell Biol*, 8:464-478, 2007.
Asher et al., "Two separate metalloproteinase activities are responsible for the shedding and processing of the NG2 proteoglycan in vitro," *Mol Cell Neurosci*, 29(1):82-96, 2005.
Avraamides et al., "Integrins in angiogenesis and lymphangiogenesis," *Nat Rev Cancer*, 8:604-617, 2008.
Baren et al., "mRNA profiling of the cancer degradome in oesophago-gastric adenocarcinoma," *Br J Cancer*, 107:143-149, 2012.
Belguise et al., "Activation of FOXO3a by the Green Tea Polyphenol Epigallocatechin-3-Gallate Induces Estrogen Receptor a Expression Reversing Invasive Phenotype of Breast Cancer Cells," *Cancer Res*, 67(12):5763-5770, 2007.
Bergers et al., "Tumorigenesis and the angiogenic switch," *Nat Rev Cancer*, 3:401-410, 2003.

(Continued)

*Primary Examiner* — Misook Yu
(74) *Attorney, Agent, or Firm* — Fish & Richardson P.C.

(57) ABSTRACT

Provided herein are proteins that inhibit both the metalloprotease activity and disintegrin activity of human ADAM8, wherein the protein comprises an antigen-binding domain that: (i) binds specifically to human ADAM8; and (ii) binds to an epitope within human ADAM8 that includes at least one amino acid within the sequence of SEQ ID NO: 1, nucleic acids, vectors, compositions, and methods of use thereof (e.g., methods of treatment and methods of diagnosing).

28 Claims, 50 Drawing Sheets

Specification includes a Sequence Listing.

(56) References Cited

OTHER PUBLICATIONS

Boder et al., "Yeast surface display for screening combinatorial polypeptide libraries," *Nature Biotechnology*, 15(6):553-557, 1997.
Boyle, "Triple-negative breast cancer: epidemiological considerations and recommendations," *Ann Oncol*, 23(Suppl 6):vi7-vi12, 2012.
Bridges et al., "ADAM-Integrin Interactions: potential integrin regulated ectodomain shedding activity," *Curr Pharm Des*, 11:837-847, 2005.
Cristofanilli et al., "Circulating tumor cells, disease progression, and survival in metastatic breast cancer," *N Engl J Med*, 351:781-791, 2004.
Das et al., "Abstract 23: Antibody targeting of ADAM8 for treatment of triple-negative breast cancer," *AACR Annual Meeting 2017*, 4 pages, 2017 (Abstract Only).
Das et al., "miR-720 is a downstream target of an ADAM8-induced ERK signaling cascade that promotes the migratory and invasive phenotype of triple-negative breast cancer cells," *Breast Cancer Res*, 18(1):40, 19 pages, 2016.
Davidson et al., "A high-throughput shotgun mutagenesis approach to mapping B-cell antibody epitopes," *Immunology*, 143:13-20, 2014.
Dent et al., "Triple-Negative Breast Cancer: Clinical Features and Patterns of Recurrence," *Clin Cancer Res*, 13(15):4429-4434, 2007.
Desgrosellier et al., "Integrins in cancer: biological implications and therapeutic opportunities," *Nat Rev Cancer*, 10:9-22, 2010.
Duffy et al., "Role of ADAMs in cancer formation and progression," *Clin Cancer Res*, 15:1140-1144, 2009.
Duffy et al.," The ADAMs family of proteases: new biomarkers and therapeutic targets for cancer," *Clin Proteomics*, 8(1):9, 13 pages, 2011.
EP Search Report in European Appln. No. 14798014, dated Dec. 6, 2016, 7 pages.
Eyles et al., "Tumor cells disseminate early, but immunosurveillance limits metastatic outgrowth, in a mouse model of melanoma," *J Clin Invest*, 120:2030-2039, 2010.
Forozan et al., "Molecular cytogenetic analysis of 11 new breast cancer cell lines," *Br J Cancer*, 81(8):1328-1334, 1999.
Fourie et al., "Catalytic Activity of ADAM8, ADAM15, and MDC-L (ADAM28) on Synthetic Peptide Substrates and in Ectodomain Cleavage of CD23*," *J Biol Chem*, 278(33):30469-30477, 2003.
GenBank Accession No. EAW61326.1, "ADAM metallopeptidase domain 8, isoform CRA_b [*Homo sapiens*]," 3 pages, dated Mar. 23, 2015.
Gradishar et al., "Phase III Trial of Nanoparticle Albumin-Bound Paclitaxel Compared With Polyethylated Castor Oil-Based Paclitaxel in Women With Breast Cancer," *J Clin Oncol*, 23(31):7794-7803, 2005.
Gradishar et al., "Significantly longer progression-free survival with nab-paclitaxel compared with docetaxel as first-line therapy for metastatic breast cancer," *J Clin Oncol*, 27(22):3611-3619, 2009.
Greiner et al., "Confocal backscattering-based detection of leukemic cells in flowing blood samples," *Cytometry A*, 79:874-883, 2011.
Guaiquil et al., "ADAM8 is a negative regulator of retinal neovascularization and of the growth of heterotopically injected tumor cells in mice," *J Mol Med*, 88:497-505, 2010.
Hall et al., "Structure of human ADAM-8 catalytic domain complexed with batimastat," Acta Crystallogr Sect F Struc Biol Cryst Commun, 68(Pt 6):616-621, 2012.
Harada et al., "Monoclonal antibody G6K12 specific for membrane-associated differentiation marker of human stratified squamous epithelia and squamous cell carcinoma," *Oral Pathol Med*, 22(4):145-152, 1993.
Harris, "Hypoxia—a key regulatory factor in tumour growth," *Nat Rev Cancer*, 2:38-47, 2002.
Hawinkels et al., "VEGF release by MMP-9 mediated heparan sulphate cleavage induces colorectal cancer angiogenesis," *Eur J Cancer*, 44:1904-1913, 2008.
He et al., "Overexpression of a disintegrin and metalloprotease 8 in human gliomas is implicated in tumor progression and prognosis," Med Oncol, 29(3):2032-2037, 2012.
Huang et al., "Upregulation of a disintegrin and metalloprotease 8 is associated with progression and prognosis of patients with gastric cancer," *Transl Res*, 166(6):602-613, 12 pages, 2015.
Hwu et al., "Assessment of the role of circulating breast cancer cells in tumor formation and metastatic potential using n vivo flow cytometry," J Biomed Opt, 16(4):040501, 3 pages, 2011.
Inai et al., "Immunohistochemical detection of an enamel protein-related epitope in rat bone an an early stage of osteogenesis," *Histochemistry*, 99(5):355-362, 1993.
Intemational Search Report and Written Opinion in International Appln. No. PCT/US2014/037857, dated Nov. 11, 2014, 17 pages.
International Preliminary Report on Patentability in International Appln. No. PCT/US2014/037857, dated Nov. 13, 2014, 14 pages.
International Preliminary Report on Patentability in International Appln. No. PCT/US2020/035280, dated Dec. 9, 2021, 8 pages.
International Search Report and Written Opinion in International Appln. No. PCT/US2020/035280, dated Sep. 11, 2020, 16 pages.
Ishikawa et al., "ADAM8 as a Novel Serological and Histochemical Marker for Lung Cancer," *Clin Cancer Res*, 10(24):8363-8370, 2004.
Isticato et al., "Surface Display of Recombinant Proteins on Bacillus subtilis Spores," *J Bacterial*, 183(21):5294-6301, 2001.
Jiang et al., "Expression of ADAM8 and its clinical values in diagnosis and prognosis of hepatocellular carcinoma," *Tumor Biol*, 33(6):2167-2172, 2012.
Kaufman et al., "Amplification and expression of sequences cotransfected with a modular dihydrofolate reductase complementary dna gene," *J Mol Biol*, 159(4):601-621, 1982.
Kelly et al., "Metalloprotease-disintegrin ADAM8: expression analysis and targeted deletion in mice," *Dev Dyn*, 232:221-231, 2005.
Kim et al., "Inhibitor of DNA binding 1 activates vascular endothelial growth factor through enhancing the stability and activity of hypoxia-inducible factor-1 alpha," *Mol Cancer Res*, 5:321-329, 2007.
Koller et al., "ADAM8/MS2/CD156, an emerging drug target in the treatment of inflammatory and invasive pathologies," *Curr Pharm Des*, 15:2272-2281, 2009.
Lee et al., "ADAM10 is upregulaled in melanoma metastasis compared with primary melanoma," *J Invest Dermatol*, 130:763-773, 2009.
Linderholm et al., "Significantly higher levels of vascular endothelial growth factor (VEGF) and shorter survival times for patients with primary operable triple-negative breast cancer," *Ann Oncol*, 20:1639-1646, 2009.
Lohela et al., "VEGFs and receptors involved in angiogenesis versus lymphangiogenesis," *Curr Opin Cell Biol*, 21:154-165, 2009.
Lyons et al., "Endogenous light scattering as an optical signature of circulating tumor cell clusters," *Biomed Opt Express*, 7(3):1042-1050, 9 pages, 2016.
Majmundar et al., "Hypoxia—inducible factors and the response to hypoxic stress," Mol Cell, 40:294-309, 2010.
Maretzky et al., "Migration of growth factor-stimulated epithelial and endothelial cells depends on EGFR transactivation by ADAM17," Nat Commun, 2:229, 18 pages, 2011.
Marks et al., "By-passing immunization: Human antibodies from V-gene libraries displayed on phage," *Journal of Molecular Biology*, 222(3):581-597, 1991.
Martin et al., "The role of ADAM 15 in glomerular mesangial cell migration," *J Biol Chem*, 277(37):33683-33689, 7 pages, 2002.
McLaughlin et al., "The RasGAP gene, RASAL2, is a tumor and metastasis suppressor," *Cancer Cell*, 24(3):365-278, 2013.
Mierke, "Role of the endothelium during tumor cell metastasis: is the endothelium a barrier or a promoter for cell invasion and metastasis," *Biophys*, 2008:183516, 14 pages, 2008.
Mineva et al., "Epigallocatechin-3-Gallate Inhibits Stem-Like Inflammatory Breast Cancer Cells," *PLoS One*, 8(9):e73464, 2013.
Mineva et al., "Inhibition of RelB by 1,25-dihydroxyvitamin D3 promotes sensitivity of breast cancer cells to radiation," *J Cell Physiol*, 220:593-599, 2009.
Minn et al., "Genes that mediate breast cancer metastasis to lung," *Nature*, 436:518-524, 2005.

(56) References Cited

OTHER PUBLICATIONS

Mohammed et al., "Prognostic significance of vascular endothelial cell growth factors -A, -C and -D in breast cancer and their relationship with angio- and lymphangiogenesis," *Br J Cancer*, 96:1092-1100, 2007.
Mulder et al., "Characterization of two human monoclonal antibodies reactive with HLA-B12 and HLA-B60, respectively, raised by in vitro secondary immunization of peripheral blood lymphocytes," Immunol, 36 (3):186-192, 1993.
Naumov et al., "Role of angiogenesis in human tumor dormancy: animal models of the angiogenic switch," *Cell Cycle*, 5:1779-1787, 2006.
Nelson et al., "Demystified . . . Monoclonal antibodies," *Mol Pathol*, 53(3):111-117, 2000.
Pascal et al., "HDX Workbench: Software for the Analysis of H/D Exchange MS Data," J Am Soc Mass 0002US1 Spectrom, 23(9):1512-1521, 2012.
Pierce et al., "Levels of specific glycans significantly distinguish lymph node-positive from lymph node-negative breast cancer patients," *Glycobiology*, 20:1283-1288, 2010.
Pogoda et al., "Analysis of pattern, time and risk factors influencing recurrence in triple-negative breast cancer patients," *Med Oncol*, 30(1):388-395, 8 pages, 2013.
Price et al., "Beta-1 Integrins mediate tumour cell adhesion to quiescent endothelial cells in vitro," Br J Cancer, 74:1762-1766, 1996.
Rao et al., "α9β1: A Novel Osteoclast Integrin That Regulates Osteoclast Formation and Functiontt," *J Bone Miner Res*, 21(10):1657-1665, 2006.
Richens et al., "The detection of ADAM8 protein on cells of the human immune system and the demonstration of its expression on peripheral blood B cells, dendritic cells and monocyte subsets," Immunobiology, 212:29-38, 2007.
Roemer et al., "Increased mRNA expression of ADAMs in renal cell carcinoma and their association with clinical outcome," *Oncol Rep*, 11(2):529-536, 2004.
Roemer et al., "The membrane proteases adams and hepsin are differentially expressed in renal cell carcinoma are they potential tumor markers," J Urol, 172:2162-2166, 2001.
Romagnoli et al., "ADAM8 expression in invasive breast cancer promotes tumor dissemination and metastasis," *EMBO Mol Med*, 6(2):278-294, 2014.
Romagnoli et al., "Epithelial-to-mesenchymal transition induced by TGF-beta1 is mediated by Blimp-1-dependent repression of BMP-5," *Cancer Res*, 72:6268-6278, 2005.
Roy et al., "Potential of fluorescent metalloproteinase substrates for cancer detection," *Clin Biochem*, 44:1434-1439, 2011.
Schlomann et al., "The Metalloprotease Disintegrin ADAM8," *J Biol Chem*, 277:48210-48219, 2002.
Scott et al., "Unifying metastasis—integrating intravasation, circulation and end-organ colonization," *Nat Rev Cancer*, 12:445-446, 2012.
Srinivasan et al., "N-glycosylation regulates ADAM8 processing and activation," *J Biol Chem*, 289(48):33676-33688, 2014.
Sriraman et al., "Regulated expression of ADAM8 (a disintegrin and metalloprotease domain 8) in the mouse ovary: evidence for a regulatory role of luteinizing hormone, progesterone receptor, and epidermal growth factor-like growth factors," *Biol Reprod*, 78:1038-1048, 2008.
Stauber et al., "Rapid generation of monoclonal antibody-secreting hybridomas against African horse sickness virus by in vitro immunization and the fusion/cloning technique," *J Immunol Methods*, 161(2):157-168, 1993.
Steeg, "Tumor metastasis: mechanistic insights and clinical challenges," *Nat Med*, 12:895-904, 2006.
Stone et al., "Structure-function analysis of the ADAM family of disintegrin-like and metalloproteinase-containing proteins (review)," *J Protein Chem*, 18(4):447-465, 1999.
Takeda et al., "Crystal structures of VAP1 reveal ADAMs' MDC domain architecture and its unique C-shaped scaffold," *EMBO J*, 25(11):2388-2396, 2006.
Takeda, "ADAM and ADAMTS Family Proteins and Snake Venom Metalloproteinases: A Structural Overview," *Toxins*, 8(5), pii:E155, 35 pages, 2016.
Toh et al., "Immune predictors of cancer progression," *Immunol Res*, 53:229-234, 6 pages, 2012.
Urlaub et al., "Isolation of Chinese hamster cell mutants deficient in dihydrofolate reductase activity," *Proc Natl Acad Sci USA*, 77:4216-4220, 1980.
Valkovskaya et al., "ADAM8 expression is associated with increased invasiveness and reduced patient survival in pancreatic cancer," *J Cell Mol Med*, 11(5):1162-1174, 2007.
Valkovskaya, "Hypoxia-dependent expression of ADAM8 in human pancreatic cancer cell lines," *Exp Oncol*, 30(2):129-132, 2008.
Van de Vijver et al., "A gene-expression signature as a predictor of survival in breast cancer," *N Engl J Med*, 347:1999-2009, 2002.
Venkateswaran et al., "Production of anti-fibroblast growth factor receptor monoclonal antibodies by in vitro immunization," *Hybridoma*, 11(6):729-739, 1992.
Vitetta et al., "Redesigning nature's poisons to create anti-tumor reagents," *Science*, 238:1098-1104, 1987.
Volk et al., "Nab-paclitaxel Efficacy in the Orthotopic Model of Human Breast Cancer Is Significantly Enhanced by Concurrent Anti-Vascular Endothelial Growth Factor A Therapy," *Neoplasia*, 10(6):613-623, 2008.
Wang et al., "Oestrogen signalling inhibits invasive phenotype by repressing RelB and its target BCL2," *Nat Cell Biol*, 9:470-478, 2007.
Yang et al., "Expression of a disintegrin and metalloprotease 8 is associated with cell growth and poor survival in colorectal cancer," *BMC Cancer*, 14:568-579, 12 pages, 2014.
Yoshiyama et al., "CD156 (human ADAM8): expression, primary amino acid sequence, and gene location," *Genomics*, 41(1):56-62, 1997.
Zhang et al., "A Renewable Tissue Resource of Phenotypically Stable, Biologically and Ethnically Diverse, Patient-Derived Human Breast Cancer Xenograft Models," *Cancer Res*, 73(15):4885-4897, 2013.
Zhang et al., "Establishment of Patient-Derived Xenograft (PDX) Models of Human Breast Cancer," *Curr Protoc Mouse Biol*, 3(1):21-29, 2013.
Zhang et al., "High ADAM8 Expression is Associated with Poor Prognosis in Patients with Hepatocellular Carcinoma," *Pathol Oncol Res*, 19(1):79-88, 2013.
Zhang et al., "High expression of ADAM8 correlates with poor prognosis in hepatocellular carcinoma," *Surgeon*, 11(2):67-71, 2013.
Zhang et al., "Prognostic and clinical implication of a disintegrin and metalloprotease 8 expression in pediatric rnedulloblastoma," *J Neurol Sci*, 323(1-2):46-51, 2012.
Zhong et al., "Distinct Functions of Natural ADAM-15 Cytoplasmic Domain Variants in Human Mammary Carcinoma," *Mol Cancer Res*, 6:383-394, 2009.
Zielinski et al., "ADAM8 in squamous cell carcinoma of the head and neck: a retro0002US1 Spective study," BMC Cancer, 12:76, 5 pages, 2012.

* cited by examiner

| ADAM8 Antibody | Isotype | Subclass | Light Chain |
|---|---|---|---|
| ADP1 | IgG | 2c | κ |
| ADP2 | IgG | 2b | κ |
| ADP3 | IgG | 1 | κ |
| ADP4 | IgG | 2b | κ |
| ADP5 | IgG | 2c | κ |
| ADP6 | IgG | 1 | κ |
| ADP7 | IgG | 1 | κ |
| ADP8 | IgG | 1 | κ |
| ADP9 | IgG | 1 | κ |
| ADP10 | IgG | 1 | κ |
| ADP11 | IgG | 1 | κ |
| ADP12 | IgG | 1 | κ |
| ADP13 | IgG | 1 | κ |
| ADP14 | IgG | 2c | κ |
| ADP16 | IgG | 2c | κ |
| ADP17 | IgG | 1 | κ |
| ADP18 | IgG | 1 | κ |
| ADP19 | IgG | 1 | κ |

FIG. 3

| ADAM8 Antibody | Binding to Cell Surface ADAM8 in FACS (MFI) | | | | | |
|---|---|---|---|---|---|---|
| | HEK293-ADAM8 | | | HEK293-Empty vector | | |
| | 10 μg/ml | 1 μg/ml | 0.1 μg/ml | 10 μg/ml | 1 μg/ml | 0.1 μg/ml |
| ADP1 | 185.7 | 171.2 | 46.8 | 3.1 | 3.1 | 3.1 |
| ADP2 | 158.1 | 156.5 | 58.4 | 2.6 | 2.7 | 2.9 |
| ADP3 | 86.9 | 96.5 | 51.8 | 2.8 | 2.7 | 2.7 |
| ADP4 | 160.8 | 140.0 | 47.4 | 2.6 | 2.7 | 2.7 |
| ADP5 | 149.0 | 105.9 | 26.8 | 2.7 | 2.8 | 3.1 |
| ADP6 | 62.4 | 65.4 | 28.2 | 2.7 | 2.7 | 2.9 |
| ADP7 | 68.1 | 63.1 | 25.8 | 2.7 | 2.9 | 2.8 |
| ADP8 | 48.6 | 53.1 | 17.0 | 2.6 | 2.6 | 2.6 |
| ADP9 | 62.1 | 61.1 | 22.1 | 3.2 | 2.9 | 2.7 |
| ADP10 | 67.2 | 58.2 | 18.7 | 3.2 | 2.8 | 2.7 |
| ADP11 | 56.6 | 64.2 | 24.1 | 3.1 | 2.7 | 2.6 |
| ADP12 | 106.7 | 68.7 | 17.4 | 3.1 | 3.1 | 3.0 |
| ADP13 | 62.2 | 21.1 | 7.1 | 2.6 | 2.7 | 2.6 |
| ADP14 | 58.6 | 17.9 | 5.9 | 3.3 | 3.2 | 3.0 |
| ADP16 | 147.3 | 89.6 | 24.6 | 2.6 | 2.9 | 2.9 |
| ADP17 | 53.6 | 63.8 | 25.5 | 2.8 | 2.7 | 2.8 |
| ADP18 | 53.7 | 61.0 | 23.5 | 2.8 | 2.8 | 2.7 |
| ADP19 | 59.0 | 52.9 | 17.5 | 2.6 | 2.6 | 3.0 |
| mIgG | 4.0 | 3.2 | 3.3 | 4.0 | 3.1 | 3.1 |
| Test bleed | 65.2 | 161.5 | 87.9 | 3.7 | 3.7 | 3.0 |

FIG. 4

| ADAM8 Antibody | ADAM8 Binding | | | |
|---|---|---|---|---|
| | ELISA | Biacore | | |
| | EC50(nM) | $k_a$ (1/Ms) | $k_d$ (1/s) | KD (M) |
| ADP1 | 0.032 | 7.04E+04 | 3.15E-04 | 4.47E-09 |
| ADP2 | 0.029 | 8.95E+04 | 2.99E-04 | 3.34E-09 |
| ADP3 | 0.049 | 3.47E+04 | 6.34E-04 | 1.83E-08 |
| ADP4 | 0.041 | 3.52E+04 | 2.55E-02 | 7.23E-08 |
| ADP5 | 0.059 | 9.51E+03 | 9.27E-05 | 9.75E-09 |
| ADP6 | 0.059 | 2.62E+05 | 4.07E-03 | 1.55E-08 |
| ADP7 | 0.091 | 1.68E+04 | 8.89E-04 | 5.29E-08 |
| ADP8 | 0.097 | 3.14E+03 | 1.48E-04 | 4.72E-08 |
| ADP9 | 0.053 | 2.78E+04 | 1.37E-03 | 4.92E-08 |
| ADP10 | 0.091 | 2.45E+03 | 7.52E-05 | 3.07E-08 |
| ADP11 | 0.097 | 5.07E+03 | 1.09E-04 | 2.14E-08 |
| ADP12 | 0.061 | 4.97E+04 | 4.14E-04 | 8.33E-09 |
| ADP13 | 0.054 | 3.54E+04 | 4.60E-05 | 1.30E-09 |
| ADP14 | 0.531 | 2.32E+04 | 6.12E-04 | 2.64E-08 |
| ADP16 | 0.053 | 7.27E+04 | 0.005121 | 7.05E-08 |
| ADP17 | 0.049 | 6.78E+03 | 1.26E-04 | 1.86E-08 |
| ADP18 | 0.024 | 8.05E+03 | 1.23E-04 | 1.53E-08 |
| ADP19 | 0.085 | 1.60E+04 | 1.45E-04 | 9.11E-09 |

FIG. 5

| Epitope | Antibody | ADP10 | ADP17 | ADP18 | ADP19 | ADP11 | ADP8 | ADP5 | ADP13 | ADP2 | ADP1 | ADP12 | ADP7 | ADP9 | ADP6 | ADP4 | ADP3 | ADP16 | ADP14 |
|---|---|---|---|---|---|---|---|---|---|---|---|---|---|---|---|---|---|---|---|
| 1 | ADP10 | 91% | 90% | 88% | 82% | 91% | 90% | 59% | 44% | 24% | 26% | 16% | 37% | 47% | 68% | 49% | 14% | 45% | -13% |
| | ADP17 | 90% | 93% | 88% | 90% | 94% | 92% | 45% | 65% | 38% | 52% | 42% | 47% | 57% | 63% | 53% | 32% | 35% | -26% |
| | ADP18 | 91% | 94% | 90% | 89% | 94% | 91% | 32% | 49% | 30% | 21% | 13% | 34% | 50% | 60% | 46% | 7% | 45% | -29% |
| | ADP19 | 90% | 93% | 91% | 88% | 92% | 92% | 79% | 37% | -4% | 16% | 3% | 26% | 31% | 34% | 33% | 0% | 25% | -24% |
| | ADP11 | 91% | 93% | 90% | 88% | 94% | 92% | 87% | 47% | 10% | -3% | 9% | 48% | 50% | 46% | 24% | 3% | 37% | 5% |
| | ADP8 | 92% | 92% | 88% | 84% | 93% | 91% | 85% | 44% | 2% | 8% | 4% | 17% | 37% | 42% | 20% | 6% | 25% | -27% |
| | ADP5 | 91% | 93% | 92% | 86% | 94% | 94% | 81% | 54% | 14% | 26% | 8% | 42% | 22% | 37% | 33% | 4% | 54% | -30% |
| 2 | ADP13 | 52% | 56% | 23% | 66% | 27% | 46% | 27% | 92% | 85% | 80% | 89% | -9% | -3% | 19% | 47% | 3% | 12% | -18% |
| 3 | ADP2 | 26% | 26% | 11% | 10% | 13% | 11% | 1% | 94% | 91% | 83% | 90% | 91% | 85% | 93% | 94% | 93% | 41% | -10% |
| | ADP1 | 24% | 7% | 12% | 6% | 13% | 9% | 3% | 89% | 91% | 78% | 90% | 88% | 85% | 94% | 95% | 95% | 34% | 1% |
| | ADP12 | 31% | 15% | 7% | 42% | 6% | 6% | -17% | 94% | 90% | 85% | 90% | 83% | 79% | 85% | 89% | 80% | 22% | -25% |
| | ADP7 | 64% | 61% | 40% | 48% | 54% | 48% | 87% | 33% | 66% | 77% | 60% | 87% | 83% | 91% | 88% | 73% | 86% | -29% |
| | ADP9 | 58% | 61% | 34% | 49% | 39% | 42% | 68% | 52% | 81% | 83% | 79% | 88% | 84% | 87% | 89% | 84% | 90% | -30% |
| | ADP6 | 40% | 38% | 17% | 57% | 18% | 30% | -5% | 22% | 76% | 76% | 69% | 89% | 84% | 93% | 95% | 78% | 87% | 6% |
| | ADP4 | 35% | 35% | 9% | 28% | 11% | 25% | 3% | 32% | 61% | 76% | 53% | 85% | 82% | 91% | 92% | 66% | 84% | -25% |
| | ADP3 | 34% | 16% | 15% | 16% | 15% | -1% | 6% | 31% | 89% | 80% | 89% | 89% | 87% | 93% | 92% | 93% | 89% | 6% |
| 4 | ADP16 | 35% | 7% | 7% | 26% | 12% | -2% | -3% | 47% | 43% | 56% | 34% | 79% | 81% | 89% | 86% | 72% | 88% | -7% |
| 5 | ADP14 | 46% | 32% | 19% | 39% | 27% | 6% | 15% | 40% | 40% | 62% | 13% | 60% | 70% | 83% | 75% | 57% | 20% | 82% |

FIG. 6

| ADAM8 Antibody | Crossreactivity to Related ADAMs (ELISA, OD450 nm) | | | |
|---|---|---|---|---|
| | ADAM8 | ADAM9 | ADAM12 | ADAM10 |
| ADP1 | 2.68 | 0.07 | 0.07 | 0.06 |
| NC | 0.08 | 0.07 | 0.07 | 0.07 |
| PC | 2.95 | 0.18 | 0.17 | 0.17 |
| ADP2 | 2.76 | 0.07 | 0.14 | 0.16 |
| NC | 0.07 | 0.15 | 0.09 | 0.12 |
| PC | 2.65 | 0.22 | 0.60 | 0.33 |
| ADP3 | 2.31 | 0.15 | 0.16 | 0.17 |
| ADP4 | 2.78 | 0.13 | 0.10 | 0.10 |
| ADP5 | 3.00 | 0.12 | 0.13 | 0.13 |
| ADP6 | 2.35 | 0.12 | 0.11 | 0.11 |
| ADP7 | 2.71 | 0.12 | 0.12 | 0.14 |
| ADP8 | 2.69 | 0.15 | 0.13 | 0.14 |
| ADP9 | 2.46 | 0.10 | 0.09 | 0.11 |
| ADP11 | 2.79 | 0.10 | 0.15 | 0.10 |
| ADP12 | 2.55 | 0.12 | 0.11 | 0.16 |
| ADP13 | 2.64 | 0.12 | 0.12 | 0.09 |
| ADP14 | 2.68 | 0.13 | 0.18 | 0.14 |
| ADP16 | 2.81 | 0.14 | 0.13 | 0.18 |
| ADP18 | 2.55 | 0.13 | 0.11 | 0.12 |
| ADP19 | 2.83 | 0.20 | 0.12 | 0.17 |
| NC | 0.26 | 0.20 | 0.20 | 0.21 |
| PC | 3.01 | 3.06 | 1.17 | 2.06 |
| ADP10 | 2.57 | 0.16 | 0.24 | 0.26 |
| NC | 0.26 | 0.20 | 0.20 | 0.21 |
| PC | 3.01 | 3.06 | 1.17 | 2.06 |
| ADP17 | 2.99 | 0.09 | 0.09 | 0.08 |
| NC | 0.07 | 0.10 | 0.09 | 0.06 |
| PC | 3.08 | 2.77 | 2.51 | 2.83 |

FIG. 8

| ADAM8 Antibody | Functional Assay | | |
|---|---|---|---|
| | MP Activity | DI Activity | |
| | CD23 cleavage<br>% inhibition | α9β1 integrin binding to ADAM8<br>% inhibition | Transendothelial migration<br>% inhibition |
| ADP1 | 72.6 ± 6.4 | 58.4 ± 17.3 | 54.6 ± 1.9 |
| ADP2 | 62.6 ± 23.0 | 72.0 ± 9.8 | 37.6 ± 3.8 |
| ADP3 | 79.9 ± 16.5 | 69.3 ± 11.9 | 44.5 ± 11.0 |
| ADP4 | 77.3 ± 14.6 | 9.5 ± 7.9 | 22.2 ± 2.4 |
| ADP5 | 95.5 ± 3.6 | 36.3 ± 6.9 | 43.8 ± 11.4 |
| ADP6 | 86.6 ± 6.3 | 47.9 ± 11.5 | 54.1 ± 7.9 |
| ADP12 | 95.5 ± 6.0 | 60.4 ± 12.5 | 35.0 ± 18.2 |
| ADP13 | 79.1 ± 11.7 | 78.5 ± 6.5 | 54.5 ± 14.3 |
| ADP19 | 88.7 ± 10.9 | 72.4 ± 14.2 | 35.1 ± 15.0 |
| MAB1031 | 65.8 ± 14.5 | 63.4 ± 10.0 | 42.4 ± 4.7 |

FIG. 10

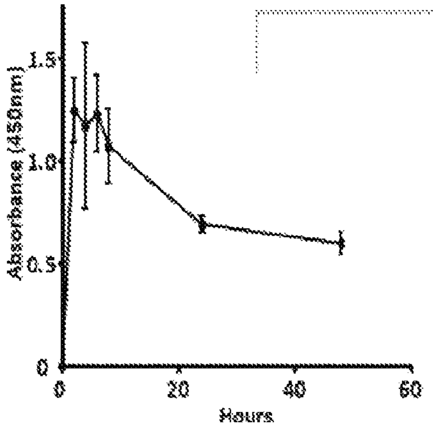
FIG. 23A
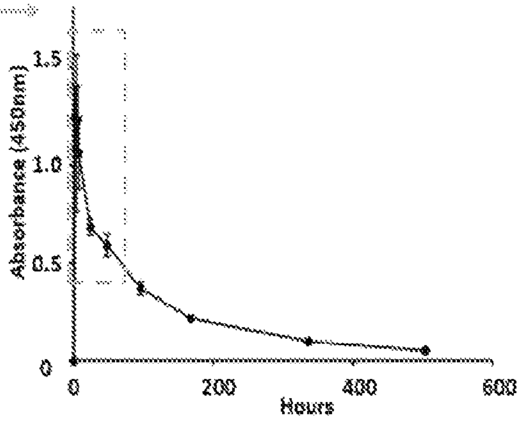
FIG. 23B
| Time (hr) | Concentration (nM) |
|---|---|
| 0 | 0 |
| 2 | 1271 ± 186 |
| 4 | 1017 ± 201 |
| 6 | 1001 ± 133 |
| 8 | 1055 ± 185 |
| 24 | 782 ± 31 |
| 48 | 617 ± 31 |
| 96 | 375 ± 33 |
| 168 | 246 ± 16 |
| 336 | 108 ± 16 |
| 504 | 56 ± 7 |
FIG. 23C

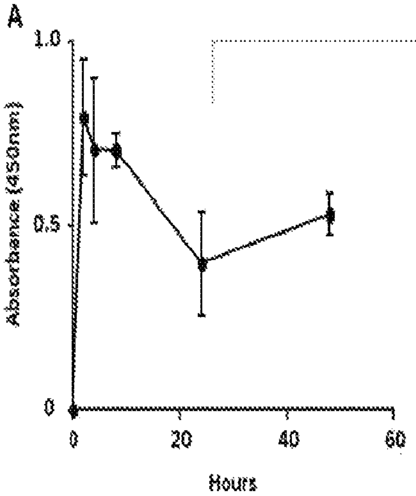
FIG. 24A
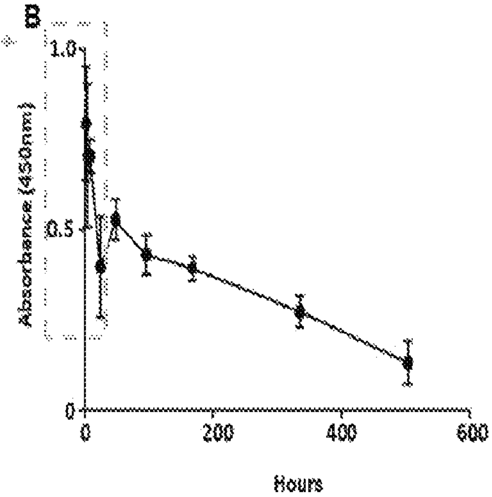
FIG. 24B
C
| [illegible] | [illegible] |
|---|---|
| 0 | 0 |
| 2 | 785±157 |
| 4 | 706±198 |
| 8 | 704±46 |
| 24 | 398±146 |
| 48 | 528±67 |
| 96 | 432±55 |
| 168 | 395±33 |
| 336 | 275±48 |
| 504 | 130±61 |
FIG. 24C
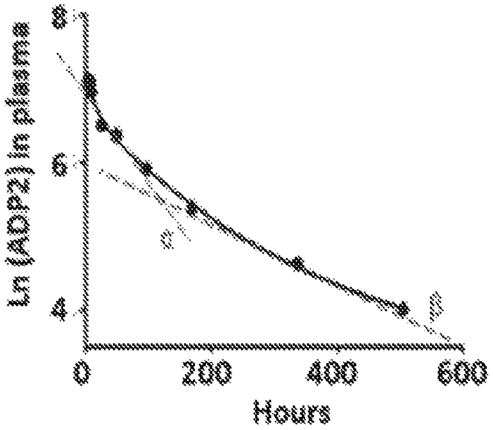
FIG. 25A
| ADP2 Parameters | Values |
|---|---|
| AUC to last point | 127996 |
| Ke(1/hr) | 0.00469 |
| T1/2 (hours) | 147.8 |
| T1/2 (days) | 6.2 |
| Total AUC | 139851 |
| Clearance (mL/min) | 0.1537 |
FIG. 25B
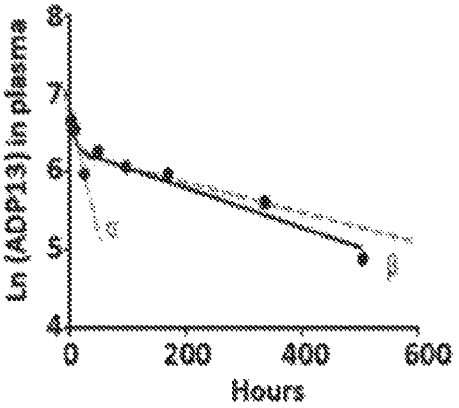
FIG. 25C
| ADP13 Parameters | Values |
|---|---|
| AUC to last point | 168444 |
| Ke(1/hr) | 0.00284 |
| T1/2 (hours) | 244 |
| T1/2 (days) | 10.2 |
| Total AUC | 215275 |
| Clearance (mL/min) | 0.1 |
FIG. 25D

| ADP2 | |
|---|---|
| Time (hr) | Concentration (nM) |
| 0 | 0 |
| 2 | 1155 ± 101 |
| 50 | 2241 ± 562 |
| 100 | 4087 ± 1296 |
| 172 | 1610 ± 153 |
| 174 | 3644 ± 834 |

| ADP13 | |
|---|---|
| Time (hr) | Concentration (nM) |
| 0 | 0 |
| 2 | 944 ± 149 |
| 50 | 1496 ± 212 |
| 100 | 3273 ± 1032 |
| 172 | 2628 ± 386 |
| 174 | 3543 ± 1103 |

| Binding Reactivity ( % WT) | | | |
|---|---|---|---|
| Mutation | ADP2 Fab HS | ADP13 Fab HS | Control Ab |
| R431A | 26.2 (18) | 79.6 (9) | 91.0 (16) |
| E444A | 17.6 (10) | 70.8 (26) | 85.6 (4) |
| G445A | 30.7 (0) | 9.7 (3) | 78.4 (13) |
| Q447A | 46.5 (40) | -0.9 (13) | 90.2 (11) |
| K458A | 28.0 (15) | 13.5 (1) | 77.0 (9) |
| V459A | 55.6 (21) | 27.8 (1) | 84.6 (12) |
| A462S | 50.1 (63) | 24.7 (69) | 84.1 (4) |
| R482A | 113.1 (47) | 8.3 (8.5) | 91.6 (36) |

FIG. 38

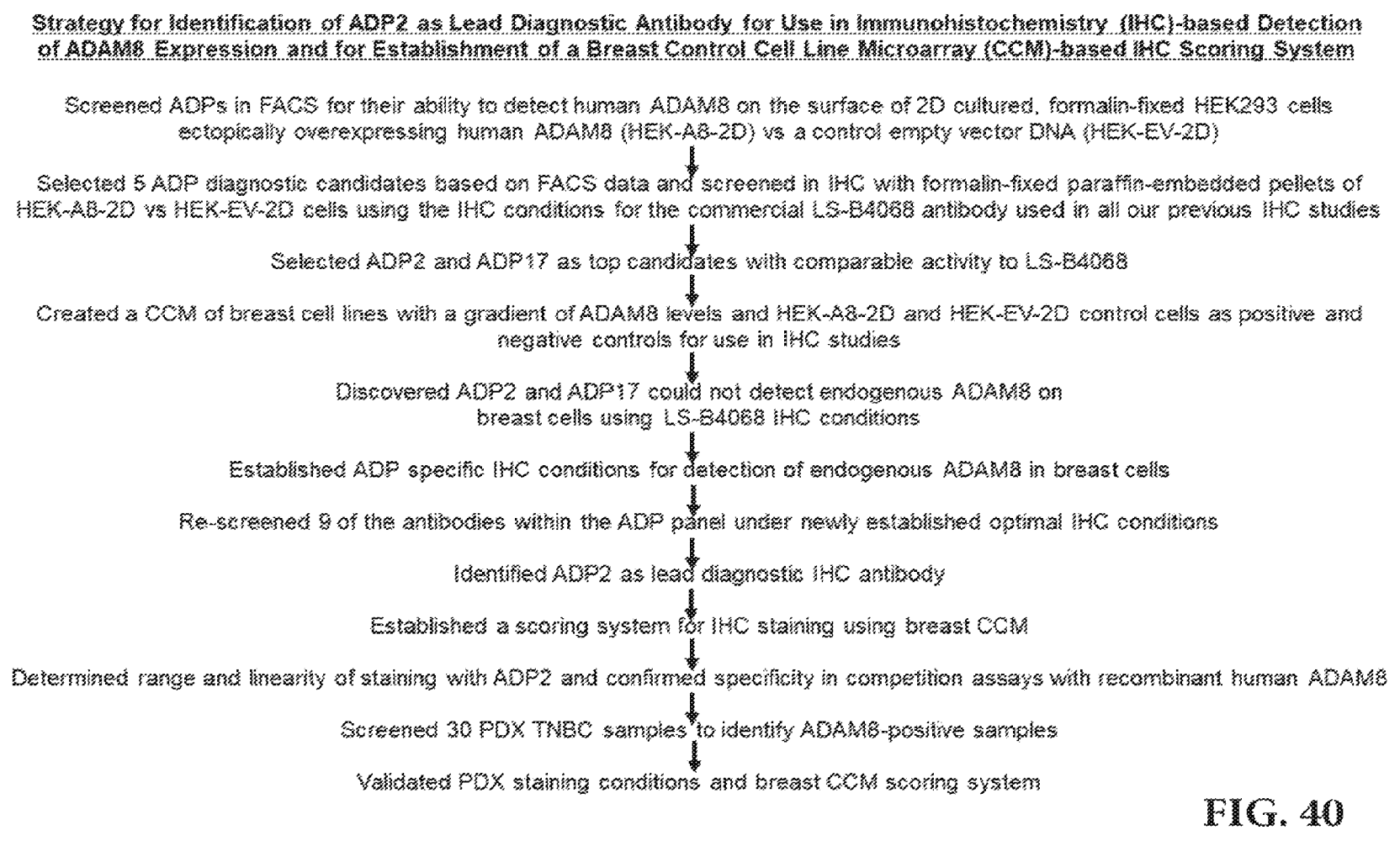

Strategy for Identification of ADP2 as Lead Diagnostic Antibody for Use in Immunohistochemistry (IHC)-based Detection of ADAM8 Expression and for Establishment of a Breast Control Cell Line Microarray (CCM)-based IHC Scoring System

Screened ADPs in FACS for their ability to detect human ADAM8 on the surface of 2D cultured, formalin-fixed HEK293 cells ectopically overexpressing human ADAM8 (HEK-A8-2D) vs a control empty vector DNA (HEK-EV-2D)

↓

Selected 5 ADP diagnostic candidates based on FACS data and screened in IHC with formalin-fixed paraffin-embedded pellets of HEK-A8-2D vs HEK-EV-2D cells using the IHC conditions for the commercial LS-B4068 antibody used in all our previous IHC studies

↓

Selected ADP2 and ADP17 as top candidates with comparable activity to LS-B4068

↓

Created a CCM of breast cell lines with a gradient of ADAM8 levels and HEK-A8-2D and HEK-EV-2D control cells as positive and negative controls for use in IHC studies

↓

Discovered ADP2 and ADP17 could not detect endogenous ADAM8 on breast cells using LS-B4068 IHC conditions

↓

Established ADP specific IHC conditions for detection of endogenous ADAM8 in breast cells

↓

Re-screened 9 of the antibodies within the ADP panel under newly established optimal IHC conditions

↓

Identified ADP2 as lead diagnostic IHC antibody

↓

Established a scoring system for IHC staining using breast CCM

↓

Determined range and linearity of staining with ADP2 and confirmed specificity in competition assays with recombinant human ADAM8

↓

Screened 30 PDX TNBC samples to identify ADAM8-positive samples

↓

Validated PDX staining conditions and breast CCM scoring system

FIG. 40

ANTI-ADAM8 ANTIBODIES AND USES OF THE SAME

CROSS-REFERENCE TO RELATED APPLICATIONS

This application is a National Stage entry of PCT/US2020/035280, filed on May 29, 2020, which claims priority to U.S. Provisional Patent Application Ser. No. 62/855,575, filed May 31, 2019; the entire contents of each of which is herein incorporated by reference.

STATEMENT AS TO FEDERALLY SPONSORED RESEARCH

This invention was made with government support under grants CA194955, CA200161, and CA239942 awarded by the National Institutes of Health. The government has certain rights in the invention.

TECHNICAL FIELD

The present disclosure relates generally to the fields of immunology and cancer biology. More specifically, the present disclosure relates to the use of proteins to treat cancer and to identify those patients that can benefit from this treatment.

BACKGROUND

ADAM8 was found to be non-essential under physiological conditions, as evidenced by normal development, lack of pathological defects, and a normal life span of ADAM8-deficient mice. Under normal conditions in most human tissues and cells, ADAM8 mRNA is either undetectable or low, and protein expression is either limited to low levels or to an inactive cytoplasmic state. However, elevated ADAM8 expression has been detected in breast cancer and many other solid tumors, including adrenal, bone, brain, colorectal, esophageal, gastric, head and neck, hepatocellular, lung, pancreatic, prostate, renal, and thyroid cancers, as well as in lymphomas and leukemias. Overexpression of ADAM8 in solid tumors has been correlated with either a higher tumor grade, a more metastatic phenotype and/or poorer patient prognosis. Overall, the ADAM8 cell surface protein constitutes a crucial player in multiple steps of tumorigenesis and is a promising target for a large number of patients with aggressive ADAM8-driven cancers. Development of an anti-ADAM8 antagonist antibody could revolutionize treatment of patients affected by these cancers by providing an effective and tolerable therapeutic option, and reducing the mortality associated with metastatic disease.

SUMMARY

The present invention relates to the discovery of a new class of proteins that target the disintegrin (DI) domain of ADAM8 and inhibit the activity of both the metalloproteinase (MP) and disintegrin (DI) domains of ADAM8. The effectiveness of these proteins indicates that the DI domain of ADAM8 has its own independent function and plays a role in maintaining the overall protein structure and in bridging/aligning the catalytic and substrate recognition activities necessary for proper MP domain functionality.

Provided herein are proteins that inhibit both the metalloprotease activity and disintegrin activity of human ADAM8, wherein the protein includes an antigen-binding domain that: (i) binds specifically to human ADAM8; and (ii) binds to an epitope within human ADAM8 that includes at least one amino acid within the sequence of: DCGPPEDCRNRCCNSTTCQLAE-GAQCAHGTCCQECKVKPAGELCRPKKDMCDLEEF CDGRHPECPEDAF (SEQ ID NO: 1).

In some embodiments of any of the proteins described herein, the protein binds to human ADAM8 with a $K_D$ of about 0.1 nM to about 100 nM. In some embodiments of any of the proteins described herein, the protein binds to human ADAM8 with a $K_D$ of about 0.1 nM to about 10 nM.

In some embodiments of any of the proteins described herein, the protein includes a single polypeptide. In some embodiments of any of the proteins described herein, the antigen-binding domain is a VHH domain, a VNAR domain, or a scFv. In some embodiments of any of the proteins described herein, the protein is selected from the group consisting of: a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, and a tandem-scFv.

In some embodiments of any of the proteins described herein, the protein includes two or more polypeptides. In some embodiments of any of the proteins described herein, the protein is selected from the group consisting of: an antibody, a VHH-scAb, a VHH-Fab, a Dual scFab, a $F(ab')_2$, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG (H)-V, V(H)—IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, an 1mmTAC, an IgG-IgG conjugate, a Cov-X-Body, and a $scFv1\text{-}PEG\text{-}scFv_2$.

In some embodiments of any of the proteins described herein, the protein is an antibody that is an IgG antibody. In some embodiments of any of the proteins described herein, the IgG antibody is an IgG1, IgG2, IgG3, or IgG4 antibody. In some embodiments of any of the proteins described herein, the IgG antibody can comprise a lamba light chain or a kappa light chain. In some embodiments of any of the proteins described herein, the antibody is a monospecific antibody. In some embodiments of any of the proteins described herein, the antibody is a bispecific antibody. In some embodiments of any of the proteins described herein, the antigen-binding domain includes heavy chain variable domain CDRs of GFSFPDYY (SEQ ID NO: 2), IRDSANGYTT (SEQ ID NO: 3), and ARYSRYYGMDY (SEQ ID NO: 4), and light chain variable domain CDRs of QTVNYD (SEQ ID NO: 5), FAS (SEQ ID NO: 6), and QQDYSAPWT (SEQ ID NO: 7). In some embodiments of any of the proteins described herein, the antigen-binding domain includes a light chain variable domain sequence of: SIVMTQTPKILLVSAGDRVTITCKASQTVNY-DVAWYQQKPGQSPKPVIYFASNRYTG VPDRFTGSGFGTDFTFTISTVQAED-LAVYFCQQDYSAPWTFGGGTKLEIK (SEQ ID NO: 8). In some embodiments of any of the proteins described herein, the antigen-binding domain includes a heavy chain variable domain sequence of: EVKLVESGG-GLVQPGGSLSLSCAASGFSFPDYYMSWVRQPPGKA- LEWLGFIRDSAN GYTTEYIASVKGRFTFSRDNSQSI-LYLQMNALRAEDSATYYCARYSRYYGMDYWGQ GTSVTVSS (SEQ ID NO: 10).

In some embodiments of any of the proteins described herein, the antigen-binding domain includes heavy chain variable domain CDRs of GYTFTDYY (SEQ ID NO: 12), ISPNIGGA (SEQ ID NO: 13), and TRGGSSYPYFYAMDY (SEQ ID NO: 14), and light chain variable domain CDRs of QSLLYSSNQKKY (SEQ ID NO: 15), WAS (SEQ ID NO: 16), and QQFYSYPYT (SEQ ID NO: 17). In some embodiments of any of the proteins described herein, the antigen-binding domain includes a light chain variable domain sequence of: DIVMSQSPSSLAVSVGEKVTMSCK-SSQSLLYSSNQKKYLAWYQQKPGQSPKLLIYW ASTRESGVPDRFTGSGSGTD FTLTISSVKAED-LAVYYCQQFYSYPYTFGGGTKLEINR (SEQ ID NO: 18). In some embodiments of any of the proteins described herein, the antigen-binding domain includes a heavy chain variable domain sequence of: EVQLQQSG-PEMVKPGTSVKISCKASGYTFTDYY-INWVKQSHGKSLEWIGDISPNIGG ATYNPKFKGKAILTVDKSARTAYMELRSLTSED-SAVYCCTRGGSSYPYFYAMDYWG QGTSVTVSS (SEQ ID NO: 20).

In some embodiments of any of the proteins described herein, the antigen-binding domain includes heavy chain variable domain CDRs of GFTFSDAW (SEQ ID NO: 22), IRGKVNNLAT (SEQ ID NO: 23), and LGRYDATYAMDY (SEQ ID NO: 24), and light chain variable domain CDRs of QSLVHSDGNTY (SEQ ID NO: 25), KLS (SEQ ID NO: 26), and SQSTHVPWT (SEQ ID NO: 27). In some embodiments of any of the proteins described herein, the antigen-binding domain includes a light chain variable domain sequence of: DVVMTQTPLSLPVSLGDQASIS-CRSSQSLVHSDGNTYLHWYLQKPGQSPKLLIYKLS NRFSGVPDRFSGSGSGTDF TLKISRVEAE-DLGVYFCSQSTHVPWTFGGGTKLEIK (SEQ ID NO: 28). In some embodiments of any of the proteins described herein, the antigen-binding domain includes a heavy chain variable domain sequence of: EVKLEESGG-GLVQPGGSMKLSCAASGFTFSDAWMDWVRQS-PEKGLEWVAEIRGKV NNLATYYVESVKGRFTISRDD-SKSSVYLQMNSLRAEDTGIYYCLGRYDATYAMDY WGQGTSVTVSS (SEQ ID NO: 30).

In some embodiments of any of the proteins described herein, the antigen-binding domain includes heavy chain variable domain CDRs of GFSFTDYY (SEQ ID NO: 32), IRDSANGYTA (SEQ ID NO: 33), and ARYSRYYAMDY (SEQ ID NO: 34), and light chain variable domain CDRs of QSVNYD (SEQ ID NO: 35), FAS (SEQ ID NO: 36), and QQDYSSPWT (SEQ ID NO: 37). In some embodiments of any of the proteins described herein, the antigen-binding domain includes a light chain variable domain sequence of: FIVMTQTPKILLVSAGDRITITCKASQSVNY-DVAWYQQKPGQSPKPVIYFASNRYTGV PDRFTGSGFGTDFTFTISTVQAEDLAVYFCQQD-YSSPWTFGGGTKLEIK (SEQ ID NO: 38). In some embodiments of any of the proteins described herein, the antigen-binding domain includes a heavy chain variable domain sequence of: EVKLVESGG-GLVQPGGSLSLSCETSGFSFTDYYMIWVRQPPGKA-LEWLGFIRDSANG YTAEYIASVKGRFTFSRDNSQSI-LYLQMNALRAEDSATYYCARYSRYYAMDYWGQ GTSVTVAP (SEQ ID NO: 40).

In some embodiments of any of the proteins described herein, the antigen-binding domain includes heavy chain variable domain CDRs of GYTFTDYN (SEQ ID NO: 42), INPNNGGT (SEQ ID NO: 43), and ARKRGLGQAWLAY (SEQ ID NO: 44), and light chain variable domain CDRs of QSLLYSGNQKNY (SEQ ID NO: 45), GAS (SEQ ID NO: 46), and QNDHSYPLT (SEQ ID NO: 47). In some embodiments of any of the proteins described herein, the antigen-binding domain includes a light chain variable domain sequence of: DIVMTQSPSSRSVSAGEKVTMSCK-SSQSLLYSGNQKNYLAWYQQKPGQPPKLLIYG ASTRESGVPDRFTGSGSGTDFTLTISSVQAED-LAVYYCQNDHSYPLTFGAGTKLELK (SEQ ID NO: 48). In some embodiments of any of the proteins described herein, the antigen-binding domain includes a heavy chain variable domain sequence of: EVQLQQSGPELVKP-GASVKIPCKASGYTFTDYNMDWVKQSHGKSLD-WIGDINPNNG GTIYNQKFKGKATLTVDKSSSTAYMELRSLTSED-TAVYYCARKRGLGQAWLAYWG QGTLVTVSA (SEQ ID NO: 50).

In some embodiments of any of the proteins described herein, the antigen-binding domain includes heavy chain variable domain CDRs of GFTFSYAW (SEQ ID NO: 52), IRSKANNYAT (SEQ ID NO: 53), and MGRYDAAYGMDY (SEQ ID NO: 54), and light chain variable domain CDRs of QSLVHSNGITY (SEQ ID NO: 55), KVS (SEQ ID NO: 56), and SQSTHVPWT (SEQ ID NO: 57). In some embodiments of any of the proteins described herein, the antigen-binding domain includes a light chain variable domain sequence of: DVVMTQTPLSLPVSLGYQASISCRSSQSLVHSNGI-TYLHWYLQKPGQSPKWYKVSN RFSGVPDRFSGSGSGTDF TLKISRVEAE-DLGVYFCSQSTHVPWTFGGGTKLEIK (SEQ ID NO: 58). In some embodiments of any of the proteins described herein, the antigen-binding domain includes a heavy chain variable domain sequence of: EVKLEESGG-GLVQPGGSMKLSCAASGFTFSYAWMDWVRQS-PEKGLEWVAEIRSKA NNYATYYAESVKGRFTISRND-SKSSVYLQMNSLRIEDTGIYYCMGRYDAAYGMDY WGQGTSVTVSS (SEQ ID NO: 60).

In some embodiments of any of the proteins described herein, the protein competitively binds to human ADAM8 with an antigen-binding domain including: (i) a light chain variable domain of SEQ ID NO: 8 and a heavy chain variable domain of SEQ ID NO: 10; (ii) a light chain variable domain of SEQ ID NO: 18 and a heavy chain variable domain of SEQ ID NO: 20; (iii) a light chain variable domain of SEQ ID NO: 28 and a heavy chain variable domain of SEQ ID NO: 30; (iv) a light chain variable domain of SEQ ID NO: 38 and a heavy chain variable domain of SEQ ID NO: 40; (v) a light chain variable domain of SEQ ID NO: 48 and a heavy chain variable domain of SEQ ID NO: 50; or (vi) a light chain variable domain of SEQ ID NO: 58 and a heavy chain variable domain of SEQ ID NO: 60.

In some embodiments of any of the proteins described herein, the antigen-binding domain binds to an epitope within human ADAM8 that includes at least one amino acid within the sequence of: CCNSTTCQLAE-GAQCAHGTCCQECK (SEQ ID NO: 86) or RNRCCN-STTCQLAEGAQCAHGTCCQECK (SEQ ID NO: 104).

In some embodiments of any of the proteins described herein, the antigen-binding domain includes heavy chain variable domain CDRs of GFSFPDYY (SEQ ID NO: 2), IRDSANGYTT (SEQ ID NO: 3), and ARYSRYYGMDY (SEQ ID NO: 4), and light chain variable domain CDRs of QTVNYD (SEQ ID NO: 5), FAS (SEQ ID NO: 6), and QQDYSAPWT (SEQ ID NO: 7).

In some embodiments of any of the proteins described herein, the antigen-binding domain includes a light chain variable domain sequence of: SIVMTQTPKILL-VSAGDRVTITCKASQTVNY-DVAWYQQKPGQSPKPVIYFASNRYTG VPDRFTGSGFGTDFTFTISTVQAED-LAVYFCQQDYSAPWTFGGGTKLEIK (SEQ ID NO: 8).

In some embodiments of any of the proteins described herein, the antigen-binding domain includes a heavy chain variable domain sequence of: EVKLVESGG-GLVQPGGSLSLSCAASGFSFPDYYMSWVRQPPGKA-LEWLGFIRDSAN GYTTEYIASVKGRFTFSRDNSQSI-LYLQMNALRAEDSATYYCARYSRYYGMDYWGQ GTSVTVSS (SEQ ID NO: 10).

In some embodiments of any of the proteins described herein, the protein competitively binds to human ADAM8 with an antigen-binding domain including: (i) a light chain variable domain of SEQ ID NO: 18 and a heavy chain variable domain of SEQ ID NO: 20; (ii) a light chain variable domain of SEQ ID NO: 28 and a heavy chain variable domain of SEQ ID NO: 30; (iii) a light chain variable domain of SEQ ID NO: 38 and a heavy chain variable domain of SEQ ID NO: 40; (iv) a light chain variable domain of SEQ ID NO: 48 and a heavy chain variable domain of SEQ ID NO: 50; or (v) a light chain variable domain of SEQ ID NO: 58 and a heavy chain variable domain of SEQ ID NO: 60.

In some embodiments of any of the proteins described herein, the antigen-binding domain binds to an epitope within human ADAM8 that includes at least one amino acid within the sequence of: LAE-GAQCAHGTCCQECKVKPAGEL-CRPKKDMCDLEEFCDGRHPECPEDAF (SEQ ID NO: 87).

In some embodiments of any of the proteins described herein, the antigen-binding domain includes heavy chain variable domain CDRs of GYTFTDYY (SEQ ID NO: 12), ISPNIGGA (SEQ ID NO: 13), and TRGGSSYPYFYAMDY (SEQ ID NO: 14), and light chain variable domain CDRs of QSLLYSSNQKKY (SEQ ID NO: 15), WAS (SEQ ID NO: 16), and QQFYSYPYT (SEQ ID NO: 17).

In some embodiments of any of the proteins described herein, the antigen-binding domain includes a light chain variable domain sequence of: DIVMSQSPSSLAVSVGEKVTMSCKSSQSLLYSSNQK-KYLAWYQQKPGQSPKLLIYW ASTRESGVPDRFTGSGSGTD FTLTISSVKAED-LAVYYCQQFYSYPYTFGGGTKLEINR (SEQ ID NO: 18).

In some embodiments of any of the proteins described herein, the antigen-binding domain includes a heavy chain variable domain sequence of: EVQLQQSG-PEMVKPGTSVKISCKASGYTFTDYY-INWVKQSHGKSLEWIGDISPNIGG ATYNPKFKGKAILTVDKSARTAYMELRSLTSED-SAVYCCTRGGSSYPYFYAMDYWG QGTSVTVSS (SEQ ID NO: 20).

In some embodiments of any of the proteins described herein, the protein competitively binds to human ADAM8 with an antigen-binding domain including: (i) a light chain variable domain of SEQ ID NO:8 and a heavy chain variable domain of SEQ ID NO: 10; (ii) a light chain variable domain of SEQ ID NO: 38 and a heavy chain variable domain of SEQ ID NO: 40; or (iii) a light chain variable domain of SEQ ID NO: 48 and a heavy chain variable domain of SEQ ID NO: 50.

In some embodiments of any of the proteins described herein, the antigen-binding domain binds to an epitope within human ADAM8 that includes at least one amino acid within the sequence of: DCGPPEDCRNRCCNSTTCQ (SEQ ID NO: 88).

In some embodiments of any of the proteins described herein, the antigen-binding domain includes heavy chain variable domain CDRs of GFTFSDAW (SEQ ID NO: 22), IRGKVNNLAT (SEQ ID NO: 23), and LGRYDATYAMDY (SEQ ID NO: 24), and light chain variable domain CDRs of QSLVHSDGNTY (SEQ ID NO: 25), KLS (SEQ ID NO: 26), and SQSTHVPWT (SEQ ID NO: 27).

In some embodiments of any of the proteins described herein, the antigen-binding domain includes a light chain variable domain sequence of: DVVMTQTPLSLPVSLGDQASISCRSSQSLVHSDGN-TYLHWYLQKPGQSPKLLIYKLS NRFSGVPDRFSGSGSGTDF TLKISRVEAE-DLGVYFCSQSTHVPWTFGGGTKLEIK (SEQ ID NO: 28).

In some embodiments of any of the proteins described herein, the antigen-binding domain includes a heavy chain variable domain sequence of: EVKLEESGG-GLVQPGGSMKLSCAASGFTFSDAWMDWVRQS-PEKGLEWVAEIRGKV NNLATYYVESVKGRFTISRDD-SKSSVYLQMNSLRAEDTGIYYCLGRYDATYAMDY WGQGTSVTVSS (SEQ ID NO: 30).

In some embodiments of any of the proteins described herein, the protein competitively binds to human ADAM8 with an antigen-binding domain including: (i) a light chain variable domain of SEQ ID NO: 8 and a heavy chain variable domain of SEQ ID NO: 10; (ii) a light chain variable domain of SEQ ID NO: 38 and a heavy chain variable domain of SEQ ID NO: 40; (iii) a light chain variable domain of SEQ ID NO: 48 and a heavy chain variable domain of SEQ ID NO: 50; or (iv) a light chain variable domain of SEQ ID NO: 58 and a heavy chain variable domain of SEQ ID NO: 60.

In some embodiments of any of the proteins described herein, the protein includes a human Fc domain.

In some embodiments of any of the proteins described herein, the protein further includes a conjugated toxin or a therapeutic agent.

Provided herein are nucleic acids encoding any of the proteins described herein, vectors including any of the nucleic acids described herein, and mammalian cells including any of the nucleic acids described herein or any of the vectors described herein.

Provided herein are methods of producing a protein that includes: (a) culturing a mammalian cell (e.g., any of the mammalian cells described herein) in a liquid culture medium under conditions sufficient to produce the protein; and (b) recovering the protein from the mammalian cell or the liquid culture medium. In some embodiments of any of the methods described herein, the method further includes: (c) isolating the protein recovered in step (b). In some embodiments of any of the methods described herein, the method further includes: (d) formulating the protein isolated in step (c) into a pharmaceutical composition.

Also provided herein are pharmaceutical compositions produced by any of the methods described herein.

Also provided herein are pharmaceutical compositions including a therapeutically effective amount of any of the proteins described herein.

Also provided herein are kits that include any of the proteins described herein or any of the pharmaceutical compositions described herein.

Also provided herein are methods for inhibiting migration and/or invasion of an ADAM8 expressing cell in a subject that include administering to the subject a therapeutically effective amount of any of the proteins described herein or any of the pharmaceutical compositions described herein.

In some embodiments of any of the methods described herein, the cell is an ADAM8-associated cancer cell. In some embodiments of any of the methods described herein, the ADAM8-associated cancer cell is from a cancer selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia. In some embodiments of any of the methods described herein, the cancer cell is a triple negative breast cancer cell.

Provided herein are methods of decreasing the risk of developing a metastasis or developing an additional metastasis over a period of time in a subject identified as having an ADAM8-associated cancer that include administering to the subject a therapeutically effective amount of any of the proteins described herein or any of the pharmaceutical compositions described herein. In some embodiments of any of the methods described herein, the ADAM8-associated cancer is selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia. In some embodiments of any of the methods described herein, the ADAM8-associated cancer is triple negative breast cancer. In some embodiments of any of the methods described herein, the metastasis or additional metastasis is one or more to a bone, lymph nodes, brain, lung, liver, skin, chest wall including bone, cartilage and soft tissue, abdominal cavity, contralateral breast, soft tissue, muscle, bone marrow, ovaries, adrenal glands, and pancreas. In some embodiments of any of the methods described herein, the period of time is about 1 month to about 5 years.

Provided herein are methods of inhibiting the growth of a solid tumor in a subject identified as having an ADAM8-associated cancer that include administering to the subject a therapeutically effective amount of any of the proteins described herein or any of the pharmaceutical compositions described herein.

In some embodiments of any of the methods described herein, the growth of a solid tumor is primary growth of a solid tumor. In some embodiments of any of the methods described herein, the growth of a solid tumor is recurrent growth of a solid tumor. In some embodiments of any of the methods described herein, the growth of a solid tumor is metastatic growth of a solid tumor. In some embodiments of any of the methods described herein, the ADAM8-associated cancer is selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, and bone cancer. In some embodiments of any of the methods described herein, the ADAM8-associated cancer is triple negative breast cancer.

Provided herein are methods of inhibiting the growth or proliferation of a hematological cancer in a subject identified as having an ADAM8-associated cancer that include administering to the subject a therapeutically effective amount of any of the proteins described herein or any of the pharmaceutical compositions described herein.

In some embodiments of any of the methods described herein, the hematological cancer is a leukemia. In some embodiments of any of the methods described herein, the hematological cancer is a lymphoma.

Also provided herein are methods of killing an ADAM8-associated cancer cell in a subject that include: administering to the subject a therapeutically effective amount of any of the proteins described herein or any of the pharmaceutical compositions described herein.

In some embodiments of any of the methods described herein, the ADAM8-associated cancer cell is from a cancer selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia. In some embodiments of any of the methods described herein, the cancer cell is a triple negative breast cancer cell.

Provided herein are methods of treating an ADAM8-associated cancer in a subject that include: administering to a subject identified as having an ADAM8-associated cancer a therapeutically effective amount of any of the proteins described herein or any of the pharmaceutical compositions described herein.

In some embodiments of any of the methods described herein, the ADAM8-associated cancer is selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia.

In some embodiments of any of the methods described herein, the ADAM8-associated cancer is triple negative breast cancer.

In some embodiments of any of the methods described herein, the method further includes administering to the subject a therapeutically effective amount of a chemotherapeutic agent, a targeted therapy, or an immunotherapy. In some embodiments of any of the methods described herein, the chemotherapeutic agent is an antimetabolite, a plant alkaloid, a microtubule inhibitor, an anthracycline, a taxol, a platinum agent, or an alkylating agent. In some embodiments of any of the methods described herein, the targeted therapy is an angiogenesis or a kinase inhibitor. In some embodiments of any of the methods described herein, the immunotherapy is an inhibitor of PD-1, PD-L1, CTLA-4, LAG-3, CD70, CD80, ICOS, TIGIT, or IDO. In some embodiments of any of the methods described herein, the immunotherapy is a chimeric antigen receptor (CAR) T-cell therapy.

Provided herein are methods of identifying a protein including an antigen-binding domain that binds specifically to human ADAM8 and has the ability to inhibit both the metalloprotease activity and disintegrin activity of human ADAM8 that include: (a) identifying a protein including an antigen-binding domain that binds to an epitope within human ADAM8 that includes at least one amino acid within the sequence of: DCGPPEDCRNRCCNSTTCQLAE-GAQCAHGTCCQECKVKPAGELCRPKKDMCDLEEF CDGRHPECPEDAF (SEQ ID NO: 1).

In some embodiments of any of the methods described herein, the method further includes confirming the ability of the identified protein to inhibit the metalloprotease activity and disintegrin activity of human ADAM8. In some embodiments of any of the methods described herein, step (a) includes identifying a protein including an antigen-binding domain that binds to an epitope within human ADAM8 that includes at least one amino acid within the sequence of: CCNSTTCQLAEGAQCAHGTCCQECK (SEQ ID NO: 86) or RNRCCNSTTCQLAEGAQCAHGTCCQECK (SEQ ID NO: 104).

In some embodiments of any of the methods described herein, step (a) includes identifying a protein including an antigen-binding domain that binds to an epitope within human ADAM8 that includes at least one amino acid within the sequence of: LAEGAQCAHGTCCQECKVKPAGEL-CRPKKDMCDLEEFCDGRHPECPEDAF (SEQ ID NO: 87).

In some embodiments of any of the methods described herein, step (a) includes identifying a protein including an antigen-binding domain that binds to an epitope within human ADAM8 that includes at least one amino acid within the sequence of: DCGPPEDCRNRCCNSTTCQ (SEQ ID NO: 88).

Also provided herein are methods of diagnosing an ADAM8-associated cancer in a subject that include: (a) contacting a biological sample from the subject with any of the proteins described herein; (b) determining a level of the protein specifically bound to the biological sample; and (c) identifying the subject as having an ADAM8-associated cancer if the level of the protein specifically bound to the biological sample is elevated as compared to a control level. In some embodiments of any of the methods described herein, the biological sample is a biopsy tissue sample. In some embodiments of any of the methods described herein, the biological sample is not a fixed tissue sample. In some embodiments of any of the methods described herein, the biological sample is a fresh, frozen tissue sample.

Some embodiments of any of the methods described herein further include, prior to step (a), trypsinizing the biological sample. In some embodiments of any of the methods described herein, step (b) comprises the use of fluorescence-activated cell sorting.

In some embodiments of any of the methods described herein, the biological sample is a fixed tissue sample. In some embodiments of any of the methods described herein, the fixed tissue sample is a formalin-fixed paraffin-embedded (FFPE) tissue sample. Some embodiments of any of the methods described herein further include, before step (a), fixing the tissue sample. Some embodiments of any of the methods described herein further include, before step (a), decrosslinking the fixed tissue sample. In some embodiments of any of the methods described herein, the decrosslinking of the fixed tissue sample is performed using a Tris-EDTA-based, basic buffer. In some embodiments of any of the methods described herein, the decrosslinking is performed for 40 to 80 minutes at a temperature of about 65° C. to about 95° C. In some embodiments of any of the methods described herein, the decrosslinking of the fixed tissue sample is performed using an alkaline endopeptidase. In some embodiments of any of the methods described herein, the alkaline endopeptidase is a serine protease.

In some embodiments of any of the methods described herein, the protein comprises a detectable label. In some embodiments of any of the methods described herein, step (b) comprises detecting the detectable label. In some embodiments of any of the methods described herein, the detectable label is a heavy metal, a fluorophore, or an enzyme.

In some embodiments of any of the methods described herein, the protein does not comprise a detectable label, and step (b) comprises the use of an agent that binds specifically to the protein specifically bound to the biological sample. In some embodiments of any of the methods described herein, the agent comprises an antibody. In some embodiments of any of the methods described herein, the agent comprises a detectable label. In some embodiments of any of the methods described herein, step (b) comprises detecting the detectable label. In some embodiments of any of the methods described herein, the detectable label comprises a heavy metal, a fluorophore, or an enzyme.

In some embodiments of any of the methods described herein, step (b) comprises imaging the biological sample. In some embodiments of any of the methods described herein, step (b) comprises performing immunohistochemistry or immunofluorescence.

In some embodiments of any of the methods described herein, the biological sample is a liquid biopsy sample. In some embodiments of any of the methods described herein, the liquid biopsy sample is a blood sample, a cerebrospinal fluid sample, a pleural effusion sample or an ascites sample. Some embodiments of any of the methods described herein further include obtaining the liquid biopsy sample from the subject. Some embodiments of the methods described herein further include, before step (a), concentrating the cells in the liquid biopsy sample. Some embodiments of any of the methods described herein further include, before step (a), fixing the liquid biopsy sample. In some embodiments of any of the methods described herein, step (b) comprises performing fluorescence-activated cell sorting. Some embodiments of any of the methods described herein further include, before step (a), lysing cells in the liquid biopsy sample. In some embodiments of any of the methods described herein, step (b) comprises performing an enzyme-linked immunosorbent assay. In some embodiments of any of the methods described herein, the protein comprises a detectable label. In some embodiments of any of the methods described herein, step (b) comprises detecting the detectable label. In some embodiments of any of the methods described herein, the detectable label is a heavy metal, a fluorophore, or an enzyme. In some embodiments of any of the methods described herein, the protein does not comprise a detectable label, and step (b) comprises the use of an agent that binds specifically to the protein specifically bound to the biological sample. In some embodiments of any of the methods described herein, the agent comprises an antibody. In some embodiments of any of the methods described herein, the agent comprises a detectable label.

Some embodiments of any of the methods described herein further include, after step (c), (d) selecting a therapeutically effective amount of the protein used in step (a) for treatment of the subject identified as having an ADAM8-associated cancer. Some embodiments of any of the methods described herein further include, after step (c), (d) administering a therapeutically effective amount of the protein used in step (a) to the subject identified as having an ADAM8-associated cancer.

Some embodiments of any of the methods described herein further include, after step (c), (d) administering a therapeutically effective amount of a chemotherapeutic agent, a targeted therapy, or an immunotherapy. In some embodiments of any of the methods described herein, the chemotherapeutic agent is an antimetabolite, a plant alkaloid, a microtubule inhibitor, an anthracycline, a taxol, a platinum agent, or an alkylating agent. In some embodiments of any of the methods described herein, the targeted therapy is an angiogenesis or a kinase inhibitor. In some embodiments of any of the methods described herein, the immunotherapy is an inhibitor of PD-1, PD-L1, CTLA-4, LAG-3, CD70, CD80, ICOS, TIGIT, or IDO. In some embodiments of any of the methods described herein, the immunotherapy is a chimeric antigen receptor (CAR) T-cell therapy. Some embodiments of any of the methods described herein further include, after step (c), determining the stage of the ADAM8-associated cancer in the subject based on the level of the protein specifically bound to the biological sample.

In some embodiments of any of the methods described herein, the subject is suspected of having an ADAM8-associated cancer. In some embodiments of any of the methods described herein, the subject is presenting with one or more symptoms of an ADAM8-associated cancer. In some embodiments of any of the methods described herein, the ADAM8-associated cancer is a cancer selected from the group of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia. In some embodiments of any of the methods described herein, the ADAM8-associated cancer is triple negative breast cancer. In some embodiments of any of the methods described herein, the ADAM8-associated cancer is a hematological cancer. In some embodiments of any of the methods described herein, the hematological cancer is a leukemia. In some embodiments of any of the methods described herein, the hematological cancer is lymphoma.

In some embodiments of any of the methods described herein, the biological sample is obtained from a metastasis. In some embodiments of any of the methods described herein, the metastasis is obtained from bone, lymph node, brain, lung, liver, skin, chest wall (including bone, cartilage and soft tissue), abdominal cavity, contralateral breast, soft tissue, muscle, bone marrow, ovaries, adrenal glands, and pancreas.

Also provided herein are methods of determining the efficacy of treatment of an ADAM8-associated cancer in a subject that include: (a) contacting a first biological sample obtained from a subject having an ADAM8-associated cancer at first time point with any of the proteins described herein; (b) determining a first level of the protein specifically bound to the first biological sample; (c) contacting a second biological sample obtained from the same subject at a second time point with the protein, wherein the subject has been administered a treatment against an ADAM8-associated cancer between the first and second time points; (d) determining a second level of the protein specifically bound to the second biological sample; and (e) determining the treatment as being effective in a subject having a decreased second level as compared to the first level, or determining the treatment as not being effective in a subject having about the same or an increased second level as compared to the first level.

In some embodiments of any of the methods described herein, the subject has previously been diagnosed as having an ADAM8-associated cancer. Some embodiments of any of the methods described herein further include recording the determination in step (e) in the subject's medical record.

In some embodiments of any of the methods described herein, step (e) comprises determining the treatment as being effective in the subject. Some embodiments of any of the methods described herein further include, after step (e), selecting one or more additional doses of the treatment for the subject. Some embodiments of any of the methods described herein further include, after step (e), administering one or more additional doses of the treatment to the subject.

In some embodiments of any of the methods described herein, step (e) comprises determining the treatment was not effective in the subject. Some embodiments of any of the methods described herein further include, after step (e), selecting an alternative treatment for the subject. Some embodiments of any of the methods described herein further include, after step (e), administering an alternative treatment to the subject.

Some embodiments of any of the methods described herein further include administering the treatment to the subject between the first and second time points.

In some embodiments of any of the methods described herein, the treatment comprises the protein used in steps (a) and (c). In some embodiments of any of the methods described herein, the treatment comprises the protein conjugated to a cytotoxin or therapeutic agent. In some embodiments of any of the methods described herein, treatment comprises a chemotherapeutic agent, a targeted therapy, or an immunotherapy. In some embodiments of any of the methods described herein, the chemotherapeutic agent is an antimetabolite, a plant alkaloid, a microtubule inhibitor, an anthracycline, a taxol, a platinum agent, or an alkylating agent. In some embodiments of any of the methods described herein, the targeted therapy is an angiogenesis or a kinase inhibitor. In some embodiments of any of the methods described herein, the immunotherapy is an inhibitor of PD-1, PD-L1, CTLA-4, LAG-3, CD70, CD80, ICOS, TIGIT, or IDO. In some embodiments of any of the methods described herein, the immunotherapy is a chimeric antigen receptor (CAR) T-cell therapy.

In some embodiments of any of the methods described herein, the first and second biological samples are tissue samples. In some embodiments of any of the methods described herein, the tissue samples are biopsy tissue samples. In some embodiments of any of the methods described herein, the tissue samples are not fixed tissue samples. In some embodiments of any of the methods described herein, the tissue sample is a fresh, frozen tissue sample. Some embodiments of any of the methods described herein further include, prior to step (a), trypsinizing the tissue samples. In some embodiments of any of the methods described herein, step (b) comprises the use of fluorescence-activated cell sorting.

In some embodiments of any of the methods described herein, the tissue samples are fixed tissue samples. In some embodiments of any of the methods described herein, the fixed tissue samples are formalin-fixed paraffin-embedded (FFPE) tissue samples. Some embodiments of any of the methods described herein further include, before step (a), fixing the tissue samples. Some embodiments of any of the methods described herein further include, before step (a), decrosslinking the fixed tissue samples. In some embodiments of any of the methods described herein, the decrosslinking of the fixed tissue samples is performed using a Tris-EDTA-based, basic buffer. In some embodiments of any of the methods described herein, the decrosslinking is performed for 40 to 80 minutes at a temperature of about 65° C. to about 95° C. In some embodiments of any of the methods described herein, the decrosslinking of the fixed tissue sample is performed using an alkaline endopeptidase. In some embodiments of any of the methods described herein, the alkaline endopeptidase is a serine protease.

In some embodiments of any of the methods described herein, the protein comprises a detectable label. In some embodiments of any of the methods described herein, step (b) comprises detecting the detectable label. In some embodiments of any of the methods described herein, the detectable label is a heavy metal, a fluorophore, or an enzyme.

In some embodiments of any of the methods described herein, the protein does not comprise a detectable label, and steps (b) and (d) comprises the use of an agent that binds specifically to the protein specifically bound to the first and second biological samples, respectively. In some embodiments of any of the methods described herein, the agent comprises an antibody. In some embodiments of any of the methods described herein, the agent comprises a detectable label. In some embodiments of any of the methods described herein, steps (b) and (d) comprise detecting the detectable label. In some embodiments of any of the methods described herein, the detectable label comprises a heavy metal, a fluorophore, or an enzyme.

In some embodiments of any of the methods described herein, steps (b) and (d) comprise imaging the first and second biological samples. In some embodiments of any of the methods described herein, the determining in steps (b) and (d) comprise performing immunohistochemistry or immunofluorescence.

In some embodiments of any of the methods described herein, the first and second biological samples are liquid biopsy samples. In some embodiments of any of the methods described herein, the liquid biopsy samples are blood samples, cerebrospinal fluid samples, pleural effusion samples or ascites samples.

Some embodiments of any of the methods described herein further include concentrating cells in the biological sample(s). Some embodiments of any of the methods described herein further include, before steps (a) and (c), fixing the biological samples. In some embodiments of any of the methods described herein, steps (b) and (d) comprise performing fluorescence-activated cell sorting. Some embodiments of any of the methods described herein further include, before steps (a) and (c), lysing cells in the liquid biopsy sample. In some embodiments of any of the methods described herein, steps (b) and (d) comprise performing an enzyme-linked immunosorbent assay. In some embodiments of any of the methods described herein, the protein comprises a detectable label. In some embodiments of any of the methods described herein, step (b) comprises detecting the detectable label. In some embodiments of any of the methods described herein, the detectable label is a heavy metal, a fluorophore, or an enzyme.

In some embodiments of any of the methods described herein, the protein does not comprise a detectable label, and steps (b) and (d) comprise the use of an agent that binds specifically to the protein specifically bound to the biological sample. In some embodiments of any of the methods described herein, the agent comprises an antibody. In some embodiments of any of the methods described herein, the agent comprises a detectable label.

Also provided herein are kits that include any of the proteins described herein or any of the pharmaceutical compositions described herein. Also provided herein are kits that include any of the proteins described herein and instructions for performing any of the methods described herein. Some embodiments of any of the kits described herein further include one or more of: a positive and/or a negative control sample(s); a negative control antibody; an agent that binds specifically to the protein; and a reagent necessary for detection of a tag or enzyme activity.

The term “a” and “an” refers to one or to more than one (i.e., at least one) of the grammatical object of the article. By way of example, “a protein” encompasses one protein and more than one protein.

The term “conservative mutation” refers to a mutation that does not change the amino acid encoded at the site of the mutation (due to codon degeneracy).

Modifications can be introduced into a nucleotide sequence by standard techniques known in the art, such as site-directed mutagenesis, PCR-mediated mutagenesis, and CRISPR technology. Conservative amino acid substitutions are ones in which the amino acid residue is replaced with an amino acid residue having a similar side chain. Families of amino acid residues having similar side chains have been defined in the art. These families include amino acids with basic side chains (e.g., histidine, lysine and arginine), acidic side chains (e.g., glutamic acid and aspartic acid), uncharged polar side chains (e.g., asparagine, glycine, glutamine, serine, threonine, tyrosine, cysteine, and tryptophan), nonpolar side chains (e.g., alanine, valine, leucine, isoleucine, proline, phenylalanine, and methionine), beta-branched side chains (e.g., threonine, valine and isoleucine), and aromatic side chains (e.g., tyrosine, phenylalanine, tryptophan, and histidine).

The term “nucleic acid” or “polynucleotide” refers to deoxyribonucleic acid (DNA) or ribonucleic acid (RNA), or a combination thereof, in either single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the nucleic acids described herein, the nucleic acid is DNA. In some embodiments of any of the nucleic acids described herein, the nucleic acid is RNA.

Unless otherwise specified, a “nucleotide sequence encoding an amino acid sequence” includes all nucleotide sequences that are degenerate versions of each other and thus encode the same amino acid sequence.

The terms “protease” and “proteinase” are used interchangeably and refer to an enzyme that cleaves proteins into smaller peptides. Non-limiting examples of proteases and proteinases include ADAM8 metalloprotease or ADAM8 metalloproteinase. A metalloproteinase can be abbreviated as MP.

The term “transfect”, “transformed” or “transduced” refers to a process by which exogenous nucleic acid is transferred or introduced into a cell. A “transfected”, “transformed”, or “transduced” mammalian cell is one that has been transfected, transformed, or transduced with exogenous nucleic acid and can lead to ectopic or exogenous expression of protein.

The term "endogenous" expression refers to proteins that are expressed naturally from the mammalian cell genome.

The term "expression" refers to the transcription and/or translation of a particular nucleotide sequence encoding a protein.

The term "subject" refers to any mammal. In some embodiments, the subject is a rabbit, a sheep, a goat, a pig, a canine (e.g., a dog), a feline (e.g., a cat), a rodent (e.g., a mouse, a guinea pig, a hamster, or a rat), an equine (e.g., a horse), a bovine, simian (e.g., a monkey (e.g., a rhesus monkey, a cynomolgus monkey, a marmoset, or a baboon), or an ape (e.g., a gorilla, a chimpanzee, an orangutan, or a gibbon), or a non-human primate), or a human. In some embodiments, the subject has or is at risk of developing cancer. In some embodiments, the subject or "subject suitable for treatment" may be a non-human mammal, especially mammals that are conventionally used as models for demonstrating therapeutic efficacy in humans may be used, such as mice, rabbits, dogs, primates, or rats.

A treatment is "therapeutically effective" when it results in a reduction in one or more of the number, severity, and frequency of one or more symptoms of a disease state (e.g., cancer) in a subject (e.g., a human). In some embodiments, a therapeutically effective amount of a protein or a pharmaceutical composition can inhibit the growth of cancer, e.g., tumors and/or tumor cells, improve overall survival of a patient suffering from or at risk for cancer, and/or improve the outcome of other cancer treatments. In some embodiments, a treatment can reduce cancer progression, reduce the histopathological severity of a cancer, and/or reduce the risk of re-occurrence of a cancer.

The term "cancer" includes a variety of cancerous growths, e.g., primary tumors, recurrent tumors, metastatic tumors, and malignantly transformed cells, tissues, or organs, irrespective of histopathologic type or stage of invasiveness.

An "ADAM8-associated cancer" refers to a cancer characterized by a population of cancer cells that expressed increased levels and/or activity of ADAM8, e.g., compared to a control cell. For example, an ADAM8-associated cancer can be selected from the group of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma, and leukemia. In some examples, an ADAM8-associated cancer is a triple negative breast cancer.

An "ADAM8-associated cancer cell" refers to a cancer cell of an ADAM8-associated cancer. For example, an ADAM8 associated cancer cell can be from an ADAM8 associated cancer selected from the group of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma, and leukemia. In some examples, an ADAM8-associated cancer cell is a triple negative breast cancer cell.

A metastatic tumor can arise from a multitude of primary tumor types, including but not limited to those of breast, lung, colon, bone, prostate, and liver origin. Metastases develop, e.g., when tumor cells shed from a primary tumor, adhere to vascular endothelium, invade the vasculature, penetrate into surrounding tissues, and grow to form independent tumors at sites separate from a primary tumor. In some examples, a metastatic tumor may form after a period of latency and/or dormancy (e.g., months, or years).

The term "triple negative breast cancer" or "TNBC" refers to a breast cancer characterized by a population of breast cancer cells that are estrogen receptor (ER)-negative, progesterone receptor (PR)-negative and human epidermal growth factor receptor 2 (HER2)-negative. In some examples, a TNBC is also characterized by a population of breast cancer cells that have a mutation in the breast cancer gene 1 (BRCA1) and/or breast cancer gene 2 (BRCA2) gene. In some examples, a breast cancer is determined to be a TNBC based on immunohistochemistry staining of a breast tissue biopsy sample.

The term "population" when used before a noun means two or more of the specific noun. For example, the phrase "a population of cancer cells" means "two or more cancer cells". Non-limiting examples of cancer cells are described herein.

A "chemotherapeutic agent" refers to a chemical compound useful in the treatment of cancer. Chemotherapeutic agents include, e.g., "anti-hormonal agents" or "endocrine therapeutics," which act to regulate, reduce, block, or inhibit the effects of hormones that can promote the growth of cancer. Non-limiting examples of chemotherapeutic agents include: alkylating agents, plant alkaloid, microtubule inhibitors, anthracyclines (e.g., doxorubicin), taxols (e.g., Paclitaxel), platinum agents, antimetabolites, e.g., purine antagonists, pyrimidine antagonists, and/or folate antagonists; antibiotics, e.g., bleomycin, and/or mitomycin; inorganic ions, e.g, cisplatin; and nitrosureas. Additional classes, subclasses, and examples of chemotherapeutic agents are known in the art.

Individuals considered at risk for developing metastasis may benefit from the present disclosure, e.g., because prophylactic treatment can begin before there is any evidence and/or diagnosis of metastasis. In some examples, the subject of any of the methods described herein may have previously received cancer treatment (e.g., any of the cancer treatments described herein).

Skilled practitioners will appreciate that a patient can be diagnosed, e.g., by a medical professional, e.g., a physician or a nurse (or a veterinarian, as appropriate for the subject being diagnosed), using any method known in the art, e.g., by assessing a patient's medical history, employing imaging techniques, or performing diagnostic tests.

Skilled practitioners will also appreciate that treatment need not be administered to a subject by the same individual who diagnosed the subject (or the same individual who prescribed the treatment for the subject). Treatment can be administered (and/or administration can be supervised), e.g., by the diagnosing and/or prescribing individual, and/or any other individual (e.g., infusion nurse), including the subject her/him/themselves (e.g., where the subject is capable of self-administration).

Also contemplated by the present disclosure is administration of a protein (e.g., any of the proteins described herein), a pharmaceutical composition (e.g., any of the pharmaceutical compositions described herein) to a subject in combination with a chemotherapeutic agent (e.g., any of the chemotherapeutic agents described herein), a targeted therapy (e.g., any of the targeted therapies described herein), an immunotherapy (e.g., any of the immunotherapies described herein), or a radiation therapy (e.g., using γ-radiation, electron beams, neutron beams, and/or radioactive isotopes). In some embodiments of any of the methods described herein, the chemotherapeutic agent is an antimetabolite, a plant alkaloid, a microtubule inhibitor, an anthracycline, a taxol, a platinum agent, or an alkylating agent. In some embodiments of any of the methods described herein, the targeted therapy is an angiogenesis or a kinase inhibitor. In some embodiments of any of the methods described herein, the immunotherapy is an inhibitor of PD-1, PD-L1, CTLA-4, LAG-3, CD70, CD80, ICOS, TIGIT, or IDO. In some embodiments of any of the methods described herein, the immunotherapy is a chimeric antigen receptor (CAR) T-cell therapy.

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features, and advantages of the disclosure will be apparent from the following detailed description and figures, and from the claims.

BRIEF DESCRIPTION OF DRAWINGS

FIG. 3 is a table showing the isotype, subclass and type of light chain for each ADP antibody.

FIG. 4 is a table that demonstrates the ability of each ADP to bind to native ADAM8 ectopically expressed on the cell surface. Fluorescent Activated Cell Sorting (FACS) analysis was performed using HEK293 cells stably overexpressing full-length ADAM8 (HEK293-ADAM8) or empty vector DNA (HEK293-Empty Vector), as a control for binding specificity, as a function of decreasing antibody concentration. Mean Fluorescent Intensity (MFI) indicates the extent of binding of each antibody. As negative and positive controls normal mouse IgG (mIgG) and a test bleed sample from a mouse injected with recombinant human ADAM8 (rHuADAM8) were used, respectively.

FIG. 5 is a table showing the binding affinity of each ADP antibody to rHuADAM8 determined through Enzyme-linked immunosorbent assays (ELISA) and surface plasmon resonance (Biacore™) assays. The half maximal effective concentration ($EC_{50}$) [nM] for each ADP obtained in ELISA assays is presented. Furthermore, binding kinetics, such as association rate constant ($k_a$), dissociation rate constant ($k_d$) and equilibrium dissociation constant (KD) obtained through Biacore surface plasmon resonance studies are shown.

FIG. 6 is a table showing the epitope binning analysis of ADP antibodies. The binding of each ADP [indicated in the "Antibody" column] to rHuADAM8 was challenged with excess of a second competitor ADP (indicated in the top row of the table). Percentages indicate extent of cross-competition for ADAM8. High levels of cross-competition, defined as equal to or greater than 75% (marked in black), delineate five ADP epitope clusters, which have been labelled Epitope 1 through 5. White boxes are the values obtained for competition with self.

FIG. 8 is a table demonstrating that all ADP antibodies have specific binding to ADAM8 and do not cross-react with related ADAM proteins ADAM9, ADAM12 or ADAM15. ELISA assays were performed with recombinant ADAM proteins. Normal mouse IgG was used as a negative control (NC) and indicates the level of general non-specific binding. A test bleed sample from a rHuADAM8 injected mouse was used as a positive control (PC).

FIG. 10 is a table showing the dual antagonist MP and DI inhibitory activity of ADP antibodies in cell-based functional assays. MP activity was assessed using a CD23 cleavage assay. Percent inhibition of MP activity was calculated as a decrease in the cleavage of the ADAM8 target protein CD23 in the supernatant of HEK293 cells co-expressing CD23 and full-length ADAM8, following ADP treatment vs treatment with isotype-matched control IgG (set to 100%). DI activity was assessed in two assays: binding of α9β1 integrin to ADAM8 and transendothelial migration (TEM), both processes mediated through an active DI domain. Percent inhibition of DI activity was calculated as a decrease in the adhesion of Chinese Hamster Ovary (CHO) cells expressing α9β1 integrin to rHuADAM8 and a decrease in the ability of MDA-MB-231 ADAM8-expressing TNBC cells to move through a layer of human umbilical vein endothelial cells (HUVEC), following treatment with ADP vs control IgG (set to 100%). Inhibitory activity of the prototype dual antagonist MAB1031 antibody, that was used in U.S. Patent Publication No. 2016/0130365, was also determined. Mean±standard deviation (S.D.) from 3 independent experiments is given in each case.

Figure 20A:
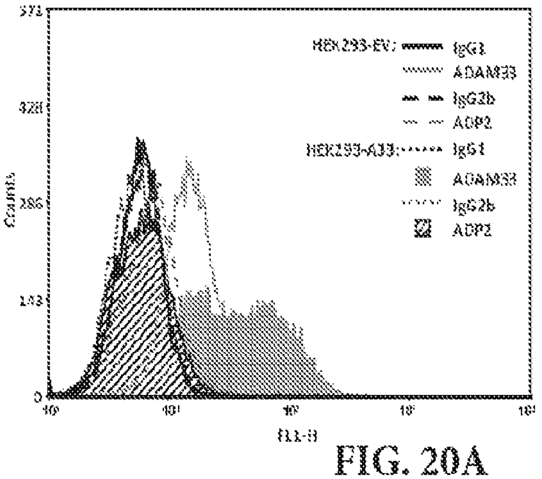

FIG. 20A is a graph showing the number of cells demonstrating fluorescence using FACS analysis in HEK293-ADAM33 (A33) and control HEK293-Empty Vector (EV) after exposure to ADP2 antibody. An ADAM33 antibody was used as a positive control. Both antibodies were matched with their respective control isotype IgG.

Figure 20B:
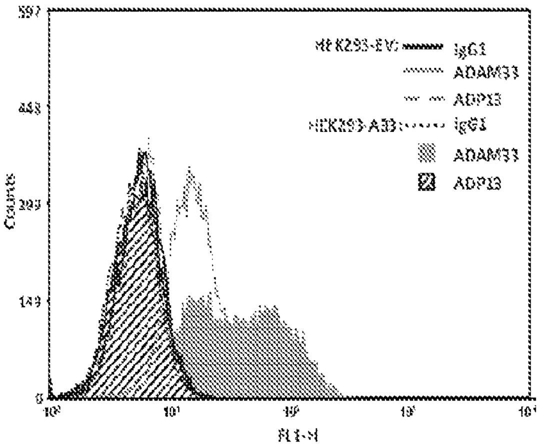

FIG. 20B is a graph showing the number of cells demonstrating fluorescence using FACS analysis in HEK293-ADAM33 (A33) and control HEK293-Empty Vector (EV) after exposure to ADP13 antibody. An ADAM33 antibody was used as a positive control. Both antibodies were matched with their respective control isotype IgG.

Figure 21A:
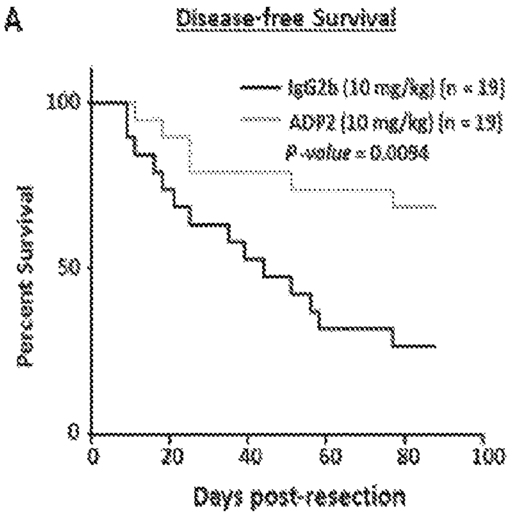

FIG. 21A is a Kaplan-Meier curve of the ability of ADP2 to increase disease-free survival of mice with pre-existing MDA-MB-231 TNBC cell line-derived orthotopic tumors when administered in a neoadjuvant (tumor resection) treatment protocol vs its isotype-matched control IgG. n=number of animals/group. P-values were calculated using a Log-rank test.

Figure 21B:
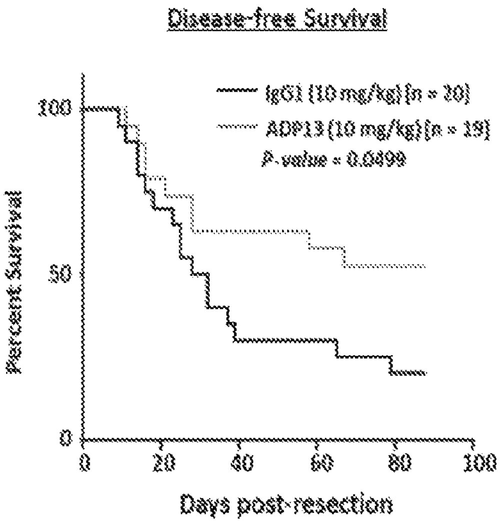

FIG. 21B is a Kaplan-Meier curve of the ability of ADP13 to increase disease-free survival of mice with pre-existing MDA-MB-231 TNBC cell line-derived orthotopic tumors when administered in a neoadjuvant (tumor resection) treatment protocol vs its isotype-matched control IgG. n=number of animals/group. P-values were calculated using a Log-rank test.

Figure 21C:
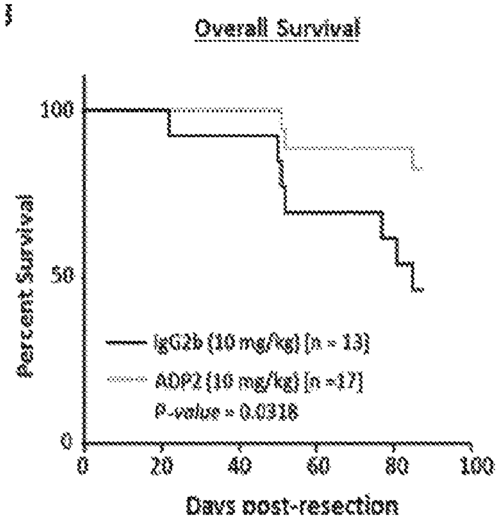

FIG. 21C is a Kaplan-Meier curve of the ability of ADP2 to increase overall survival of mice with pre-existing MDA-MB-231 TNBC cell line-derived orthotopic tumors when administered in a neoadjuvant (tumor resection) treatment protocol vs its isotype-matched control IgG. n=number of animals/group. P-values were calculated using a Log-rank test.

Figure 21D:
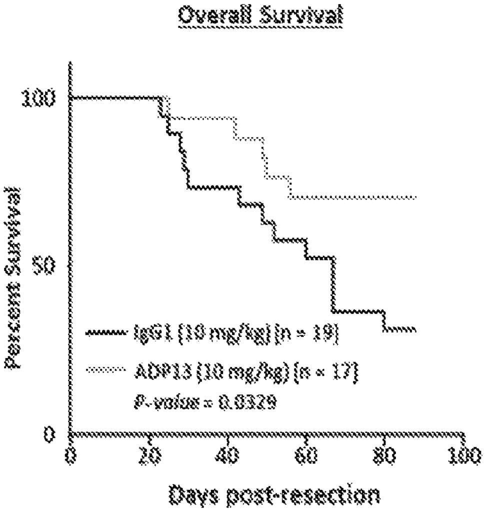

FIG. 21D is a Kaplan-Meier curve of the ability of ADP13 to increase overall survival of mice with pre-existing MDA-MB-231 TNBC cell line-derived orthotopic tumors when administered in a neoadjuvant (tumor resection) treatment protocol vs its isotype-matched control IgG. n=number of animals/group. P-values were calculated using a Log-rank test.

Figures 22A, 22B:
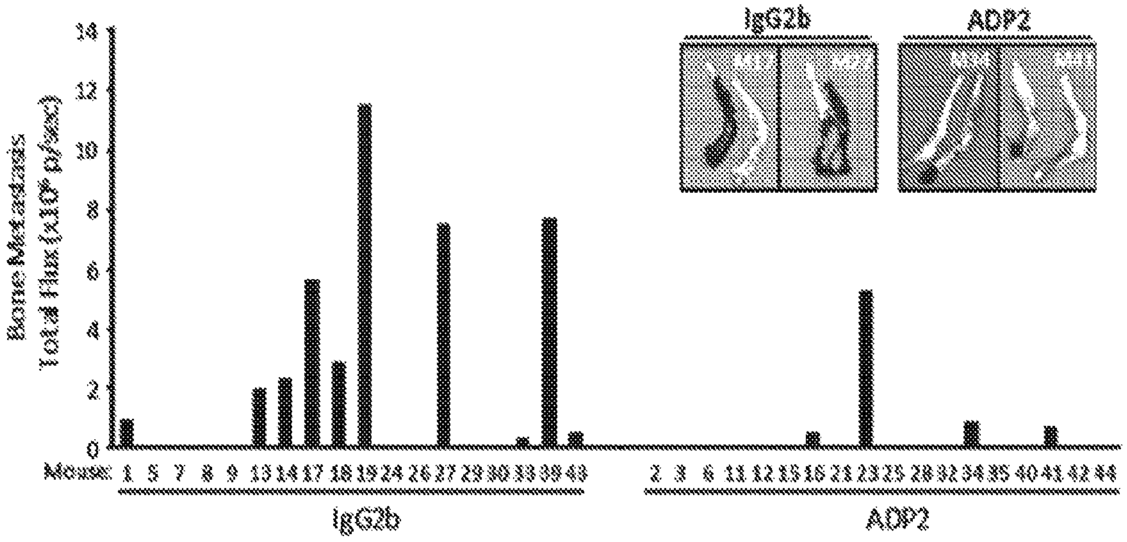

FIG. 22A is a bar graph showing the presence and extent of bone metastases determined using biophotonic imaging of dissected bones for detection of activity from the luciferase tag expressed in MDA-MB-231 cells in mice that had pre-existing MDA-MB-231 TNBC cell line-derived orthotopic tumors and were administered isotype control IgG2b.

FIG. 22B is a bar graph showing the presence and extent of bone metastases determined using biophotonic imaging of dissected bones for detection of activity from the luciferase tag expressed in MDA-MB-231 cells in mice that had pre-existing MDA-MB-231 TNBC cell line-derived orthotopic tumors and were administered ADP2 antibody in a neoadjuvant (tumor resection) treatment protocol. Representative images of isolated bones from individual mice (M) are shown in top panel. Top left panel representing bones from mice administered with isotype control IgG2b. Top right panel representing bones from mice administered with ADP2 antibody. A grey color on the bone indicates a small to moderate size metastasis. A black color on the bone corresponds to a large metastatic lesion. A white color on the bone indicates no metastasis.

Figures 22C, 22D:
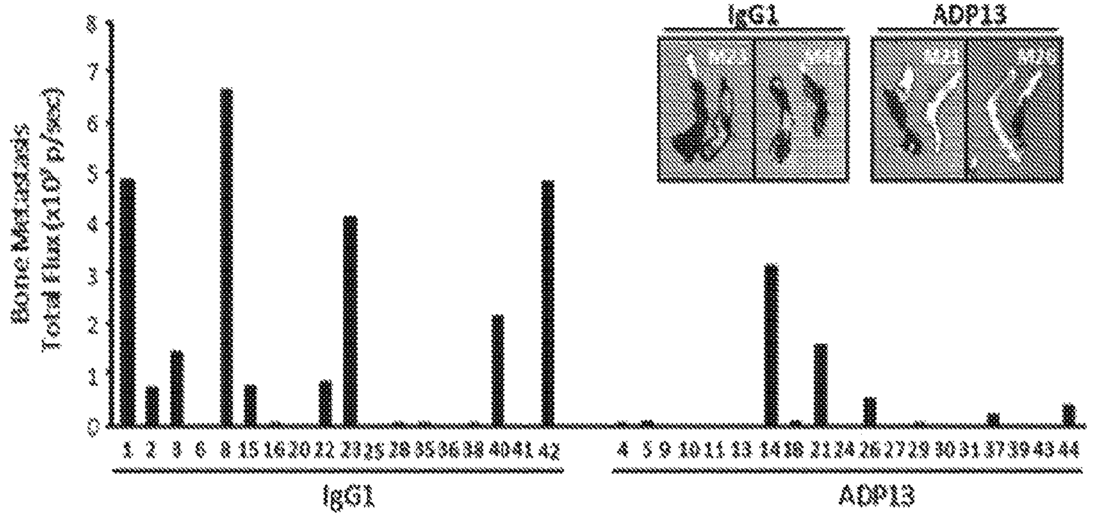

FIG. 22C is a bar graph showing the presence and extent of bone metastases determined using biophotonic imaging of dissected bones for detection of activity from the luciferase tag expressed in MDA-MB-231 cells in mice that had pre-existing MDA-MB-231 TNBC cell line-derived orthotopic tumors and were administered isotype control IgG1.

FIG. 22D is a bar graph showing the presence and extent of bone metastases determined using biophotonic imaging of dissected bones for detection of activity from the luciferase tag expressed in MDA-MB-231 cells in mice that had pre-existing MDA-MB-231 TNBC cell line-derived orthotopic tumors and were administered ADP13 antibody in a neoadjuvant (tumor resection) treatment protocol. Representative images of isolated bones from individual mice (M) are shown in top panel. Top left panel representing bones from mice administered with isotype control IgG1. Top right panel representing bones from mice administered with ADP13 antibody. A grey color on the bone indicates a small to moderate size metastasis. A black color on the bone corresponds to a large metastatic lesion. A white color on the bone indicates no metastasis.

FIG. 23A is a graph showing the pharmacokinetic profile of ADP2 48 hours post i.p. injection of a single 10 mg/kg dose of ADP2 into NOD/SCID mice. The concentration of ADP2 protein in plasma, isolated from the blood of the injected mice at various time points (0 hours, 2 hours, 4 hours, 6 hours, 8 hours, 24 hours, and 48 hours) was determined in three independent ELISA runs, in which rHuADAM8 was used for ADP2 capture and an anti-Mouse IgG-horseradish peroxidase (HRP) secondary for signal detection. number of mice, n=3.

FIG. 23B is a graph showing the pharmacokinetic profile of ADP2 over a 21-day period post i.p. injection of a single 10 mg/kg dose of ADP2 into NOD/SCID mice. The concentration of ADP2 protein in plasma, isolated from the blood of the injected mice at various time points (0 hours, 2 hours, 4 hours, 6 hours, 8 hours, 24 hours, 48 hours, 96 hours, 168 hours, 336 hours, and 504 hours) was determined in three independent ELISA runs, in which rHuADAM8 was used for ADP2 capture and an anti-Mouse IgG-HRP secondary for signal detection.

FIG. 23C is a table showing the specific ADP2 concentration values (nM)+/−standard deviation (S.D.) at the individual time points of mice used in FIG. 23B.

FIG. 24A is a graph showing the pharmacokinetic profile of ADP13 48 hours post i.p. injection of a single 10 mg/kg dose of ADP13 into NOD/SCID mice. ADP13 plasma concentration from blood collected at each time point (0 hours, 2 hours, 4 hours, 6 hours, 8 hours, 24 hours, and 48 hours) was determined in three independent ELISA runs.

FIG. 24B is a graph showing the pharmacokinetic profile of ADP13 over a 21-day period post i.p. injection of a single 10 mg/kg dose of ADP13 into NOD/SCID mice. ADP13 plasma concentration from blood collected at each time point (0 hours, 2 hours, 4 hours, 6 hours, 8 hours, 24 hours, 48 hours, 96 hours, 168 hours, 336 hours, and 504 hours) was determined in three independent ELISA runs.

FIG. 24C is a table showing the specific ADP13 concentration values (nM)+/−standard deviation (S.D.) at the individual time points of mice used in FIG. 24B.

FIG. 25A is a graphic representation of the experimental decay for ADP2. The ADP2 semi-log plasma concentration curves were plotted and found to be composed each of a distribution phase alpha-phase (α) and an elimination phase beta-phase (β).

FIG. 25B is a table showing specific PK parameters (area under the curve (AUC), elimination rate constant (Ke), half-time (T½) and clearance) for ADP2.

FIG. 25C is a graphic representation of the experimental decay for ADP13. The ADP13 semi-log plasma concentration curves were plotted and found to be composed each of a distribution phase alpha-phase (α) and an elimination phase beta-phase (β).

FIG. 25D is a table showing specific PK parameters (area under the curve (AUC), elimination rate constant (Ke), half-time (T½) and clearance) for ADP13.

Figures 26A, 26B, 26C:
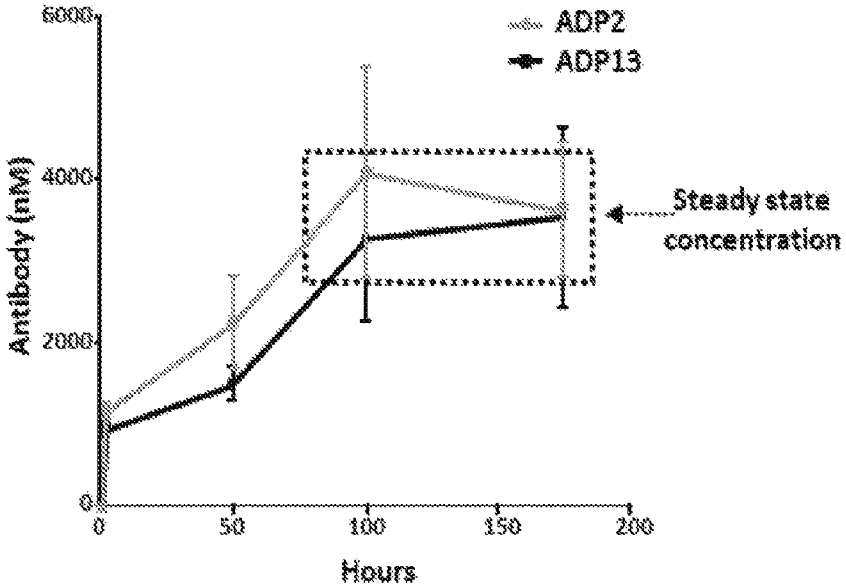

FIG. 26A is a graph showing plasma ADP2 and ADP13 concentration over time (in hours) following a treatment regimen composed of a loading dose of 20 mg/kg antibody followed by maintenance doses of 10 mg/kg (3×/week) in NOD/SCID mice. Dotted box indicates achievement of steady state concentration. Values are obtained from three independent ELISA runs of plasma isolated from the blood of mice (n=3/time point) treated with ADP2 or ADP13 based on the proposed loading/maintenance dose regimen.

FIG. 26B is a table showing the specific ADP2 concentration values (nM)+/−standard deviation (S.D.) at each time point of FIG. 26A.

FIG. 26C is a table showing the specific ADP13 concentration values (nM)+/−standard deviation (S.D.) at each individual time point of FIG. 26A.

Figure 27:
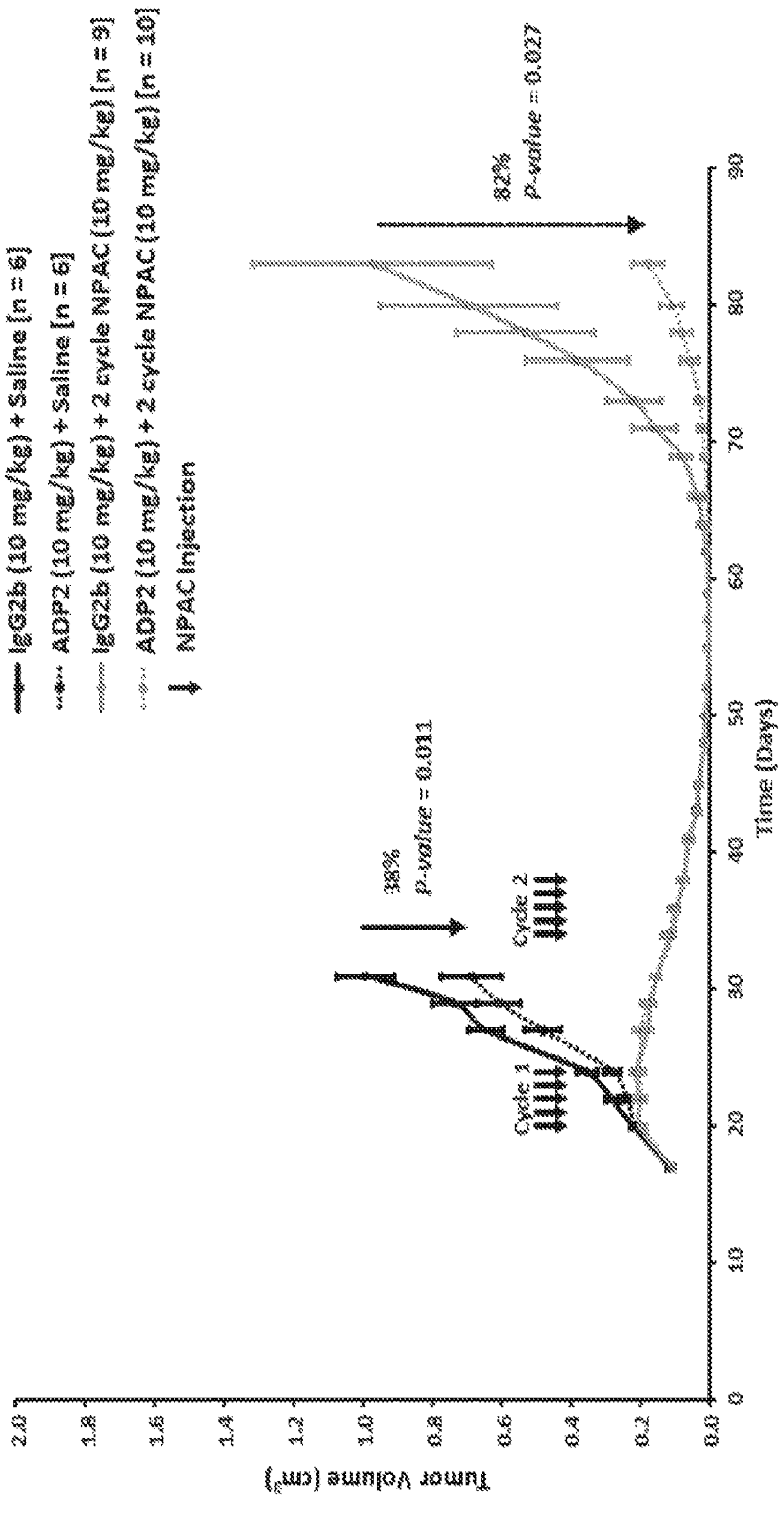

FIG. 27 is a graph showing tumor volume (Mean±standard error of mean (S.E.M.)) over time in a tumor regrowth model. Mice carrying pre-existing MDA-MB-231-luciferase-tagged cell-derived orthotopic tumors were treated with control IgG2b+Saline, ADP2+Saline, IgG2b+Nanoparticle Albumin-Bound Paclitaxel (NPAC) or the combination of ADP2+NPAC (n=number of animals/group). NPAC (in saline) was administered in 2 cycles of 5 consecutive intravenous (i.v.) treatments with one week of rest in between; an equivalent volume of vehicle saline was also given. ADP2 or IgG2b were administered i.p. 3×/week. Percentages indicate level of inhibition of tumor growth vs corresponding control group. P-values were determined using a Student's t-test.

Figure 28A:
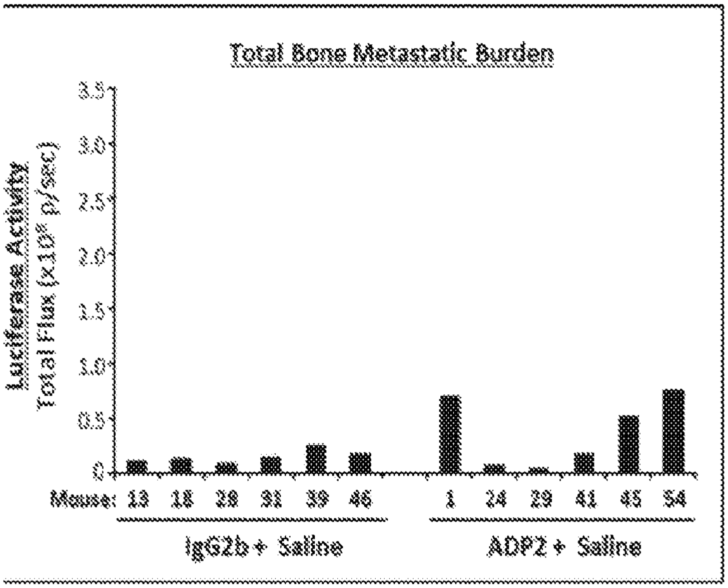

FIG. 28A is a bar graph showing the presence and extent of bone metastasis from TNBC tumors of mice used in FIG. 27 (IgG2b+Saline vs ADP2+Saline) using biphotonic imaging of dissected bones for detection of activity from the luciferase tag expressed in MDA-MB-231 cells.

Figure 28B:
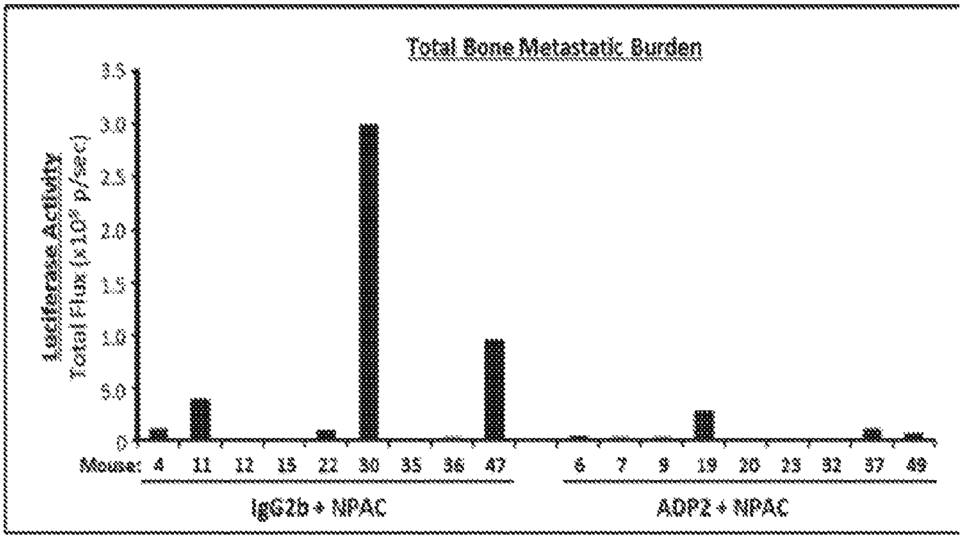

FIG. 28B is a bar graph showing the presence and extent of total bone metastasis from TNBC tumors of mice used in FIG. 27 (IgG2b+NPAC vs ADP2+NPAC) using biphotonic imaging of dissected bones for detection of activity from the luciferase tag expressed in MDA-MB-231 cells.

Figure 28C:
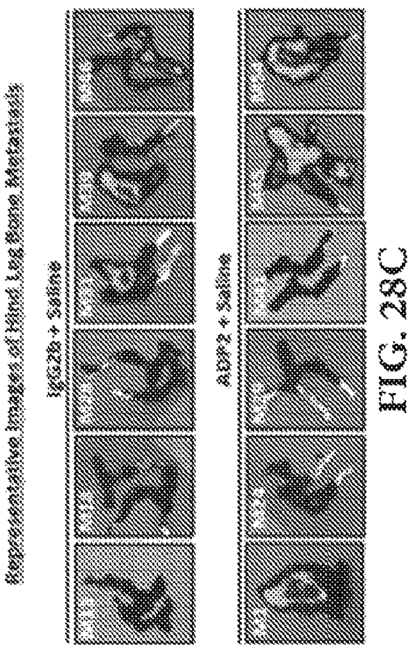

FIG. 28C is a collection of images showing all hind leg bone metastases from individual mice (M) treated with IgG2b+Saline or ADP2+Saline as in FIG. 28A. A grey color on the bone indicates a small to moderate-sized metastasis. A black color on the bone corresponds to a large metastatic lesion. A white color on the bone indicates no metastasis.

Figure 28D:
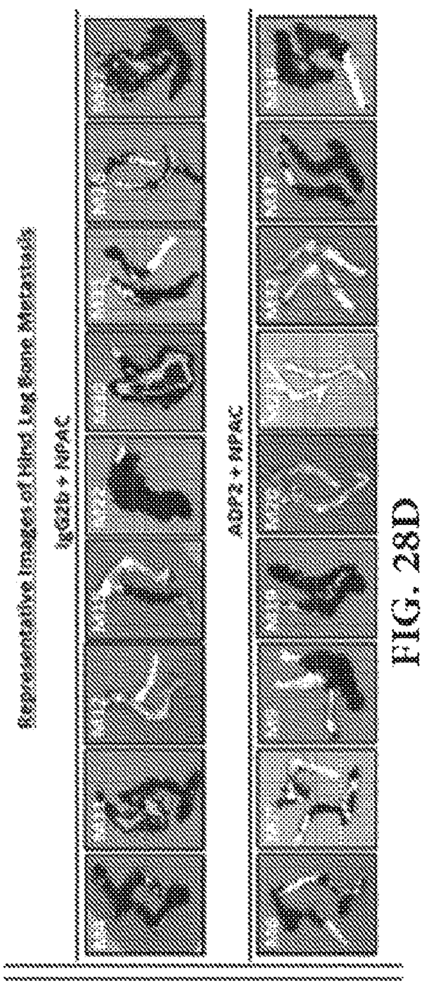

FIG. 28D is a collection of images showing all hind leg bone metastases from individual mice (M) treated with IgG2b+NPAC or ADP2+NPAC as in FIG. 28B. A grey color on the bone indicates a small to moderate-sized metastasis. A black color on the bone corresponds to a large metastatic lesion. A white color on the bone indicates no metastasis.

Figure 29A:
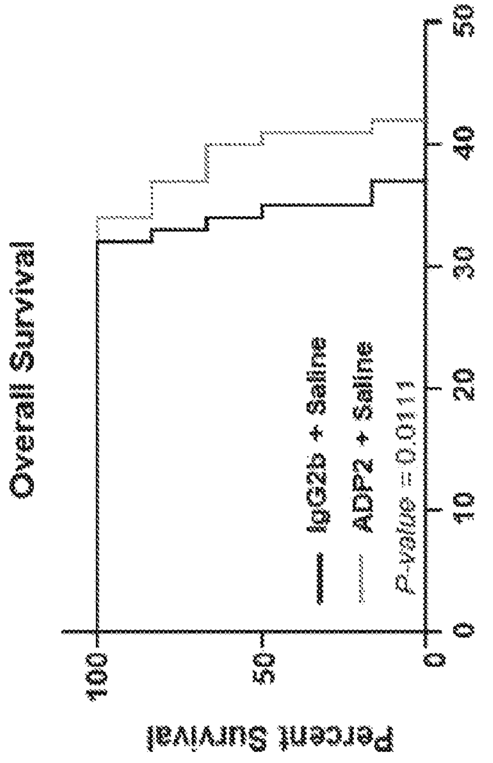

FIG. 29A is a Kaplan-Meier curve of the ability of ADP2 monotherapy (IgG2b+Saline vs ADP2+Saline) to increase overall survival in the mice used in FIG. 27. Statistical significance was determined using a Log-rank test; P-values=0.0111.

Figure 29B:
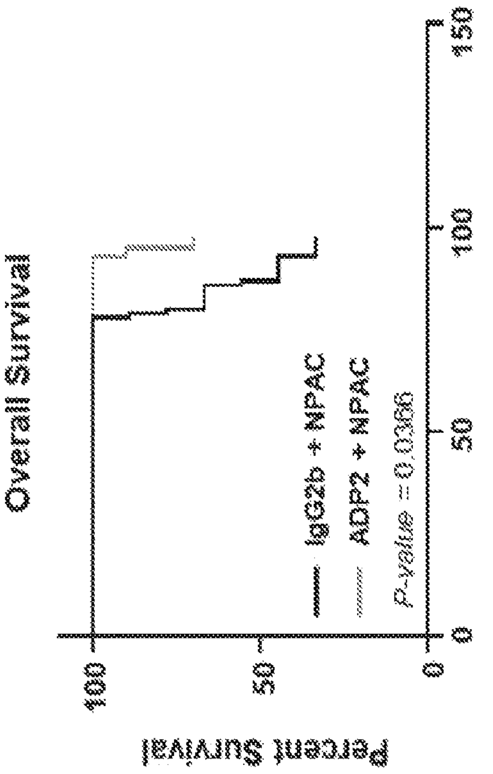

FIG. 29B is a Kaplan-Meier curve of the ability of combination therapy with NPAC (IgG2b+NPAC vs ADP2+NPAC) to increase overall survival in the mice used in FIG. 27. Statistical significance was determined using a Log-rank test; P-values=0.0366.

Figure 30:
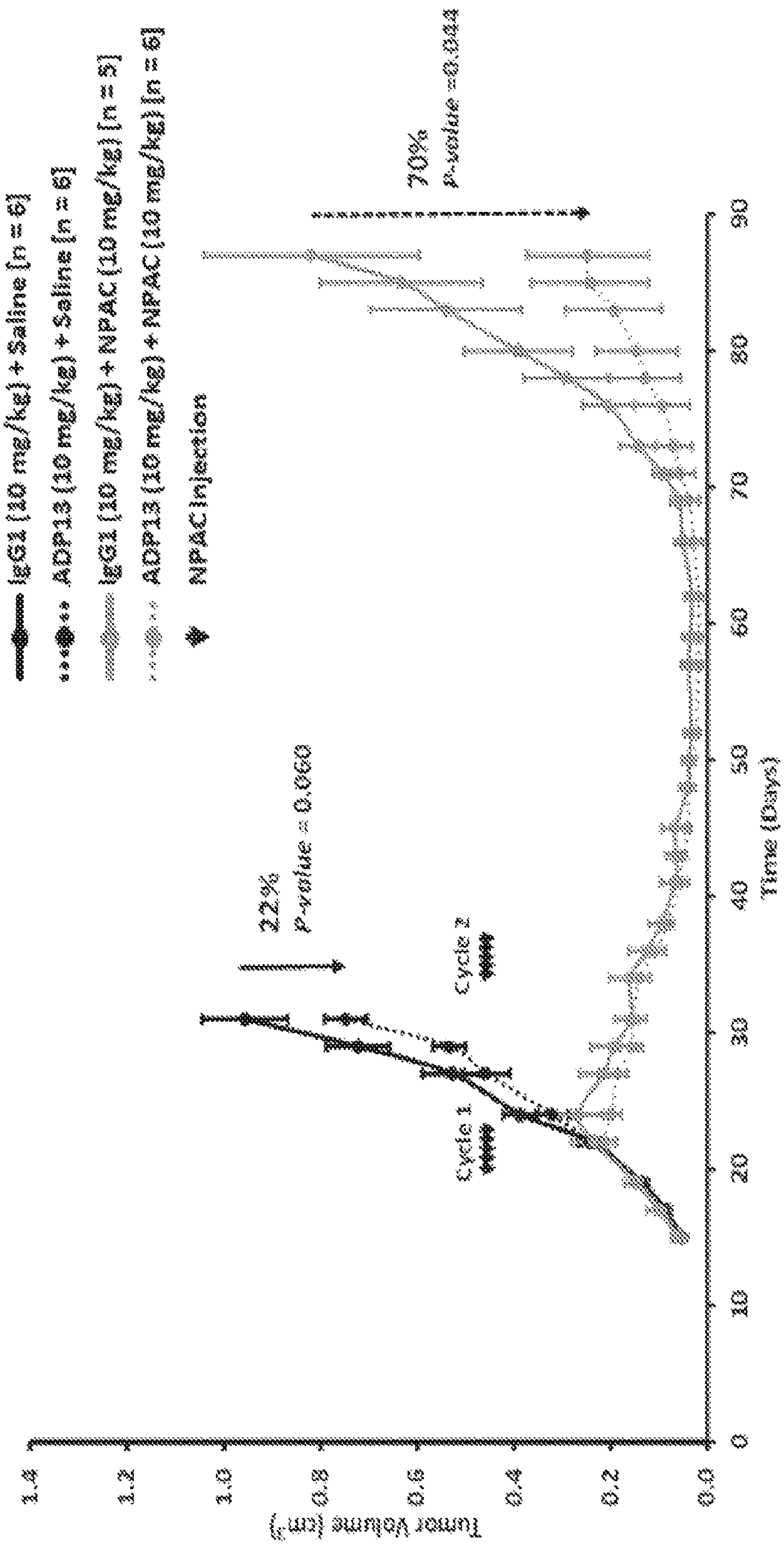

FIG. 30 is a graph showing tumor volume (Mean±S.E.M.) over time in a tumor regrowth model. Mice carrying pre-existing MDA-MB-231-luciferase-tagged cell-derived orthotopic tumors were treated with control IgG1+Saline, ADP13+Saline, IgG1+NPAC or ADP13+NPAC (n=number of animals/group). NPAC (in saline) was administered in 2 cycles of 5 consecutive i.v. treatments with one week of rest in between; an equivalent volume of vehicle saline was also given. ADP13 or IgG1 were administered i.p. 3×/week. Percentages indicate level of inhibition of tumor growth vs corresponding control group. P-values were determined using a Student's t-test.

Figure 31A:
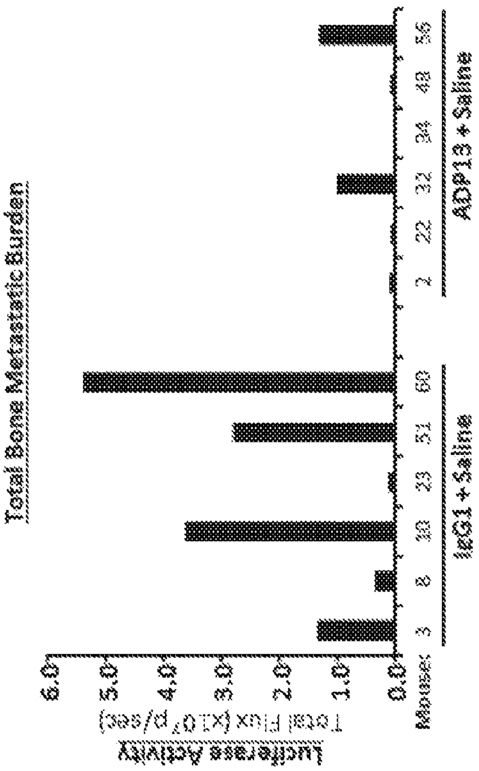

FIG. 31A is a bar graph showing the presence and extent of total bone metastasis from TNBC tumors of mice used in FIG. 30 (IgG1+Saline vs ADP13+Saline) using biphotonic imaging of dissected bones for detection of activity from the luciferase tag expressed in MDA-MB-231 cells.

Figure 31B:
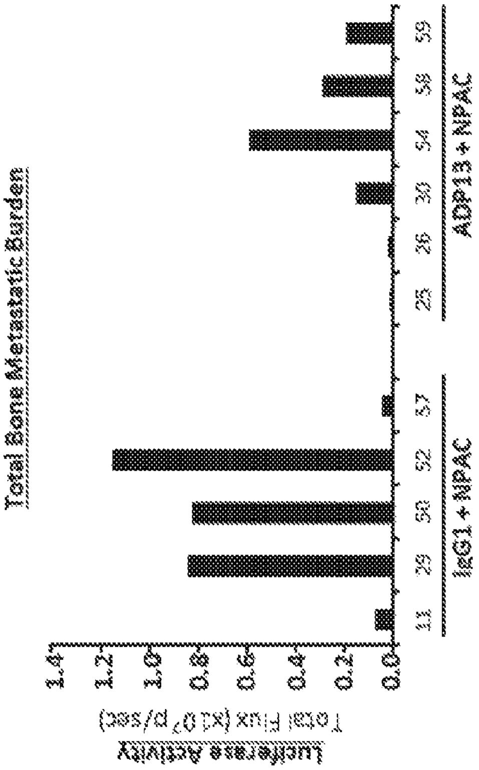

FIG. 31B is a bar graph showing the presence and extent of bone metastasis from TNBC tumors of mice used in FIG. 30 (IgG1+NPAC vs ADP13+NPAC) using biphotonic imaging of dissected bones for detection of activity from the luciferase tag expressed in MDA-MB-231 cells.

Figure 31C:
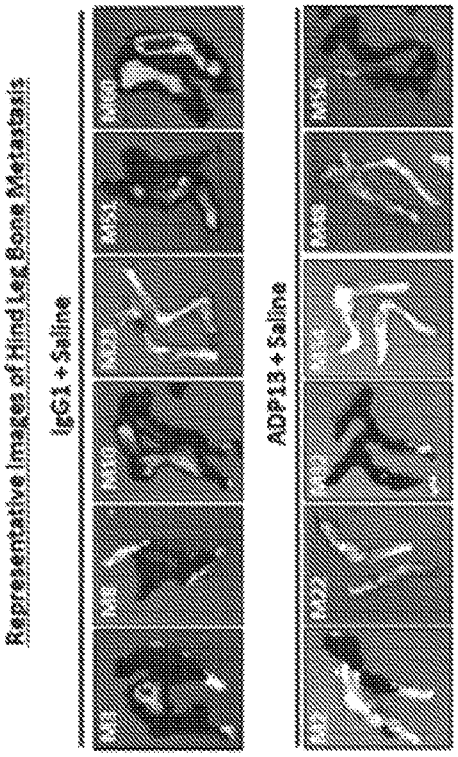

FIG. 31C is a collection of images showing all hind leg bone metastases from individual mice (M) treated with IgG1+Saline or ADP13+Saline as in FIG. 31A. A grey color on the bone indicates a small to moderate-sized metastasis. A black color on the bone corresponds to a large metastatic lesion. A white color on the bone indicates no metastasis.

Figure 31D:
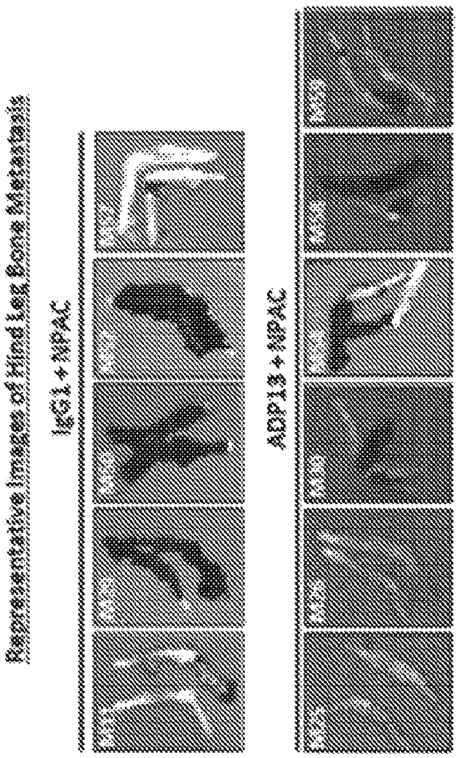

FIG. 31D is a collection of images showing all hind leg bone metastases from individual mice (M) treated with IgG1+NPAC or ADP13+NPAC as in FIG. 31B. A grey color on the bone indicates a small to moderate-sized metastasis. A black color on the bone corresponds to a large metastatic lesion. A white color on the bone indicates no metastasis.

Figure 32A:
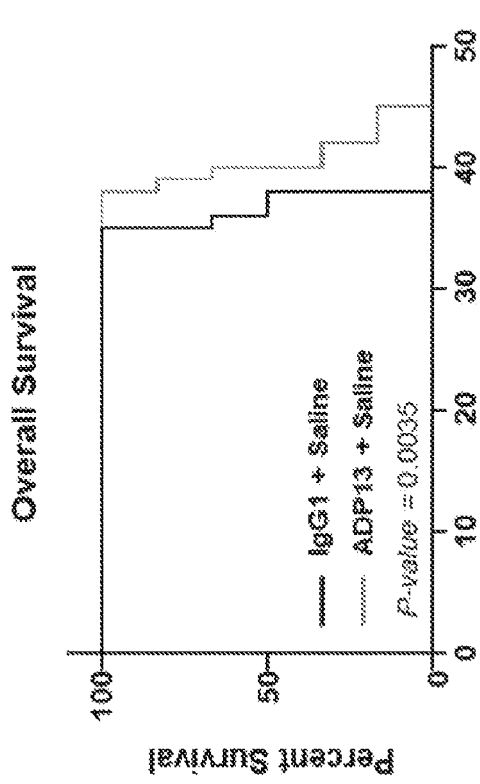

FIG. 32A is a Kaplan-Meier curve of the ability of ADP13 monotherapy (IgG1+Saline vs ADP13+Saline) to increase overall survival in the mice used in FIG. 30. Statistical significance was determined using a Log-rank test; P-values=0.0035.

Figure 32B:
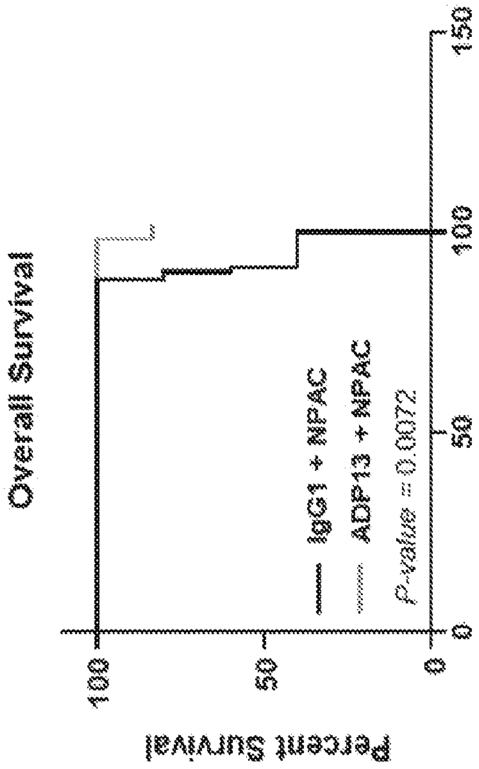
Figure 32C:
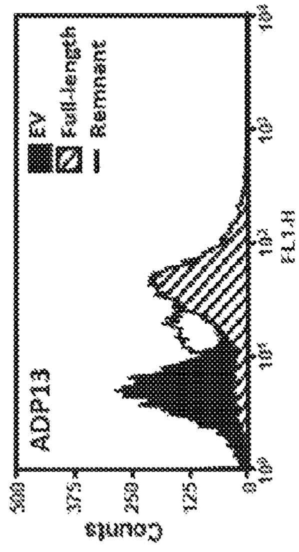

FIG. 32B is a Kaplan-Meier curve of the ability of combination therapy with NPAC (IgG1+NPAC vs ADP13+NPAC) to increase overall survival in the mice used in FIG. 30. Statistical significance was determined using a Log-rank test; P-values=0.0072.

Figure 33A:
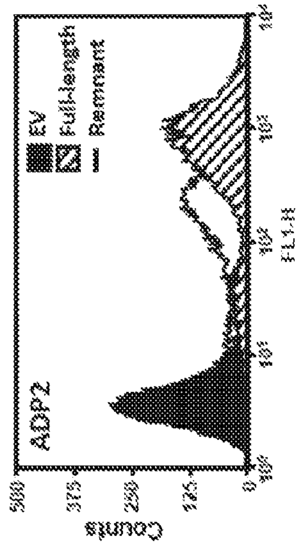

FIG. 33A is a fluorescent-activated cell sorting (FACS) analysis histogram of HEK293 cells stably expressing either empty vector control DNA (EV), full-length ADAM8 or remnant ADAM8 (which lacks the promodomain and MP domain) showing ADP2 binding to the disintegrin (DI) region of ADAM8.

Figure 33B:
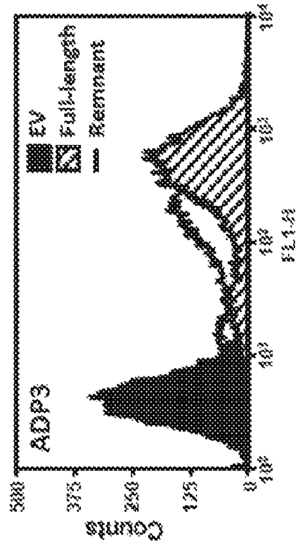

FIG. 33B is a FACS analysis histogram of HEK293 cells stably expressing either EV, full-length ADAM8 or remnant ADAM8 showing ADP3 binding to the DI region of ADAM8.

FIG. 33C is a FACS analysis histogram of HEK293 cells stably expressing either EV, full-length ADAM8 or remnant ADAM8 showing ADP13 binding to the DI region of ADAM8.

Figure 33D:
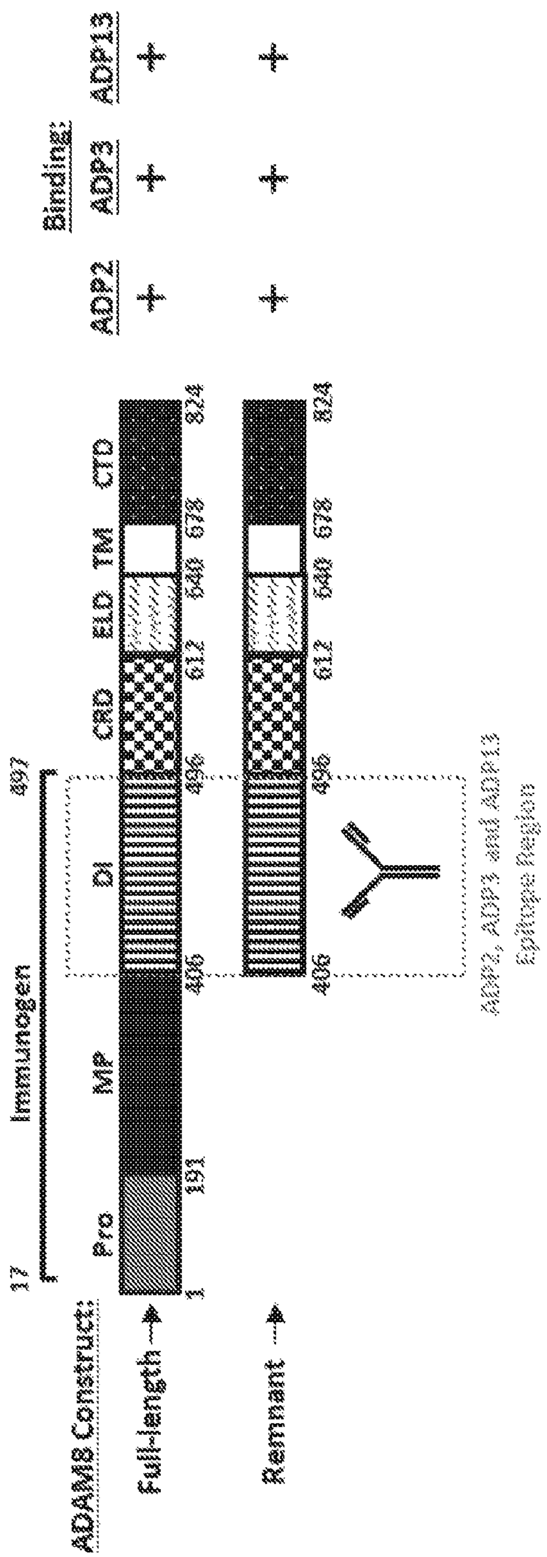

FIG. 33D is a schematic representation of the ADAM8 constructs used in FIGS. 33A-C, with domain information and amino acid numbers, as well as the immunogen injected into mice for generation of the ADP antibodies. The identified ADP2, ADP3 and ADP13 epitope binding region is indicated (dotted grey box). ADAM8 domains: Pro—pro-domain; MP—metalloproteinase; DI—disintegrin; CDR—cysteine-rich; ELD—EGF-like; TM—transmembrane; CTD—cytoplasmic domain.

Figure 34:
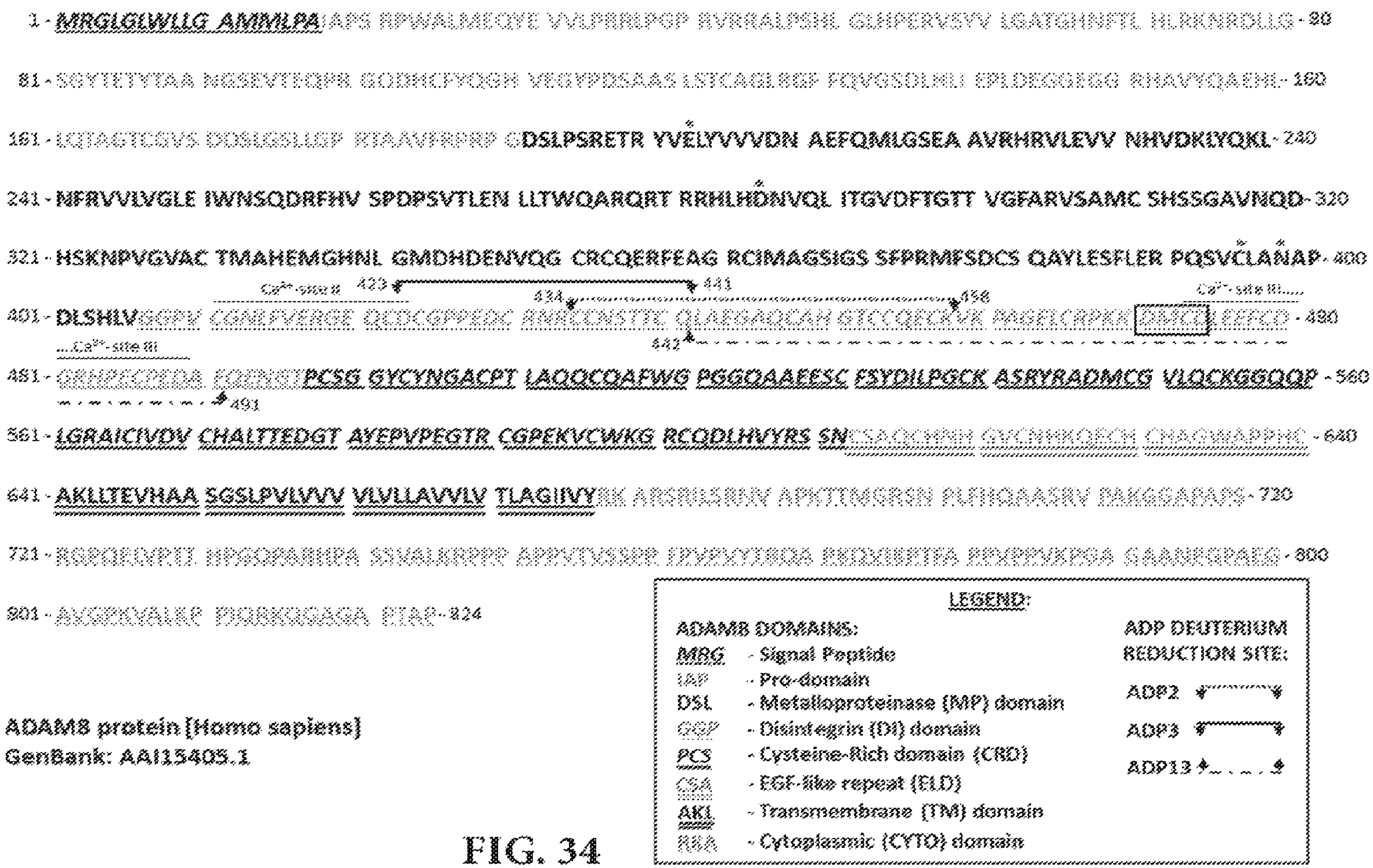

FIG. 34 is a diagram indicating the epitopes at the peptide level within the DI domain of human ADAM8 to which ADP2, ADP3 or ADP13 bind, as identified using hydrogen deuterium exchange (HDX) mass spectrometry analysis. HDX mass spectrometry analysis with rHuADAM8 in the presence or absence of ADP2, ADP3 or ADP13 identified the indicated protected peptide sequences as judged by a decrease in deuterium exchange level upon antibody binding. These peptides are thus identified as containing the epitope amino acid sequences of ADAM8 for specific ADP2, ADP3 and ADP13 antibody binding. Calcium ion binding site I (involving the 4 starred amino acids in the MP domain), and sites II and III in the DI domain are indicated. The integrin binding region (DMCD, open box) within the "disintegrin mobile hairpin loop" is stabilized by disulfide bonds and calcium binding to the adjacent site III. The first 3 amino acids for each ADAM8 domain are given in the inset box. The GenBank number for human ADAM8 is AAI15405.1

Figure 35:
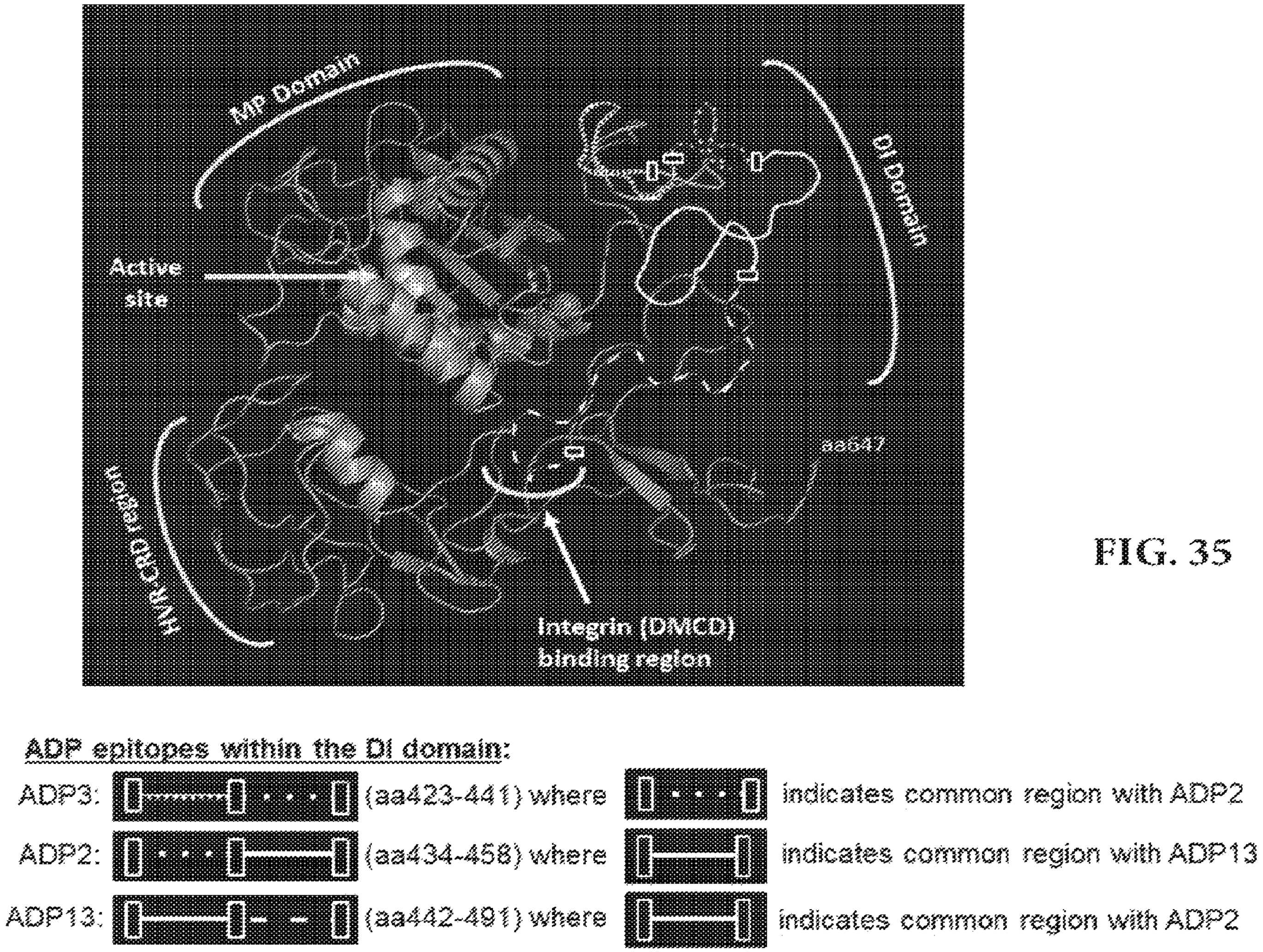

FIG. 35 is an image of a 3D model of the extracellular structure of ADAM8 as predicted using Swiss-model software and the crystal structure of ADAM22 as a template. The ADAM8 ectodomain structure (residues 195-647, which include the MP, DI, CRD and ELD domains) was predicted. Peptides of ADP2, ADP3 and ADP13 binding, identified from the HDX mass spectrometry analysis in FIG. 34 are indicated, including common regions. The MP domain with its active catalytic site, the DI domain with its integrin binding region and the hypervariable region (HVR) of the CDR domain are also shown.

Figure 36A:
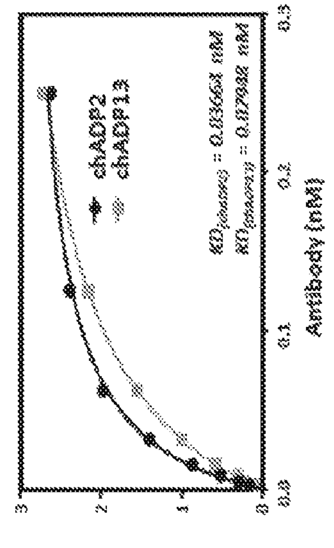

FIG. 36A is a graph showing binding of chimeric ADP2 and ADP13 antibodies composed of mouse ADP V regions and human IgG1 C regions (chADP2 and chADP13) to human ADAM8 (rHuADAM8) using ELISA assays over a concentration range from 0 to 2.5 nM. $KD_{(chADP2)}$ is 0.03664 nM. $KD_{(chADP13)}$ is 0.07948 nM.

Figure 36B:
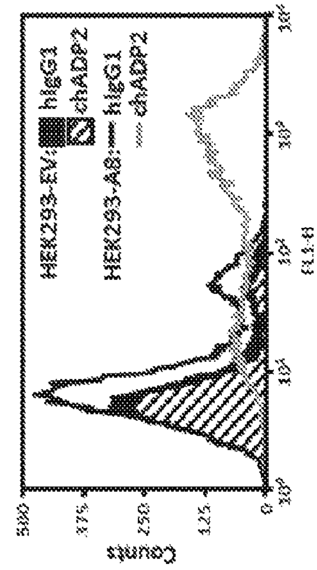

FIG. 36B is a FACS analysis histogram of HEK293 cells stably expressing either empty vector control DNA (HEK293-EV) or full-length ADAM8 (HEK293-A8) showing chADP2 binding to native ADAM8. Human IgG1 (hIgG1) was used as an antibody isotype-matched control.

Figure 36C:
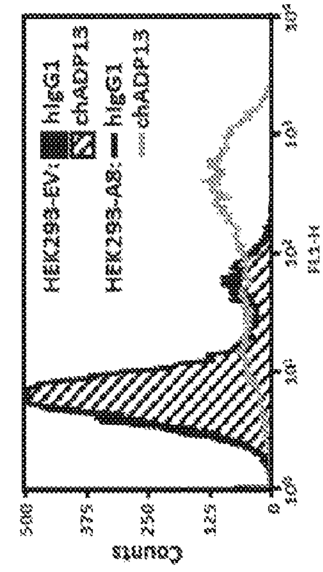

FIG. 36C is a FACS analysis histogram of HEK293 cells stably expressing either empty vector control DNA (HEK293-EV) or full-length ADAM8 (HEK293-A8) showing chADP13 binding to native ADAM8. Human IgG1 (hIgG1) was used as an antibody isotype-matched control.

Figure 37A:
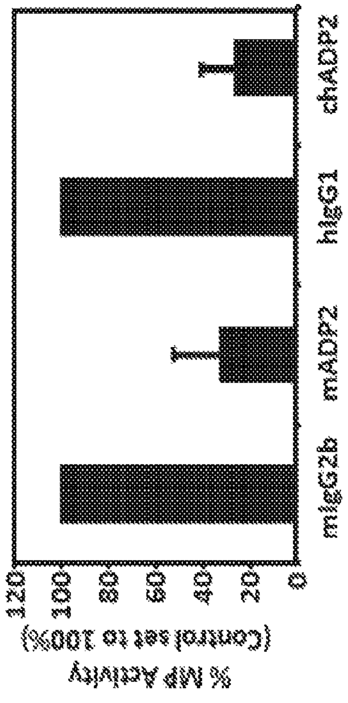

FIG. 37A is a bar graph showing the ability of chimeric ADP2 (chADP2) and mouse ADP2 (mADP2) treatment to inhibit MP activity as assessed using CD23 cleavage as in FIG. 10. Human IgG1 (hIgG1) and mouse IgG2b (mIgG2b) were used as controls, as appropriate.

Figure 37B:
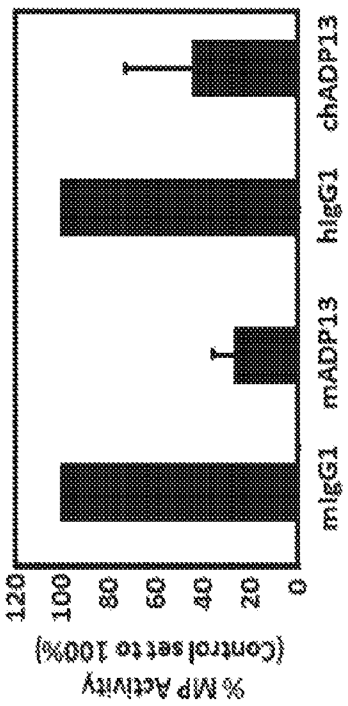

FIG. 37B is a bar graph showing the ability of chimeric ADP13 (chADP13) and mouse ADP13 (mADP13) treatment to inhibit MP activity as assessed using CD23 cleavage, as in FIG. 10. Human IgG1 (hIgG1) or mouse IgG1 (mIgG1) were used as controls, as appropriate.

Figure 37C:
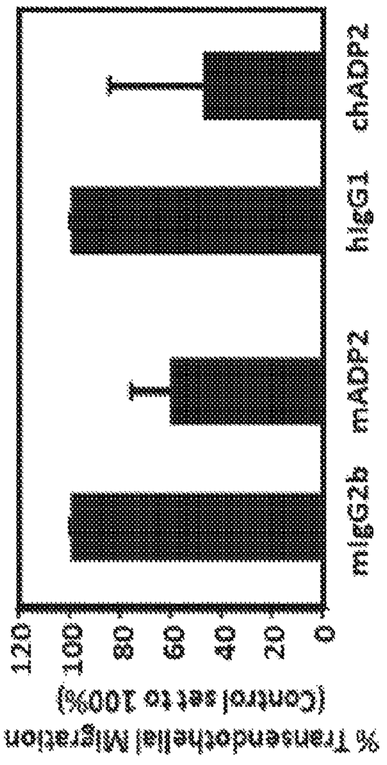

FIG. 37C is a bar graph showing the ability of chADP2 vs mADP2 to inhibit DI activity using transendothelial migration (TEM) assays as in FIG. 10. Levels of activity seen with control IgGs (mIgG2b, hIgG1) were set to 100%. Values are Mean±S.D. from three independent experiments.

Figure 37D:
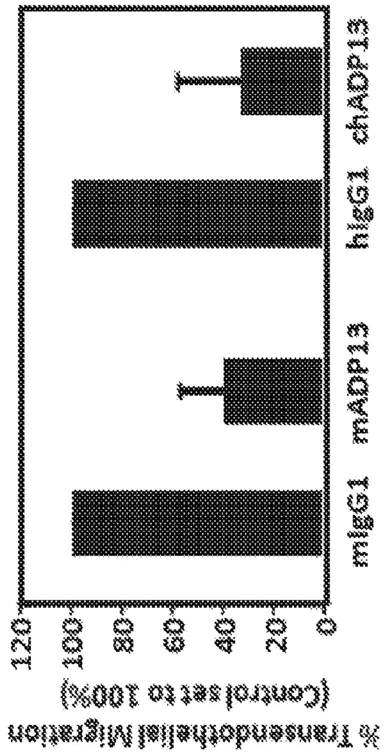

FIG. 37D is a bar graph showing the ability of chADP13 vs mADP13 to inhibit DI activity using transendothelial migration (TEM) assays as in FIG. 10. Levels of activity seen with control IgGs (mIgG1, hIgG1) were set to 100%. Values are Mean±S.D. from three independent experiments.

FIG. 38 is a table showing the amino acid residues important for ADP2 and ADP13 binding to ADAM8 identified using shotgun mutagenesis. Mean binding reactivity (in duplicate samples) of the test ADP2 and ADP13 antigen-binding fragments (Fabs), under high stringency (HS) conditions, and of the positive control ADAM8 antibody (Control Ab), to the mutated ADAM8 protein residues at the indicated positions (Mutation) is listed as a percentage of binding to the corresponding wild type (WT) residue. The range of binding reactivity (maximum-minimum) in each case is indicated in parentheses. Amino acids that reached the threshold guidelines for critical binding residues (i.e., control antibody binding >70% of WT and test antibody binding <20% of WT binding) are shown in closed boxes. Mutations in these amino acid positions resulted in a significant reduction of ADP2 and ADP13 Fab binding, but no reduction of control antibody binding. Dotted boxes show residues of secondary importance, i.e., that did not reach the <20% of WT binding criterion for critical residues but still led to a substantial reduction in ADP2 and ADP13 Fab binding activity. This in combination with their proximity to critical residues indicates that they are part of the antibody epitope.

Figure 39A:
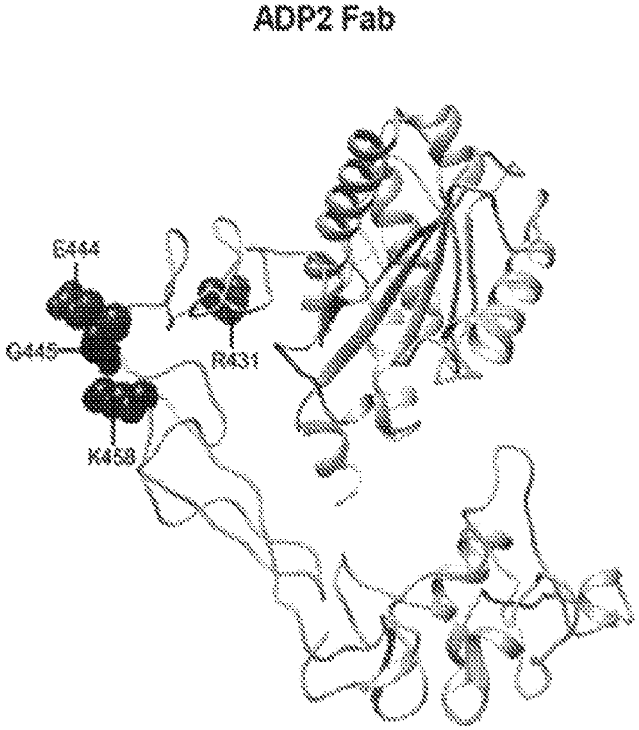

FIG. 39A is a graphic representation of the extracellular structure of ADAM8 with epitope amino acid residues for ADP2 Fab binding, identified through shotgun mutagenesis, indicated. Residues were visualized on a crystal structure model of ADAM8 based on the structure of vascular apoptosis-inducing protein-1 (PDB ID #2ERP, Takeda et al., *EMBO J.* 25:2388-2396, 2006). E444 is an ADP2 Fab critical binding residue. R431, G445, and K458 are secondary binding residues for ADP2 Fab.

Figure 39B:
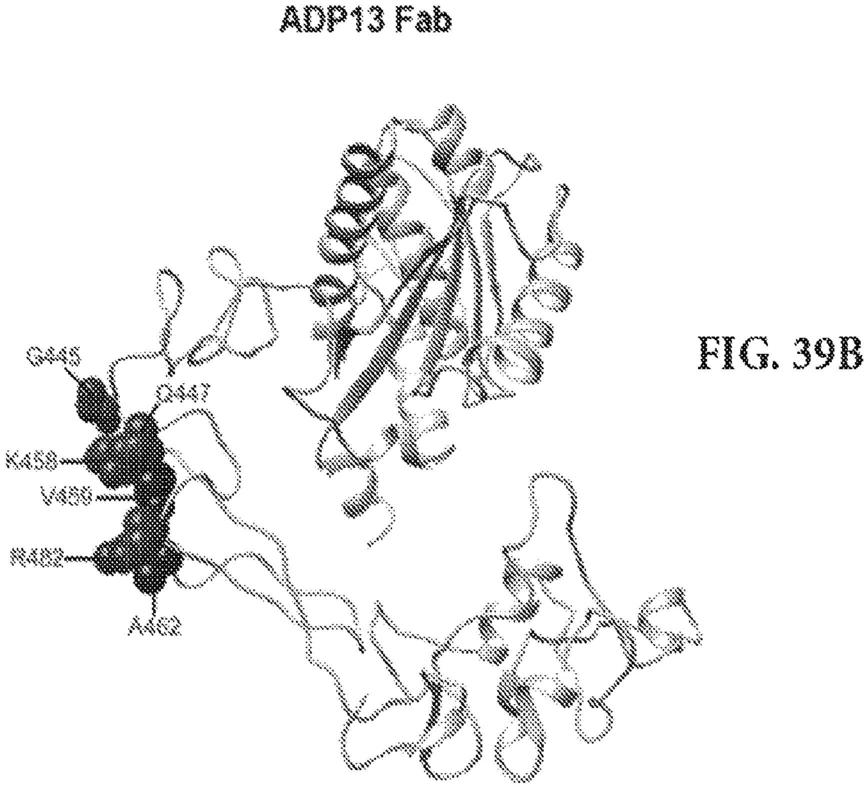

FIG. 39B is a graphic representation of the extracellular structure of ADAM8 with epitope amino acid residues for ADP13 Fab binding, identified through shotgun mutagenesis, indicated. Residues were visualized on a crystal structure model of ADAM8 based on the structure of vascular apoptosis-inducing protein-1 (PDB ID #2ERP, Takeda et al., *EMBO J.* 25:2388-2396, 2006). G445, Q447, K458, and R482 are ADP13 Fab critical binding residues. V459 and A462 are secondary binding residues for ADP13 Fab.

FIG. 40 is a diagram of the strategy with steps used to identify ADP2 as a diagnostic antibody for use in immunohistochemistry (IHC)-based detection of ADAM8 expression on cancer cells and patient-derived xenograft (PDX) tumor tissue samples and to establish a breast control cell line microarray (CCM) with a gradient of low, medium, and high ADAM8 levels for quantitation of tissue sample staining.

Figure 41A:
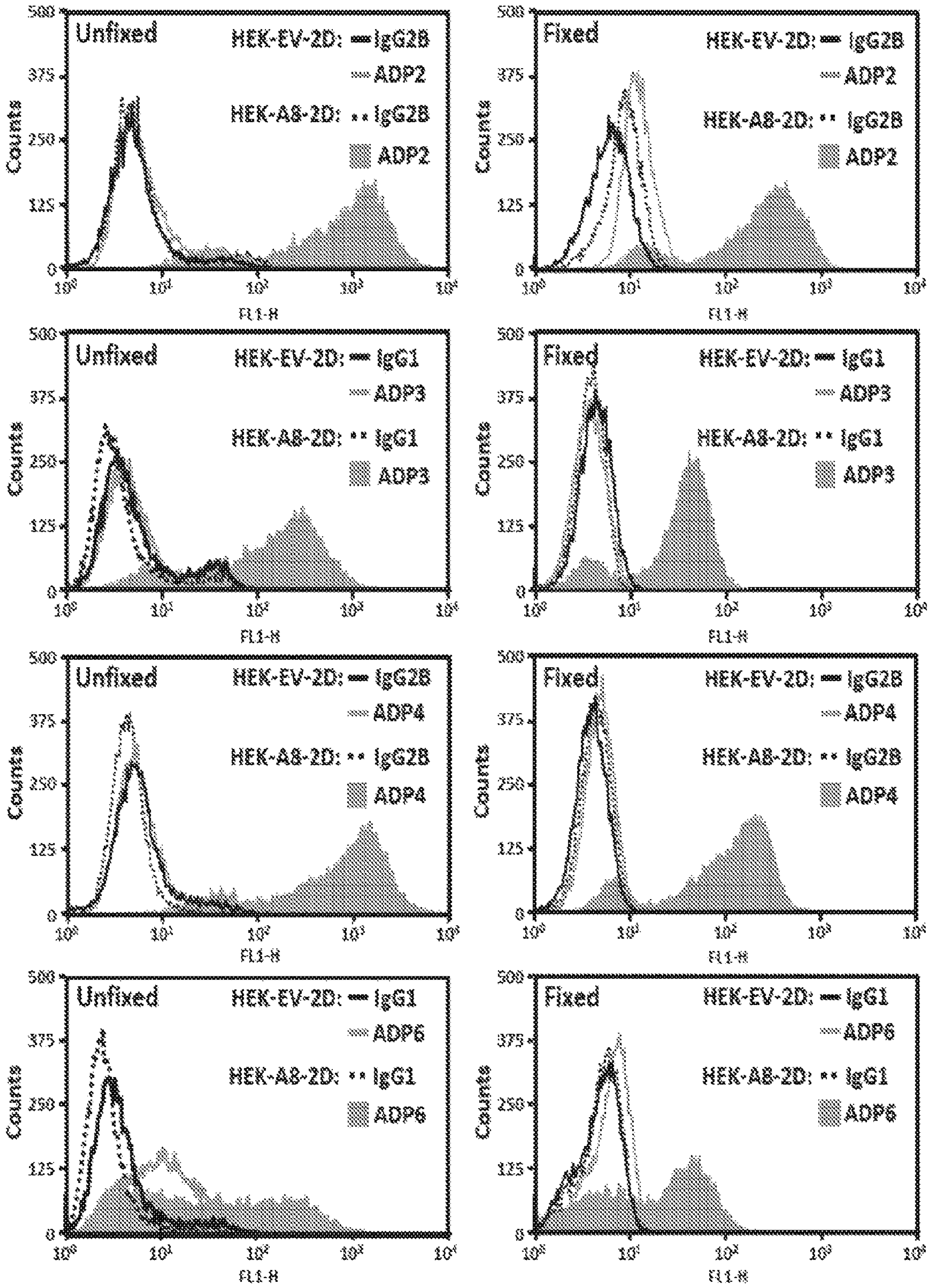

FIG. 41A are FACS analysis histograms demonstrating that the ADP antibodies retain their ability to recognize ADAM8 on the cell surface under fixed conditions. ADP2, ADP3, ADP4 and ADP6 were tested in FACS analysis using 2D cultured HEK293-ADAM8 cells, which ectopically (exogenously) overexpress full-length ADAM8 (HEK-A8-2D), or HEK293-Empty vector DNA cells (HEK-EV-2D) under native/unfixed conditions (left panels) or following fixation (right panels) versus appropriate IgG controls.

Figure 41B:
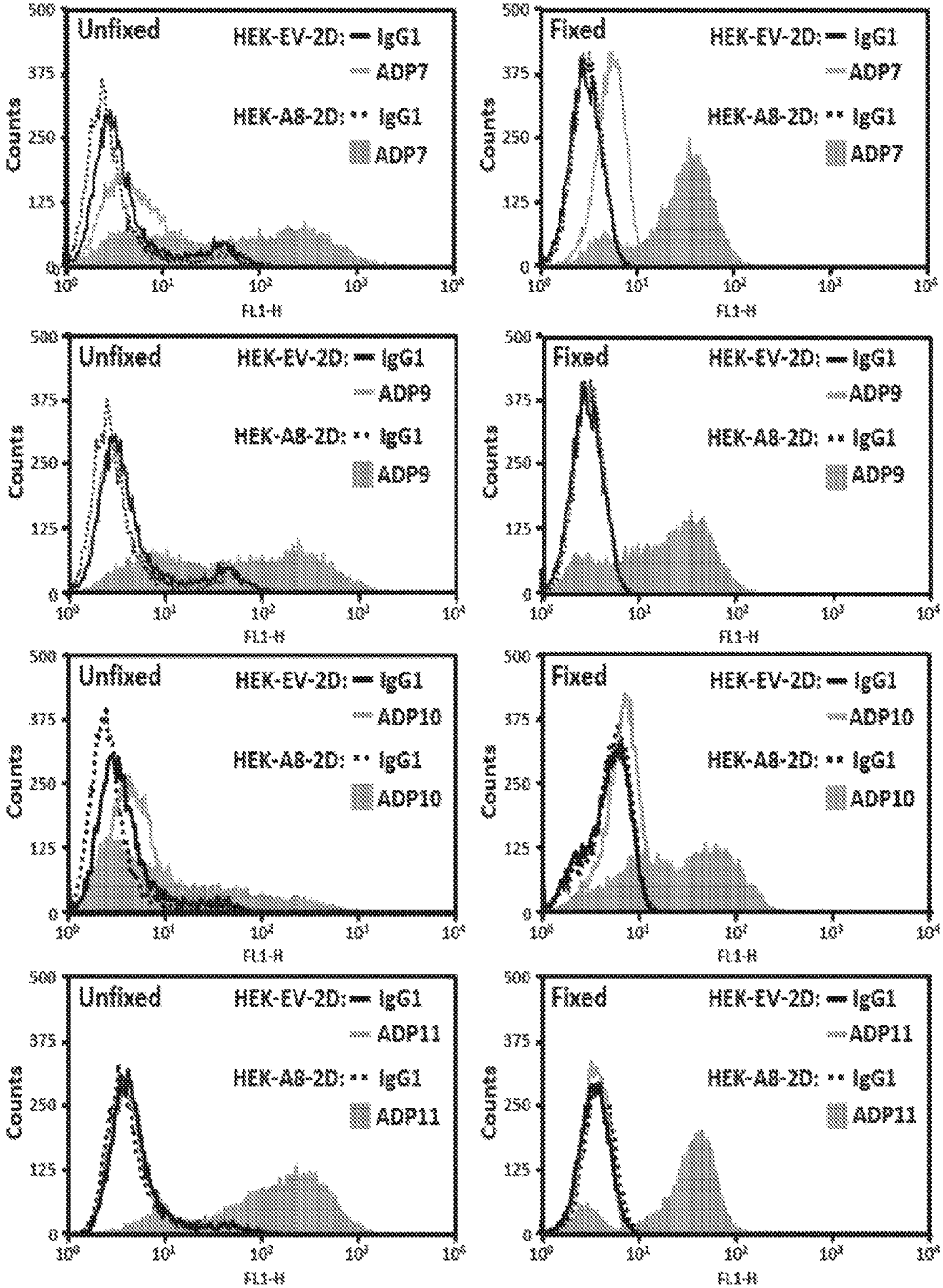

FIG. 41B are FACS analysis histograms demonstrating that the ADP antibodies retain their ability to recognize ADAM8 on the cell surface under fixed conditions. ADP7, ADP9, ADP10 and ADP11 were tested in FACS analysis using 2D cultured HEK293-ADAM8 cells, which ectopically (exogenously) overexpress full-length ADAM8 (HEK-A8-2D), or HEK293-Empty vector DNA cells (HEK-EV-2D) under native/unfixed conditions (left panels) or following fixation (right panels) versus appropriate IgG controls.

Figure 41C:
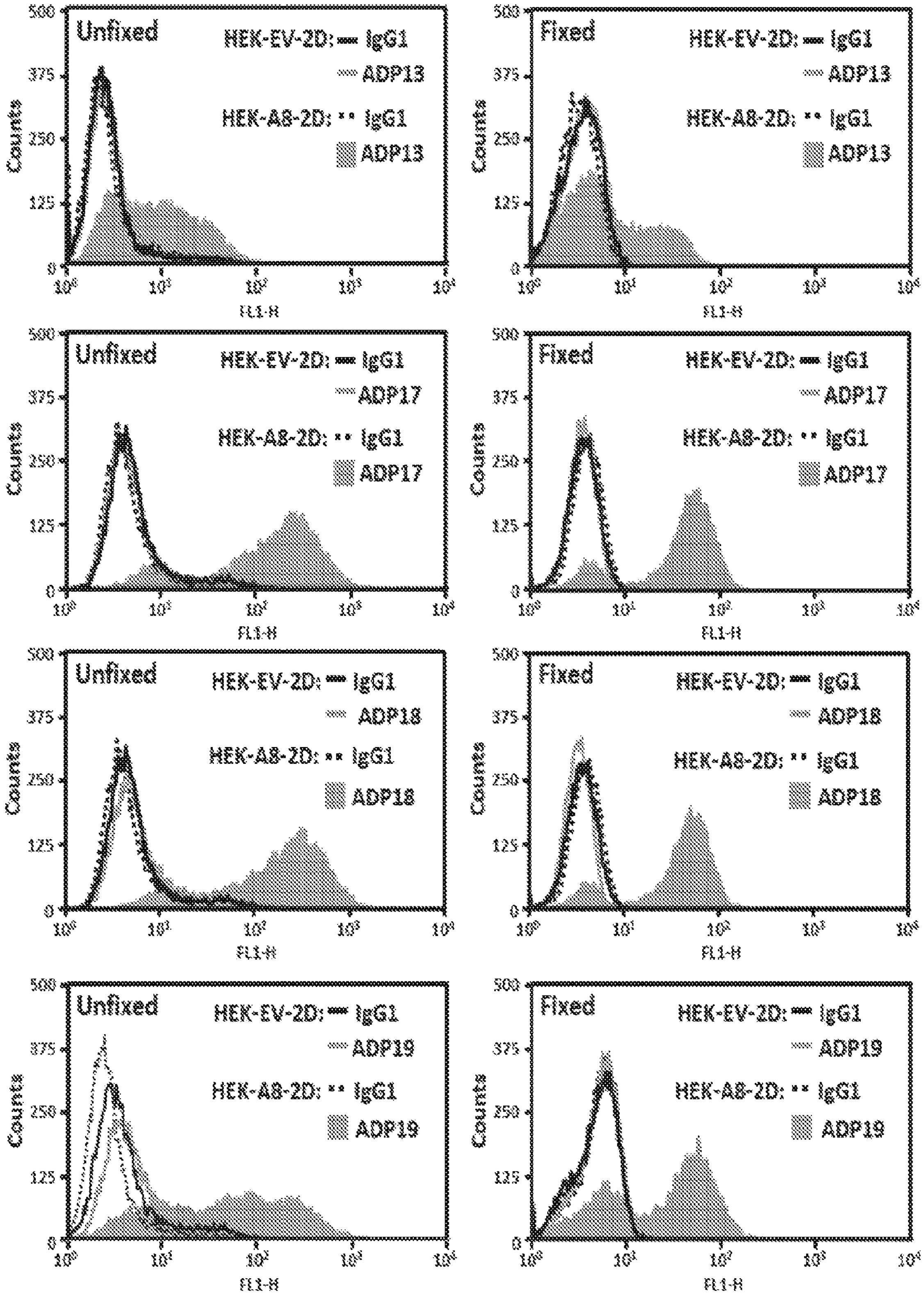

FIG. 41C are FACS analysis histograms demonstrating that the ADP antibodies retain their ability to recognize ADAM8 on the cell surface under fixed conditions. ADP13, ADP17, ADP18 and ADP19 were tested in FACS analysis using 2D cultured HEK293-ADAM8 cells, which ectopically (exogenously) overexpress full-length ADAM8 (HEK-A8-2D), or HEK293-Empty vector DNA cells (HEK-EV-2D) under native/unfixed conditions (left panels) or following fixation (right panels) versus appropriate IgG controls.

Figure 42:
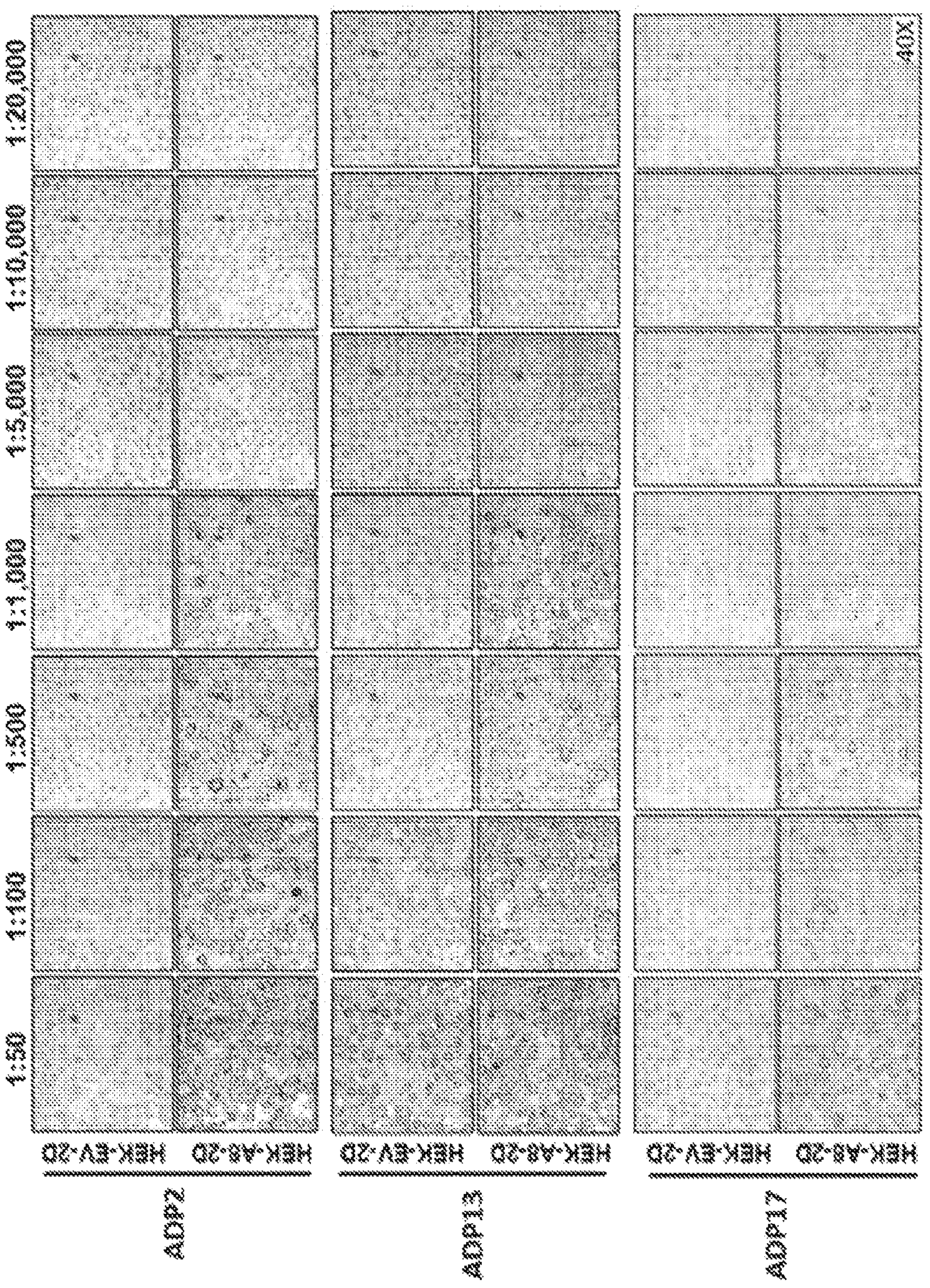

FIG. 42 are images showing that ADP2, ADP13 and ADP17 can detect ectopically (exogenously) expressed ADAM8 in HEK293-ADAM8 using IHC conditions optimized for the LS-B4068 ADAM8 antibody. Images are at 40× magnification.

Figure 43:
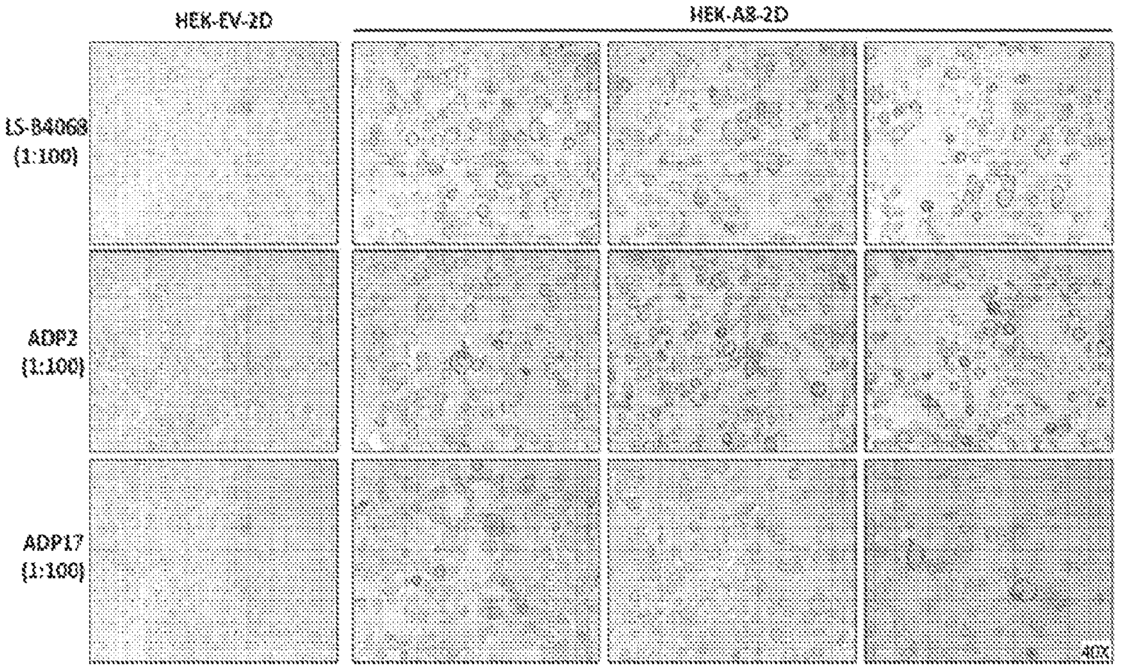

FIG. 43 are images demonstrating that ADP2 and ADP17 are comparable to LS-B4068 in detecting exogenously expressed ADAM8 in HEK293-ADAM8 cells. IHC was performed as above in FIG. 42 with 2D cultured HEK293-ADAM8 (HEK-A8-2D) and HEK293-Empty Vector (HEK-EV-2D) cells and 1:100 dilutions of LS-B4068, ADP2 and ADP17. Images are at 40× magnification.

Figure 44:
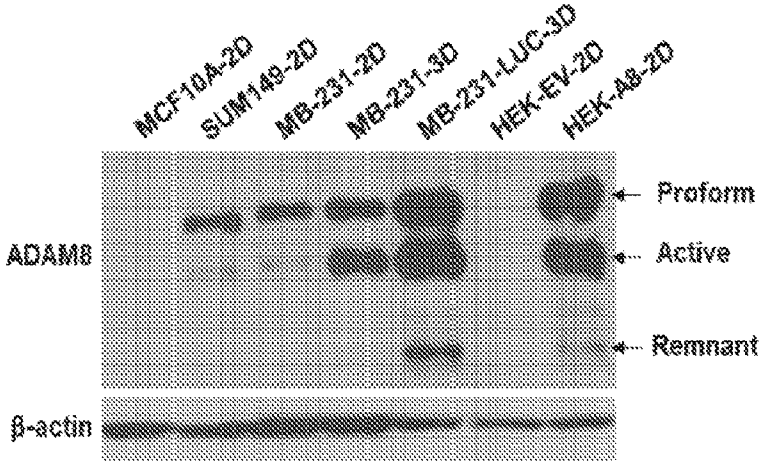

FIG. 44 is a Western blot image comparing the levels of endogenously expressed ADAM8 in untransformed breast cells and breast cancer cells versus exogenously expressed ADAM8 in HEK293-ADAM8 cells, while β-actin was used as a loading control. MCF10A-2D, MDA-MB-231-2D and MDA-MB-231-3D cells were selected to create a breast CCM with a gradient of low, medium, and high ADAM8 levels. HEK-EV-2D and HEK-A8-2D cells were selected as negative and positive controls, respectively. MDA-MB-231 (MB-231) cells; 2D and 3D at the end of each cell line name indicate specific growth conditions.

Figure 45:
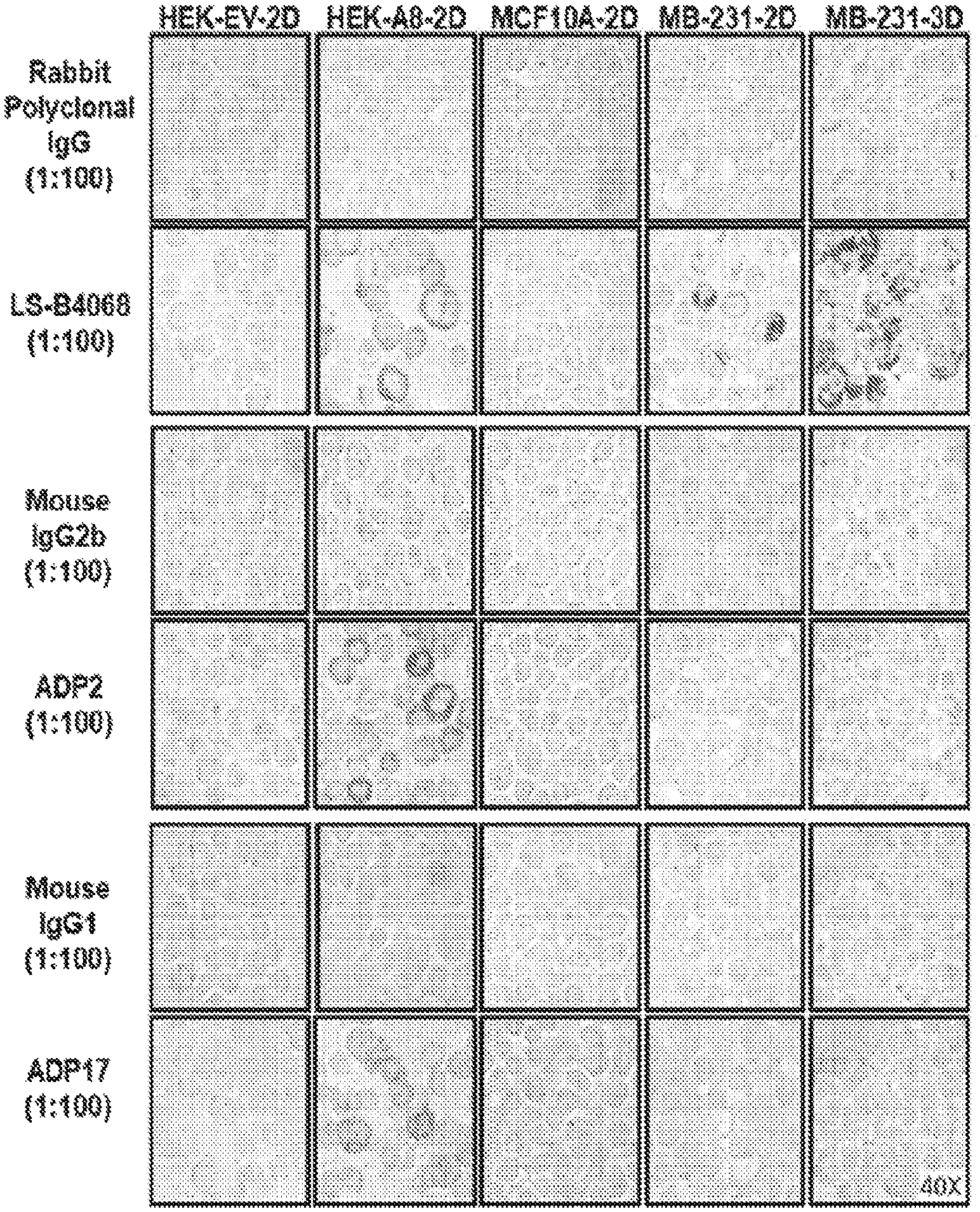

FIG. 45 are images showing that ADP2 and ADP17 detect exogenously expressed ADAM8 in HEK293 cells, but not endogenously expressed ADAM8 in breast cells under the IHC conditions optimized for the LS-B4068 antibody. IHC was performed with CCM slides and 1:100 dilutions of LS-B4068, ADP2 and ADP17 versus their isotype matched controls, rabbit polyclonal IgG, mouse IgG2b and mouse IgG1, respectively. HEK293-Empty Vector (HEK-EV), HEK293-ADAM8 (HEK-A8) and MDA-MB-231 (MB-231) cells; 2D and 3D at the end of each cell line name indicate specific growth conditions. Images are at 40× magnification.

Figure 46:
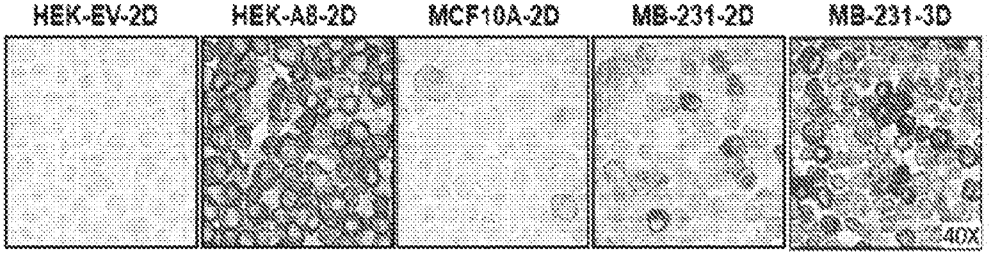

FIG. 46 are images demonstrating ADAM8 staining in the breast CCM under the optimized conditions for use of ADP antibodies in IHC. IHC was performed with ADP2 as a prototype ADP antibody (at 1:100 dilution) and with CCM slides. HEK293-Empty Vector (HEK-EV), HEK293-ADAM8 (HEK-A8) and MDA-MB-231 (MB-231) cells; 2D and 3D at the end of each cell line name indicate specific growth conditions. Images are at 40× magnification.

Figure 47A:
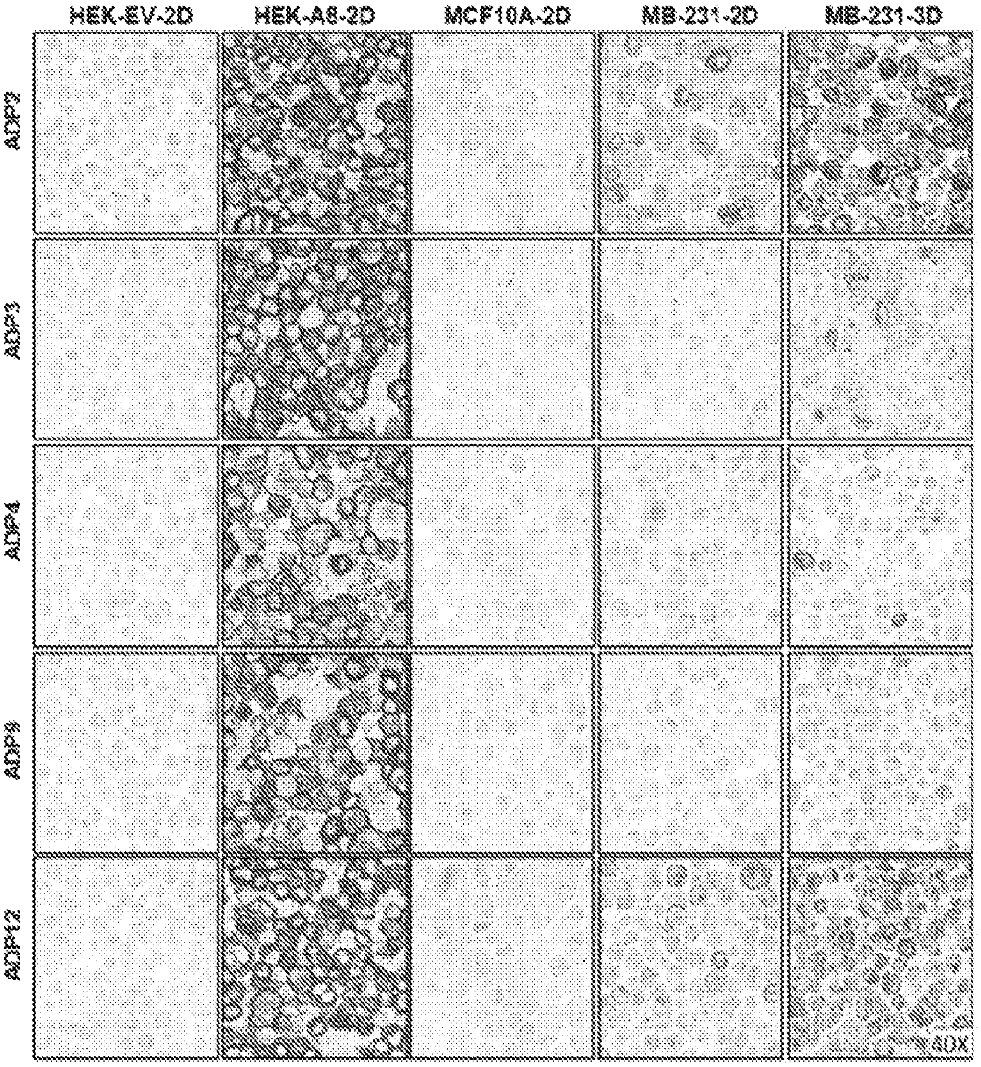

FIG. 47A are images comparing the IHC activity of ADP2 versus other antibodies within the ADP panel. The activity of ADP2 versus ADP3, ADP4, ADP9 and ADP12, at 1:100 dilutions, was compared using fresh slides of the breast CCM (described in FIG. 46) and the optimal staining conditions for use of ADP antibodies in IHC. Images are at 40× magnification.

Figure 47B:
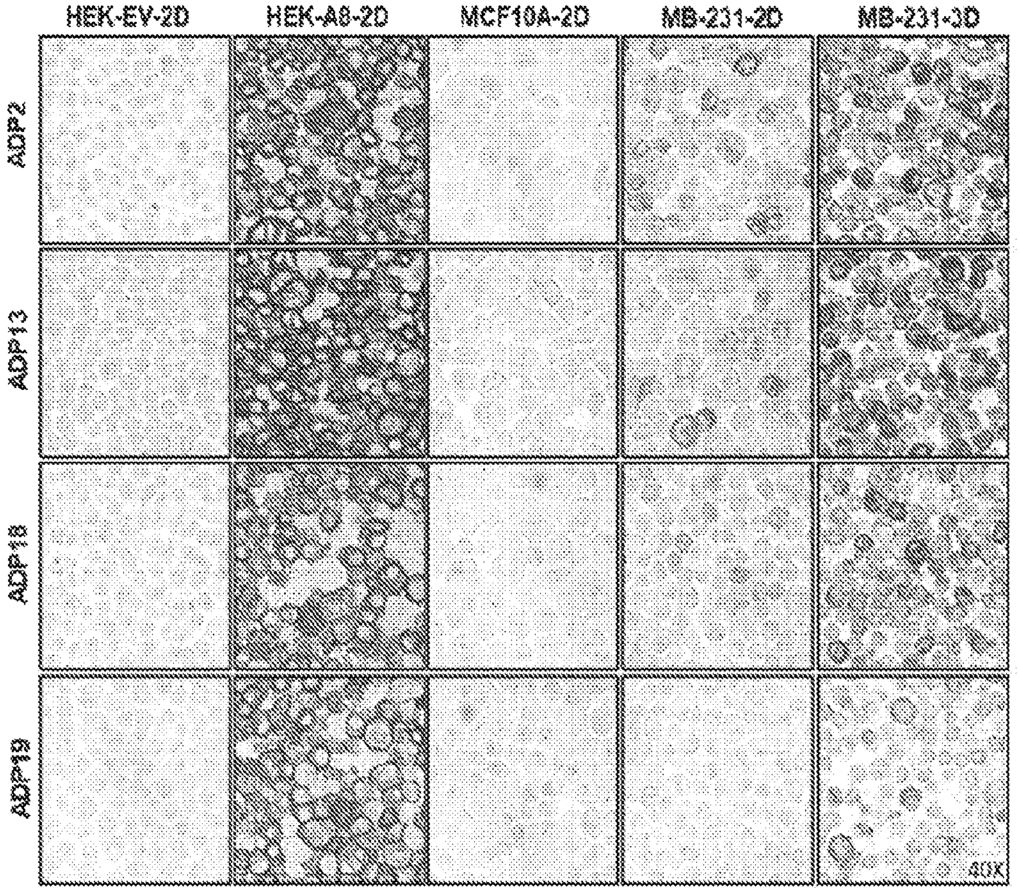

FIG. 47B are images comparing the IHC activity of ADP2 versus other antibodies within the ADP panel. The activity of ADP2 versus ADP13, ADP18, and ADP19, at 1:100 dilutions, was compared using fresh slides of the breast CCM (described in FIG. 46) and the new optimal staining conditions for use of ADP antibodies in IHC. Images are at 40× magnification.

Figure 48:
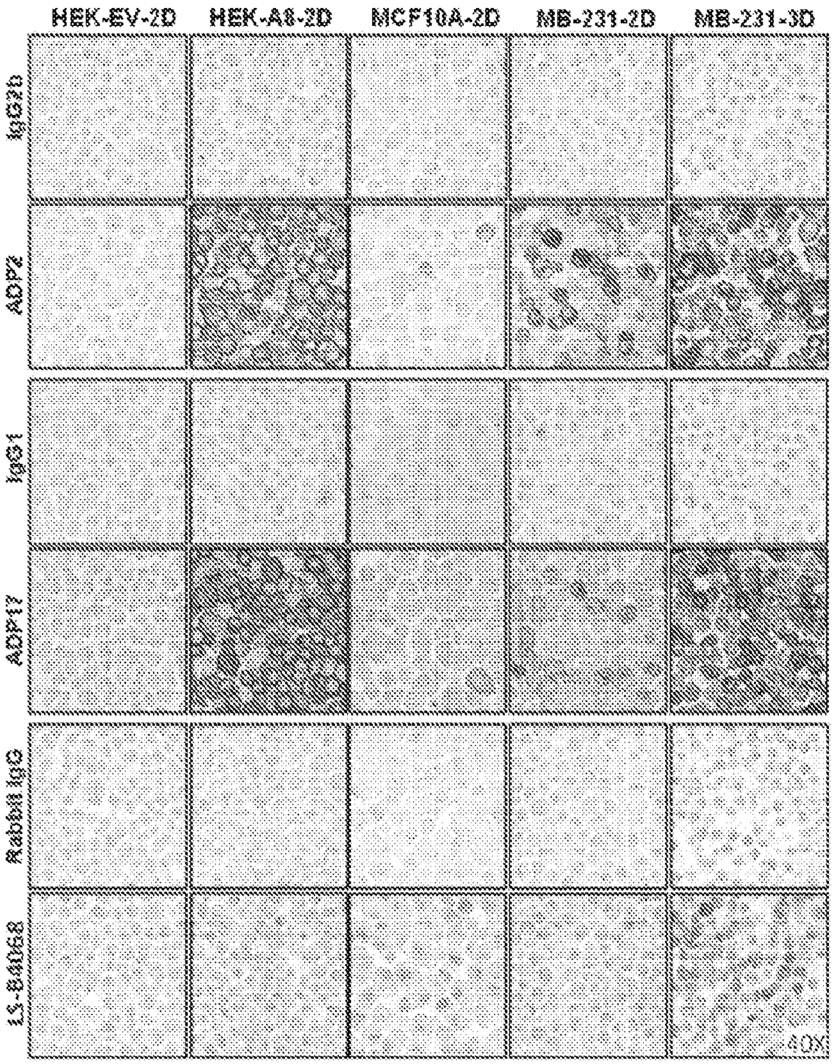

FIG. 48 are images comparing the performance of ADP2, ADP17 and LS-B4068 versus their control IgGs, at 1:100 dilutions, using slides of the CCM (described in FIG. 46) and the new optimal IHC staining conditions for ADP antibodies. Images are at 40× magnification.

Figure 49:
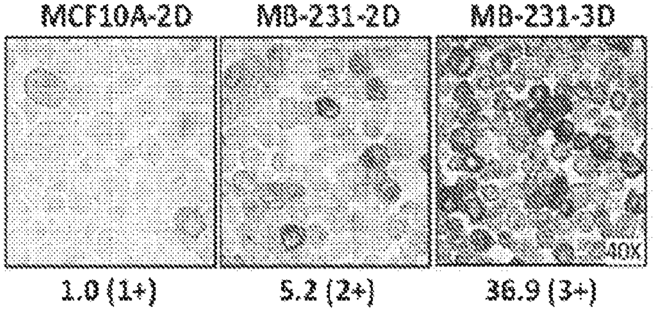

FIG. 49 are images showing the IHC scoring system established using the breast specific CCM. Cells, grown in 2D or 3D conditions, were either processed in a single block to generate the breast specific CCM (described in FIG. 46) and slides analyzed by IHC using ADP2 (with ADP optimal staining conditions and 1:100 dilution) or protein extracted and subjected to Western blotting using the LS-C20181 anti-ADAM8 antibody. A stepwise ~5-7-fold increase in relative active ADAM8 levels (indicated below images), and a low, medium, and high percent cell culture staining positivity was seen between the three cell lines of breast origin in Western blotting and IHC, respectively. Based on active ADAM8 levels and culture positivity, these cells were defined as having a simple 1+, 2+ and 3+ ADAM8 IHC staining score (indicated below images in parentheses). Images are at 40× magnification.

Figure 50:
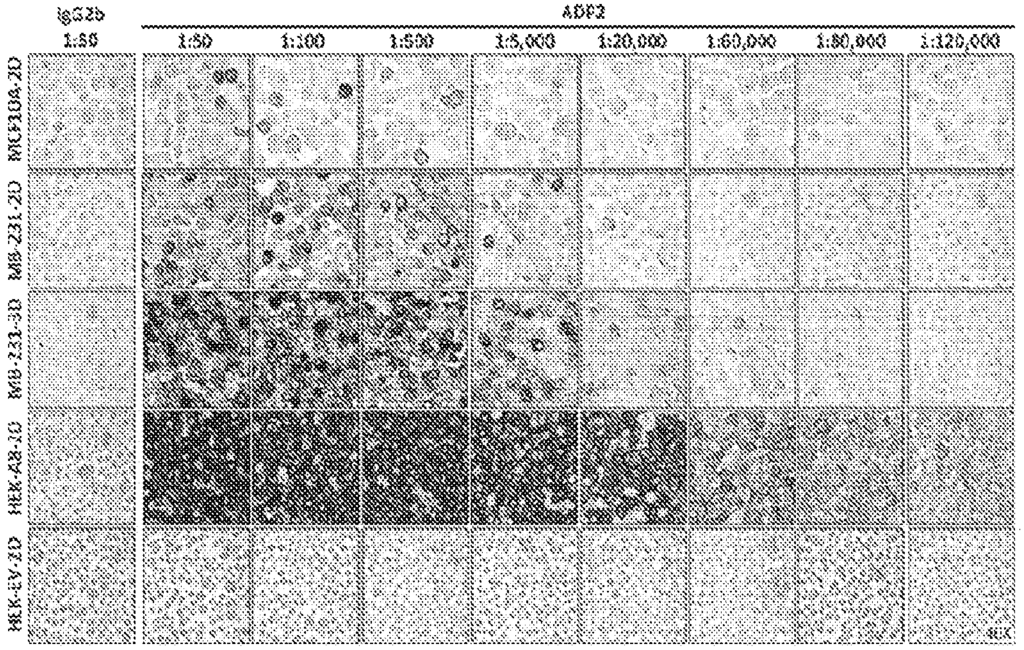

FIG. 50 are images demonstrating the range and linearity of ADP2 ADAM8 IHC staining. IHC was performed using slides of the CCM (described in FIG. 46) and a range of ADP2 dilutions from 1:50 to 1:120,000 under the optimized ADP staining conditions versus control IgG2b at 1:50. Images are at 40× magnification.

Figure 51:
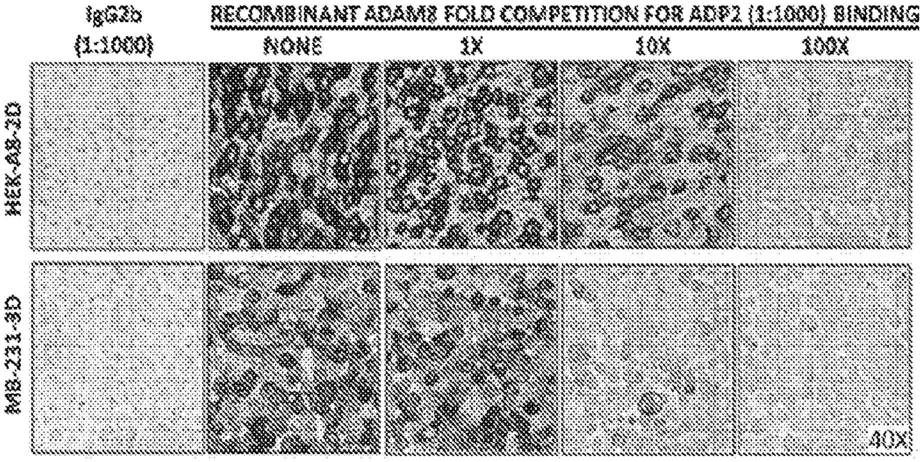

FIG. 51 are images demonstrating the specificity of ADP2 IHC staining for ADAM8. ADP2 at 1:1000 dilution was pre-incubated overnight at 4° C. in the absence or presence of 1×, 10× or 100× molar equivalents of purified recombinant human ADAM8 protein and used in HEK293-ADAM8 (HEK-A8)-2D and MDA-MB-231 (MB-231)-3D IHC. Images are at 40× magnification.

Figure 52:
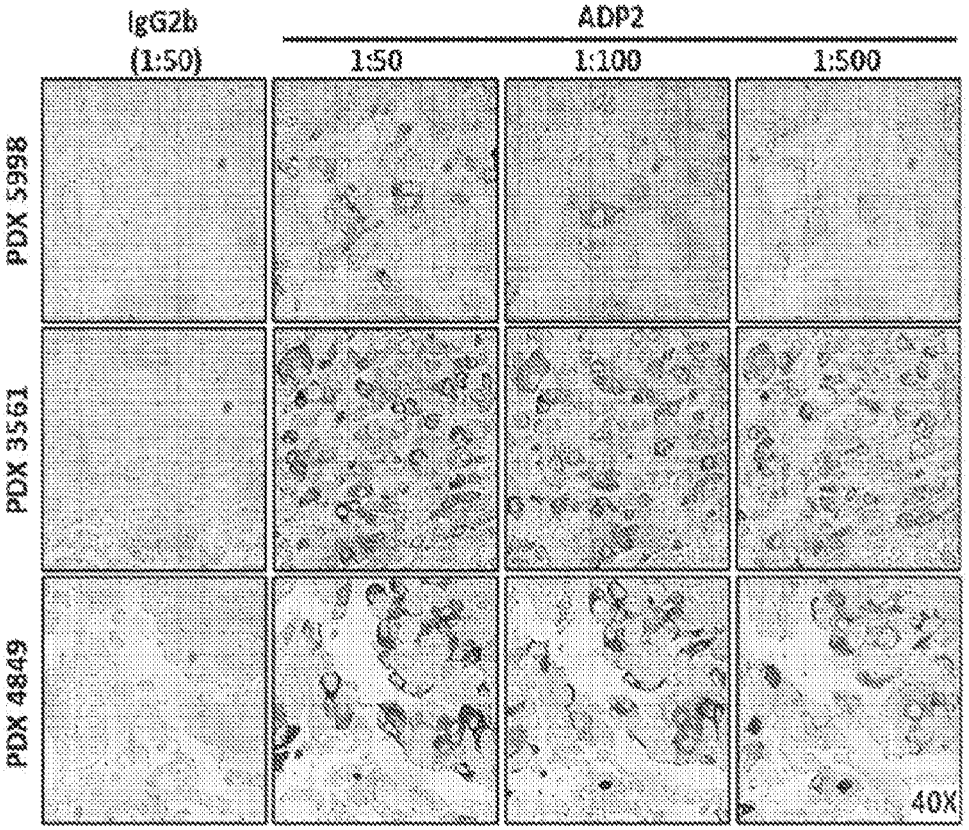

FIG. 52 are images demonstrating the ability of ADP2 to detect ADAM8 in TNBC patient-derived xenograft (PDX) tumor samples. IHC was performed using ADP2 at dilutions of 1:50, 1:100 and 1:500 versus its isotype-matched control IgG2b at 1:50 and TNBC PDX samples 5998, 3561, and 4849, which were found previously to have high ADAM8 expression based on a preliminary IHC screen of 30 PDX samples with LS-B4068 and ADP2. Images are at 40× magnification.

Figure 53A:
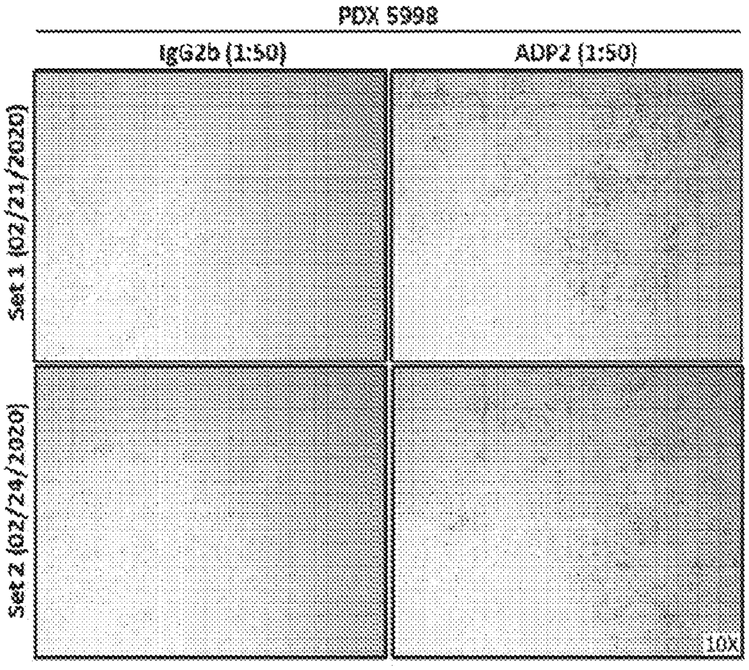

FIG. 53A are images demonstrating ADP2 IHC staining is reproducible in TNBC PDX samples. Two sets of single section slides of PDX 5998 tumors were subjected on different days to IHC using ADP2 and its isotype-matched control IgG2b at 1:50 dilutions. Images are at 10× magnification.

Figure 53B:
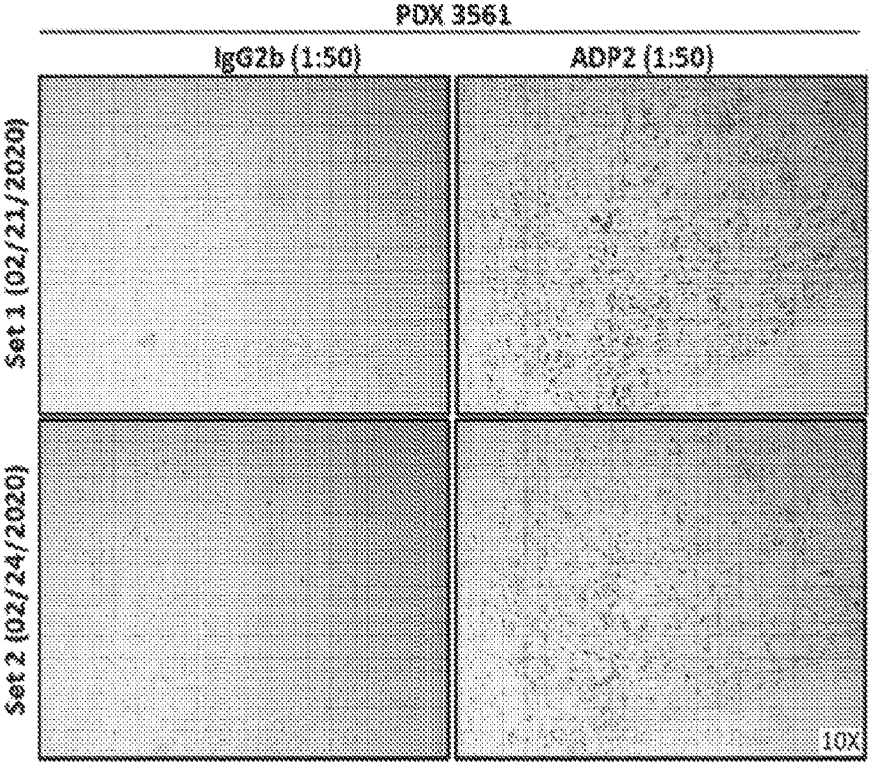

FIG. 53B are images demonstrating ADP2 IHC staining is reproducible in TNBC PDX samples. Two sets of single section slides of PDX 3561 tumors were subjected on different days to IHC using ADP2 and its isotype-matched control IgG2b at 1:50 dilutions. Images are at 10× magnification.

Figure 53C:
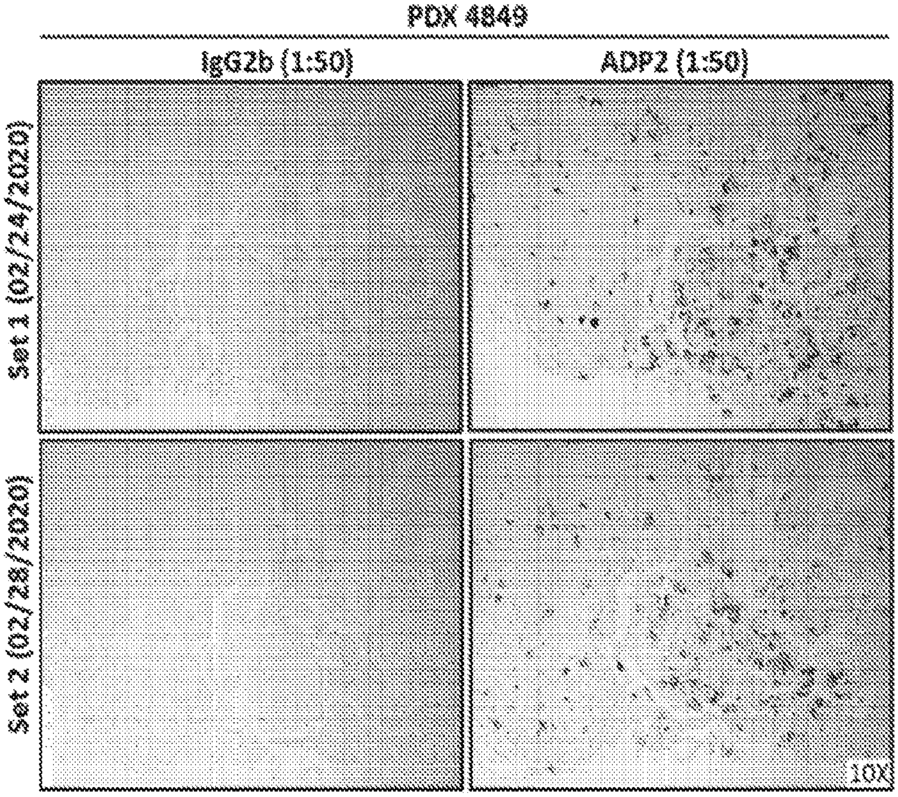

FIG. 53C are images demonstrating ADP2 IHC staining is reproducible in TNBC PDX samples. Two sets of single section slides of PDX 4849 tumors were subjected on different days to IHC using ADP2 and its isotype-matched control IgG2b at 1:50 dilutions. Images are at 10× magnification.

Figure 54:
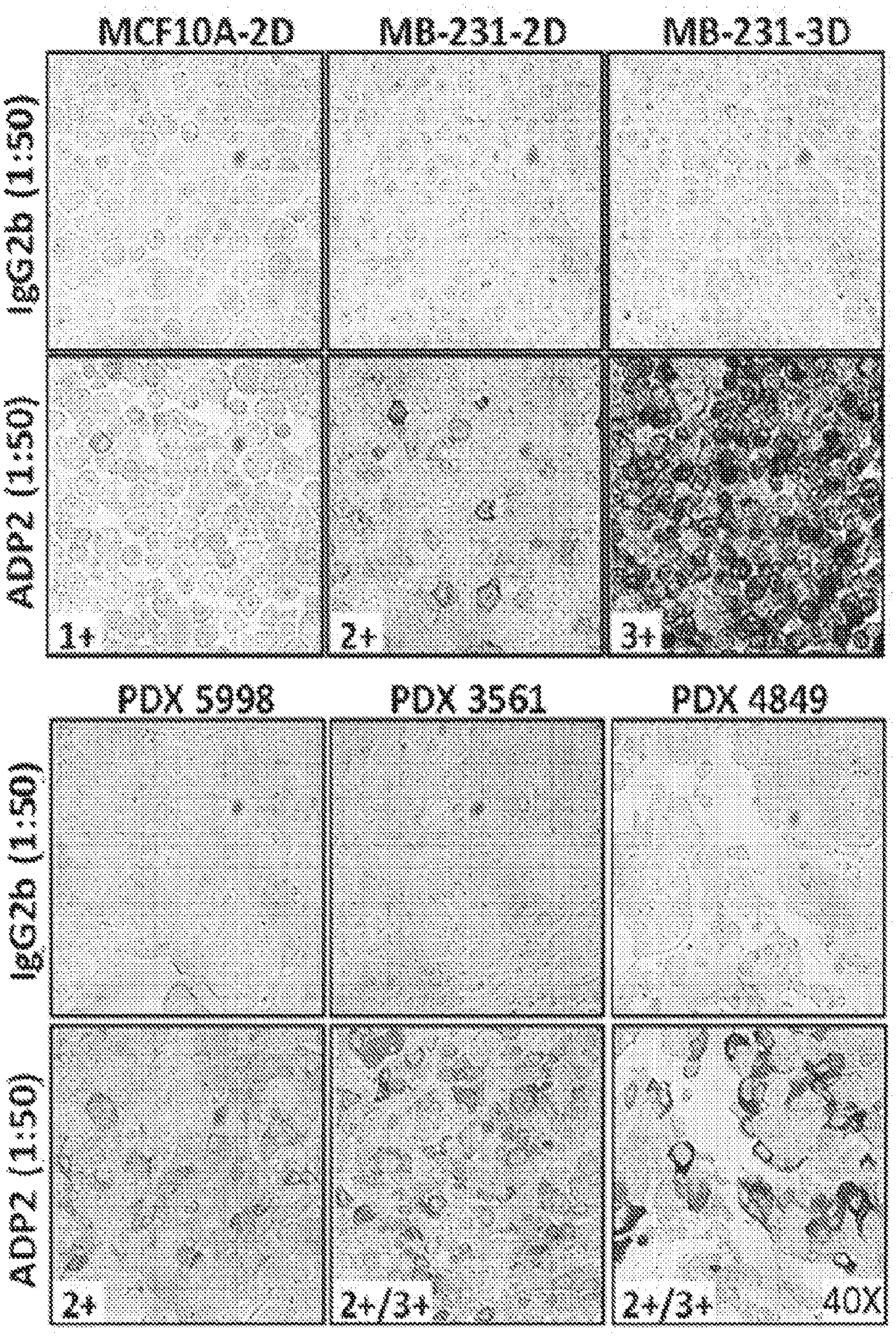

FIG. 54 are images showing the ADAM8 IHC scores for TNBC PDX samples are within the range of the CCM. ADP2 or its isotype-matched control IgG2b was used at a 1:50 dilution in IHC of the breast CCM (top panels) and the TNBC PDX 5998, PDX 3561, and PDX 4849 samples (lower panels). PDX staining scores were determined by direct visual comparison to the breast lines within the CCM (described in FIG. 46) and their IHC scores as established in FIG. 49. Sample scores are indicated at the bottom left corner of each image. Images are at 40× magnification.

DETAILED DESCRIPTION

Provided herein are proteins that inhibit both the metalloprotease activity and disintegrin activity of human ADAM8, wherein the protein includes an antigen-binding domain that: (i) binds specifically to human ADAM8; and (ii) binds to an epitope within human ADAM8 that includes at least one (e.g., at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68 amino acids) amino acid within the sequence of: DCGPPEDCRNRCCNSTTCQLAE-GAQCAHGTCCQECKVKPAGELCRPKKDMCDLEEF CDGRHPECPEDAF (SEQ ID NO: 1).

Provided herein are nucleic acid sequences encoding any of the proteins described herein, vectors including any of the nucleic acids described herein, and mammalian cells including any of the nucleic acids described herein or any of the vectors described herein.

Provided herein are methods of producing a protein that includes: (a) culturing a mammalian cell (e.g., any of the mammalian cells described herein) in a liquid culture medium under conditions sufficient to produce the protein; and (b) recovering the protein from the mammalian cell or the liquid culture medium. In some embodiments of any of the methods described herein, the method further includes: (c) isolating the protein recovered in step (b). In some embodiments of any of the methods described herein, the method further includes: (d) formulating the protein isolated in step (c) into a pharmaceutical composition.

Also provided herein are pharmaceutical compositions produced by any of the methods described herein.

Also provided herein are pharmaceutical compositions including a therapeutically effective amount of any of the proteins described herein.

Also provided herein are kits that include any of the proteins described herein or any of the pharmaceutical compositions described herein.

Also provided herein are methods for inhibiting migration and/or invasion of an ADAM8 expressing cell in a subject that include administering to the subject a therapeutically effective amount of any of the proteins described herein or any of the pharmaceutical compositions described herein.

Provided herein are methods of decreasing the risk of developing a metastasis or developing an additional metastasis over a period of time in a subject identified as having an ADAM8-associated cancer that include administering to the subject a therapeutically effective amount of any of the proteins described herein or any of the pharmaceutical compositions described herein.

Provided herein are methods of inhibiting the growth of a solid tumor in a subject identified as having an ADAM8-associated cancer that include administering to the subject a therapeutically effective amount of any of the proteins described herein or any of the pharmaceutical compositions described herein.

Provided herein are methods of inhibiting the growth or proliferation of a hematological cancer in a subject identified as having an ADAM8-associated cancer that include administering to the subject a therapeutically effective amount of any of the proteins described herein or any of the pharmaceutical compositions described herein.

Also provided herein are methods of killing an ADAM8-associated cancer cell in a subject that include: administering to the subject a therapeutically effective amount of any of the proteins described herein or any of the pharmaceutical compositions described herein.

Provided herein are methods of treating an ADAM8-associated cancer in a subject that include: administering to a subject identified as having an ADAM8-associated cancer a therapeutically effective amount of any of the proteins described herein or any of the pharmaceutical compositions described herein.

Provided herein are methods of identifying a protein including an antigen-binding domain that binds specifically to human ADAM8 and has the ability to inhibit both the metalloprotease activity and disintegrin activity of human ADAM8 that include: (a) identifying a protein including an antigen-binding domain that binds to an epitope within human ADAM8 that includes at least one amino acid (e.g., at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68 amino acids) within the sequence of: DCGPPEDCRNRCCNSTTCQLAE-GAQCAHGTCCQECKVKPAGELCRPKKDMCDLEEF CDGRHPECPEDAF (SEQ ID NO: 1).

ADAM8

ADAM8 is a type I transmembrane protein that belongs to the ADAM (A Disintegrin And Metalloprotease) family. ADAM8 mediates cell adhesion, cell migration, and proteolysis of various substrates, including receptors and ligands for cytokines and immunoglobulins (Ig), cell adhesion molecules and extracellular matrix components.

Figure 1A:
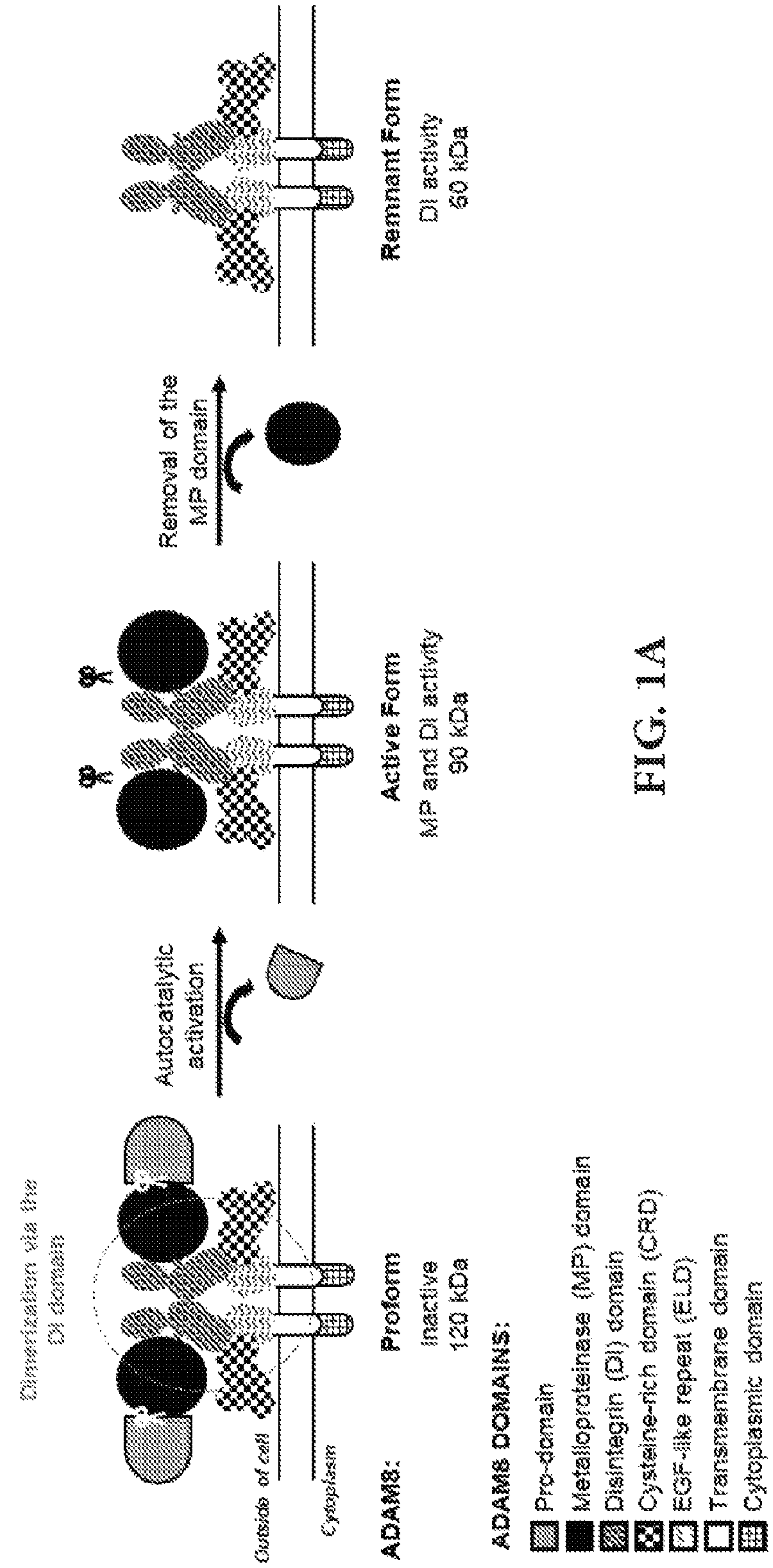
FIG. 1A is a schematic representation of human ADAM8, its various domains, forms and activities. Synthesized as an inactive "Proform", the transmembrane ADAM8 protein can dimerize or multimerize and autocatalytically clip off its Prodomain. This processing generates a 90 kDa "Active" membrane-anchored form with Metalloproteinase (MP) and Disintegrin (DI) activities. Active ADAM8 can further be clipped to a 60 kDa "Remnant" form, which lacks the MP domain and therefore has only DI activity. The molecular weight and activity status of each form is indicated.
Figure 1B:
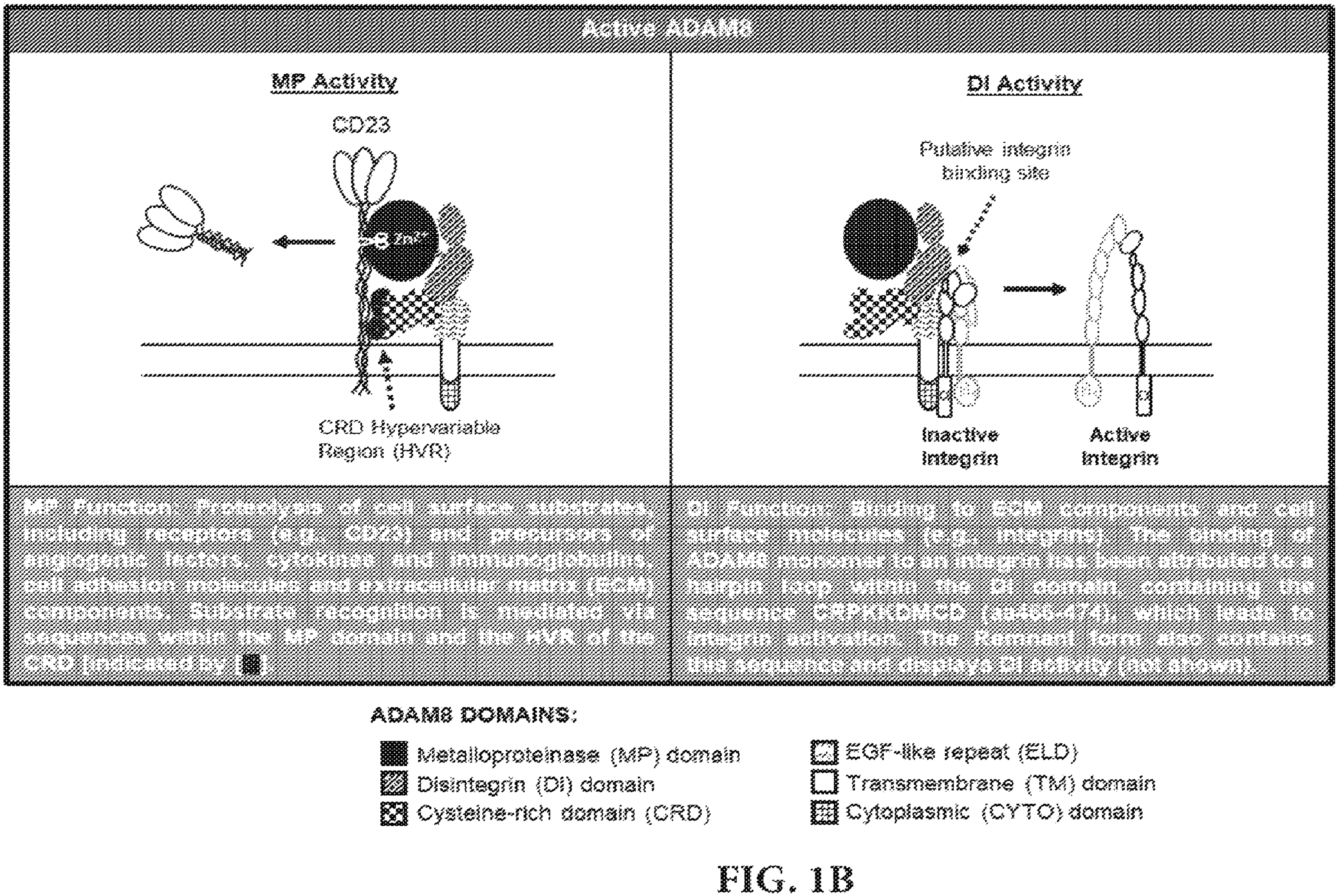
FIG. 1B is a schematic representation of the MP and DI functions of "Active ADAM8" using example substrates CD23 and Integrin. MP function: proteolysis of cell surface substrates including receptors (e.g., CD23) and precursors of angiogenic factors, cytokines and immunoglobulins, cell adhesion molecules and extracellular matrix (ECM) components. Substrate recognition is mediated via sequences within the MP domain and the hypervariable region (HVR) of the Cysteine-rich domain (CRD). DI function: binding to ECM components and cell surface molecules (e.g., integrins). The binding of ADAM8 monomer to an integrin has been attributed to a hairpin loop within the DI domain, containing the sequence CRPKKDMCD (aa466-474) (SEQ ID NO: 89), which leads to integrin activation. The Remnant form also contains this sequence and displays DI activity (not shown).

Human ADAM8 is synthesized as an inactive 120 kDa (824 amino acid) proform with a signal peptide (amino acids 1-16), which is clipped off upon entry into the rough endoplasmic reticulum on its way to the cell surface, and an inhibitory amino terminal prodomain (amino acids 17-191). Upon dimerization or multimerization, ADAM8 autocatalytically removes its prodomain, leading to the formation of a 90 kDa membrane-anchored "active" form, which has four functional extracellular domains: the metalloproteinase (MP, amino acids 192-406), disintegrin (DI, amino acids 407-496), cysteine-rich domain (CRD, amino acids 497-612), and EGF-like domain (ELD, amino acids 613-640) (FIG. 1A and FIG. 34). These are followed by a transmembrane region (TM, amino acids 641-678) and a cytoplasmic tail (CYTO, amino acids 679-824). Active ADAM8 has both MP and DI activities, but can be further processed by removal of the MP domain to a transmembrane 60 kDa Remnant form (amino acids 407-824). ADAM8 Remnant consists of the DI, CRD, and ELD domains, and the TM and CYTO (FIG. 1A), and retains DI activity (FIG. 1B).

The crystal structure of the human ADAM8 MP domain with batimastat, a broad-spectrum inhibitor of metalloproteinases, revealed an overall similarity to other members of the ADAM family, including a characteristic central five-stranded β-sheet, four long α-helices and one short N-terminal α-helix (Hall et al., *Acta Crystallogr Sect F Struc Biol Cryst Commun,* 68(Pt 6):616-621, 2012). The MP catalytic active site has a characteristic $Zn^{2+}$ ion binding consensus sequence: HEXXHXXGXXH (amino acids 334-344) (SEQ ID NO: 90). The three histidines (H, underlined) coordinate the binding of $Zn^{2+}$ while the glutamic acid (E, bold) functions as part of a catalytic base within the active site cleft; consistently, an E335Q mutation inhibits protease activity (Srinivasan et al., *J Biol Chem,* 289(48): 33676-22688, 2014). The MP domain of Active ADAM8 modulates cellular signals through its sheddase activity by cleaving proteins on the cancer cell surface (FIG. 1B), including receptors such as the CD23 receptor for IgE, pro-angiogenic cytokines (see below), growth factors, as well as components of the extracellular matrix. The 90 amino acid-DI domain in ADAM8 Active and Remnant forms mediates cell adhesion, notably by direct binding to and activation of integrins, including β1-integrin (as depicted for the Active form in FIG. 1B). The DI and CRD domains of ADAM8 are rich in cysteine residues, which play critical roles in maintaining a tight 3D structure. Specifically, highly conserved cysteine residues form disulfide linkages between the two halves of the DI domain and with the amino terminal portion of the CRD domain that result in the formation of a rigid C-shaped structure. This structure is further stabilized by binding of calcium ions to two distinct sites at either end of the DI domain ($Ca^{2+}$-binding site II and $Ca^{2+}$-binding site III, respectively). At the base of this C-shape structure is a loop of variable length and amino acid sequence within the CRD domain, which has been termed the hypervariable region (HVR). The HVR aligns the MP active site and has been implicated in binding/recognition of substrates and their correct processing by the MP domain (FIG. 1B). An additional calcium ion site ($Ca^{2+}$-binding site I), located within the MP domain and in proximity to the DI domain, is also essential for MP activity. Finally, while the ADAM8 DI domain lacks a typical RGD integrin binding sequence, it contains a consensus integrin binding (D/S)XCD sequence, e.g., DMCD (aa471-474), which in other ADAM proteins is located at the tip of a highly mobile hairpin loop (FIG. 1B). The present invention is based, at least in part, on the discovery that the binding of antibodies to the DI domain of ADAM8 inhibits the activities of both its DI and MP domains, which is believed to be necessary for a significant therapeutic effect in ADAM8-associated cancer patients.

An exemplary human wildtype ADAM8 is or includes the sequence of SEQ ID NO: 91, 93, 95, 97, or 99. Non-limiting examples of nucleotide sequences encoding a wildtype ADAM8 protein are or include SEQ ID NO: 92, 94, 96, 98, or 100.

```
Human Wildtype ADAM8 Protein Transcript Variant 1
                                                              (SEQ ID NO: 91)
MRGLGLWLLGAMMLPAIAPSRPWALMEQYEVVLPWRLPGPRVRRALPSHLGLHPERVSYVLGATGHNFTLHLRKN

RDLLGSGYTETYTAANGSEVTEQPRGQDHCFYQGHVEGYPDSAASLSTCAGLRGFFQVGSDLHLIEPLDEGGEGG

RHAVYQAEHLLQTAGTCGVSDDSLGSLLGPRTAAVFRPRPGDSLPSRETRYVELYVVVDNAEFQMLGSEAAVRHR

VLEVVNHVDKLYQKLNFRVVLVGLEIWNSQDRFHVSPDPSVTLENLLTWQARQRTRRHLHDNVQLITGVDFTGTT

VGFARVSAMCSHSSGAVNQDHSKNPVGVACTMAHEMGHNLGMDHDENVQGCRCQERFEAGRCIMAGSIGSSFPRM

FSDCSQAYLESFLERPQSVCLANAPDLSHLVGGPVCGNLFVERGEQCDCGPPEDCRNRCCNSTTCQLAEGAQCAH

GTCCQECKVKPAGELCRPKKDMCDLEEFCDGRHPECPEDAFQENGTPCSGGYCYNGACPTLAQQCQAFWGPGGQA

AEESCFSYDILPGCKASRYRADMCGVLQCKGGQQPLGRAICIVDVCHALTTEDGTAYEPVPEGTRCGPEKVCWKG

RCQDLHVYRSSNCSAQCHNHGVCNHKQECHCHAGWAPPHCAKLLTEVHAASGSLPVFVVVVLVLLAVVLVTLAGI

IVYRKARSRILSRNVAPKTTMGRSNPLFHQAASRVPAKGGAPAPSRGPQELVPTTHPGQPARHPASSVALKRPPP

APPVTVSSPPFPVPVYTRQAPKQVIKPTFAPPVPPVKPGAGAANPGPAEGAVGPKVALKPPIQRKQGAGAPTAP

(NCBI Accession No. NM_001109.5)

Human Wildtype ADAM8 Transcript Variant 1 cDNA
                                                              (SEQ ID NO: 92)
atgcgcggcctcgggctctggctgctgggcgcgatgatgctgcctgcgattgcccccagccggccctgggccctc

atggagcagtatgaggtcgtgttgccgtggcgtctgccaggcccccgagtccgccgagctctgccctcccacttg

ggcctgcacccagagagggtgagctacgtccttggggccacagggcacaacttcaccctccacctgcggaagaac

agggacctgctgggctccggctacacagagacctatacggctgccaatggctccgaggtgacggagcagcctcgc

gggcaggaccactgcttctaccagggccacgtagaggggtacccggactcagccgccagcctcagcacctgtgcc
```

-continued ggcctcaggggtttcttccaggtggggtcagacctgcacctgatcgagcccctggatgaaggtggcgagggcgga cggcacgccgtgtaccaggctgagcacctgctgcagacggccgggacctgcggggtcagcgacgacagcctgggc agcctcctgggaccccggacggcagccgtcttcaggcctcggcccggggactctctgccatcccgagagacccgc tacgtggagctgtatgtggtcgtggacaatgcagagttccagatgctggggagcgaagcagccgtgcgtcatcgg gtgctggaggtggtgaatcacgtggacaagctatatcagaaactcaacttccgtgtggtcctggtgggcctggag atttggaatagtcaggacaggttccacgtcagccccgaccccagtgtcacactggagaacctcctgacctggcag gcacggcaacggacacggcggcacctgcatgacaacgtacagctcatcacgggtgtcgacttcaccgggactacc gtggggtttgccagggtgtccgccatgtgctcccacagctcaggggctgtgaaccaggaccacagcaagaacccc gtgggcgtggcctgtaccatggcccatgagatgggccacaacctgggcatggaccatgatgagaacgtccagggc tgccgctgccaggaacgcttcgaggccggccgctgcatcatggcgggcagcattggctccagtttccccaggatg ttcagtgactgcagccaggcctacctggagagctttttggagcggccgcagtcggtgtgcctcgccaacgcccct gacctcagccacctggtgggcggccccgtgtgtgggaacctgtttgtggagcgtggggagcagtgcgactgcggc ccccccgaggactgccggaaccgctgctgcaactctaccacctgccagctggctgagggggcccagtgtgcgcac ggtacctgctgccaggagtgcaaggtgaagccggctggtgagctgtgccgtcccaagaaggacatgtgtgacctc gaggagttctgtgacggccggcaccctgagtgcccggaagacgccttccaggagaacggcacgccctgctccggg ggctactgctacaacggggcctgtcccacactggcccagcagtgccaggccttctgggggccaggtgggcaggct gccgaggagtcctgcttctcctatgacatcctaccaggctgcaaggccagccggtacagggctgacatgtgtggc gttctgcagtgcaagggtgggcagcagcccctggggcgtgccatctgcatcgtggatgtgtgccacgcgctcacc acagaggatggcactgcgtatgaaccagtgcccgagggcacccggtgtggaccagagaaggtttgctggaaagga cgttgccaggacttacacgtttacagatccagcaactgctctgcccagtgccacaaccatggggtgtgcaaccac aagcaggagtgccactgccacgcgggctgggccccgccccactgcgcgaagctgctgactgaggtgcacgcagcg tccgggagcctccccgtcttcgtggtggtggttctggtgctcctggcagttgtgctggtcaccctggcaggcatc atcgtctaccgcaaagcccggagccgcatcctgagcaggaacgtggctcccaagaccacaatggggcgctccaac cccctgttccaccaggctgccagccgcgtgccggccaagggcggggctccagccccatccaggggcccccaagag ctggtccccaccacccacccgggccagcccgcccgacacccggcctcctcggtggctctgaagaggccgcccccct gctcctccggtcactgtgtccagcccacccttcccagttcctgtctacacccggcaggcaccaaagcaggtcatc aagccaacgttcgcacccccagtgcccccagtcaaacccggggctggtgcggccaaccctggtccagctgagggt gctgttggcccaaaggttgccctgaagcccccccatccagaggaagcaaggagccggagctcccacagcaccctag Human Wildtype ADAM8 Protein Transcript Variant 2

(SEQ ID NO: 93)

MRGLGLWLLGAMMLPAIAPSRPWALMEQYEVVLPWRLPGPRVRRALPSHLGLHPERVSYVLGATGHNFTLHLRKN

RDLLGSGYTETYTAANGSEVTEQPRGQDHCFYQGHVEGYPDSAASLSTCAGLRGFFQVGSDLHLIEPLDEGGEGG

RHAVYQAEHLLQTAGTCGVSDDSLGSLLGPRTAAVFRPRPGDSLPSRETRYVELYVVVDNAEFQMLGSEAAVRHR

VLEVVNHVDKLYQKLNFRVVLVGLEIWNSQDRFHVSPDPSVTLENLLTWQARQRTRRHLHDNVQLITGVDFTGTT

VGFARVSAMCSHSSGAVNQDHSKNPVGVACTMAHEMGHNLGMDHDENVQGCRCQERFEAGRCIMAGSIGSSFPRM

FSDCSQAYLESFLERPQSVCLANAPDLSHLVGGPVCGNLFVERGEQCDCGPPEDCRNRCCNSTTCQLAEGAQCAH

GTCCQECKVKPAGELCRPKKDMCDLEEFCDGRHPECPEDAFQENGTPCSGGYCYNGACPTLAQQCQAFWGPGGQA

AEESCFSYDILPGCKASRYRADMCGVLQCKGGQQPLGRAICIVDVCHALTTEDGTAYEPVPEGTRCGPEKVCWKG

-continued
RCQDLHVYRSSNCSAQCHNHGVCNHKQECHCHAGWAPPHCAKLLTEVHAGCQPRAGQGRGSSPIQGPPRAGPHHP

PGPARPTPGLLGGSEEAAPCSSGHCVQPTLPSSCLHPAGTKAGHQANVRTPSAPSQTRGWCGQPWSS (NCBI Accession No. NM_001164489.1)

Human Wildtype ADAM8 Transcript Variant 2 cDNA (SEQ ID NO: 94)

atgcgcggcctcgggctctggctgctgggcgcgatgatgctgcctgcgattgcccccagccggccctgggccct catggagcagtatgaggtcgtgttgccgtggcgtctgccaggcccccgagtccgccgagctctgccctcccactt gggcctgcacccagagagggtgagctacgtccttggggccacagggcacaacttcaccctccacctgcggaagaa cagggacctgctgggctccggctacacagagacctatacggctgccaatggctccgaggtgacggagcagcctcg cgggcaggaccactgcttctaccagggccacgtagaggggtacccggactcagccgccagcctcagcacctgtgc cggcctcaggggtttcttccaggtggggtcagacctgcacctgatcgagcccctggatgaaggtggcgagggcgg acggcacgccgtgtaccaggctgagcacctgctgcagacggccgggacctgcggggtcagcgacgacagcctggg cagcctcctgggaccccggacggcagccgtcttcaggcctcggcccggggactctctgccatcccgagagacccg ctacgtggagctgtatgtggtcgtggacaatgcagagttccagatgctggggagcgaagcagccgtgcgtcatcg ggtgctggaggtggtgaatcacgtggacaagctatatcagaaactcaacttccgtgtggtcctggtgggcctgga gatttggaatagtcaggacaggttccacgtcagccccgaccccagtgtcacactggagaacctcctgacctggca ggcacggcaacggacacggcggcacctgcatgacaacgtacagctcatcacgggtgtcgacttcaccgggactac cgtggggtttgccagggtgtccgccatgtgctcccacagctcaggggctgtgaaccaggaccacagcaagaaccc cgtgggcgtggcctgtaccatggcccatgagatgggccacaacctgggcatggaccatgatgagaacgtccaggg ctgccgctgccaggaacgcttcgaggccggccgctgcatcatggcgggcagcattggctccagtttccccaggat gttcagtgactgcagccaggcctacctggagagctttttggagcggccgcagtcggtgtgcctcgccaacgcccc tgacctcagccacctggtgggcggccccgtgtgtgggaacctgtttgtggagcgtggggagcagtgcgactgcgg ccccccccgaggactgccggaaccgctgctgcaactctaccacctgccagctggctgaggggggcccagtgtgcgca cggtacctgctgccaggagtgcaaggtgaagccggctggtgagctgtgccgtcccaagaaggacatgtgtgacct cgaggagttctgtgacggccggcaccctgagtgcccggaagacgccttccaggagaacggcacgccctgctccgg gggctactgctacaacggggcctgtcccacactggcccagcagtgccaggccttctgggggccaggtgggcaggc tgccgaggagtcctgcttctcctatgacatcctaccaggctgcaaggccagccggtacagggctgacatgtgtgg cgttctgcagtgcaagggtgggcagcagcccctggggcgtgccatctgcatcgtggatgtgtgccacgcgctcac cacagaggatggcactgcgtatgaaccagtgcccgagggcacccggtgtggaccagagaaggtttgctggaaagg acgttgccaggacttacacgtttacagatccagcaactgctctgcccagtgccacaaccatggggtgtgcaacca caagcaggagtgccactgccacgcgggctgggccccgccccactgcgcgaagctgctgactgaggtgcacgcagg ctgccagccgcgtgccggccaagggcggggctccagccccatccaggggcccccaagagctggtccccaccaccc acccgggccagcccgcccgacacccggcctcctcggtggctctgaagaggccgcccccctgctcctccggtcactg tgtccagcccacccttcccagttcctgtctacacccggcaggcaccaaagcaggtcatcaagccaacgttcgcac ccccagtgcccccagtcaaacccggggctggtgcggccaaccctggtccagctga Human Wildtype ADAM8 Protein Transcript Variant 3

(SEQ ID NO: 95)

MRGLGLWLLGAMMLPGPAPREGELRPWGHRAQLHPPPAEEQGPAGLRLHRDLYGCQWLRGDGAASRAGPLLLPGP

RRGVPGLSRQPQHLCRPQVGSDLHLIEPLDEGGEGGRHAVYQAEHLLQTAGTCGVSDDSLGSLLGPRTAAVFRPR

PGDSLPSRETRYVELYVVVDNAEFQMLGSEAAVRHRVLEVVNHVDKLYQKLNFRVVLVGLEIWNSQDRFHVSPDP

SVTLENLLTWQARQRTRRHLHDNVQLITGVDFTGTTVGFARVSAMCSHSSGAVNQDHSKNPVGVACTMAHEMGHN

LGMDHDENVQGCRCQERFEAGRCIMAGSIGSSFPRMFSDCSQAYLESFLERPQSVCLANAPDLSHLVGGPVCGNL

FVERGEQCDCGPPEDCRNRCCNSTTCQLAEGAQCAHGTCCQECKVKPAGELCRPKKDMCDLEEFCDGRHPECPED

-continued

AFQENGTPCSGGYCYNGACPTLAQQCQAFWGPGGQAAEESCFSYDILPGCKASRYRADMCGVLQCKGGQQPLGRA

ICIVDVCHALTTEDGTAYEPVPEGTRCGPEKVCNHKQECHCHAGWAPPHCAKLLTEVHAASGSLPVFVVVVLVLL

AVVLVTLAGIIVYRKARSRILSRNVAPKTTMGRSNPLFHQAASRVPAKGGAPAPSRGPQELVPTTHPGQPARHPA

SSVALKRPPPAPPVTVSSPPFPVPVYTRQAPKQGAVGPKVALKPPIQRKQGAGAPTAP (NCBI Accession No. NM_001164490.1)

Human Wildtype ADAM8 Transcript Variant 3 cDNA (SEQ ID NO: 96)

atgcgcggcctcgggctctggctgctgggcgcgatgatgctgcctgggcctgcacccagagagggtgagctacg tccttggggccacagggcacaacttcaccctccacctgcggaagaacagggacctgctgggctccggctacacag agacctatacggctgccaatggctccgaggtgacggagcagcctcgcgggcaggaccactgcttctaccagggcc acgtagaggggtacccggactcagccgccagcctcagcacctgtgccggcctcaggtggggtcagacctgcacct gatcgagcccctggatgaaggtggcgagggcggacggcacgccgtgtaccaggctgagcacctgctgcagacggc cgggacctgcggggtcagcgacgacagcctgggcagcctcctgggaccccggacggcagccgtcttcaggcctcg gcccggggactctctgccatcccgagagacccgctacgtggagctgtatgtggtcgtggacaatgcagagttcca gatgctggggagcgaagcagccgtgcgtcatcgggtgctggaggtggtgaatcacgtggacaagctatatcagaa actcaacttccgtgtggtcctggtgggcctggagatttggaatagtcaggacaggttccacgtcagccccgaccc cagtgtcacactggagaacctcctgacctggcaggcacggcaacggacacggcggcacctgcatgacaacgtaca gctcatcacgggtgtcgacttcaccgggactaccgtggggtttgccagggtgtccgccatgtgctcccacagctc aggggctgtgaaccaggaccacagcaagaaccccgtgggcgtggcctgtaccatggcccatgagatgggccacaa cctgggcatggaccatgatgagaacgtccagggctgccgctgccaggaacgcttcgaggccggccgctgcatcat ggcgggcagcattggctccagtttccccaggatgttcagtgactgcagccaggcctacctggagagctttttgga gcggccgcagtcggtgtgcctcgccaacgcccctgacctcagccacctggtgggcggccccgtgtgtgggaacct gtttgtggagcgtggggagcagtgcgactgcggcccccccgaggactgccggaaccgctgctgcaactctaccac ctgccagctggctgagggggcccagtgtgcgcacggtacctgctgccaggagtgcaaggtgaagccggctggtga gctgtgccgtcccaagaaggacatgtgtgacctcgaggagttctgtgacggccggcaccctgagtgcccggaaga cgccttccaggagaacggcacgccctgctccgggggctactgctacaacggggcctgtcccacactggcccagca gtgccaggccttctgggggccaggtgggcaggctgccgaggagtcctgcttctcctatgacatcctaccaggctg caaggccagccggtacagggctgacatgtgtggcgttctgcagtgcaagggtgggcagcagcccctggggcgtgc catctgcatcgtggatgtgtgccacgcgctcaccacagaggatggcactgcgtatgaaccagtgcccgagggcac ccggtgtggaccagagaaggtgtgcaaccacaagcaggagtgccactgccacgcgggctgggccccgccccactg cgcgaagctgctgactgaggtgcacgcagcgtccgggagcctccccgtcttcgtggtggtggttctggtgctcct ggcagttgtgctggtcaccctggcaggcatcatcgtctaccgcaaagcccggagccgcatcctgagcaggaacgt ggctcccaagaccacaatggggcgctccaacccccctgttccaccaggctgccagccgcgtgccggccaagggcgg ggctccagccccatccaggggcccccaagagctggtccccaccacccacccgggccagcccgcccgacacccggc ctcctcggtggctctgaagaggccgcccccctgctcctccggtcactgtgtccagcccacccttcccagttcctgt ctacacccggcaggcaccaaagcagggtgctgttggcccaaaggttgccctgaagcccccccatccagaggaagca aggagccggagctcccacagcaccctag Mouse Wildtype ADAM8 Protein Transcript Variant 1

(SEQ ID NO: 97)

MLGLWLLSVLWTPAVAPGPPLPHVKQYEVVWPRRLAASRSRRALPSHWGQYPESLSYALGTSGHVFTLHLRKNRD

LLGSSYTETYSAANGSEVTEQLQEQDHCLYQGHVEGYEGSAASISTCAGLRGFFRVGSTVHLIEPLDADEEGQHA

MYQAKHLQQKAGTCGVKDTNLNDLGPRALEIYRAQPRNWLIPRETRYVELYVVADSQEFQKLGSREAVRQRVLEV

-continued

VNHVDKLYQELSFRVVLVGLEIWNKDKFYISRYANVTLENFLSWREQNLQGQHPHDNVQLITGVDFIGSTVGLAK

VSALCSRHSGAVNQDHSKNSIGVASTMAHELGHNLGMSHDEDIPGCYCPEPREGGGCIMTESIGSKFPRIFSRCS

KIDLESFVTKPQTGCLTNVPDVNRFVGGPVCGNLFVEHGEQCDCGTPQDCQNPCCNATTCQLVKGAECASGTCCH

ECKVKPAGEVCRLSKDKCDLEEFCDGRKPTCPEDAFQQNGTPCPGGYCFDGSCPTLAQQCRDLWGPGARVAADSC

YTFSIPPGCNGRMYSGRINRCGALYCEGGQKPLERSFCTFSSNHGVCHALGTGSNIDTFELVLQGTKCEEGKVCM

DGSCQDLRVYRSENCSAKCNNHGVCNHKRECHCHKGWAPPNCVQRLADVSDEQAASTSLPVSVVVVLVILVAAMV

IVAGIVIYRKAPRQIQRRSVAPKPISGLSNPLFYTRDSSLPAKNRPPDPSETVSTNQPPRPIVKPKRPPPAPPGA

VSSSPLPVPVYAPKIPNQFRPDPPTKPLPELKPKQVKPTFAPPTPPVKPGTGGTVPGATQGAGEPKVALKVPIQK

R (NCBI Accession No. NM_007403.3)

Mouse Wildtype ADAM8 Transcript Variant 1 cDNA (SEQ ID NO: 98)

atgcttggcctctggctgctcagcgtcttatggacaccagcagtagcccctggacctcctttgccccatgtgaaa cagtatgaagtggtttggcctcggcgcctagctgcatcccgctcccgcagagccctgccctcccactggggccag tacccagagagtctgagctatgctcttgggaccagcgggcacgttttcaccctgcaccttcgaaagaacagggac ctgctgggctcaagctacacagagacctactcagctgccaatggctctgaggtgacagagcaactgcaggagcag gaccattgcctctaccaaggccatgtggaagggtacgagggctcagctgccagtattagcacctgtgctggcctc aggggctttttccgagttgggtccactgtccacttgattgagcctctggatgctgatgaagaggggcaacatgcg atgtatcaggcaaagcatctgcaacagaaggctgggacctgtggggtcaaagataccaacctgaatgacctaggg cctcgggcattagaaatatacagggctcagccacggaactggctgatacccagagaaacccgctatgtggagttg tatgtggttgcagacagccaagagttccagaagttggggagcagagaggccgtgcgccagcgagtgctggaggtt gtaaaccacgtggacaagctttatcaggaactcagttttcgagttgtcctggtgggcctggagatctggaacaag gacaaattctacatcagccgctatgccaacgtgacactggagaacttcttgtcctggagggaacagaacttgcaa gggcagcacccacatgacaacgtgcaacttatcacgggggttgatttcattgggagcactgttggactggctaag gtgtctgccctgtgttcccgtcactccggagctgtgaatcaggaccactccaagaactccattggtgtagcctcc accatggcccatgagctgggccacaacctgggcatgagccatgatgaggacattccaggatgctactgtcctgaa ccacgggagggtggtggctgcatcatgaccgaaagcatcggctccaagttccccaggatattcagcaggtgtagc aagattgacctagagtcattcgtgacaaaaccccagacaggctgcctgaccaatgttccagatgtcaaccggttc gtgggtggccctgtgtgtggaaacctgtttgtggagcatggagagcagtgtgactgtggcacacctcaggactgt caaaacccctgctgcaatgccaccacttgccagctggtcaagggggcagagtgtgccagtggtacctgttgtcat gaatgcaaggtgaagccagctggagaggtgtgtcgtctcagtaaggacaaatgtgacctggaggagttctgtgat ggccggaagccaacatgtcccgaagatgccttccaacagaatggcactccctgcccagggggctactgctttgat gggagctgtcccaccctggcacagcagtgccgggatctgtgggggccaggtgctcgggtagcagccgactcctgc tatacctttagcatccctccgggctgcaatgggaggatgtactctggcaggatcaaccggtgtggagcgctgtac tgtgagggaggccagaagccccttgaacgctccttctgcactttctcctccaaccatggagtctgccatgctctt ggcacaggcagcaacattgacacctttgagctggtattgcagggcaccaagtgcgaggagggaaaggtttgcatg gatggaagctgccaggacctccgtgtatacagatctgaaaactgctctgctaaatgcaacaaccatggggtatgc aaccacaagagggagtgccactgtcacaagggctgggcaccacccaactgtgtacagcggctggcagatgtatca gatgaacaagcagcgtctacgagcctcccagtcagtgtggttgtggtcttggtgatcctggtggctgcgatggtc atcgtggcaggcatcgtcatctaccgaaaggctccgagacaaatccagaggaggagtgtggcacccaagcctatc tcggggctctccaacccccctattctacacaaggggacagcagcctgccagctaagaacaggcctccagacccttct gagacagtttctaccaaccagcccccaagacccatagtgaaaccaaagaggcctcccccctgcacctccaggtgct gtgtccagttcaccactcccagttcctgtttatgccccaaagataccaaatcagtttagacctgatcctcccacc -continued aagcccctcccagagctgaaacccaagcaggtcaagccaacctttgcacccccgacaccaccagtcaagcccggg actggagggacggtgcctggagcaactcagggagctggtgagccaaaggttgctctgaaggtccccatccagaag aggtga Mouse Wildtype ADAM8 Protein Transcript Variant 2

(SEQ ID NO: 99)

MLGLWLLSVLWTPVAPGPPLPHVKQYEVVWPRRLAASRSRRALPSHWGQYPESLSYALGTSGHVFTLHLRKNRDL

LGSSYTETYSAANGSEVTEQLQEQDHCLYQGHVEGYEGSAASISTCAGLRGFFRVGSTVHLIEPLDADEEGQHAM

YQAKHLQQKAGTCGVKDTNLNDLGPRALEIYRAQPRNWLIPRETRYVELYVVADSQEFQKLGSREAVRQRVLEVV

NHVDKLYQELSFRVVLVGLEIWNKDKFYISRYANVTLENFLSWREQNLQGQHPHDNVQLITGVDFIGSTVGLAKV

SALCSRHSGAVNQDHSKNSIGVASTMAHELGHNLGMSHDEDIPGCYCPEPREGGGCIMTESIGSKFPRIFSRCSK

IDLESFVTKPQTGCLTNVPDVNRFVGGPVCGNLFVEHGEQCDCGTPQDCQNPCCNATTCQLVKGAECASGTCCHE

CKVKPAGEVCRLSKDKCDLEEFCDGRKPTCPEDAFQQNGTPCPGGYCFDGSCPTLAQQCRDLWGPGARVAADSCY

TFSIPPGCNGRMYSGRINRCGALYCEGGQKPLERSFCTFSSNHGVCHALGTGSNIDTFELVLQGTKCEEGKVCMD

GSCQDLRVYRSENCSAKCNNHGVCNHKRECHCHKGWAPPNCVQRLADVSDEQAASTSLPVSVVVVLVILVAAMVI

VAGIVIYRKAPRQIQRRSVAPKPISGLSNPLFYTRDSSLPAKNRPPDPSETVSTNQPPRPIVKPKRPPPAPPGAV

SSSPLPVPVYAPKIPNQFRPDPPTKPLPELKPKQVKPTFAPPTPPVKPGTGGTVPGATQGAGEPKVALKVPIQKR (NCBI Accession No. NM_001291066.2)

Mouse Wildtype ADAM8 Transcript Variant 2 cDNA (SEQ ID NO: 100)

atgcttggcctctggctgctcagcgtcttatggacaccagtagcccctggacctcctttgccccatgtgaaacag tatgaagtggtttggcctcggcgcctagctgcatcccgctcccgcagagccctgccctcccactggggccagtac ccagagagtctgagctatgctcttgggaccagcgggcacgttttcaccctgcaccttcgaaagaacagggacctg ctgggctcaagctacacagagacctactcagctgccaatggctctgaggtgacagagcaactgcaggagcaggac cattgcctctaccaaggccatgtggaagggtacgagggctcagctgccagtattagcacctgtgctggcctcagg ggctttttccgagttgggtccactgtccacttgattgagcctctggatgctgatgaagaggggcaacatgcgatg tatcaggcaaagcatctgcaacagaaggctgggacctgtggggtcaaagataccaacctgaatgacctagggcct cgggcattagaaatatacagggctcagccacggaactggctgatacccagagaaacccgctatgtggagttgtat gtggttgcagacagccaagagttccagaagttggggagcagagaggccgtgcgccagcgagtgctggaggttgta aaccacgtggacaagctttatcaggaactcagttttcgagttgtcctggtgggcctggagatctggaacaaggac aaattctacatcagccgctatgccaacgtgacactggagaacttcttgtcctggagggaacagaacttgcaaggg cagcacccacatgacaacgtgcaacttatcacgggggttgatttcattgggagcactgttggactggctaaggtg tctgccctgtgttcccgtcactccggagctgtgaatcaggaccactccaagaactccattggtgtagcctccacc atggcccatgagctgggccacaacctgggcatgagccatgatgaggacattccaggatgctactgtcctgaacca cgggagggtggtggctgcatcatgaccgaaagcatcggctccaagttccccaggatattcagcaggtgtagcaag attgacctagagtcattcgtgacaaaaccccagacaggctgcctgaccaatgttccagatgtcaaccggttcgtg ggtggccctgtgtgtggaaacctgtttgtggagcatggagagcagtgtgactgtggcacacctcaggactgtcaa aacccctgctgcaatgccaccacttgccagctggtcaagggggcagagtgtgccagtggtacctgttgtcatgaa tgcaaggtgaagccagctggagaggtgtgtcgtctcagtaaggacaaatgtgacctggaggagttctgtgatggc cggaagccaacatgtcccgaagatgccttccaacagaatggcactccctgcccagggggctactgctttgatggg agctgtcccaccctggcacagcagtgccgggatctgtgggggccaggtgctcgggtagcagccgactcctgctat acctttagcatccctccgggctgcaatgggaggatgtactctggcaggatcaaccggtgtggagcgctgtactgt gagggaggccagaagccccttgaacgctccttctgcactttctcctccaaccatggagtctgccatgctcttggc -continued

```
acaggcagcaacattgacacctttgagctggtattgcagggcaccaagtgcgaggagggaaaggtttgcatggat

ggaagctgccaggacctccgtgtatacagatctgaaaactgctctgctaaatgcaacaaccatggggtatgcaac

cacaagagggagtgccactgtcacaagggctgggcaccacccaactgtgtacagcggctggcagatgtatcagat

gaacaagcagcgtctacgagcctcccagtcagtgtggttgtggtcttggtgatcctggtggctgcgatggtcatc

gtggcaggcatcgtcatctaccgaaaggctccgagacaaatccagaggaggagtgtggcacccaagcctatctcg

gggctctccaacccccctattctacacaagggacagcagcctgccagctaagaacaggcctccagacccttctgag

acagtttctaccaaccagcccccaagacccatagtgaaaccaaagaggcctcccccctgcacctccaggtgctgtg

tccagttcaccactcccagttcctgtttatgccccaaagataccaaatcagtttagacctgatcctcccaccaag

cccctcccagagctgaaacccaagcaggtcaagccaacctttgcacccccgacaccaccagtcaagcccgggact

ggagggacggtgcctggagcaactcagggagctggtgagccaaaggttgctctgaaggtccccatccagaagagg

tga
```

ADAM8 in Breast Cancer Patients

Breast cancer is the most frequently diagnosed cancer and the leading cause of cancer-related deaths worldwide among women (World Health Organization) with 600,000 breast cancer deaths yearly, mainly from metastatic disease. Large-scale transcriptional analyses identified ADAM8 as one of the most overexpressed genes in breast cancer compared to normal breast tissue (Romagnoli et al., *EMBO Mol Med,* 6(2): 278-294, 2014). High ADAM8 levels were an independent predictor of both poor disease-free and overall survival. Breast cancers are heterogeneous with different tumor drivers identified in distinct patient subpopulations. In many cases, breast tumors are driven by aberrant receptor signaling, e.g., the estrogen receptor a (ER), or the epidermal growth factor receptor 2 (HER2).

In the past two decades, tremendous advances have been made with the introduction of targeted therapies against these receptors: hormone modulators (e.g. tamoxifen) for ER-positive tumors, and the humanized anti-HER2 antibody (trastuzumab) for HER2-positive tumors. However, approximately 15% of breast tumors, termed triple-negative breast cancers (TNBCs), are devoid of elevated levels of ER, HER2, or progesterone receptor expression, and have thus not benefitted from these recent treatment advances. ADAM8 mRNA levels were significantly higher in Grade 3 vs. Grade 1 and 2 breast cancers and especially in basal-like tumors, known to be mostly TNBCs. In immunohistochemistry (IHC) studies, 34.0% of primary patient TNBC tumor samples, and 48.2% of all breast cancer-derived metastases displayed high ADAM8 levels whereas normal mammary tissue was negative (n=50) (Romagnoli et al., *EMBO Mol Med,* 6(2):278-294, 2014). TNBCs are highly aggressive and occur preferentially in women who are younger or of African-American descent.

Due to the lack of elevated expression of hormone and HER2 receptors, treatment options for TNBCs are restricted to chemotherapy and radiation, which are insufficient to block tumor progression or metastatic dissemination, and have severe side effects. Patients frequently recur with locoregional disease or distant metastasis. The main sites of metastasis include the bones, lymph nodes, brain, lungs, and liver, but skin, chest wall (including bone, cartilage, and soft tissue), contralateral breast, soft tissue, bone marrow, ovary, adrenal gland, and even pancreatic spread have been observed. Furthermore, IHC of samples from patients with a particularly aggressive TNBC subclass termed Triple-Negative Inflammatory Breast Cancer were ADAM8-positive. Specifically, 45.5% of primary and 50.0% of axillary lymph node metastases expressed high levels of ADAM8. In addition, elevated ADAM8 mRNA or protein levels were also detected in HER2+ breast cancers and in 13.5% of premalignant Ductal Carcinoma in Situ (DCIS) samples from patients who later progressed to malignant breast cancer (Romagnoli et al., *EMBO Mol Med,* 6(2): 278-294, 2014). Due to their enhanced ability to spread compared to other breast tumor types and the poor response rate to Standard of Care (SoC) treatments, TNBCs account for more than 25% of breast cancer deaths, despite having a lower incidence rate.

Mouse and Cell-Based Mechanistic Studies of ADAM8 Role in Breast Cancer

Stable ADAM8 knockdown (KD) in MDA-MB-231 TNBC cells resulted in profound tumor growth inhibition (TGI, percent reduction in mean tumor volume) in an orthotopic mammary fat pad (MFP) model (Romagnoli et al., *EMBO Mol Med,* 6(2): 278-294, 2014). Notably, female NOD/SCID mice injected with Control MDA-MB-231 TNBC cells [containing a control shRNA and thus retaining high levels of ADAM8] started to develop tumors within 2 weeks, which progressed rapidly to 1 $cm^3$ (the experimental endpoint). In contrast, tumors derived from ADAM8 KD MDA-MB-231 TNBC cells [stably expressing shADAM8 RNA and thus with substantially reduced ADAM8 expression] failed to grow beyond a palpable size (0.05 $cm^3$) even after more than 4 weeks. Tumors derived from ADAM8 KD MDA-MB-231 TNBC cells displayed reduced angiogenesis, shed fewer circulating tumor cells (CTCs) and CTC clusters (CTCCs) into the bloodstream, and displayed a substantial reduction in metastasis to the brain (Romagnoli et al., *EMBO Mol Med,* 6(2): 278-294, 2014; Lyons et al., *Biomed Opt Express,* 7(3): 1042-1050, 2016).

In a follow-up experiment, in which cells were injected directly into the mouse blood stream through the heart, ADAM8 KD TNBC cells were unable to colonize distant organs while mice with ADAM8-expressing TNBC cells formed large metastases in a variety of organs, including bones, brain, and lungs. Consistently, in TNBC cells in culture, a reduction in ADAM8 levels strongly diminished secretion of pro-angiogenic factors, in vitro angiogenesis, and migratory and invasive properties (Romagnoli et al., *EMBO Mol Med,* 6(2): 278-294, 2014). Furthermore, hypoxic areas in control MDA-MB-231 tumors were often associated with elevated ADAM8 staining, which was consistent with cell culture models where growth under hypoxic conditions (1% 02 for 24 h) led to increased ADAM8 levels (Romagnoli et al., *EMBO Mol Med,* 6(2): 278-294, 2014). Overall, studies conducted in cell-based and orthotopic mouse models revealed that ADAM8 promotes tumor growth and dissemination by stimulating: (i) angiogenesis via the cleavage and release of cell-bound precursor proteins into active angiogenic factors, such as VEGF-A, PDGF-AA, angiogenin, and placenta growth factors, through its MP domain activity, and (ii) tumor cell intra/extravasation and metastasis via activation of β1-integrin and enhancement of interactions between cancer cells and endothelial cells lining blood vessel walls, through its DI domain activity (Romagnoli et al., *EMBO Mol Med,* 6(2): 278-294, 2014) (FIG. 1B).

The proteins provided herein show significant specificity, e.g., the proteins provided herein strongly inhibit both the ADAM8 MP and DI activities, but fail to interact with closely related ADAM8, ADAM12, ADAM15 or ADAM33. The data herein also demonstrate that the proteins provided herein very effectively inhibit the MP domain of ADAM8 responsible for tumor growth, as well as, the DI domain of ADAM8, which is critical to stop tumor dissemination, the ultimate cause of patient mortality.

Proteins

Provided herein are proteins that inhibit both the metalloprotease activity and disintegrin activity of human ADAM8, wherein the protein includes an antigen-binding domain that: (i) binds specifically to human ADAM8; and (ii) binds to an epitope within human ADAM8 that includes at least one (e.g., at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, or at least 25, at least 26, at least 27, at least 28, at least 29, at least 30, at least 31, at least 32, at least, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68 amino acids) amino acid within the sequence of:

(SEQ ID NO: 1)
DCGPPEDCRNRCCNSTTCQLAEGAQCAHGTCCQECKVKPAGELCRPKKD

MCDLEEFCDGRHPECPEDAF.

In some embodiments of any of the proteins described herein, the protein binds to an epitope within human ADAM8 that includes about 1 amino acid to about 60 amino acids (e.g., about 1 amino acid to about 55 amino acids, about 1 amino acid to about 50 amino acids, about 1 amino acid to about 45 amino acids, about 1 amino acid to about 40 amino acids, about 1 amino acid to about 35 amino acids, about 1 amino acid to about 30 amino acids, about 1 amino acid to about 25 amino acids, about 1 amino acid to about 20 amino acids, about 1 amino acid to about 15 amino acids, about 1 amino acid to about 10 amino acids, about 1 amino acid to about 5 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 to about 25 amino acids, about 5 amino acids to about 20 amino acids, about 5 amino acids to about 15 amino acid, about 5 amino acids to about 10 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acid, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 60 amino acids, about 40 amino acids to about 55 amino acids, about 40 amino acids to about 50 amino acids, about 40 amino acids to about 45 amino acids, about 45 amino acids to about 60 amino acids, about 45 amino acids to about 55 amino acids, about 45 amino acids to about 50 amino acids, about 50 amino acids to about 60 amino acids, about 50 amino acids to about 55 amino acids, or about 55 amino acids to about 60 amino acids) within the sequence of:

(SEQ ID NO: 1)
DCGPPEDCRNRCCNSTTCQLAEGAQCAHGTCCQECKVKPAGELCRPKKD

MCDLEEFCDGRHPECPEDAF.

In some embodiments of any of the proteins described herein, the protein binds to human ADAM8 with a $K_D$ of about 0.1 nM to about 250 nM (e.g., about 0.1 nM to about 200 nM, about 0.1 nM to about 150 nM, about 0.1 nM to about 100 nM, about 0.1 nM to about 80 nM, about 0.1 nM to about 60 nM, about 0.1 nM to about 40 nM, about 0.1 nM to about 20 nM, about 0.1 nM to about 10 nM, about 0.1 nM to about 5 nM, about 0.1 nM to about 1 nM, about 1 nM to about 250 nM, about 1 nM to about 200 nM, about 1 nM to about 150 nM, about 1 nM to about 100 nM, about 1 nM to about 80 nM, about 1 nM to about 60 nM, about 1 nM to about 40 nM, about 1 nM to about 20 nM, about 1 nM to about 10 nM, about 1 nM to about 5 nM, about 5 nM to about 250 nM, about 5 nM to about 200 nM, about 5 nM to about 150 nM, about 5 nM to about 100 nM, about 5 nM to about 80 nM, about 5 nM to about 60 nM, about 5 nM to about 40 nM, about 5 nM to about 20 nM, about 5 nM to about 10 nM, about 10 nM to about 250 nM, about 10 nM to about 200 nM, about 10 nM to about 150 nM, about 10 nM to about 100 nM, about 10 nM to about 80 nM, about 10 nM to about 60 nM, about 10 nM to about 40 nM, about 10 nM to about 20 nM, about 20 nM to about 250 nM, about 20 nM to about 200 nM, about 20 nM to about 150 nM, about 20 nM to about 100 nM, about 20 nM to about 80 nM, about 20 nM to about 60 nM, about 20 nM to about 40 nM, about 40 nM to about 250 nM, about 40 nM to about 200 nM, about 40 nM to about 150 nM, about 40 nM to about 100 nM, about 40 nM to about 80 nM, about 40 nM to about 60 nM, about 60 nM to about 250 nM, about 60 nM to about 200 nM, about 60 nM to about 150 nM, about 60 nM to about 100 nM, about 60 nM to about 80 nM, about 80 nM to about 250 nM, about 80 nM to about 200 nM, about 80 nM to about 150 nM, about 80 nM to about 100 nM, about 100 nM to about 250 nM, about 100 nM to about 200 nM, about 100 nM to about 150 nM, about 150 nM to about 250 nM, about 150 nM to about 200 nM, or about 200 nM to about 250 nM).

In some embodiments of any of the proteins described herein, the protein binds to human ADAM8 with a $K_D$ of less than $1\times10^{-7}$M, less than $1\times10^{-8}$ M, less than $1\times10^{-9}$M, less than $1\times10^{-10}$ M, less than $1\times10^{-11}$ M, less than $1\times10^{-12}$ M, or less than $1\times10^{-13}$M.

In some embodiments of any of the proteins described herein, the protein binds to human ADAM8 with a $K_D$ of about $1\times10^{-3}$ M to about $1\times10^{-13}$ M, about $1\times10^{-3}$ M to about $1\times10^{-12}$ M, about $1\times10^{-3}$M to about $1\times10^{-11}$M, about $1\times10^{-3}$M to about $1\times10^{-10}$ M, about $1\times10^{-3}$ M to about $1\times10^{-9}$M, about $1\times10^{-3}$M to about $1\times10^{-8}$ M, about $1\times10^{-3}$ M to about $1\times10^{-7}$M, about $1\times10^{-3}$ M to about $1\times10^{-6}$ M, about $1\times10^{-3}$ M to about $1\times10^{-5}$M, about $1\times10^{-4}$M to about $1\times10^{-13}$M, about $1\times10^{-4}$ M to about $1\times10^{-12}$ M, about $1\times10^{-4}$ M to about $1\times10^{-11}$M, about $1\times10^{-4}$ M to about $1\times10^{-10}$ M, about $1\times10^{-4}$M to about $1\times10^{-9}$M, about $1\times10^{-4}$M to about $1\times10^{-8}$ M, about $1\times10^{-4}$ M to about $1\times10^{-7}$M, about $1\times10^{-4}$M to about $1\times10^{-6}$ M, about $1\times10^{-4}$ M to about $1\times10^{-5}$ M, about $1\times10^{-5}$ M to about $1\times10^{-13}$M, about $1\times10^{-5}$M to about $1\times10^{-12}$M, about $1\times10^{-5}$M to about $1\times10^{-11}$ M, about $1\times10^{-5}$ M to about $1\times10^{-10}$ M, about $1\times10^{-5}$M to about $1\times10^{-9}$ M, about $1\times10^{-5}$ M to about $1\times10^{-8}$ M, about $1\times10^{-5}$ M to about $1\times10^{-7}$ M, about $1\times10^{-5}$ M to about $1\times10^{-6}$M, about $1\times10^{-6}$M to about $1\times10^{-8}$ M, about $1\times10^{-6}$ M to about $1\times10^{-13}$M, about $1\times10^{-6}$ M to about $1\times10^{-12}$ M, about $1\times10^{-6}$ M to about $1\times10^{-11}$M, about $1\times10^{-6}$ M to about $1\times10^{-10}$ M, about $1\times10^{-6}$ M to about $1\times10^{-9}$M, about $1\times10^{-6}$ M to about $1\times10^{-8}$ M, about $1\times10^{-6}$ M to about $1\times10^{-7}$ M, about $1\times10^{-7}$ M to about $1\times10^{-13}$ M, about $1\times10^{-7}$ M to about $1\times10^{-12}$ M, about $1\times10^{-7}$M to about $1\times10^{-11}$M, about $1\times10^{-7}$M to about $1\times10^{-10}$ M, about $1\times10^{-7}$ M to about $1\times10^{-9}$ M, about $1\times10^{-7}$ M to about $1\times10^{-8}$ M, about $1\times10^{-8}$ M to about $1\times10^{-13}$M, about $1\times10^{-8}$ M to about $1\times10^{-12}$M, about $1\times10^{-8}$ M to about $1\times10^{-11}$M, about $1\times10^{-8}$ M to about $1\times10^{-10}$ M, about $1\times10^{-8}$ M to about $1\times10^{-9}$M, about $1\times10^{-9}$ M to about $1\times10^{-13}$M, about $1\times10^{-9}$M to about $1\times10^{-12}$ M, about $1\times10^{-9}$M to about $1\times10^{-11}$M, about $1\times10^{-9}$M to about $1\times10^{-10}$ M, about $1\times10^{-10}$ M to about $1\times10^{-13}$ M, about $1\times10^{-10}$ M to about $1\times10^{-12}$ M, about $1\times10^{-10}$ M to about $1\times10^{-11}$M, about $1\times10^{-11}$M to about $1\times10^{-13}$ M, about $1\times10^{-11}$M to about $1\times10^{-12}$ M, or about $1\times10^{-12}$M to about $1\times10^{-13}$M (inclusive).

In some embodiments of any of the proteins described herein, the protein includes a single polypeptide. In some embodiments of any of the proteins described herein, the antigen-binding domain is a VHH domain, a VNAR domain, or a scFv. In some embodiments of any of the proteins described herein, the protein is selected from the group consisting of: a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, and a tandem-scFv.

In some embodiments of any of the proteins described herein, the protein includes two or more polypeptides. In some embodiments of any of the proteins described herein, the protein is selected from the group consisting of: an antibody, a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG (H)-V, V(H)—IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, an ImmTAC, an IgG-IgG conjugate, a Cov-X-Body, and a scFv1-PEG-$scFv_2$.

In some embodiments of any of the proteins described herein, the protein is an antibody that is an IgG antibody. In some embodiments of any of the proteins described herein, the IgG antibody is an IgG1, IgG2, IgG3, or IgG4 antibody. In some embodiments of any of the proteins described herein, the antibody is a monospecific antibody. In some embodiments of any of the proteins described herein, the antibody is a multi-specific (e.g., bispecific antibody, e.g., a knobs-in-hole bispecific antibody). In some embodiments of any of the proteins described herein, the antibody is a bispecific antibody.

In some embodiments of any of the proteins described herein, the antigen-binding domain includes heavy chain variable domain CDRs of GFSFPDYY (SEQ ID NO: 2), IRDSANGYTT (SEQ ID NO: 3), and ARYSRYYGMDY (SEQ ID NO: 4), and light chain variable domain CDRs of QTVNYD (SEQ ID NO: 5), FAS (SEQ ID NO: 6), and QQDYSAPWT (SEQ ID NO: 7). In some embodiments of any of the proteins described herein, the antigen-binding domain includes a light chain variable domain sequence of: SIVMTQTPKILLVSAGDRVTITCKASQTVNY-DVAWYQQKPGQSPKPVIYFASNRYTG VPDRFTGSGFGTDFTFTISTVQAED-LAVYFCQQDYSAPWTFGGGTKLEIK (SEQ ID NO: 8). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 8. In some embodiments of any of the proteins described herein, the antigen-binding domain includes a light chain variable domain sequence of SEQ ID NO: 8, except that it includes about 1 to about 6 amino acid substitutions (e.g., 1, 2, 3, 4, 5, or 6 amino acid substitutions) in SEQ ID NO: 8. In some embodiments of any of the proteins described herein, the light chain variable domain sequence is encoded by a nucleic acid including a sequence that is at least 95% (e.g., at least 96%, at least 97%, at least 98%, at least 99%, or 100%) identical to SEQ ID NO: 9. In some embodiments of any of the proteins described herein, the antigen-binding domain includes a heavy chain variable domain sequence of: EVKLVESGGGLVQPGGSLSLS-CAASGFSFPDYYMSWVRQPPGKALEWLGFIRDSAN GYTTEYIASVKGRFTFSRDNSQSILYLQMNALRAED-SATYYCARYSRYYGMDYWGQ GTSVTVSS (SEQ ID NO: 10). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 10. In some embodiments of any of the proteins described herein, the antigen-binding domain includes a heavy chain variable domain sequence of SEQ ID NO: 10, except that it includes about 1 to about 6 amino acid substitutions (e.g., 1, 2, 3, 4, 5, or 6 amino acid substitutions) in SEQ ID NO: 10. In some embodiments of any of the proteins described herein, the heavy chain variable domain sequence is encoded by a nucleic acid including a sequence that is at least 95% (e.g., at least 96%, at least 97%, at least 98%, at least 99%, or 100%) identical to SEQ ID NO: 11.

In some embodiments of any of the proteins described herein, the antigen-binding domain includes heavy chain variable domain CDRs of GYTFTDYY (SEQ ID NO: 12), ISPNIGGA (SEQ ID NO: 13), and TRGGSSYPYFYAMDY (SEQ ID NO: 14), and light chain variable domain CDRs of QSLLYSSNQKKY (SEQ ID NO: 15), WAS (SEQ ID NO: 16), and QQFYSYPYT (SEQ ID NO: 17). In some embodiments of any of the proteins described herein, the antigen-binding domain includes a light chain variable domain sequence of: DIVMSQSPSSLAVSVGEKVTMSCK-SSQSLLYSSNQKKYLAWYQQKPGQSPKLLIYW ASTRESGVPDRFTGSGSGTD FTLTISSVKAED-LAVYYCQQFYSYPYTFGGGTKLEINR (SEQ ID NO: 18). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 18. In some embodiments of any of the proteins described herein, the antigen-binding domain includes a light chain variable domain sequence of SEQ ID NO: 18, except that it includes about 1 to about 6 amino acid substitutions (e.g., 1, 2, 3, 4, 5, or 6 amino acid substitutions) in SEQ ID NO: 18. In some embodiments of any of the proteins described herein, the light chain variable domain sequence is encoded by a nucleic acid including a sequence that is at least 95% (e.g., at least 96%, at least 97%, at least 98%, at least 99%, or 100%) identical to SEQ ID NO: 19. In some embodiments of any of the proteins described herein, the antigen-binding domain includes a heavy chain variable domain sequence of: EVQLQQSG-PEMVKPGTSVKISCKASGYTFTDYY-INWVKQSHGKSLEWIGDISPNIGG ATYNPKFKGKAILTVDKSARTAYMELRSLTSED-SAVYCCTRGGS SYPYFYAMDYWG QGTSVTVSS (SEQ ID NO: 20). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 20. In some embodiments of any of the proteins described herein, the antigen-binding domain includes a heavy chain variable domain sequence of SEQ ID NO: 20, except that it includes about 1 to about 6 amino acid substitutions (e.g., 1, 2, 3, 4, 5, or 6 amino acid substitutions) in SEQ ID NO: 20. In some embodiments of any of the proteins described herein, the heavy chain variable domain sequence is encoded by a nucleic acid including a sequence that is at least 95% (e.g., at least 96%, at least 97%, at least 98%, at least 99%, or 100%) identical to SEQ ID NO: 21.

In some embodiments of any of the proteins described herein, the antigen-binding domain includes heavy chain variable domain CDRs of GFTFSDAW (SEQ ID NO: 22), IRGKVNNLAT (SEQ ID NO: 23), and LGRYDATYAMDY (SEQ ID NO: 24), and light chain variable domain CDRs of QSLVHSDGNTY (SEQ ID NO: 25), KLS (SEQ ID NO: 26), and SQSTHVPWT (SEQ ID NO: 27). In some embodiments of any of the proteins described herein, the antigen-binding domain includes a light chain variable domain sequence of: DVVMTQTPLSLPVSLGDQASIS-CRSSQSLVHSDGNTYLHWYLQKPGQSPKLLIYKLS NRFSGVPDRFSGSGSGTDF TLKISRVEAE-DLGVYFCSQSTHVPWTFGGGTKLEIK (SEQ ID NO: 28). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 28. In some embodiments of any of the proteins described herein, the antigen-binding domain includes a light chain variable domain sequence of SEQ ID NO: 28, except that it includes about 1 to about 6 amino acid substitutions (e.g., 1, 2, 3, 4, 5, or 6 amino acid substitutions) in SEQ ID NO: 28. In some embodiments of any of the proteins described herein, the light chain variable domain sequence is encoded by a nucleic acid including a sequence that is at least 95% (e.g., at least 96%, at least 97%, at least 98%, at least 99%, or 100%) identical to SEQ ID NO: 29. In some embodiments of any of the proteins described herein, the antigen-binding domain includes a heavy chain variable domain sequence of: EVKLEESGG-GLVQPGGSMKLSCAASGFTFSDAWMDWVRQS-PEKGLEWVAEIRGKV NNLATYYVESVKGRFTISRDD-SKSSVYLQMNSLRAEDTGIYYCLGRYDATYAMDY WGQGTSVTVSS (SEQ ID NO: 30). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 30. In some embodiments of any of the proteins described herein, the antigen-binding domain includes a heavy chain variable domain sequence of SEQ ID NO: 30, except that it includes about 1 to about 6 amino acid substitutions (e.g., 1, 2, 3, 4, 5, or 6 amino acid substitutions) in SEQ ID NO: 30. In some embodiments of any of the proteins described herein, the heavy chain variable domain sequence is encoded by a nucleic acid including a sequence that is at least 95% (e.g., at least 96%, at least 97%, at least 98%, at least 99%, or 100%) identical to SEQ ID NO: 31.

In some embodiments of any of the proteins described herein, the antigen-binding domain includes heavy chain variable domain CDRs of GFSFTDYY (SEQ ID NO: 32), IRDSANGYTA (SEQ ID NO: 33), and ARYSRYYAMDY (SEQ ID NO: 34), and light chain variable domain CDRs of QSVNYD (SEQ ID NO: 35), FAS (SEQ ID NO: 36), and QQDYSSPWT (SEQ ID NO: 37). In some embodiments of any of the proteins described herein, the antigen-binding domain includes a light chain variable domain sequence of: FIVMTQTPKILLVSAGDRITITCKASQSVNY-DVAWYQQKPGQSPKPVIYFASNRYTGV PDRFTGSGFGTDFTFTISTVQAEDLAVYFCQQD-YSSPWTFGGGTKLEIK (SEQ ID NO: 38). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 38. In some embodiments of any of the proteins described herein, the antigen-binding domain includes a light chain variable domain sequence of SEQ ID NO: 38, except that it includes about 1 to about 6 amino acid substitutions (e.g., 1, 2, 3, 4, 5, or 6 amino acid substitutions) in SEQ ID NO: 38. In some embodiments of any of the proteins described herein, the light chain variable domain sequence is encoded by a nucleic acid including a sequence that is at least 95% (e.g., at least 96%, at least 97%, at least 98%, at least 99%, or 100%) identical to SEQ ID NO: 39. In some embodiments of any of the proteins described herein, the antigen-binding domain includes a heavy chain variable domain sequence of: EVKLVESGG-GLVQPGGSLSLSCETSGFSFTDYYMIWVRQPPGKA-LEWLGFIRDSANG YTAEYIASVKGRFTFSRDNSQSI-LYLQMNALRAEDSATYYCARYSRYYAMDYWGQ GTSVTVAP (SEQ ID NO: 40). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 40. In some embodiments of any of the proteins described herein, the antigen-binding domain includes a heavy chain variable domain sequence of SEQ ID NO: 40, except that it includes about 1 to about 6 amino acid substitutions (e.g., 1, 2, 3, 4, 5, or 6 amino acid substitutions) in SEQ ID NO: 40. In some embodiments of any of the proteins described herein, the heavy chain variable domain sequence is encoded by a nucleic acid including a sequence that is at least 95% (e.g., at least 96%, at least 97%, at least 98%, at least 99%, or 100%) identical to SEQ ID NO: 41.

In some embodiments of any of the proteins described herein, the antigen-binding domain includes heavy chain variable domain CDRs of GYTFTDYN (SEQ ID NO: 42), INPNNGGT (SEQ ID NO: 43), and ARKRGLGQAWLAY (SEQ ID NO: 44), and light chain variable domain CDRs of QSLLYSGNQKNY (SEQ ID NO: 45), GAS (SEQ ID NO: 46), and QNDHSYPLT (SEQ ID NO: 47). In some embodiments of any of the proteins described herein, the antigen-binding domain includes a light chain variable domain sequence of: DIVMTQSPSSRSVSAGEKVTMSCK-SSQSLLYSGNQKNYLAWYQQKPGQPPKLLIYG ASTRESGVPDRFTGSGSGTDFTLTISSVQAED-LAVYYCQNDHSYPLTFGAGTKLELK (SEQ ID NO: 48). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 48. In some embodiments of any of the proteins described herein, the antigen-binding domain includes a light chain variable domain sequence of SEQ ID NO: 48, except that it includes about 1 to about 6 amino acid substitutions (e.g., 1, 2, 3, 4, 5, or 6 amino acid substitutions) in SEQ ID NO: 48. In some embodiments of any of the proteins described herein, the light chain variable domain sequence is encoded by a nucleic acid including a sequence that is at least 95% (e.g., at least 96%, at least 97%, at least 98%, at least 99%, or 100%) identical to SEQ ID NO: 49. In some embodiments of any of the proteins described herein, the antigen-binding domain includes a heavy chain variable domain sequence of: EVQLQQSGPELVKP-GASVKIPCKASGYTFTDYNMDWVKQSHGKSLD-WIGDINPNNG GTIYNQKFKGKATLTVDKSSSTAYMELRSLTSED-TAVYYCARKRGLGQAWLAYWG QGTLVTVSA (SEQ ID NO: 50). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 50. In some embodiments of any of the proteins described herein, the antigen-binding domain includes a heavy chain variable domain sequence of SEQ ID NO: 50, except that it includes about 1 to about 6 amino acid substitutions (e.g., 1, 2, 3, 4, 5, or 6 amino acid substitutions) in SEQ ID NO: 50. In some embodiments of any of the proteins described herein, the heavy chain variable domain sequence is encoded by a nucleic acid including a sequence that is at least 95% (e.g., at least 96%, at least 97%, at least 98%, at least 99%, or 100%) identical to SEQ ID NO: 51.

In some embodiments of any of the proteins described herein, the antigen-binding domain includes heavy chain variable domain CDRs of GFTFSYAW (SEQ ID NO: 52), IRSKANNYAT (SEQ ID NO: 53), and MGRYDAAYGMDY (SEQ ID NO: 54), and light chain variable domain CDRs of QSLVHSNGITY (SEQ ID NO: 55), KVS (SEQ ID NO: 56), and SQSTHVPWT (SEQ ID NO: 57). In some embodiments of any of the proteins described herein, the antigen-binding domain includes a light chain variable domain sequence of: DVVMTQTPLSLPVSLGYQASISCRSSQSLVHSNGI-TYLHWYLQKPGQSPKWYKVSN RFSGVPDRFSGSGSGTDF TLKISRVEAE-DLGVYFCSQSTHVPWTFGGGTKLEIK (SEQ ID NO: 58). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 58. In some embodiments of any of the proteins described herein, the antigen-binding domain includes a light chain variable domain sequence of SEQ ID NO: 58, except that it includes about 1 to about 6 amino acid substitutions (e.g., 1, 2, 3, 4, 5, or 6 amino acid substitutions) in SEQ ID NO: 58. In some embodiments of any of the proteins described herein, the light chain variable domain sequence is encoded by a nucleic acid including a sequence that is at least 95% (e.g., at least 96%, at least 97%, at least 98%, at least 99%, or 100%) identical to SEQ ID NO: 59. In some embodiments of any of the proteins described herein, the antigen-binding domain includes a heavy chain variable domain sequence of: EVKLEESGG-GLVQPGGSMKLSCAASGFTFSYAWMDWVRQS-PEKGLEWVAEIRSKA NNYATYYAESVKGRFTISRND-SKSSVYLQMNSLRIEDTGIYYCMGRYDAAYGMDY WGQGTSVTVSS (SEQ ID NO: 60). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 60. In some embodiments of any of the proteins described herein, the antigen-binding domain includes a heavy chain variable domain sequence of SEQ ID NO: 60, except that it includes about 1 to about 6 amino acid substitutions (e.g., 1, 2, 3, 4, 5, or 6 amino acid substitutions) in SEQ ID NO: 60. In some embodiments of any of the proteins described herein, the heavy chain variable domain sequence is encoded by a nucleic acid including a sequence that is at least 95% (e.g., at least 96%, at least 97%, at least 98%, at least 99%, or 100%) identical to SEQ ID NO: 61.

In some embodiments of any of the proteins described herein, the protein competitively binds to human ADAM8 with an antigen-binding domain including: (i) a light chain variable domain of SEQ ID NO: 8 and a heavy chain variable domain of SEQ ID NO: 10; (ii) a light chain variable domain of SEQ ID NO: 18 and a heavy chain variable domain of SEQ ID NO: 20; (iii) a light chain variable domain of SEQ ID NO: 28 and a heavy chain variable domain of SEQ ID NO: 30; (iv) a light chain variable domain of SEQ ID NO: 38 and a heavy chain variable domain of SEQ ID NO: 40; (v) a light chain variable domain of SEQ ID NO: 48 and a heavy chain variable domain of SEQ ID NO: 50; or (vi) a light chain variable domain of SEQ ID NO: 58 and a heavy chain variable domain of SEQ ID NO: 60.

In some embodiments of any of the proteins described herein, the antigen-binding domain includes heavy chain variable domain CDRs of GFTFSDAW (SEQ ID NO: 62), IRNKANSHAT (SEQ ID NO: 63), and TRDGGYYAWFAY (SEQ ID NO: 64), and light chain variable domain CDRs of QSIVHSDGNTY (SEQ ID NO: 65), RVS (SEQ ID NO: 66), and FHGSHIPLT (SEQ ID NO: 67). In some embodiments of any of the proteins described herein, the antigen-binding domain includes a light chain variable domain sequence of: GALLTQTPLSLPVSLGDQVSISCRSSQSIVHSDGN-TYLEWYLQKPGQSPKLLIYRVSN RFSGVPDRFSGSGSGTDF TLKISRVEAE-DLGIYYCFHGSHIPLTFGAGTKLELK (SEQ ID NO: 68). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 68. In some embodiments of any of the proteins described herein, the antigen-binding domain includes a light chain variable domain sequence of SEQ ID NO: 68, except that it includes about 1 to about 6 amino acid substitutions (e.g., 1, 2, 3, 4, 5, or 6 amino acid substitutions) in SEQ ID NO: 68. In some embodiments of any of the proteins described herein, the light chain variable domain sequence is encoded by a nucleic acid including a sequence that is at least 95% (e.g., at least 96%, at least 97%, at least 98%, at least 99%, or 100%) identical to SEQ ID NO: 69. In some embodiments of any of the proteins described herein, the antigen-binding domain includes a heavy chain variable domain sequence of: EVKFEESGG-GLVQPGGSMKLSCAASGFTFSDAWMDWVRQS-PEKGLEWVAEIRNKA NSHATYYAESVKGRFTISRDD-SKSTVYLQMNSLRAEDTGIYYCTRDGGYYAWFAY WGQGTLVTVSA (SEQ ID NO: 70). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 70. In some embodiments of any of the proteins described herein, the antigen-binding domain includes a heavy chain variable domain sequence of SEQ ID NO: 70, except that it includes about 1 to about 6 amino acid substitutions (e.g., 1, 2, 3, 4, 5, or 6 amino acid substitutions) in SEQ ID NO: 70. In some embodiments of any of the proteins described herein, the heavy chain variable domain sequence is encoded by a nucleic acid including a sequence that is at least 95% (e.g., at least 96%, at least 97%, at least 98%, at least 99%, or 100%) identical to SEQ ID NO: 71.

In some embodiments of any of the proteins described herein, the antigen-binding domain includes heavy chain variable domain CDRs of GFTFSDAW (SEQ ID NO: 72), IRNKANNHAT (SEQ ID NO: 73), and TRDGGYYAWFAY (SEQ ID NO: 74), and light chain variable domain CDRs of QSIVHSDGNTY (SEQ ID NO: 75), KVS (SEQ ID NO: 76), and FHGSHIPLT (SEQ ID NO: 77). In some embodiments of any of the proteins described herein, the antigen-binding domain includes a light chain variable domain sequence of: GVLMTQTPLSLPVSLGDQASISCRSSQ-SIVHSDGNTYLEWYLQKPGQSPKLLLYKVS NRFSGVPDRFSGSGSGTDF TLKISRVEAE-DLGVYYCFHGSHIPLTFGAGTKLELK (SEQ ID NO: 78). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 78. In some embodiments of any of the proteins described herein, the antigen-binding domain includes a light chain variable domain sequence of SEQ ID NO: 78, except that it includes about 1 to about 6 amino acid substitutions (e.g., 1, 2, 3, 4, 5, or 6 amino acid substitutions) in SEQ ID NO: 78. In some embodiments of any of the proteins described herein, the light chain variable domain sequence is encoded by a nucleic acid including a sequence that is at least 95% (e.g., at least 96%, at least 97%, at least 98%, at least 99%, or 100%) identical to SEQ ID NO: 79. In some embodiments of any of the proteins described herein, the antigen-binding domain includes a heavy chain variable domain sequence of: EVKFEESGG-GLVQPGGSMKLSCAASGFTFSDAWMDWVRQS-PEKGLEWVAEIRNKA NNHATYYAESVKGRFTISRDD-SKSSVYLQMNSLRAEDTGIYYCTRDGGYYAWFAY WGQGTLVTVSA (SEQ ID NO: 80). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 80. In some embodiments of any of the proteins described herein, the antigen-binding domain includes a heavy chain variable domain sequence of SEQ ID NO: 80, except that it includes about 1 to about 6 amino acid substitutions (e.g., 1, 2, 3, 4, 5, or 6 amino acid substitutions) in SEQ ID NO: 80. In some embodiments of any of the proteins described herein, the heavy chain variable domain sequence is encoded by a nucleic acid including a sequence that is at least 95% (e.g., at least 96%, at least 97%, at least 98%, at least 99%, or 100%) identical to SEQ ID NO: 81.

In some embodiments of any of the proteins described herein, the antigen-binding domain binds to an epitope within human ADAM8 that includes at least one amino acid (e.g., at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, or at least 24 amino acids) within the sequence of: CCNSTTCQLAE-GAQCAHGTCCQECK (SEQ ID NO: 86).

In some embodiments of any of the proteins described herein, the antigen-binding domain binds to an epitope within human ADAM8 that includes at least one amino acid (e.g., at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, or at least 27 amino acids) within the sequence of: RNRCCNSTTCQLAEGAQCAHGTCCQECK (SEQ ID NO: 104). In some embodiments of any of the proteins described herein, the antigen-binding domain includes heavy chain variable domain CDRs of GFSFPDYY (SEQ ID NO: 2), IRDSANGYTT (SEQ ID NO: 3), and ARYSRYYGMDY (SEQ ID NO: 4), and light chain variable domain CDRs of QTVNYD (SEQ ID NO: 5), FAS (SEQ ID NO: 6), and QQDYSAPWT (SEQ ID NO: 7). In some embodiments of any of the proteins described herein, the antigen-binding domain includes a light chain variable sequence of: SIVMTQTPKILLVSAGDRVTITCK-ASQTVNYDVAWYQQKPGQSPKPVIYFASNRYTG VPDRFTGSGFGTDFTFTISTVQAED-LAVYFCQQDYSAPWTFGGGTKLEIK (SEQ ID NO: 8). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 8. In some embodiments of any of the proteins described herein, the antigen-binding domain includes a light chain variable domain sequence of SEQ ID NO: 8, except that it includes about 1 to about 6 amino acid substitutions (e.g., 1, 2, 3, 4, 5, or 6 amino acid substitutions) in SEQ ID NO: 8. In some embodiments of any of the proteins described herein, the antigen-binding domain includes a heavy chain variable domain sequence of: EVKLVESGGGLVQPGGSLSLSCAASGFSFPDYYMSWVRQPPGKALEWLGFIRDSAN GYTTEYIASVKGRFTFSRDNSQSILYLQMNALRAEDSATYYCARYSRYYGMDYWGQ GTSVTVSS (SEQ ID NO: 10). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 10. In some embodiments of any of the proteins described herein, the antigen-binding domain includes a heavy chain variable domain sequence of SEQ ID NO: 10, except that it includes about 1 to about 6 amino acid substitutions (e.g., 1, 2, 3, 4, 5, or 6 amino acid substitutions) in SEQ ID NO: 10. In some embodiments of any of the proteins described herein, the protein competitively binds to human ADAM8 with an antigen-binding domain that includes: (i) a light chain variable domain of SEQ ID NO: 18 and a heavy chain variable domain of SEQ ID NO: 20; (ii) a light chain variable domain of SEQ ID NO: 28 and a heavy chain variable domain of SEQ ID NO: 30; (iii) a light chain variable domain of SEQ ID NO: 38 and a heavy chain variable domain of SEQ ID NO: 40; (iv) a light chain variable domain of SEQ ID NO: 48 and a heavy chain variable domain of SEQ ID NO: 50; or (v) a light chain variable domain of SEQ ID NO: 58 and a heavy chain variable domain of SEQ ID NO: 60.

In some embodiments of any of the proteins described herein, the antigen-binding domain binds to an epitope within human ADAM8 that includes at least one amino acid (e.g., at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least, at least 33, at least 34, at least 35, at least 36, at least 37, at least 38, at least 39, at least 40, at least 41, at least 42, at least 43, at least 44, at least 45, at least 46, at least 47, at least 48, or at least 49 amino acids) within the sequence of: LAEGAQCAHGTCCQECKVKPAGELCRPKKDMCDLEEFCDGRHPECPEDAF (SEQ ID NO: 87).

In some embodiments of any of the proteins described herein, the antigen-binding domain includes heavy chain variable domain CDRs of GYTFTDYY (SEQ ID NO: 12), ISPNIGGA (SEQ ID NO: 13), and TRGGSSYPYFYAMDY (SEQ ID NO: 14), and light chain variable domain CDRs of QSLLYSSNQKKY (SEQ ID NO: 15), WAS (SEQ ID NO: 16), and QQFYSYPYT (SEQ ID NO: 17). In some embodiments of any of the proteins described herein, the antigen-binding domain includes a light chain variable domain sequence of: DIVMSQSPSSLAVSVGEKVTMSCKSSQSLLYSSNQKKYLAWYQQKPGQSPKLLIYW ASTRESGVPDRFTGSGSGTD FTLTISSVKAEDLAVYYCQQFYSYPYTFGGGTKLEINR (SEQ ID NO: 18). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 18. In some embodiments of any of the proteins described herein, the antigen-binding domain includes a light chain variable domain sequence of SEQ ID NO: 18, except that it includes about 1 to about 6 amino acid substitutions (e.g., 1, 2, 3, 4, 5, or 6 amino acid substitutions) in SEQ ID NO: 18. In some embodiments of any of the proteins described herein, the antigen-binding domain includes a heavy chain variable domain sequence of: EVQLQQSGPEMVKPGTSVKISCKASGYTFTDYYINWVKQSHGKSLEWIGDISPNIGG ATYNPKFKGKAILTVDKSARTAYMELRSLTSEDSAVYCCTRGGSSYPYFYAMDYWG QGTSVTVSS (SEQ ID NO: 20). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 20. In some embodiments of any of the proteins described herein, the antigen-binding domain includes a heavy chain variable domain sequence of SEQ ID NO: 20, except that it includes about 1 to about 6 amino acid substitutions (e.g., 1, 2, 3, 4, 5, or 6 amino acid substitutions) in SEQ ID NO: 20. In some embodiments of any of the proteins described herein, the protein competitively binds to human ADAM8 with an antigen-binding domain including: (i) a light chain variable domain of SEQ ID NO:8 and a heavy chain variable domain of SEQ ID NO: 10; (ii) a light chain variable domain of SEQ ID NO: 38 and a heavy chain variable domain of SEQ ID NO: 40; or (iii) a light chain variable domain of SEQ ID NO: 48 and a heavy chain variable domain of SEQ ID NO: 50.

In some embodiments of any of the proteins described herein, the antigen-binding domain binds to an epitope within human ADAM8 that includes at least one amino acid (e.g., at least two, at least three, at least four, at least five, at least six, at least seven, at least eight, at least nine, at least ten, at least 11, at least 12, at least 13, at least 14, at least 15, at least 16, at least 17, or at least 18 amino acids) within the sequence of: DCGPPEDCRNRCCNSTTCQ (SEQ ID NO: 88). In some embodiments of any of the proteins described herein, the antigen-binding domain includes heavy chain variable domain CDRs of GFTFSDAW (SEQ ID NO: 22), IRGKVNNLAT (SEQ ID NO: 23), and LGRYDATYAMDY (SEQ ID NO: 24), and light chain variable domain CDRs of QSLVHSDGNTY (SEQ ID NO: 25), KLS (SEQ ID NO: 26), and SQSTHVPWT (SEQ ID NO: 27). In some embodiments of any of the proteins described herein, the antigen-binding domain includes a light chain variable domain sequence of: DVVMTQTPLSLPVSLGDQASISCRSSQSLVHSDGNTYLHWYLQKPGQSPKLLIYKLS NRFSGVPDRFSGSGSGTDF TLKISRVEAEDLGVYFCSQSTHVPWTFGGGTKLEIK (SEQ ID NO: 28). In some embodiments of any of the proteins described herein, the antigen-binding domain includes a light chain variable domain sequence that is at least 95% (e.g., at least 96%, at least 97%, at least 98%, or at least 99%) identical to SEQ ID NO: 28. In some embodiments of any of the proteins described herein, the antigen-binding domain includes a light chain variable domain sequence of SEQ ID NO: 28, except that it includes about 1 to about 6 amino acid substitutions (e.g., 1, 2, 3, 4, 5, or 6 amino acid substitutions) in SEQ ID NO: 28. In some embodiments of any of the proteins described herein, the antigen-binding domain includes a heavy chain variable domain sequence of: EVKLEESGGGLVQPGGSMKLSCAASGFTFS- DAWMDWVRQSPEKGLEWVAEIRGKV NNLATYYVESVKGRFTISRDDSKSSVYLQMNSLRAE-DTGIYYCLGRYDATYAMDY WGQGTSVTVSS (SEQ ID NO: 30). In some embodiments of any of the proteins described herein, the antigen-binding domain includes a heavy chain variable domain sequence that is at least 95% (e.g., at least 96%, at least 97%, at least 98%, or at least 99%) identical to SEQ ID NO: 30. In some embodiments of any of the proteins described herein, the antigen-binding domain includes a heavy chain variable domain sequence of SEQ ID NO: 30, except that it includes about 1 to about 6 amino acid substitutions (e.g., 1, 2, 3, 4, 5, or 6 amino acid substitutions) in SEQ ID NO: 30. In some embodiments of any of the proteins described herein, the protein competitively binds to human ADAM8 with an antigen-binding domain including: (i) a light chain variable domain of SEQ ID NO: 8 and a heavy chain variable domain of SEQ ID NO: 10; (ii) a light chain variable domain of SEQ ID NO: 38 and a heavy chain variable domain of SEQ ID NO: 40; (iii) a light chain variable domain of SEQ ID NO: 48 and a heavy chain variable domain of SEQ ID NO: 50; or (iv) a light chain variable domain of SEQ ID NO: 58 and a heavy chain variable domain of SEQ ID NO: 60.

In some embodiments of any of the proteins described herein, the protein includes a human Fc domain (e.g., a human IgG1 Fc domain, a human IgG2 Fc domain, a human IgG3 Fc domain, or a human IgG4 Fc domain).

In some embodiments of any of the proteins described herein, the protein further includes a conjugated toxin (e.g., ozogamicin, emtansine, vedotin) or therapeutic agent. Non-limiting examples of toxins and therapeutic agents (e.g., known to be useful for the treatment of cancer) are known in the art. In some embodiments of any of the proteins described herein, the protein is conjugated to the toxin or the therapeutic agent via a cleavable linker (e.g., a disulfide bond, a hydrazone, or a peptide). In some embodiments, the cleavable linker is a protease cleavage site (e.g., a peptide linker).

Methods for determining competitive binding of two different proteins to an ADAM8 protein sequence are known in the art and include, e.g., enzyme-linked immunosorbent assays (ELISA) or surface plasmon resonance. Methods for determining the binding affinity of any of the proteins described herein are known in the art and include, e.g., surface plasmon resonance or ELISA.

Nucleic Acids, Vectors, and Mammalian Cells

Also provided herein are nucleic acids encoding any of the proteins described herein, vectors including any of the nucleic acids described herein, and mammalian cells (e.g., a CHO cell, a HEK cell or a hybridoma cell) including any of the nucleic acids described herein or any of the vectors described herein.

The term "vector" refers to a polynucleotide capable of carrying at least one exogenous nucleic acid fragment, and includes sufficient elements for expression.

In some embodiments, the vector is a plasmid, an adeno-associated viral (AAV) vector, an adenovirus, a retrovirus, a cosmid, or an artificial chromosome. Also provided are a pair of vectors that together encode a first polypeptide (e.g., an antibody light chain) and a second polypeptide (e.g., an antibody heavy chain) that together form any of the proteins described herein.

Methods of introducing vectors (e.g., expression vectors) into a mammalian cell (e.g., any of the mammalian cells described herein) are known in the art. Non-limiting examples of methods that can be used to introduce a vector (e.g., an expression vector, any of the vectors described herein) into a mammalian cell include: transfection, lipofection, electroporation, microinjection, calcium phosphate transfection, sonoporation, cell squeezing, cationic polymer transfection, optical transfection, dendrimer-based transfection, hydrodynamic delivery, magnetofection, nanoparticle transfection, or viral transduction (e.g., adeno-associated viral transduction, retroviral transduction, and lentiviral transduction).

Methods of Producing a Protein

Also provided herein are methods of producing a protein (e.g., any of the proteins described herein) that includes: (a) culturing a mammalian cell (e.g., any of the mammalian cells described herein that include nucleic acid encoding the protein or include any of the vectors described herein) in a liquid culture medium under conditions sufficient to produce the protein; and (b) recovering the protein from the mammalian cell or the liquid culture medium. In some embodiments of any of the methods described herein, the method further includes: (c) isolating the protein recovered in step (b). In some embodiments of any of the methods described herein, the method further includes: (d) formulating the protein isolated in step (c) into a pharmaceutical composition.

Also provided herein is a cell (e.g., any of the exemplary mammalian cells described herein) that includes any of the nucleic acids, vectors, or proteins described herein. Skilled practitioners will appreciate that the nucleic acids and vectors described herein can be introduced into any mammalian cell. Non-limiting examples of vectors and methods for introducing vectors and proteins into mammalian cells are described herein.

In some embodiments, the mammalian cell is a human cell, a mouse cell, a rat cell, a rabbit cell, a dog cell, a cat cell, a porcine cell, a hamster cell, or a non-human primate cell.

In some embodiments, the mammalian cell is in vitro. In some embodiments, the mammalian cell is present in a mammal.

Methods of culturing mammalian cells are well-known in the art. Mammalian cells can be maintained in vitro under conditions that favor proliferation and growth. For example, a mammalian cell can be cultured by contacting a mammalian cell (e.g., any of the mammalian cells described herein) with a cell culture medium that includes the necessary growth factors and supplements to support cell viability and growth.

Exemplary methods of introducing nucleic acids into a mammalian cell (e.g., any of the mammalian cells described herein) are described herein. Additional methods of introducing nucleic acids into a mammalian cell are known in the art.

Provided herein are methods that further include isolation of a protein (e.g., any of the proteins described herein) from a mammalian cell (e.g., any of the mammalian cells described herein) using techniques well-known in the art (e.g., size exclusion chromatography, metal-affinity chromatography, ligand-affinity chromatography, ion exchange chromatography (anion or cation), ammonium sulfate precipitation, polyethylene glycol precipitation).

Methods of detecting expression and/or activity of any of the proteins described herein are known in the art. In some embodiments, the level of expression of a protein (e.g., any of the proteins described herein) can be detected directly (e.g., detecting protein expression). Non-limiting examples of techniques that can be used to detect expression and/or activity of a protein include: ELISA, Western blotting, immunohistochemistry, or immunofluorescence.

Methods of Treatment

Provided herein are methods for inhibiting migration and/or invasion of an ADAM8 expressing cell in a subject (e.g., any of the exemplary subjects described herein) that include administering to the subject a therapeutically effective amount of any of the proteins described herein or any of the pharmaceutical compositions described herein.

In some embodiments of any of the methods described herein, the ADAM8 expressing cell is an ADAM8-associated cancer cell. In some embodiments of any of the methods described herein, the ADAM8-associated cancer cell is from a cancer selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma, and leukemia. In some embodiments of any of the methods described herein, the cancer cell is a triple negative breast cancer cell.

Also provided herein are methods of decreasing the risk of developing a metastasis or developing an additional metastasis over a period of time in a subject identified as having an ADAM8-associated cancer (e.g., any of the exemplary ADAM8-associated cancers described herein) that include administering to the subject a therapeutically effective amount of any of the proteins described herein or any of the pharmaceutical compositions described herein (e.g., as compared to a subject having a similar cancer and receiving a different treatment or receiving no treatment). In some embodiments of any of the methods described herein, the ADAM8-associated cancer is selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia.

In some embodiments of any of the methods described herein, the ADAM8-associated cancer is triple negative breast cancer. In some embodiments of any of the methods described herein, the metastasis or additional metastasis is one or more to a bone, lymph nodes, brain, lung, liver, skin, chest wall including bone, cartilage and soft tissue, abdominal cavity, contralateral breast, soft tissue, muscle, bone marrow, ovaries, adrenal glands, and pancreas.

In some embodiments of any of the methods described herein, the period of time is about 1 month to about 5 years (e.g., about 1 month to about 4 years, about 1 month to about 3.5 years, about 1 month to about 3 years, about 1 month to about 2.5 years, about 1 month to about 2 years, about 2 months to about 5 years, about 2 months to about 4 years, about 2 months to about 3.5 years, about 2 months to about 3 years, about 2 months to about 2.5 years, about 2 months to about 2 years, about 2 months to about 1.5 years, about 1 month to about 1 year, about 1 month to about 6 months, about 1 month to about 5 months, about 1 month to about 4 months, about 2 months to about 5 years, about 2 months to about 2 years, about 2 months to about 1 year, about 2 months to about 6 months, about 4 months to about 5 years, about 4 months to about 2 years, about 4 months to about 1 year, about 4 months to about 6 months, about 6 months to about 5 years, about 6 months to about 2 years, about 6 months to about 1 year, about 1 year to about 5 years, about 1 year to about 2 years, about 2 years to about 5 years, or about 4 years to about 5 years).

In some embodiments, the risk of developing a metastasis or developing an additional metastasis over a period of time in a subject identified as having an ADAM8-associated cancer is decreased by about 1% to about 99% (e.g., about 1% to about 90%, about 1% to about 80%, about 1% to about 70%, about 1% to about 60%, about 1% to about 50%, about 1% to about 40%, about 1% to about 30%, about 1% to about 20%, about 1% to about 10%, about 1% to about 5%, about 5% to about 99%, about 5% to about 90%, about 5% to about 80%, about 5% to about 70%, about 5% to about 60%, about 5% to about 50%, about 5% to about 40%, about 5% to about 30%, about 5% to about 20%, about 5% to about 10%, about 10% to about 99%, about 10% to about 90%, about 10% to about 80%, about 10% to about 70%, about 10% to about 60%, about 10% to about 50%, about 10% to about 40%, about 10% to about 30%, about 10% to about 20%, about 20% to about 99%, about 20% to about 90%, about 20% to about 80%, about 20% to about 70%, about 20% to about 60%, about 20% to about 50%, about 20% to about 40%, about 20% to about 30%, about 30% to about 99%, about 30% to about 90%, about 30% to about 80%, about 30% to about 70%, about 30% to about 60%, about 30% to about 50%, about 30% to about 40%, about 40% to about 99%, about 40% to about 90%, about 40% to about 80%, about 40% to about 70%, about 40% to about 60%, about 40% to about 50%, about 50% to about 99%, about 50% to about 90%, about 50% to about 80%, about 50% to about 70%, about 50% to about 60%, about 60% to about 99%, about 60% to about 90%, about 60% to about 80%, about 60% to about 70%, about 70% to about 99%, about 70% to about 90%, about 70% to about 80%, about 80% to about 99%, about 80% to about 90%, or about 90% to about 99%), e.g., as compared to the risk in a subject having a similar cancer receiving a different treatment or receiving no treatment.

Provided herein are methods of inhibiting the growth of a solid tumor in a subject (e.g., any of the subjects described herein) identified as having an ADAM8-associated cancer that include administering to the subject a therapeutically effective amount of any of the proteins described herein or any of the pharmaceutical compositions described herein (e.g., as compared to the growth of the solid tumor in the subject prior to treatment or the growth of a similar solid tumor in a different subject receiving a different treatment or receiving no treatment).

In some embodiments of any of the methods described herein, the growth of a solid tumor is primary growth of a solid tumor. In some embodiments of any of the methods described herein, the growth of a solid tumor is recurrent growth of a solid tumor. In some embodiments of any of the methods described herein, the growth of a solid tumor is metastatic growth of a solid tumor. In some embodiments of any of the methods described herein, the ADAM8-associated cancer is selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, and bone cancer. In some embodiments of any of the methods described herein, the ADAM8-associated cancer is triple negative breast cancer. In some embodiments, treatment results in about a 1% decrease to about 99% decrease (or any of the subranges of this range described herein) in the growth of a solid tumor in the subject (e.g., as compared to the growth of the solid tumor in the subject prior to treatment or the growth of a similar solid tumor in a different subject receiving a different treatment or receiving no treatment). The growth of a solid tumor in a subject can be assessed by a variety of different imaging methods, e.g., positron emission tomograph, X-ray computed tomography, computed axial tomography, and magnetic resonance imaging.

Provided herein are methods of inhibiting the growth or proliferation of a hematological cancer in a subject identified as having an ADAM8-associated cancer that include administering to the subject a therapeutically effective amount of any of the proteins described herein or any of the pharmaceutical compositions described herein (e.g., as compared to the growth or proliferation of the hematological cancer in the subject prior to treatment or the growth of a similar hematological cancer in a different subject receiving a different treatment or receiving no treatment). In some embodiments of any of the methods described herein, the hematological cancer is a leukemia. In some embodiments of any of the methods described herein, the hematological cancer is a lymphoma. In some embodiments, treatment results in about a 1% decrease to about 99% decrease (or any of the subranges of this range described herein) in the growth or proliferation of a hematological cancer in the subject (e.g., as compared to the growth or proliferation of the hematological cancer in the subject prior to treatment or the growth of a similar hematological cancer in a different subject receiving a different treatment or receiving no treatment). The growth or proliferation of a hematological cancer in a subject can be assessed by a variety of hematological tests.

Also provided herein are methods of killing an ADAM8-associated cancer cell in a subject that include: administering to the subject a therapeutically effective amount of any of the proteins described herein or any of the pharmaceutical compositions described herein. In some embodiments of any of the methods described herein, the killing of an ADAM8-associated cancer cell (e.g., cell death of an ADAM8-associated cancer cell) is apoptosis. In some embodiments of any of the methods described herein, the ADAM8-associated cancer cell is from a cancer selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia. In some embodiments of any of the methods described herein, the cancer cell is a triple negative breast cancer cell.

Also provided herein are methods of treating an ADAM8-associated cancer in a subject that include: administering to a subject identified as having an ADAM8-associated cancer a therapeutically effective amount of any of the proteins described herein or any of the pharmaceutical compositions described herein. In some embodiments of any of the methods described herein, the ADAM8-associated cancer is selected from the group consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia. In some embodiments of any of the methods described herein, the ADAM8-associated cancer is triple negative breast cancer.

In some embodiments of any of the methods described herein, the method further includes administering to the subject a therapeutically effective amount of a chemotherapeutic agent, a targeted therapy, or an immunotherapy. In some embodiments of any of the methods described herein, the chemotherapeutic agent is an antimetabolite, a plant alkaloid, a microtubule inhibitor, an anthracycline, a taxol, a platinum agent, or an alkylating agent. In some embodiments of any of the methods described herein, the targeted therapy is an angiogenesis or a kinase inhibitor. In some embodiments of any of the methods described herein, the immunotherapy is an inhibitor of PD-1, PD-L1, CTLA-4, LAG-3, CD70, CD80, ICOS, TIGIT, or IDO. In some embodiments of any of the methods described herein, the immunotherapy is a chimeric antigen receptor (CAR) T-cell therapy.

An immunotherapy can be administered to the patient in any of the methods described herein. The term "immunotherapy" refers to a therapeutic treatment that involves administering to a patient an agent that modulates the immune system. For example, an immunotherapy can decrease the expression and/or activity of a regulator of the immune system. In other instances, an immunotherapy can increase the expression and/or activity of a regulator of the immune system. In some instances, an immunotherapy can enhance or recruit the activity of an immune cell. In some embodiments of any of the methods described herein, the immunotherapy is an inhibitor of PD-1, PD-L1, CTLA-4, LAG-3, CD70, CD80, ICOS, TIGIT, or IDO. In some embodiments of any of the methods described herein, the immunotherapy is an antibody therapy (e.g., a conjugated therapy, a monoclonal antibody). Non-limiting examples of antibody therapies include: alemtuzumab (Campath®), bevacizumab (Mvasti™, Avastin®), dinutuximab (Unituxin®), avelumab (Bavencio®), rituximab (MabThera™, Rituxan®), elotuzumab (Empliciti™), edrecolomab (Panorex), daratumumab (Dazalex®), panitumumab (Vectibix®), pembrolizumab (Keytruda®), ramucirumab (Cyramza®), olaratumab (Lartruvo™), ofatumumab (Arzerra®), oregovomab, tremelimumab, ibritumomab (Zevalin®), mogamulizumab (Poteligeo®), denosumab (Xgeva®).

In some embodiments of any of the methods described herein, the immunotherapy is an immune checkpoint inhibitor, e.g., a CTLA-4 inhibitor, a PD-1 inhibitor, or PD-L1 inhibitor, or combinations thereof. In other embodiments of any of the methods described herein, the immunotherapy can be a cellular immunotherapy (e.g., dendritic cell therapy, natural killer cell therapy, adoptive T-cell therapy). For example, the cellular immunotherapy can be sipuleucel-T (Provenge™). In some instances, the cellular immunotherapy includes cells that express a chimeric antigen receptor (CAR). In some instances, the cellular immunotherapy can be a CAR-T cell therapy, e.g., tisagenlecleucel (Kymriah™).

In some embodiments of any of the methods described herein, the immunotherapy is a cytokine therapy (e.g., an interleukin 2 (IL-2) therapy, a granulocyte colony stimulating factor (G-CSF) therapy, an erythropoietin-alpha (EPO) therapy). A targeted therapy can be administered to the patient in any of the methods described herein. The term "targeted therapy" refers to a therapeutic agent that acts by interacting and/or binding with a specific molecular target. In some embodiments of any of the methods described herein, the targeted therapy is an angiogenesis inhibitor or a kinase inhibitor. In some embodiments of any of the methods described herein, the targeted therapy is an angiogenesis inhibitor (e.g., axitinib (Inlyta®, bevacizumab (Avastin®), cabozantinib (Cometriq®), everolimus (Afinitor®), lenalidomide (Revlimid®), lenvatinib mesylate (Lenvima®), pazopanib (Votrient®), ramucirumab (Cyramza®), regorafenib (Stivarga®), sorafenib (Nexavar®), vandetanib (Caprelsa®), ziv-aflibercept (Zaltrap®), sunitinib (Sutent®), thalidomide (Synovir, Thalomid®)). In some embodiments of any of the methods described herein, the targeted therapy is a kinase inhibitor. Non-limiting examples of kinase inhibitors include inhibitors that target EGFR, kit, ROS1, AKT, PDGFR, ABL, SRC, and mTOR. In some embodiments of any of the methods described herein, the kinase inhibitor is a tyrosine kinase inhibitor or a serine/threonine kinase inhibitor, or a combination thereof. Non-limiting examples of kinase inhibitors include, e.g., crizotinib (Xalkori®), ceritinib (Zykadia®), alectinib (Alecensa®), brigatinib (Alunbrig®), bosutinib (Bosulif®), dasatinib (Sprycel®), imatinib (Gleevec®), nilotinib (Tasigna®), ponatinib (Iclusig®), vemurafenib (Zelboraf®), dabrafenib (Tafinlar®), ibrutinib (Imbruvica®), palbociclib (Ibrance®), sorafenib (Nexavar®), ribociclib (Kisqali®), cabozantinib (Cometriq®), gefitinib (Iressa®), erlotinib (Tarceva®), lapatinib (Tykerb®), vandetanib (Caprelsa®), afatinib (Gilotrif®), osimertinib (Tagrisso®), ruxolitinib (Jakafi®), tofacitinib (Xeljanz®), trametinib (Mekinist®), axitinib (Inlyta®), lenvatinib (Lenvima®), nintedanib (OFEV®), regorafenib (Stivarga®), sunitinib (Sutent®).

In some embodiments of any of the methods described herein, the immunotherapy is a chimeric antigen receptor (CAR) T-cell therapy.

The administering, in any of the methods described herein, may be performed, e.g., at least once (e.g., at least 2-times, at least 3-times, at least 4-times, at least 5-times, at least 6-times, at least 7-times, at least 8-times, at least 9-times, at least 10-times, at least 11-times, at least 12-times, at least 13-times, at least 14-times, or at least 15-times) a week. Also contemplated are monthly administrations, e.g., administering at least once per month for at least 1 month (e.g., at least two, three, four, five, six, seven, or eight or more months, e.g., 12 or more months), and yearly (e.g., administering once a year for one or more years). Administration can be via any art-known means, e.g., intravenous, subcutaneous, intraperitoneal, oral and/or rectal administration, or any combination of known administration methods.

Administration can include administering pharmaceutical compositions formulated in any useful form. One useful pharmaceutical composition may be a combination pharmaceutical composition comprising any of the proteins described herein and an angiogenesis inhibitor, a checkpoint inhibitor, a kinase inhibitor, and/or a chemotherapeutic agent(s).

Methods of Identifying a Protein that Binds Specifically to Human ADAM8 and Inhibits Both its MP and DI Activity Also provided herein are methods of identifying a protein including an antigen-binding domain that binds specifically to human ADAM8 and has the ability to inhibit both the metalloprotease activity and disintegrin activity of human ADAM8 that include: (a) identifying a protein including an antigen-binding domain that binds to an epitope within human ADAM8 that includes at least one amino acid within the sequence of:

(SEQ ID NO: 1)
DCGPPEDCRNRCCNSTTCQLAEGAQCAHGTCCQECKVKPAGELCRPKKD

MCDLEEFCDGRHPECPEDAF.

In some embodiments of any of the methods described herein, the method further includes confirming the ability of the identified protein to inhibit the metalloprotease activity and disintegrin activity of human ADAM8.

In some embodiments of any of the methods described herein, step (a) includes identifying a protein including an antigen-binding domain that binds to an epitope within human ADAM8 that includes at least one amino acid within the sequence of:

(SEQ ID NO: 86)
CCNSTTCQLAEGAQCAHGTCCQECK
or (SEQ ID NO: 104)
RNRCCNSTTCQLAEGAQCAHGTCCQECK.

In some embodiments of any of the methods described herein, step (a) includes identifying a protein including an antigen-binding domain that binds to an epitope within human ADAM8 that includes at least one amino acid within the sequence of:

(SEQ ID NO: 87)
LAEGAQCAHGTCCQECKVKPAGELCRPKKDMCDLEEFCDGRHPECPE

DAF.

In some embodiments of any of the methods described herein, step (a) includes identifying a protein including an antigen-binding domain that binds to an epitope within human ADAM8 that includes at least one amino acid within the sequence of:

(SEQ ID NO: 88)
DCGPPEDCRNRCCNSTTCQ.

Some embodiments further include performing an animal model study of an ADAM8-associated cancer using the protein identified using any of the methods described herein.

Methods of Diagnosing

Preliminary immunohistochemistry (IHC) studies with research use only (RUO) anti-ADAM8 antibodies, indicate that a significant percentage but not all patients affected by a diverse group of aggressive cancers (e.g., those of the breast, colon, stomach, liver, pancreas, lungs, head and neck, and bones) have elevated ADAM8 levels. See Romagnoli et al., EMBO Mol Med, 6(2):278-294, 2014; Yang et al., *BMC Cancer,* 14:568-579, 2014; Huang et al., *Transl Res,* 166(6):602-613, 2015; Zhang et al., *Pathol Oncol Res,* 19(1):79-88, 2013; Valkovskaya et al., *J Cell Mol Med,* 11(5):1162-1174, 2007; Ishikawa et al., *Clin Cancer Res,* 10(24):8363-8370, 2004; Zielinski et al., *BMC Cancer,* 12:76, 2012; and Abd El-Rehim et al., *J Egypt Natl Canc Inst,* 27(1):1-9, 2015. Thus, a diagnostic assay is critical for the identification of patients with ADAM8-positive tumors who can benefit from an ADAM8-targeted therapy.

The strategy used herein to identify patients that could benefit from an ADAM8-targeted therapy includes an IHC-based assay of formalin-fixed paraffin embedded (FFPE) biopsy samples. Following cancer detection, patient tumor samples (biopsies) are taken for histologic examination and disease staging, as well as IHC analysis for detection of any known molecular markers, to guide appropriate diagnosis and treatment selection. For example, for patients with breast, gastric and gastroesophogeal cancers, biopsies are routinely analyzed by the HercepTest IHC assay (Dako), which is FDA-approved for evaluation of HER2 status and selection of candidates for Herceptin (Genentech) treatment.

Similarly, for patients with lung cancer, the anaplastic lymphoma kinase (ALK) D5F3 [Ventana] IHC assay is used to assess ALK status and identify patients who can benefit from Zykadia [Novartis] treatment. IHC is a well-accepted diagnostic technology by the FDA, does not require collection of any additional patient samples, and can be performed on automated platforms already deployed worldwide in diagnostic laboratories. These characteristics are particularly advantageous as they ensure rapid introduction of diagnostic products to the market, enabling timely patient access to new therapies. Currently, there is no FDA-approved diagnostic for detection of ADAM8-positive cancers. Herein, the identification of ADP antibodies capable of IHC-based detection of ADAM8 is described as well as IHC diagnostic antibodies that specifically recognize the target of interest under IHC conditions, that is, following fixation and retrieval of the tissue antigen from paraffin embedding.

Targeted therapies have profoundly extended and improved the quality of life for cancer patients whose tumors express specific driver genes. However, these advances would not be possible without the use of companion diagnostics that characterize the patient's tumor, providing oncologists critical information that allows them to select the most appropriate treatment regimen for a specific patient. An ADAM8 diagnostic product, based on the ADP antibodies, for detection of patients with ADAM8-positive disease can provide patients with access to a targeted therapy that can significantly improve their outcome. As ADAM8 is highly expressed on multiple aggressive tumors, such a diagnostic product has the potential to impact a large section of the overall cancer population.

Provided herein are methods of diagnosing an ADAM8-associated cancer in a subject that include: (a) contacting a biological sample from the subject with any of the proteins described herein; (b) determining a level of the protein specifically bound to the biological sample; and (c) identifying the subject as having an ADAM8-associated cancer if the level of the protein specifically bound to the biological sample is elevated as compared to a control level (e.g., a level of the protein bound to a control sample, e.g., a biological sample obtained from a subject not having or suspected of having an ADAM8-associated cancer, or a biological sample from a healthy subject with a low risk of developing an ADAM8-associated cancer).

In some examples, the biological sample is a liquid biopsy sample (e.g., blood, cerebrospinal fluid, pleural effusion, ascites). In some embodiments, the methods can further include obtaining the liquid biopsy sample from the subject.

In some embodiments, the methods can further include, prior to step (a), concentrating the cells in the liquid biopsy sample.

In some embodiments, the method can further include, prior to step (a), lysing the cells in the liquid biopsy sample. In some embodiments, step (b) can include performing an enzyme-linked immunosorbent assay (ELISA).

In some embodiments, step (b) can include the use of fluorescence-activated cell sorting. In some embodiments, step (b) can include fixing and permeabilizing the cells in the liquid biopsy sample.

In some examples, the biological sample is a tissue sample. In some examples, the tissue sample is a biopsy tissue sample. In some embodiments, the methods can further include obtaining the biopsy tissue sample from the subject.

In some examples, the tissue sample is not a fixed tissue sample (e.g., a fresh, frozen tissue sample). In some embodiments, the method can further include, prior to step (a), trypsinizing the tissue sample. In some embodiments, step (b) can include the use of fluorescence-activated cell sorting.

In some embodiments, the tissue sample can be a fixed tissue sample (e.g., a formalin-fixed paraffin-embedded (FFPE) tissue sample). In some embodiments, the methods can further include, before step (a), fixing the tissue sample. In some embodiments, the method can further include before step (a), decrosslinking the fixed tissue sample. Non-limiting examples of methods and conditions that can be used to decrosslink a tissue sample are described in the Examples. For example, decrosslinking of the fixed tissue sample can be performed using a Tris-EDTA-based, basic buffer. In some embodiments, the decrosslinking can be performed for about 40 minutes to about 80 minutes (e.g., about 40 minutes to about 75 minutes, about 40 minutes to about 70 minutes, about 40 minutes to about 65 minutes, about 40 minutes to about 60 minutes, about 40 minutes to about 55 minutes, about 40 minutes to about 50 minutes, about 40 minutes to about 45 minutes, about 45 minutes to about 80 minutes, about 45 minutes to about 75 minutes, about 45 minutes to about 70 minutes, about 45 minutes to about 65 minutes, about 45 minutes to about 60 minutes, about 45 minutes to about 55 minutes, about 45 minutes to about 50 minutes, about 50 minutes to about 80 minutes, about 50 minutes to about 75 minutes, about 50 minutes to about 70 minutes, about 50 minutes to about 65 minutes, about 50 minutes to about 60 minutes, about 50 minutes to about 55 minutes, about 55 minutes to about 80 minutes, about 55 minutes to about 75 minutes, about 55 minutes to about 70 minutes, about 55 minutes to about 65 minutes, about 55 minutes to about 60 minutes, about 60 minutes to about 80 minutes, about 60 minutes to about 75 minutes, about 60 minutes to about 70 minutes, about 60 minutes to about 65 minutes, about 65 minutes to about 80 minutes, about 65 minutes to about 75 minutes, about 65 minutes to about 70 minutes, about 70 minutes to about 80 minutes, about 70 minutes to about 75 minutes, or about 75 minutes to about 80 minutes) at a temperature of about 65° C. to about 95° C. (e.g., about 65° C. to about 94° C., about 65° C. to about 92° C., about 65° C. to about 90° C., about 65° C. to about 88° C., about 65° C. to about 86° C., about 65° C. to about 85° C., about 65° C. to about 84° C., about 65° C. to about 82° C., about 65° C. to about 80° C., about 65° C. to about 78° C., about 65° C. to about 76° C., about 65° C. to about 75° C., about 65° C. to about 74° C., about 65° C. to about 72° C., about 65° C. to about 70° C., about 65° C. to about 68° C., about 66° C. to about 95° C., about 66° C. to about 94° C., about 66° C. to about 92° C., about 66° C. to about 90° C., about 66° C. to about 88° C., about 66° C. to about 86° C., about 66° C. to about 85° C., about 66° C. to about 84° C., about 66° C. to about 82° C., about 66° C. to about 80° C., about 66° C. to about 78° C., about 66° C. to about 76° C., about 66° C. to about 75° C., about 66° C. to about 74° C., about 66° C. to about 72° C., about 66° C. to about 70° C., about 66° C. to about 68° C., about 68° C. to about 95° C., about 68° C. to about 94° C., about 68° C. to about 92° C., about 68° C. to about 90° C., about 68° C. to about 88° C., about 68° C. to about 86° C., about 68° C. to about 85° C., about 68° C. to about 84° C., about 68° C. to about 82° C., about 68° C. to about 80° C., about 68° C. to about 78° C., about 68° C. to about 76° C., about 68° C. to about 75° C., about 68° C. to about 74° C., about 68° C. to about 72° C., about 68° C. to about 70° C., about 70° C. to about 95° C., about 70° C. to about 94° C., about 70° C. to about 92° C., about 70° C. to about 90° C., about 70° C. to about 88° C., about 70° C. to about 86° C., about 70° C. to about 85° C., about 70° C. to about 84° C., about 70°

C. to about 82° C., about 70° C. to about 80° C., about 70° C. to about 78° C., about 70° C. to about 76° C., about 70° C. to about 75° C., about 70° C. to about 74° C., about 70° C. to about 72° C., about 72° C. to about 95° C., about 72° C. to about 94° C., about 72° C. to about 92° C., about 72° C. to about 90° C., about 72° C. to about 88° C., about 72° C. to about 86° C., about 72° C. to about 85° C., about 72° C. to about 84° C., about 72° C. to about 82° C., about 72° C. to about 80° C., about 72° C. to about 78° C., about 72° C. to about 76° C., about 72° C. to about 75° C., about 72° C. to about 74° C., about 74° C. to about 95° C., about 74° C. to about 94° C., about 74° C. to about 92° C., about 74° C. to about 90° C., about 74° C. to about 88° C., about 74° C. to about 86° C., about 74° C. to about 85° C., about 74° C. to about 84° C., about 74° C. to about 82° C., about 74° C. to about 80° C., about 74° C. to about 78° C., about 74° C. to about 76° C., about 74° C. to about 75° C., about 75° C. to about 95° C., about 75° C. to about 94° C., about 75° C. to about 92° C., about 75° C. to about 90° C., about 75° C. to about 88° C., about 75° C. to about 86° C., about 75° C. to about 85° C., about 75° C. to about 84° C., about 75° C. to about 82° C., about 75° C. to about 80° C., about 75° C. to about 78° C., about 76° C. to about 95° C., about 76° C. to about 94° C., about 76° C. to about 92° C., about 76° C. to about 90° C., about 76° C. to about 88° C., about 76° C. to about 86° C., about 76° C. to about 85° C., about 76° C. to about 84° C., about 76° C. to about 82° C., about 76° C. to about 80° C., about 78° C. to about 95° C., about 78° C. to about 94° C., about 78° C. to about 92° C., about 78° C. to about 90° C., about 78° C. to about 88° C., about 78° C. to about 86° C., about 78° C. to about 85° C., about 78° C. to about 84° C., about 78° C. to about 82° C., about 78° C. to about 80° C., about 80° C. to about 95° C., about 80° C. to about 94° C., about 80° C. to about 92° C., about 80° C. to about 90° C., about 80° C. to about 88° C., about 80° C. to about 86° C., about 80° C. to about 85° C., about 80° C. to about 84° C., about 80° C. to about 82° C., about 82° C. to about 95° C., about 82° C. to about 94° C., about 82° C. to about 92° C., about 82° C. to about 90° C., about 82° C. to about 88° C., about 82° C. to about 86° C., about 82° C. to about 85° C., about 82° C. to about 84° C., about 84° C. to about 95° C., about 84° C. to about 94° C., about 84° C. to about 92° C., about 84° C. to about 90° C., about 84° C. to about 88° C., about 84° C. to about 86° C., about 84° C. to about 85° C., about 85° C. to about 95° C., about 85° C. to about 94° C., about 85° C. to about 92° C., about 85° C. to about 90° C., about 85° C. to about 88° C., about 85° C. to about 86° C., about 86° C. to about 95° C., about 86° C. to about 94° C., about 86° C. to about 92° C., about 86° C. to about 90° C., about 86° C. to about 88° C., about 88° C. to about 95° C., about 88° C. to about 94° C., about 88° C. to about 92° C., about 88° C. to about 90° C., about 90° C. to about 95° C., about 90° C. to about 94° C., about 90° C. to about 92° C., about 92° C. to about 95° C., about 92° C. to about 94° C., or about 94° C. to about 95° C.).

In some embodiments, the decrosslinking of the fixed tissue sample is performed using an alkaline endopeptidase (e.g., a serine protease).

In some embodiments of any of the methods described herein, the protein comprises a detectable label. In some embodiments, step (b) comprises detecting the detectable label. In some embodiments, the detectable label is a heavy metal, a fluorophore, a chromophore, or an enzyme.

In some embodiments, the protein does not comprise a detectable label, and step (b) comprises the use of an agent that binds specifically to the protein specifically bound to the biological sample. In some embodiments, the agent comprises an antibody. In some embodiments, the agent comprises a detectable label. In some embodiments, step (b) comprises detecting the detectable label. In some embodiments, the detectable label comprises a heavy metal, a fluorophore, a chromophore, or an enzyme.

In some embodiments, step (b) comprises imaging the biological sample. In some embodiments, the determining in step (b) comprises performing immunohistochemistry or immunofluorescence.

Some embodiments of these methods further include, after step (c), (d) selecting a therapeutically effective amount of the protein used in step (a) for treatment of the subject identified as having an ADAM8-associated cancer. Some embodiments of these methods further include, after step (c), (d) administering a therapeutically effective amount of the protein used in step (a) to the subject identified as having an ADAM8-associated cancer. In some embodiments, the protein used in step (d) further comprises the protein conjugated to a toxin or a therapeutic agent.

Some embodiments of these methods further include, after step (c), (d) selecting a therapeutically effective amount of any of the proteins described herein (e.g., the same protein used in step (a) or a different protein from any of the exemplary proteins described herein) for treatment of the subject identified as having an ADAM8-associated cancer. Some embodiments of these methods further include, after step (c), (d) administering a therapeutically effective amount of any of the proteins described herein (e.g., the same protein used in step (a) or a different protein from any of the exemplary proteins described herein) to the subject identified as having an ADAM8-associated cancer. In some embodiments, the protein used in step (d) further comprises the protein conjugated to a toxin or a therapeutic agent.

Some embodiments of these methods further include, after step (c), (d) administering a therapeutically effective amount of a chemotherapeutic agent, a targeted therapy, or an immunotherapy to the subject identified as having the ADAM8-associated cancer. In some embodiments, the chemotherapeutic agent is an antimetabolite, a plant alkaloid, a microtubule inhibitor, an anthracycline, a taxol, a platinum agent, or an alkylating agent. In some embodiments, the targeted therapy is an angiogenesis or a kinase inhibitor. In some embodiments, the immunotherapy is an inhibitor of PD-1, PD-L1, CTLA-4, LAG-3, CD70, CD80, ICOS, TIGIT, or IDO. In some embodiments, the immunotherapy is a chimeric antigen receptor (CAR) T-cell therapy.

Some embodiments of these methods further include, after step (c), determining the stage of the ADAM8-associated cancer in the subject based on the level of the protein specifically bound to the biological sample.

In some embodiments, the subject is suspected of having an ADAM8-associated cancer. In some embodiments, the subject is presenting with one or more symptoms of an ADAM8-associated cancer.

In some embodiments, wherein the ADAM8-associated cancer is a cancer selected from the consisting of: breast cancer, brain cancer, head and neck cancer, thyroid cancer, esophageal cancer, lung cancer, adrenal cancer, renal cancer, liver cancer, pancreatic cancer, gastric cancer, neuroendocrine cancer, colorectal cancer, small intestine cancer, bladder cancer, ovarian cancer, cervical cancer, uterine cancer, prostate cancer, testicular cancer, skin cancer, bone cancer, lymphoma and leukemia. In some embodiments, the ADAM8-associated cancer is triple negative breast cancer. In some embodiments, the ADAM8-associated cancer is a hematological cancer. In some embodiments, the hematological cancer is a leukemia. In some embodiments, the hematological cancer is lymphoma.

In some embodiments, wherein the biological sample is obtained from a metastasis (e.g., a metastasis obtained from bone, lymph node, brain, lung, liver, skin, chest wall (including bone, cartilage and soft tissue), abdominal cavity, contralateral breast, soft tissue, muscle, bone marrow, ovaries, adrenal glands, or pancreas).

Methods of Determining the Efficacy of Treatment

Also provided herein are methods of determining the efficacy of treatment of an ADAM8-associated cancer (e.g., any of the exemplary ADAM8-associated cancers described herein) in a subject that include: (a) contacting a first biological sample obtained from a subject having an ADAM8-associated cancer at first time point with any of the proteins described herein; (b) determining a first level of the protein specifically bound to the first biological sample; (c) contacting a second biological sample obtained from the same subject at a second time point with the protein, where the subject has been administered a treatment against an ADAM8-associated cancer between the first and second time points; (d) determining a second level of the protein specifically bound to the second biological sample; and (e) determining the treatment as being effective in a subject having a decreased second level as compared to the first level, or determining the treatment as not being effective in a subject having about the same or an increased second level as compared to the first level. In some embodiments, the subject has previously been diagnosed as having an ADAM8-associated cancer. Some embodiments of these methods further include recording the determination in step (e) in the subject's medical record.

In some embodiments, step (e) comprises determining the treatment as being effective in the subject. Some embodiments of these methods further include, after step (e), selecting one or more additional doses of the treatment for the subject. Some embodiments of these methods further include, after step (e), administering one or more additional doses of the treatment to the subject.

In some embodiments, step (e) comprises determining the treatment was not effective in the subject. Some embodiments of these methods further include, after step (e), selecting an alternative treatment for the subject. Some embodiments of these methods further include, after step (e), administering an alternative treatment to the subject.

Some embodiments of these methods further include administering the treatment to the subject between the first and second time points.

In some embodiments, the treatment comprises the protein used in steps (a) and (c). In some embodiments, the treatment comprises the protein conjugated to a cytotoxin or therapeutic agent.

In some embodiments, the treatment comprises any of the proteins described herein (e.g., the same protein used in steps (a) and (c), or a different protein from any of the exemplary proteins described herein). In some embodiments, the treatment comprises the protein conjugated to a cytotoxin or therapeutic agent.

In some embodiments, the treatment comprises a chemotherapeutic agent, a targeted therapy, or an immunotherapy. In some embodiments, the chemotherapeutic agent is an antimetabolite, a plant alkaloid, a microtubule inhibitor, an anthracycline, a taxol, a platinum agent, or an alkylating agent. In some embodiments, the targeted therapy is an angiogenesis or a kinase inhibitor. In some embodiments, the immunotherapy is an inhibitor of PD-1, PD-L1, CTLA-4, LAG-3, CD70, CD80, ICOS, TIGIT, or IDO. In some embodiments, the immunotherapy is a chimeric antigen receptor (CAR) T-cell therapy.

In some embodiments, the first and second biological samples are liquid biopsy samples (e.g., blood, cerebrospinal fluid, pleural effusion, ascites). In some embodiments, the methods can further include obtaining the first and second liquid biopsy samples from the subject.

In some embodiments, the methods can further include, prior to step (a), concentrating the cells in the first and second liquid biopsy samples.

In some embodiments, step (b) can include lysing the cells in the first and second liquid biopsy samples. In some embodiments, step (b) can include performing an enzyme-linked immunosorbent assay (ELISA).

In some embodiments, step (b) can include the use of fluorescence-activated cell sorting. In some embodiments, step (b) can include fixing and permeabilizing the cells in the first and second liquid biopsy samples.

In some embodiments, steps (b) and (d) comprise imaging the first and second biological samples. In some embodiments, the determining in steps (b) and (d) comprise performing immunohistochemistry or immunofluorescence.

In some embodiments, the first and second biological samples are tissue samples (e.g., biopsy tissue samples).

In some embodiments, the tissue samples are not fixed tissue samples. In some embodiments, the tissue samples are fresh, frozen tissue samples. In some embodiments, the method further comprises, prior to step (a), trypsinizing the tissue samples. In some embodiments, step (b) comprises the use of fluorescence-activated cell sorting.

In some embodiments, the tissue samples are fixed tissue samples (e.g., formalin-fixed paraffin-embedded (FFPE) tissue samples). Some embodiments of these methods further include, before step (a), fixing the tissue samples. Some embodiments of these methods further include, before step (a), decrosslinking the fixed tissue samples. In some embodiments, the decrosslinking of the fixed tissue samples is performed using a Tris-EDTA-based, basic buffer. In some embodiments, the decrosslinking is performed for about 40 minutes to about 80 minutes (or any of the exemplary subranges of this range described herein) at a temperature of about 65° C. to about 95° C. (or any of the exemplary subranges of this range described herein).

In some embodiments, the decrosslinking of the fixed tissue samples is performed using an alkaline endopeptidase (e.g., serine protease).

In some embodiments of any of the methods described herein, the protein comprises a detectable label. In some embodiments, step (b) comprises detecting the detectable label. In some embodiments, the detectable label is a heavy metal, a fluorophore, a chromophore, or an enzyme.

In some embodiments of any of the methods described herein, the protein does not comprise a detectable label, and steps (b) and (d) comprise the use of an agent that binds specifically to the protein specifically bound to the first and second biological samples, respectively. In some embodiments, the agent comprises an antibody. In some embodiments, the agent comprises a detectable label. In some embodiments, steps (b) and (d) comprise detecting the detectable label. In some embodiments, the detectable label comprises a heavy metal, a fluorophore, a chromophore, or an enzyme.

In some embodiments, steps (b) and (d) comprise imaging the first and second biological samples. In some embodiments, the determining in steps (b) and (d) comprises performing immunohistochemistry or immunofluorescence.

In some embodiments of any of the methods described herein, the second time point is about 1 month to about 5 years (e.g., about 1 month to about 4 years, about 1 month to about 3.5 years, about 1 month to about 3 years, about 1 month to about 2.5 years, about 1 month to about 2 years, about 2 months to about 5 years, about 2 months to about 4 years, about 2 months to about 3.5 years, about 2 months to about 3 years, about 2 months to about 2.5 years, about 2 months to about 2 years, about 2 months to about 1.5 years, about 1 month to about 1 year, about 1 month to about 6 months, about 1 month to about 5 months, about 1 month to about 4 months, about 2 months to about 5 years, about 2 months to about 2 years, about 2 months to about 1 year, about 2 months to about 6 months, about 2 months to about 4 months, about 2 months to about 3 months, about 4 months to about 5 years, about 4 months to about 2 years, about 4 months to about 1 year, about 4 months to about 6 months, about 5 months to about 5 years, about 5 months to about 2 years, about 5 months to about 1 year, about 6 months to about 5 years, about 6 months to about 2 years, about 6 months to about 1 year, about 1 year to about 5 years, about 1 year to about 2 years, about 2 years to about 5 years, or about 4 years to about 5 years; or about 1 month, about 2 months, about 3 months, about 4 months, about 5 months, about 6 months, about 8 months, about 9 months, about 10 months, about 1 year, about 2 years, about 3 years, about 4 years, or about 5 years) after the first time point.

Pharmaceutical Compositions and Kits

Also provided herein are pharmaceutical compositions that include a therapeutically effective amount of any of the proteins described herein and one or more pharmaceutically or physiologically acceptable carriers, diluents, or excipients. Such pharmaceutical compositions may comprise one or more buffers, such as neutral-buffered saline, phosphate-buffered saline, and the like; one or more carbohydrates, such as glucose, mannose, dextran, and sucrose; mannitol; one or more proteins, polypeptides, or amino acids, such as glycine; one or more antioxidants; one or more chelating agents, such as EDTA or glutathione; and/or one or more preservatives.

In some embodiments, the pharmaceutical composition includes a pharmaceutically acceptable carrier (e.g., phosphate buffered saline, bacteriostatic water, or saline). Upon formulation, solutions will be administered in a manner compatible with the dosage formulation and in such amount as is therapeutically effective. The formulations are easily administered in a variety of dosage forms such as injectable solutions, injectable gels, infusions, drug-release capsules, and the like.

As used herein the term "pharmaceutically acceptable carrier" includes solvents, dispersion media, coatings, antibacterial agents, antifungal agents, and the like that are compatible with pharmaceutical administration. Supplementary active compounds can also be incorporated into any of the pharmaceutical compositions described herein.

In some embodiments, a single dose of any of the pharmaceutical compositions described herein can include a total sum amount of the protein of at least 1 mg, at least 2 mg, at least 4 mg, at least 5 mg, about 6 mg, about 8 mg, about 10 mg, about 12 mg, about 20 mg, about 30 mg, about 35 mg, about 40 mg, about 45 mg, about 50 mg, about 60 mg, about 80 mg, about 100 mg, about 120 mg, about 140 mg, about 150 mg, about 160 mg, about 180 mg, about 200 mg, about 220 mg, about 240 mg, about 250 mg, about 260 mg, about 280 mg, about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg, e.g., in a buffered solution.

The pharmaceutical compositions can be, e.g., formulated to be compatible with any intended route of administration (e.g., intravenous).

Also provided herein are kits including any of the pharmaceutical compositions described herein. In some embodiments, a kit can include a solid composition (e.g., a lyophilized composition including any of the proteins described herein) and a liquid for solubilizing the lyophilized composition.

In some embodiments, a kit can include a pre-loaded syringe including any of the pharmaceutical compositions described herein. In some embodiments, the kit includes a vial comprising any of the pharmaceutical compositions described herein (e.g., formulated as an aqueous pharmaceutical composition). In some embodiments, the kits can include instructions for performing any of the methods described herein.

Also provided herein are kits including any of the proteins described herein, and instructions for performing any of the methods described herein (e.g., diagnostic methods). In some embodiments, a kit can include instructions for use and other necessary reagents, e.g., positive and negative control samples, negative control antibodies, any of the proteins described herein and detection reagents (e.g., antibodies that bind specifically to any of the proteins described herein and reagents necessary for detection of a tag or enzyme activity); and devices (e.g., a syringe, a finger prick) or other materials for diagnosing. In some embodiments, a kit can include a solid composition (e.g., a lyophilized composition) of the proteins described herein and of the other kit reagents and liquid solutions for solubilizing the lyophilized components.

EXAMPLES

Example 1. Overview of Approach to Generate Highly Specific, Dual Antagonist Monoclonal Antibodies that Inhibit the MP and DI Domains of Human ADAM8

The hybridoma method (Nelson et al., *Mol Pathol,* 53(3): 111-117, 2000) was used to generate antibodies against a functional human ADAM8 ectodomain fragment. These monoclonal antibodies were then subjected to a multi-stage screening strategy (FIG. 2) to first isolate a panel of dual Metalloprotease (MP) and Disintegrin (DI) domain inhibitor antibodies, termed ADPs (Phase 1). The panel of ADPs was then characterized with respect to epitope, kinetics and specificity of ADAM8 binding and certain ADPs were screened in mouse models of Triple-negative breast cancer (TNBC). Two lead therapeutic candidates (ADP2 and ADP13) were identified. A third antibody (ADP3) also showed anti-tumor effect, but to a more limited extent (Phase 2). In Phase 3, additional mouse model testing (neoadjuvant tumor resection and combination therapy), amino acid sequencing, epitope mapping, and generation and functional characterization of chimeric ADP2 and ADP13 was performed. Taken together, the results showed that anti-ADAM8 dual antagonist candidate therapeutics, ADP2 and ADP13, bound to sequences within the ADAM8 DI domain, leading to reduced primary tumor growth, reduced risk of recurrence and reduced frequency and extent of metastasis, significantly improving overall survival.

Example 2. Generation of Hybridomas Producing Highly Specific, Monoclonal Antibodies Against Functional ADAM8

Recombinant human ADAM8 (rHuADAM8) ectodomain protein (aa 17-497) produced in mammalian HEK293 cells, containing both MP and DI domains and capable of autocatalytically activating itself, was purchased from ACRO Biosystems (AD8-H5223) for use as an immunogen. The activity of this recombinant protein was confirmed using functional MP and DI assays for: (a) MP domain activity: activation of a quenched fluorescent CD23 peptide; and (b) DI domain activity: binding of Chinese Hamster Ovary (CHO) cells ectopically expressing $\alpha9\beta1$ integrin to recombinant human ADAM8 coated plates.

Balb/c and SJL mice were selected for immunization in order to give the broadest range of immune response. Ten mice of each strain were pre-bled and then each injected with 50-100 μg rHuADAM8 with complete Freund's adjuvant on Day 0. On Days 14 and 35, mice were boosted with 25-50 μg rHuADAM8 with incomplete Freund's adjuvant and then bled 7 days later. These test bleed sera were evaluated for binding to rHuADAM8 using Enzyme-linked immunosorbent assays (ELISA), and for binding to native cell-surface expressed ADAM8 using HEK293-ADAM8 cells in Fluorescence-activated cell sorting (FACS) analysis to confirm a high level of anti-ADAM8 activity. Mice were given one additional boost (Day 56) prior to fusion of lymphocytes from the best responders to the Sp2/0-Ag14 myeloma cell line.

Three fusions were performed with B lymphocytes from 6 mice. Cell supernatants from resulting hybridomas, containing 0.25 to 10 μg IgG/ml, were tested to identify clones with high anti-ADAM8 activity by ELISA and FACS. Then, a novel 3 phase screening strategy (FIG. 2) was performed to isolate dual antagonist monoclonal antibodies (termed ADPs) that inhibit the two critical MP and DI domain functions of ADAM8 using cell-based assays. Four ADPs were selected and further screened against primary TNBC growth in mice, resulting in identification of ADP2 and ADP13 as lead antibodies. Extensive additional preclinical mouse testing of ADP2 and ADP13 confirmed that these dual ADAM8 inhibitory antibodies had the necessary functional characteristics, as described in U.S. Patent Publication No. 2016/0130365, to ultimately be successful therapeutic antibodies.

Example 3. Screening of Anti-ADAM8 ADP Antibodies

In Phase 1 screening, hybridomas making antibodies cross-reacting with recombinant human ADAM8, ADAM12 and ADAM15 proteins, which are closely related to ADAM8 (Takeda, *Toxins,* 8(5). pii: E155, 2016), were identified in ELISA assays and excluded from consideration. Supernatants from the remaining hybridoma clones, grown in hybridoma-serum free medium, i.e., in the absence of fetal bovine serum (FBS), to enhance antibody production, were then tested for simultaneous antagonist activity against ADAM8 MP and DI domains using cell-based assays. Hybridomas demonstrating dual antagonist activity were subcloned in two rounds by serial dilution. Following each round of subcloning, ADAM8 binding activity was confirmed in ELISA and FACS experiments. Second round subclones were isotyped, which also confirmed single clone origin, and subjected to MP/DI activity assays using cell-based functional assays. Eighteen stable subclones producing anti-human ADAM8 antibodies (termed ADPs) with dual MP and DI domain antagonist activity were identified.

In Phase 2 screening, purified ADPs were further characterized with respect to their ADAM8 binding properties [using FACS, ELISA, Biacore, epitope binning and cross-reactivity (specificity) assays], as well as their ability to inhibit the MP and DI domains of ADAM8 (in cell-based MP/DI functional assays) and to slow tumor growth in mice (using in vivo models of pre-existing TNBC cell line-derived tumors). ADP2, ADP3 and ADP13 all showed anti-tumor growth inhibitory activity in vivo. However, ADP2 and ADP13 were selected for further testing as the two most effective antibodies.

In Phase 3 screening, additional testing in vivo was performed to test the ability of the lead ADPs to reduce metastasis and improve survival (using a neoadjuvant TNBC tumor resection model followed by tissue imaging). ADP2 and ADP13 were then tested for their ability to work in combination with the chemotherapeutic agent Nanoparticle Albumin-Bound Paclitaxel (NPAC), which is a standard-of-care treatment for patients with recurrent TNBC. The results from these TNBC animal models that closely mimic patient treatment protocols validated the ability of ADP2 and ADP13, to significantly improve disease outcome when administered as monotherapies or in combination with chemotherapy.

Amino acid sequencing analysis identified the Complementarity-Determining Regions (CDRs) of ADP2, ADP13, and ADP3. With the exception of CDR L2 and CDR H1 of ADP2 and ADP13, which bear some similarity to each other, the other CDRs of the light and heavy chains of these ADPs were different. FACS analysis using cells that express ADAM8 MP and DI domains vs DI domain alone, showed that both ADP2 and ADP13 bound to the DI domain. Epitope mapping at the peptide level using hydrogen deuterium exchange (HDX) mass spectrometry peptide analysis confirmed ADP2 and ADP13 bind to the ADAM8 DI domain. Chimeras of the light chain variable domain (VL) and heavy chain variable domain (VH) of ADP2 and ADP13 with the C region of human IgG1 (chADP2 and chADP13, respectively) were generated to test for the ability of the mouse V regions to function in the context of human C regions. Binding to ADAM8 and dual MP/DI antagonist activity were retained by the two chimeras. Finally, ADP2 and ADP13 were epitope mapped at the amino acid level using shotgun mutagenesis.

Example 4. Maintenance of Hybridoma Clones and Monoclonal Antibody Preparation Anti-ADAM8 antibody producing hybridoma lines and control mouse hybridomas producing isotype-matched IgGs were grown in HyClone™ CCM1 media (GE Healthcare). Control hybridomas expressed bromodeoxyuridine (BrdU) IgG1 (clone G3G4, Developmental Studies Hybridoma Bank, U. Iowa City) and anti-*Manduca sexta* ecdysone IgG2b (clone 10F1, Developmental Studies Hybridoma Bank). All lines were confirmed mycoplasma-free using a polymerase chain reaction (PCR)-based test (Venor™GeM Mycoplasma Detection Kit, Sigma). Antibodies were purified from supernatants using recombinant Protein A affinity purification. Sterile filtered purified antibodies in 0.02 M potassium phosphate, 0.15 M sodium chloride (pH 7.2-7.4) buffer had low endotoxin levels (<2 EU/mg) and displayed >95% purity as determined by sodium dodecyl sulfate polyacrylamide gel electrophoresis (SDS-PAGE) analysis.

Example 5. ELISA Assays of ADP Binding to Recombinant Human ADAM8 (rHuADAM8)

ELISAs were performed to assess the anti-ADAM8 antibodies for binding to rHuADAM8 during preparation and screening stages, using mouse sera, hybridoma supernatants and purified mouse and chimeric ADPs. ELISA plates (96-well) were coated with 1 μg/ml rHuADAM8 (Acro Biosystems, AD8-H5223) overnight at 4° C. Plates were washed three times with phosphate buffered saline (PBS) containing 0.05% Tween 20 (PBST) and blocked with 1% bovine serum albumin (BSA) in PBST at 37° C. for 1 hr. Plates were then exposed to sera, supernatants or purified antibodies for 1 hour at 37° C.

For analysis of antibodies in the serum of mice, pre-bleed and test bleed samples in 6 dilutions ranging from 1:100 to 1:10,000,000 were tested. For analysis of antibodies in hybridoma clone and subclone supernatants, plates were subjected to 50 μl of supernatants. A test bleed sample (1:1000) and hybridoma culture medium were used as positive and negative controls, respectively. For purified antibody characterization, coated plates were incubated with eight increasing concentrations of each specific ADP ranging from $10^{-5}$ to $10^{3}$ nM. Normal mouse IgG (1 μg/ml) was used as a negative control to indicate the level of general non-specific binding and a test bleed sample (1:100) was used as a positive control. Samples were washed three times with PBST and incubated for 30 minutes at 37° C. with a secondary goat anti-mouse IgG (Fc specific)-HRP antibody (Sigma A0168, 1:5000). After washing three times with PBST, the signal was developed with addition of 100 μl of the horseradish peroxidase substrate 3,3',5,5'-Tetramethylbenzidine (TMB) for 10 minutes at room temperature, followed by quenching with 50 μl 1N HCl. Signal was read in a 96-well spectrophotometer at an optical density (OD) of 450 nm.

Example 6. FACS Analysis of ADP Binding to Native ADAM8

FACS analysis was used to assess mouse sera, hybridoma supernatants and purified mouse or chimeric ADPs for binding to native ADAM8. Variations of the same basic protocol were used. For these experiments, the human embryonic kidney (HEK) cell line 293 (HEK293), which does not naturally express ADAM8, was purchased from the American Type Culture Collection (ATCC) and maintained in medium recommended by ATCC. Stable cell lines HEK293-full-length-ADAM8 (termed HEK293-ADAM8 or Full-length), HEK293-remnant-ADAM8 (termed Remnant) and HEK293-Empty Vector (EV) were generated by transfection of HEK293 cells with full-length human ADAM8 cDNA (MGC:134985; Genbank:BC115404.1), the remnant form ADAM8 cDNA and control pCDNA3.1 Version B DNA (Invitrogen), respectively, using Lipofectamine® 2000 (Invitrogen, 11668), according to the manufacturer's directions, and selection in 500 μg/ml geneticin (G418, Teknova). ADAM8 cDNA constructs were as described previously (Romagnoli et al., *EMBO Mol Med,* 6(2): 278-294, 2014; Das et al., *Breast Cancer Res,* 18(1): 40-58, 2016; Srinivasan et al., *J Biol Chem,* 289(48): 33676-33688, 2014).

For FACS analysis, cells were trypsinized and single cell suspensions generated by passing cells through a syringe with a 21 g 1½ needle. Three hundred thousand cells per sample were resuspended in 50 μL FACS Buffer (1% BSA, 0.1% sodium azide in PBS). Cells were exposed to sera, supernatants or purified antibodies for 30 minutes on ice. For analysis of antibodies in the serum of mice, pre-bleed and test bleed samples at 1:100 dilution were used. For analysis of antibodies in hybridoma clone and subclone supernatants, cells were subjected to 10 μL of supernatant samples. Purified mouse ADPs were assessed at concentrations of 10, 1 and 0.1 μg/ml. Normal mouse IgG (1 μg/ml) was used as a negative control. For a positive technical control, staining with 1 μg/ml goat anti-mouse ADAM8 antibody AF1031 (R&D Systems) vs normal goat IgG was performed. Chimeric ADPs were tested at 2 μg/ml and human IgG1 (Sigma, 15154) was used as an antibody isotype-matched control. After incubation with primary antibodies, cells were washed three times with 1 ml of FACS buffer each time and incubated in the dark in 50 μl FACS buffer with secondary antibody. Secondary antibodies were: Alexa Fluor 488 donkey anti-mouse IgG (H+L) antibody (1:1000, Life Technologies, A-21202), Alexa Fluor 488 donkey anti-goat IgG (H+L) antibody (1:1000, Life Technologies, A-11055) and Alexa Fluor 488 goat anti-human IgG (H+L) antibody (1.25 μg, Life Technologies, A-11013). After a 20 minutes incubation with secondary antibodies, cells were washed with 1 ml of FACS buffer three times, resuspended in 400 μl of FACS buffer and analyzed by flow cytometry using a BD FACSCalibur™ machine.

Example 7. Assays for Testing of ADP Cross-Reactivity to ADAM8 Related ADAM Proteins ELISA assays were also used to test hybridoma clones, subclones and purified ADP antibodies for specificity of ADAM8 binding, i.e., binding to rHuADAM8 (Acro Biosystems, AD8-H5223) was compared to binding to closely related recombinant human ADAM proteins: ADAM9 (R&D Systems, 939-AD-020), ADAM12 (Acro Biosystems, AD2-H5228) and ADAM15 (Sino Biological, 10517-H08H). For analysis of clones and subclones, 50 μl of cell supernatants were used. A test bleed sample (1:1000) was used as a positive control. Hybridoma culture medium or a pre-bleed serum sample (1:1000) was used as a negative control. Purified mouse ADPs were assessed at 1 μg/ml vs normal mouse IgG and with a test bleed sample as a positive control. ADP binding was detected with a goat anti-mouse IgG (Fc specific)-peroxidase antibody (1:5000, Sigma-Aldrich, A0168). All ADPs showed high ADAM8 specific binding and very low cross-reactivity to related ADAM8, ADAM12 and ADAM15 proteins.

ADP2 and ADP13 were also tested for cross-reactivity to the ADAM8 related protein ADAM33 using a variation of the above FACS protocol, which included steps for cell fixation and permeabilization. FACS was performed as an ELISA assay was precluded due to the lack of commercially available recombinant ADAM33. Cell fixation and permeabilization steps were needed as ADAM33 expression in HEK293 cells is primarily intracellular. HEK293 cells were transiently transfected over a 48-hr period with an ADAM33 construct (Clone ID HsCD00419548, Harvard Plasmid Information Database) or a control EV DNA (Plasmid #25890, Addgene) using Lipofectamine® 2000. Single cell suspensions ($1\times10^{6}$ cells/ml) were prepared in FACS buffer. Cell samples (1 ml) were centrifuged, resuspended in 50 μL cold 4% paraformaldehyde and incubated for 20 minutes at 4° C. in the dark with occasional shaking. Cells were then washed once with 1 ml FACS buffer, and then twice with 0.1% saponin FACS buffer. Samples were exposed to primary antibodies in 50 μL of 0.1% saponin FACS buffer for 30 minutes at 4° C. For ADP2, ADP13 and their respective IgG2b and IgG1 isotype matched controls, 2 μg of antibody were used. An anti-ADAM33 antibody (LifeSpan Biosciences, LS-C124915) (0.3 μg) was used as a positive control; a sample was also stained with its IgG1 isotype control at the same concentration. Following primary antibody exposure, samples were washed 2× in 0.1% saponin FACS buffer and exposed to 1.25 μg secondary antibody [Alexa Fluor 488 chicken anti-mouse IgG (Life Technologies, A21200)] in 50 μL of 0.1% saponin FACS buffer for 30 minutes at 4° C. After three washes in 0.1% saponin FACS buffer, cells were resuspended in 500 μL FACS buffer and analyzed on a BD FACSCalibur™ machine.

Example 8. ADAM8 Metalloprotease (MP) Domain Activity Assays

Activation of a Quenched Fluorescent CD23 Peptide

MP domain activity of rHuADAM8 was confirmed prior to mouse immunization by assessing its ability to release fluorescence from a tagged/quenched peptide, derived from the ADAM8 target protein CD23. Briefly, duplicate samples (100 μl) of rHuADAM8 (1 μg) diluted in assay buffer (1 M Tris HCl, pH 8.0, 10 mM $CaCl_2$), 6×10-4 Brij detergent) with or without 30 mM Ethylenediaminetetraacetic acid (EDTA) were prepared. Additionally, samples (100 μl) with assay buffer plus 30 mM EDTA or assay buffer alone were prepared as controls (lacking ADAM8). EDTA is an inhibitor of ADAM8 protease enzymatic activity as it chelates the divalent cations required for MP activity. Next, 3 μl of quenched fluorescent CD23 peptide (Biozyme, PEPDAB013m001) working solution (10 mM in DMSO) was diluted (1:400) in assay buffer and 100 μl aliquots added to each experimental well. A control sample containing assay buffer alone was used to set background levels. Fluorescence was measured every hour up to 8 hr and then again at 24 hr. An increase in fluorescence was seen over time in samples with rHuADAM8, which was inhibited in the presence of the chelating agent EDTA. These results indicated that the rHuADAM8 protein had an active MP domain.

CD23 Cleavage from the Cell Surface

Cellular MP activity was measured using a modified version of the Romagnoli protocol (*EMBO Mol Med,* 6(2): 278-294, 2014). Briefly, 4×$10^5$ HEK293 cells/well were plated in 12-well plates. After 24 h, cells were co-transfected with 3 μg of a plasmid encoding C-terminal HA-tagged membrane isoform b of CD23, a well-known substrate of ADAM8 (Fourie et al., *J Biol Chem* 278(33): 30469-30477, 2003), and 1.2 μg of either full-length ADAM8 or empty vector pCDNA3.1 DNA using Lipofectamine® 2000. After 6 hours, the transfection medium was replaced with culture medium without FBS in the presence of either: (a) concentrated and dialyzed ADPs from hybridoma supernatants, or (b) purified ADPs following generation of stable subclones. Specifically, hybridoma supernatants were concentrated ~10-fold using Amicon Ultra Centrifugal Filters (EMD Millipore) and dialyzed against PBS using Micro Float-A-Lyzer dialysis units (Spectrum Labs) to remove hybridoma media. Concentrated dialyzed ADP samples were then quantified using an Easy Titer IgG Assay kit (Thermo Fisher Scientific) and concentration confirmed by Nanodrop Lite Spectrophotometer analysis.

Activity of dialyzed ADPs (20 μg/ml) from hybridoma supernatants was compared to that of similarly processed prototype anti-ADAM8 antibody MAB1031 (R&D Systems) (used in U.S. Patent Publication No. 2016/0130365) vs its isotype-matched control mouse IgG2b, to identify hybridomas with MP domain inhibitory activity. Once stable subclones were established, the MP inhibitory activity of protein A-purified ADPs was confirmed vs MAB1031, and the appropriate isotype-matched control mouse IgGs (20 μg/ml). Control IgGs used were: BrdU IgG1 (clone G3G4, Developmental Studies Hybridoma Bank, U. Iowa City), anti-*Manduca sexta* ecdysone IgG2b (clone 10F1, Developmental Studies Hybridoma Bank, U. Iowa City), and IgG2c (clone 6.3, ASB-12201, Nordic Biosite). After 16 hours of exposure to either dialyzed or purified antibodies, the serum-free media was harvested and centrifuged to remove cell debris, while cells were trypsinized and counted. Conditioned cell media (volumes corresponding to 50,000 cells per each sample) were assessed for cleaved CD23 via detection of its HA-tag in Western blotting. Whole cell extracts from lysed cells were further assessed for ADAM8 levels.

MP % inhibition was calculated as a decrease in cleaved CD23 in the conditioned media of HEK293 cells co-expressing CD23 and ADAM8, following anti-ADAM8 treatment vs treatment with isotype-matched control IgG (set to 100%). EV/CD23 co-transfected HEK293 cells were used to set background staining. MP activity studies with triple-negative inflammatory breast cancer cells were performed in essentially the same way as described above but using SUM149 cells rather than HEK293 cells.

Western Blotting

Whole-cell extracts (WCEs) from cells in culture and conditioned cell media were prepared and immunoblotted as described previously (Romagnoli et al., *EMBO Mol Med,* 6(2): 278-294, 2014). Briefly, WCE were prepared using Radioimmunoprecipitation assay buffer (RIPA, 50 mM Tris pH 7.6, 150 mM NaCl, 1% NP40, 0.1% SDS, 5 mM EDTA, 1% Sodium Sarkosyl) supplemented with Halt Protease and Phosphatase Inhibitor Single-Use Cocktail (1:100, Thermo Fisher Scientific, 78442), 0.5 M EDTA (1:100) and 1 M 1,10-Phenanthroline (1:100, Sigma, 131377) to inhibit the autocatalytic activity of ADAM8. Samples (25 μg) were subjected to immunoblotting for ADAM8 with an anti-ADAM8 antibody (LifeSpan Biosciences, LS-B4068) and for β-Tubulin, as a loading control, with an anti-β-Tubulin antibody (Sigma, T6793).

For Western blot analysis of released HA-tagged CD23 in MP assays, volumes of the conditioned media corresponding to 50,000 cells per sample, prepared as described above, were subjected to immunoblotting using an anti-HA antibody (Sigma, H6908) for detection of the CD23 HA-tag. A Precision Plus Protein Dual Color Standard (Biorad, #1610374) was used as a protein size marker.

Example 9. ADAM8 Disintegrin (DI) Domain Activity Assays

Adhesion of α9β1 Integrin Expressing Cells to rHuADAM8

ADAM8 binding to and activation of β1 integrin on the cancer cell surface is a critical step in tumor spread mediated via the activity of a functional DI domain (Romagnoli et al., *EMBO Mol Med,* 6(2): 278-294, 2014; Schlomann et al., *J Biol Chem,* 277: 48210-48219, 2002). To mimic this process and evaluate both the presence of an active DI domain on rHuADAM8 and the ability of ADPs to inhibit this activity in vitro, adhesion of Chinese Hamster Ovary (CHO) cells expressing α9β1 integrin vs the negative control αvβ3 integrin was used (Rao et al., *J Bone Miner Res,* 21(10):

1657-1665, 2006). CHO cells were maintained in DMEM high glucose (Invitrogen) supplemented with 10% FBS, 1% penicillin/streptomycin (Hyclone), L-glutamine (Gibco), non-essential amino acids (Gibco) and 100 μg/ml G418 (Teknova). Adhesion of CHO cells expressing α9β1 integrin or αvβ3 integrin to plates coated with rHuADAM8 (Acro Biosystems, AD8-H5223) was assessed as follows. Briefly, 96-well plates were coated overnight with 1.5 μg of rHuADAM8 per well, blocked with 1% BSA and washed with PBS.

To test for the presence of an active DI domain on rHuADAM8, wells were then pre-treated in duplicate for 2 hours with either PBS, 10 μg/ml neutralizing rat anti-human (31 integrin antibody (BD Pharmingen, 552828) or normal rat IgG control. A single cell suspension of CHO cells expressing α9β1 integrin ($1\times10^5$ per well) was then added and allowed to attach for 1 hour at 37° C. CHO cells expressing αvβ3 integrin, which does not interact with ADAM8, were used as an added control. Unattached cells were washed off and attached cells counted manually on a microscope using a grid drawn on the bottom of the plate. CHO cells expressing α9β1 integrin were able to bind to rHuADAM8 and this binding was inhibited by exposure to a β1 integrin neutralizing antibody. In contrast, CHO cells expressing αvβ3 integrin were unable to attach. These data indicated that rHuADAM8 had an active DI domain.

To assess the ability of ADPs to inhibit DI activity, 96-well plates coated with rHuADAM8 as above were pre-treated in duplicate for 2 hours with either PBS, 20 μg/ml of dialyzed or protein A purified ADP, MAB1031 or control isotype-matched IgGs. Unattached cells were washed off and attached cells counted as above. DI % inhibition was calculated as a decrease in adhesion of CHO cells expressing α9β1 integrin to rHuADAM8 following ADP treatment vs treatment with an isotype-matched control IgG (set to 100%). % Cell Binding=control IgG (set to 100%)−DI % inhibition, and is given as a mean±Standard Deviation (S.D.) from 3 independent experiments.

Transendothelial Migration

Transendothelial migration (TEM), the DI domain-mediated ability of ADAM8-expressing cells to move through a layer of endothelial cells, mimicking entry into a blood vessel, was used as an additional test for inhibition of DI activity by ADPs as described previously (Romagnoli et al., *EMBO Mol Med,* 6(2): 278-294, 2014). The human triple-negative breast cancer (TNBC) cell line MDA-MB-231 and the human umbilical vein endothelial cell line HUVEC were purchased from ATCC and maintained in their recommended media. MDA-MB-231-luciferase-tagged cells were generated by lentiviral infection followed by selection in G418 (500 μg/ml) as described previously (McLaughlin et al., *Cancer Cell,* 24(3): 365-278, 2013). The TNBC cell line SUM149, representative of the highly aggressive inflammatory breast cancer phenotype (Forozan et al., *Br J Cancer,* 81(8): 1328-1334, 1999) was maintained in Ham's F-12 medium (Mediatech), containing 5% FBS (Invitrogen), 5 μg/ml insulin (Sigma), 1 μg/ml hydrocortisone (Sigma), 100 units/ml penicillin and streptomycin (Hyclone) (Mineva et al., *PLoS One,* 8(9): e73464, 2013). All lines were confirmed mycoplasma-free using a PCR-based test (Venor™GeM Mycoplasma Detection Kit, Sigma). TNBC cell lines were authenticated using short tandem repeat analysis (Genetica DNA Laboratories).

Briefly, transwells (Costar) with 8-μm diameter pores were coated with a confluent monolayer of HUVEC cells. Single cell suspensions of $4\times10^4$ SUM149 cells or $1\times10^5$ MDA-MB-231 cells were pre-treated with 20 μg/ml of dialyzed or protein A purified ADP, prototype MAB1031 (R&D Systems) or their respective isotype-matched control IgGs in serum free media for 30 minutes at room temperature, layered in the upper compartment of the HUVEC-coated transwells and allowed to migrate at 37° C. After 16-24 hours incubation, cells that migrated to the lower side of the filter were quantified by crystal violet staining and OD 570 nm determination. TEM % inhibition was calculated as a decrease in transwell migration following anti-ADAM8 antibody treatment vs treatment with an isotype-matched control IgG (set to 100%).

Endothelial Cell Adhesion

To invade through a blood vessel wall, cancer cells must first adhere to the endothelial cells lining this wall in a process specifically mediated by ADAM8 DI activity. Thus, endothelial cell adhesion was used as another test for inhibition of DI activity by ADPs as described previously (Romagnoli et al., *EMBO Mol Med,* 6(2): 278-294, 2014). Briefly, $1\times10^5$ HUVEC cells were plated, in duplicate, in 48-well plates and grown for 24 hours to obtain a confluent monolayer. SUM149 cells ($5\times10^4$) were pre-treated with 20 μg/ml of ADP13 or isotype-matched control IgG1 for 30 minutes at room temperature. An untreated sample of SUM149 was used as an additional control. After antibody pre-treatment, SUM149 cells were washed twice with PBS and incubated for 20 minutes at 37° C. in 300 μl of EBM-2 Basal Medium (Lonza) supplemented with 1% FBS on top of the confluent HUVEC monolayer or in empty wells. Unattached SUM149 cells were removed by washing three times with PBS and attached cells counted in three random fields/well (n=6). The average percentage relative adhesion vs control samples set to 100% is presented.

Example 10. ADP Isotyping, Binding Kinetics and Epitope Binning

An SBA Clonotyping System-HRP kit (SouthernBiotech, 5300-05) was used to determine the isotype subclass and type of light chain for each ADP antibody. Briefly, anti-mouse-Fc capture antibody (1 μg/mL) in PBS (pH 7.4) was used to coat 96-well ELISA plates overnight at 4° C. Plates were then washed three times with PBST and blocked with 1% BSA in PBS at room temperature for 1 hour. Following another 3 washes with PBST, plates were exposed to 1:50, 1:500 and 1:5000 diluted or undiluted supernatants from second round stable ADP producing hybridoma subclones in blocking buffer for 1 hour at 37° C. HRP-conjugated secondary antibodies (anti-mouse Ig, mouse IgA, mouse IgG1, mouse IgG2a, mouse IgG2b, mouse IgG3, mouse IgM, mouse κ and mouse λ) at a dilution of 1:100 in blocking buffer were added to appropriate wells of the plate and incubated for 1 hour at 37° C. Plates were washed three times with PBST and signal developed with addition of 100 TMB for 15 minutes at room temperature. This was followed by quenching with 50 μl 1N HCl. Signal was read on a plate spectrophotometer at 450 nm. Wells incubated with an unconjugated anti-mouse Ig secondary were used to determine background signal. Positive signal in a single isotype, i.e., either IgG1, IgG2b or IgG2c subclass and light chain type for each hybridoma supernatant confirmed single subclone origin of each ADP produced.

Biacore Surface Plasmon Resonance Assays for ADP Binding Kinetics to rHuADAM8

For Biacore assays, each ADP was used as the ligand in a multiple cycle kinetics method performed on a Biacore™ T200 surface plasmon resonance system (GE Healthcare Life Sciences) machine. ADP proteins were captured using anti-mouse Fc IgG attached to a dextran matrix, and rHu-ADAM8 (Acro Biosystems, AD8-H5223) added as the analyte at concentrations ranging from 3.75 nM to 200 nM. HBS-EP+ (10 mM HEPES, 0.15 M NaCl, 3 mM EDTA, 0.05% Surfactant P20) running buffer was passed at a flow rate of 30 μl/min and antigen injected at 30 μl/min. The association and dissociation phases were carried out for 180 s and 600 s, respectively. Surface regeneration was performed for 30 s at 30 μl/min of Glycine pH 1.5. Values for association rate constant ($k_a$), dissociation rate constant ($k_d$) and equilibrium dissociation constant (KD) were calculated through the Biacore™ T200 Software.

ADP Epitope Binning by Competitive ELISA

Each purified ADP (1 μg/ml) was individually fixed on a 96-well plate overnight at 4° C. and then blocked with 1% BSA in PBST for 1 hour at 37° C. Plates were then washed three times with PBST and interacted for 1 hour with a pre-incubated mixture of biotinylated rHuADAM8 (AD8-H5223) and excess of a second competitor ADP ($ADP_C$) or control mIgG. Washed plates were then incubated with Streptavidin-HRP (1:5000 dilution) for 30 minutes at 37° C. Plates were developed with addition of 100 μl TMB for 10 minutes at room temperature, followed by quenching with 50 μl 1N HCl. OD at 450 nm was read on a plate spectrophotometer and the extent of competition between the two ADPs determined in each case. Values for percentage of competition were calculated using the formula: (1-$OD_{450}$ $ADP_C$/$OD_{450}$ control mIg) %. If the two antibodies recognize the same region of ADAM8, the numerator $OD_{450}$ $ADP_C$ will be lower, yielding a higher percentage indicative of epitope similarity. High levels of cross competition were defined as equal to or greater than 75% and used to delineate 5 ADP epitope clusters.

Example 11. siRNA Knockdown Analyses

Transient RNAi-mediated ADAM8 knockdown was performed as previously described with the following short interfering RNAs (siRNAs) (QIAGEN) (Romagnoli et al., *EMBO Mol Med,* 6(2): 278-294, 2014): siADAM8 RNA-1 (siA8-1, Hs_ADAM8_6): 5'-CGGCACCTG-CATGACAACGTA-3' (SEQ ID NO: 101); siADAM8 RNA-2 (siA8-2, Hs_ADAM8_7): 5'-CTGCGCGAAGCTGCTGACTGA-3' (SEQ ID NO: 102); AllStar negative control siRNA (Qiagen) was used in each experiment as a non-silencing control siRNA (siCtrl). siRNAs (10 nM) were introduced in cells using Lipofectamine RNAi Max Transfection Reagent (Invitrogen) by reverse transfection according to the manufacturer's protocol. Reduced ADAM8 levels were confirmed by Western blotting, as above. For functional assays, transfected cells were analyzed within 24 hours.

Soft Agar Assays

Soft agar assays were performed to evaluate the role of ADAM8 in anchorage independent growth of SUM149 TNBC cells as we have previously described (Mineva et al., *PLoS One,* 8(9): e73464, 2013). Briefly, $1.0\times10^5$ SUM149 cells in a mix of 0.4% Bacto Agar (BD Biosciences) in complete media were plated in triplicate on six-well dishes pre-coated with a 1:1 mix of 2× Ham's F-12 medium supplemented with 10% FBS and 1.6% Bacto Agar. Cells were fed three times per week with complete Ham's F-12 medium. After 3 weeks, cells were stained overnight with 0.2 mg/ml iodonitrotetrazolium chloride (Sigma) and photographed at 40× magnification. Colonies with diameters of approximately 20 microns or greater were counted using ImageJ software (NIH).

Matrigel Outgrowth Assays

Matrigel outgrowth assays were carried out to evaluate the role of ADAM8 in invasion of SUM149 cells through a collagenous extracellular matrix as described previously (Belguise et al., *Cancer Res,* 67(12): 5763-5770, 2007). Matrigel solution (BD Biosciences, 356231) was diluted with cold serum-free Ham's F-12 medium to a working concentration of 6.3 mg/ml and kept on ice until use. Two hundred microliters of diluted Matrigel was added to each well of a 24-well dish and the dish was subsequently incubated at 37° C. for 30 minutes to allow the Matrigel to solidify. For each sample, 10 μl of a single-cell suspension containing $5.0\times10^3$ SUM149 cells in Ham's F-12 media were then mixed with 190 μL of Matrigel at 4° C. and added to the preset Matrigel layer in 24-well plates, which was again incubated at 37° C. for 30 min. Lastly, 500 μL of complete growth SUM149 medium was layered on top of the cells. Cultures were incubated for 10 days and photographed at 20× magnification.

Spheroid Formation Assays

Spheroid formation assays were performed to evaluate the role of ADAM8 in SUM149 cell 3D growth in suspension. Briefly, single cell suspensions of $2\times10^4$ SUM149 cells in complete Ham's F-12 medium were plated, in triplicate, on ultra-low attachment 6-well dishes (Costar) and incubated at 37° C. After 5 and 7 days of culture, primary spheres were photographed at 20× magnification. Using a grid drawn on the bottom of the 6-well plate and the microscope objective ruler, spheroids with a diameter of 125 microns or greater were counted manually. Values shown are averages ±S.D.

Example 12. Xenograft Models for Evaluation of ADP Activity in TNBC

Tumor Formation Model

The ability of ADP13 to inhibit the establishment of ADAM8-positive SUM149 TNBC cell line derived tumors was assessed in vivo using a tumor formation mouse model. Briefly, eight-week-old female Non-Obese Diabetic/Severe Combined Immunodeficient (NOD/SCID) mice were implanted with $0.5\times10^6$ SUM149 cells in 30 μl of a 1:1 dilution of Matrigel (BD Biosciences) and Ham's F-12 medium, in the fourth inguinal mammary fat pad (MFP). ADP13 was administered at 1.5 mg/kg or 4.5 mg/kg vs control isotype matched IgG1 (G3G4 clone) at 4.5 mg/kg using i.p. injection 2×/week starting at the day of cell implantation into the MFP. Primary tumor growth was monitored by caliper measurement twice a week. Tumor volumes were calculated as (Length×Width$^2$)/2 and the mean±Standard Error of the Mean (S.E.M.) presented. Mice were sacrificed when tumors in the control group approached a volume of ~1 cm$^3$. Statistical analysis was performed using a two-tailed Student's t-test.

Pre-Existing Primary Tumor Growth Model

ADP-mediated inhibition of established, rapidly growing, primary TNBC tumors was assessed using pre-existing cell line-derived tumor mouse models. Briefly, ten-week-old female NOD/SCID mice were implanted with $0.5\times10^6$ TNBC cells (MDA-MB-231 or SUM149) in 30 μl of a 50% Matrigel (BD Biosciences) solution (1:1 Matrigel dilution+serum-free cell medium) in the fourth inguinal MFP. Tumors were allowed to form and grow undisturbed initially. When tumors reached ~50-75 mm$^3$, mice were randomly distributed into groups and treated with ADP antibody or isotype-matched control IgG in doses ranging from 1 to 30 mg/kg, as indicated. Antibody was administered 3×/week using i.p. injection. Tumor volume was measured 3×/week using calipers and calculated, as above. Mice were sacrificed when average tumor growth in the control group approached 1 $cm^3$. Significance was determined using a two-tailed Student's t-test.

Neoadjuvant Treatment Protocol

To test whether ADP monotherapy can decrease metastasis and improve outcome, a neoadjuvant treatment, surgical resection protocol was performed. MDA-MB-231-luciferase tagged cells, which preferentially metastasize to the bone, were injected in the MFP of ten-week old female NOD/SCID mice as above. Once tumors reached a volume of ~50-75 $mm^3$, mice were treated with 10 mg/kg ADP2, ADP13 or their control IgGs in i.p injection 3×/week. Tumors in all treatment groups were surgically removed when a volume of ~200 $mm^3$ was reached in the control IgG treated group (about a week after treatment initiation). Following surgical removal of tumors, antibody treatment was continued for 12 weeks. Mouse health was assessed 3×/week and recurrence of a tumor at the primary site detected using palpation. Mice were sacrificed when recurrent tumors reached 0.9 $cm^3$. Kaplan-Meier curves for disease-free survival and overall survival were generated using Prism software. Statistical significance was determined using a Log rank test.

At sacrifice, either due to the presence of a large recurrent tumor or at the end of the experiment (Day 88 post-resection), mice were also assessed for metastases using biophotonic imaging of dissected bones on a Xenogen IVIS-200 machine for detection of activity from the luciferase tag expressed in MDA-MB-231 cells. Total flux indicates the presence and extent of metastasis in dissected bones. Representative images of hind leg bone metastases are shown, e.g., in FIGS. 22B, 22D, 28C, 28D, 31C and 31D. A grey color on the bone indicates a small to medium metastasis. A black color on the bone corresponds to a large metastatic lesion. A white color on the bone indicates no metastasis.

Combinatorial Treatment Protocol

In the clinical setting, new therapies are tested initially in combination with standard of care chemotherapy so that patients are not put in a position of having to choose between a proven, while not necessarily efficient, therapy and a new experimental drug. In the preclinical setting, this strategy is mimicked by testing combination regimens in tumor regression and regrowth mouse models, where full disease regression is driven by multiple cycles of chemotherapy and regrowth delayed by the new agent being studied (Volk et al., *Neoplasia,* 10(6): 613-623, 2008).

To test ADP2 and ADP13 therapy under these conditions, a combinatorial regimen with the TNBC standard-of-care chemotherapeutic Nanoparticle Albumin-Bound Paclitaxel (NPAC, brand name Abraxane®) was selected. NPAC is more stable than unmodified paclitaxel and has demonstrated greater efficacy in clinical trials compared to both paclitaxel or docetaxel (Gradishar et al., *J Clin Oncol,* 23(31): 7794-7803, 2005; Gradishar et al., *J Clin Oncol,* 27(22): 3611-3619, 2009).

To determine an appropriate NPAC dose, NOD/SCID mice bearing MDA-MB-231-luciferase tagged cell line derived tumors, obtained as above, were treated with 5 consecutive i.v. doses (1 cycle) ranging up to 30 mg/kg NPAC (in carrier saline). The maximum effective dose of NPAC with no substantial adverse effects was 10 mg/kg in these mice [Tumor Growth Inhibition (TGI)=78%;]. Thus, to fully regress primary tumors, for the combinatorial studies 2 consecutive cycles of NPAC were performed.

Female NOD/SCID mice were injected with MDA-MB-231-luciferase-tagged cells as described above and tumor growth followed. On Day 19 after cell implantation, mice bearing well-established, rapidly growing ~150 $mm^3$ tumors were divided into 4 groups. Treatment was initiated on Day 20 to the groups as follows: a) Isotype-matched control IgG+Saline, b) ADP+Saline, c) IgG+NPAC and d) ADP+NPAC. NPAC was administered in 2 cycles of 5 consecutive i.v. treatments of 10 mg/kg NPAC with one week of rest in between; an equivalent volume of vehicle saline was also given. ADP2, ADP13 or their respective isotype-matched controls (IgG2b and IgG1) were administered i.p. 3×/week. Antibodies were administered using the dosing regimen proposed from Pharmacokinetic (PK) studies to achieve steady state concentrations in the blood of mice (see below). A first loading dose of 20 mg/kg was followed by maintenance doses of 10 mg/kg 3×/week. Antibody treatment was started concurrently with the first NPAC cycle and continued throughout the time course. Tumor volume (Mean±S.E.M.) over time is presented. The endpoint for evaluation of TGI was an average tumor volume approaching 1 $cm^3$ in the IgG+Saline vs ADP+Saline groups, and in the IgG+NPAC vs ADP+NPAC groups. Percentages indicate level of inhibition of tumor growth vs corresponding control group. Statistical significance was determined using a Student's t-test.

When individual mice in the experiment reached humane endpoint (the IACUC protocol allowed tumor volume of ~1.5 $cm^3$ or a size of ~2.0 cm in any one direction for this model), survival lengths (in days) were plotted into Kaplan-Meier curves comparing IgG+Saline vs ADP+Saline and IgG+NPAC vs ADP+NPAC. Statistical significance was determined using a Log-rank test. At sacrifice, all bones were dissected and examined for metastases using biophotonic imaging for luciferase activity. IgG+Saline vs ADP+Saline and IgG+NPAC vs ADP+NPAC groups were analyzed as above.

Example 13. PK Studies of ADP2 and ADP13

PK studies of ADP2 and ADP13 in mice were performed using ELISA assays as described below. First, to establish a relationship between optical density (OD) reading and antibody concentration, ADP2 and ADP13 standard curves were established. Blood samples from untreated NOD/SCID mice (n=6) were collected by submandibular puncture according to IACUC guidelines. Blood samples (100 μl) were collected from each mouse in Eppendorf tubes containing 40 μl of EDTA (0.5M) and pooled together. Tubes were then centrifuged at 1,300 g for 15 minutes and the resulting top layer of clear plasma was removed, aliquoted and frozen at −80° C. until time of analysis. Next, 96-well ELISA plates (Medisorp) were coated overnight at 4° C. with 100 μl of rHuADAM8 or BSA at 1.0 μg/ml in reagent diluent (10% FBS in 1×PBS, pH 7.4). Plates were washed three times with wash buffer (1×PBS with 0.05% Tween 20) and blocked with 100 μl of Blocking solution (1% BSA in 1×PBS with 0.05% Tween 20) for 1 hour at 37° C. Then, 100 μl of plasma samples (1:5000 dilution in reagent diluent) spiked with either ADP2, ADP13 antibodies or their isotype matched IgGs (8 concentrations ranging from 0.021 nM to 0.250 nM), or left untreated, were added to wells. Microplates were incubated for 2 hours at 37° C. Bound primary antibodies were detected with a goat anti-mouse IgG (whole molecule)-horseradish peroxidase conjugate (1:2500 in reagent diluent) for 30 minutes at 37° C. Signal was developed using a 1-Step Ultra TMB-ELISA Substrate Solution (Thermo Fisher Scientific) as per manufacturer's recommendations. Briefly, 100 μl were added to each well for 20 minutes in the dark. The reaction was stopped with 50 μl/well 2N sulfuric acid, and OD read at 450 nm on a microplate reader. Specific binding was defined by subtraction of the binding observed in wells with plasma from untreated mice (unspecific binding) from that observed in the wells with spiked samples. Control IgG samples were negative for binding as expected.

Three independent ELISA assays for each antibody were performed and analyzed separately before the results were averaged to establish robust concentration standard curves for ADP2 and ADP13. These assays followed current FDA bioanalytical recommendations. Specifically, over 6 concentrations of each ADP were used and intra- and inter-assay precision with less than 20% coefficient of variation and accuracy within 20% of the nominal concentration were confirmed.

Generation of these concentration standard curves enabled PK analysis of ADP2 and ADP13 following injection in mice. Female NOD/SCID mice (n=63) were weighed the day before injection. Each animal received a single i.p. injection of ADP2 or ADP13 at a dose of 10 mg/kg. Following sacrifice using $CO_2$ asphyxiation and a secondary method of cervical dislocation, blood samples (n=3 mice per time point) were collected by intra-cardiac puncture at 2 hours, 4 hours, 6 hours (only for ADP2), 8 hours, 24 hours, 48 hours, 96 hours, 7 days, 14 days, and 21 days. Approximatively 500 μl of blood was collected in an Eppendorf tube containing 70 μl of EDTA (0.5 M, pH 8.0) and plasma was isolated as described above. The specific concentration values Mean (nM)+/−S.D. of ADP2 or ADP13 protein in plasma were determined in three independent ELISA runs using the previously established ADP standard curves. These values were then used to determine the PK profiles for both antibodies using SAS software. Ln (concentration) vs time for ADP2 and ADP13 was plotted. Based on visual evaluation, the best estimate on what points constitute the terminal beta phase was made.

For ADP2, this was 96 hours while for ADP13 it was 48 hr. Linear regression was applied on the plots to determine the elimination rate constant (Ke), which was then used to calculate the $T_{1/2}$ in hours and days. The area under curve (AUC) from the origin out to the last observed quantifiable concentration ($C_{last}$=504 hr) was determined using the linear trapezoidal method. The extrapolated area from 504 to infinity was calculated as $C_{last}$/Ke, which was added to the truncated AUC to yield the total AUC. The clearance (Cl) which is determined physiologically by blood flow to the organ that metabolizes or clears the drug, was calculated as the ratio Dose/(total AUC) converted to ml/min. Volume of distribution (Vd) was not calculated as the absolute systemic availability with the extravascular dosage route is unknown. The decay pattern was bi-exponential, and a "non-compartmental" approach was used to calculate the above values.

Based on the PK parameters obtained for the two antibodies, a treatment regimen composed of a loading dose of 20 mg/kg ADP followed by maintenance doses of 10 mg/kg 3× per week was proposed to establish steady state concentrations needed for long term treatment experiments. To confirm that the proposed dosing regimen results in the desired steady state, female NOD/SCID mice (n=30) received an i.p. injection of either 20 mg/kg ADP2 or ADP13 followed by injections of 10 mg/kg on days 2, 4 and 7. Blood samples (n=3 mice per time point) were collected by intra-cardiac puncture 2 hours after each antibody injection. On day 7, blood samples were also collected from 3 mice before the time of next dosing. Plasma was isolated and analyzed as above for antibody concentration over time, which confirmed the effectiveness of the regimen.

Example 14. ADP2 and ADP13 Cloning and Sequencing/CDR Determination and Chimera Synthesis RNA was extracted from hybridoma lines and subjected to 5' cDNA synthesis, and 5' RACE using primers specific for amplifying mouse $V_L$ and $V_H$ chain DNA. The products were analyzed by agarose gel electrophoresis. Bands running in the correct positions, i.e., between 500-700 base pairs, were visualized for each hybridoma, and cloned using TOPO (Thermo Fisher Scientific). These cloned DNAs were PCR-amplified, and purified by gel electrophoresis. Individual cloned DNAs were recovered from the gels and subjected to DNA sequencing. Analysis of multiple samples per $V_L$ and $V_H$ chain DNA confirmed the findings. CDR analysis of the sequencing data was performed using VBASE2 (vbase2.org). The DNA and resulting amino acid sequence for the $V_L$ and $V_H$ chains are presented.

Chimeras of the $V_L$ and $V_H$ chain DNAs were made with germline human IgG1 $C_L$ and $C_H$ regions, respectively using DNA ligation. Resulting chimeric chADP2-IgG1 (SEQ ID NO: 82 and SEQ ID NO: 83) and chADP13-IgG1 (SEQ ID NO: 84 and SEQ ID NO: 85) proteins were synthesized in CHO cells, and affinity purified using Protein A. Purified chimeric proteins were tested for their ability to bind ADAM8 (using ELISA and FACS) and to inhibit ADAM8 MP and DI domain activity (in CD23 cleavage and transendothelial migration assays), as described above.

Example 15. Epitope Mapping of ADP2 and ADP13 Binding to Human ADAM8

Mapping to Native ADAM8 Using Deletion Construct Analysis

To delineate the epitope binding regions of ADP2 and ADP13, FACS analysis was performed with HEK293 cells stably expressing either EV DNA, full-length ADAM8 or remnant ADAM8 (which lacks the pro- and MP domains). Cells were prepared using the basic FACS protocol described above, with 2 μg of ADP2 or ADP13 as the primary antibodies and 1.25 μg of Alexa Fluor 488 donkey anti-mouse IgG (H+L) (Life Technologies, A-21202) as the secondary antibody, and analyzed on a BD FACSCalibur™ machine. ADP2 and ADP13 were found to bind to both full-length and remnant ADAM8 expressing cells. Given the immunogen used to generate these antibodies contained only the MP and DI domains, and the DI domain is the only common region between the two expression constructs used in this analysis, the data point to the DI domain as the broad epitope region for ADP2 and ADP13 binding.

Mapping by Hydrogen/Deuterium Exchange (HDX)

To confirm the region of ADP binding and map it at the peptide level HDX analysis was performed. First, pepsin/protease XIII digestion and liquid chromatography-mass spectrometry (LC-MS) with rHuADAM8 were used to generate peptides and assess the extent of protein coverage provided by this method. Recombinant human ADAM8 (8 μg, 1031-AD-020, R&D Systems) in 130 μl control buffer (50 mM phosphate, 100 mM sodium chloride at pH 7.4) was denatured by adding 130 μl of 4 M guanidine hydrochloride, 0.85 M TCEP buffer (final pH 2.5) and incubating the mixture for 3 minutes at 10° C. The mixture was then subjected to pepsin/protease XIII digestion using a pepsin/ protease XIII (w/w, 1:1) column. The resultant peptides were analyzed using an ultra-performance (UP) LC-MS system comprised of a Waters Acquity UPLC coupled to a Q Exactive plus Hybrid Quadrupole-Orbitrap Mass Spectrometer (Thermo). The peptides were separated on a 50 mm×1 mm C8 column with a 16.5 min gradient from 2-30% solvent B (0.2% formic acid in acetonitrile). Solvent A was 0.2% formic acid in water. The injection valve, enzyme column and their related connecting tubing were inside a cooling box maintained at 20° C. The second switching valve, C8 column and their related connecting stainless steel tubing were inside a chilled circulating box maintained at −6° C. Peptide identification was done through searching MS/MS data against the human ADAM8 sequence with Mascot. The mass tolerance for the precursor and product ions were 7 ppm and 0.02 Da, respectively. Sequence coverage of 69.7% to 74% was achieved for rHuADAM8, primarily due to autocatalytic clipping of the prodomain, as expected. Next, HDX with pepsin/protease XIII digestion was carried out.

Human ADAM8 (8 μg in 20 μl) or 20 μl ADAM8 mixed with ADP2, ADP13 or ADP3 (8 μg: 24 μg) was incubated with 110 μl deuterium oxide labeling buffer (50 mM sodium phosphate, 100 mM sodium chloride at pH 7.4) for 0 s, 60 s, 600 s, or 3600 s at 10° C. Hydrogen/deuterium exchange was quenched by adding 130 μl of 4 M guanidine hydrochloride, 0.85 M TCEP buffer (final pH 2.5). Subsequently, the quenched samples were subjected to on column pepsin/protease XIII digestion and LC-MS analysis as described above. The mass spectra were recorded in MS only mode. Raw MS data was processed using HDX WorkBench software for the analysis of hydrogen/deuterium exchange MS data (Pascal et al., *J. Am. Soc. Mass Spectrom.* 23 (9), 1512-1521, 2012). The deuterium levels were calculated using the average mass difference between the deuterated peptide and its native form (t0). The deuterium levels at the various peptides were monitored from the mass shift on LC-MS. Deuterium buildup curves over exchange time for all peptides were plotted and ADAM8 sequences with reduction in deuterium uptake levels upon binding to antibody identified.

Mapping by Shotgun Mutagenesis

The specific amino acid residues that mediate the interaction between ADP2 or ADP13 and ADAM8 were identified using shotgun mutagenesis paired with high-throughput flow cytometry. This was performed as described in Davidson and Doranz (Immunology 143:13-20, 2014). Specifically, a library of human ADAM8 expression constructs was prepared with single alanine mutations introduced into each amino acid residue from 192 to 497 except when alanine was the original amino acid—in which case, it was mutated to serine. This mutation library comprises the MP and DI domains of ADAM8 and was generated by high-throughput, site-directed mutagenesis. The constructs were transfected into HEK293 human embryonic kidney cells and arrayed in 384-well microplates. Only one mutated ADAM8 protein was expressed, in its native configuration, in an individual clone. These individual clones were grown in culture and their expression on the surface of HEK293 cells was confirmed using flow cytometry with a positive control anti-ADAM8 antibody (Control Ab) whose binding is not affected by the amino acid changes. Clones were then screened for binding to either ADP2 or ADP13 as test antibodies to determine which amino acid changes affect test antibody binding to ADAM8. Additionally, HEK293 cells were transfected with a wild-type (WT) ADAM8 construct or empty vector DNA, as a positive and negative control, respectively. A variety of experimental parameters were optimized for high-throughput flow cytometry including blocking buffer, and primary and secondary antibody concentrations, to identify the optimal conditions for screening. Through these studies ADP2 and ADP13 were determined to be high affinity binding antibodies. Notably, for antibodies that bind with high affinity, it is harder to identify critical amino acid binding residues unless stringency is increased.

Thus, for these studies antigen-binding fragments (Fabs) of ADP2 and ADP13, which bind with lower affinity than the full antibody, were generated. In addition, higher binding stringency conditions were tested, such as increased pH, salinity, and temperature, and/or increased washing, to weaken binding sufficiently to allow identification of critical binding residues in flow cytometry. The final experimental flow cytometry conditions were: primary antibody incubation with ADP2 Fab (0.50 μg/ml), ADP13 Fab (5.00 μg/ml) and Control Ab (0.16 μg/ml) for 60 minutes in flow cytometry buffer containing 10% goat serum in PBS ($Ca^{2+}$ and $Mg^{2+}$ free). Secondary antibody incubation was performed for 30 minutes with an Alexa Fluor 488 AffiniPure F(ab')2 fragment specific goat anti-mouse IgG (1:200, Jackson ImmunoResearch 115-546-006) for detection of ADP Fab binding and Alexa Fluor 488 AffiniPure goat anti-mouse IgG (H+L) [1:400, Jackson ImmunoResearch 115-545-003] for Control Ab binding. Samples were washed three times after primary antibody incubation and twice after secondary antibody incubation with PBS ($Ca^{2+}$ and Mg' free). Next, HEK293 cells expressing WT or mutated ADAM8 proteins or EV DNA were incubated with ADP2 or ADP13 Fabs or Control Ab at their optimal concentrations. Fab binding was detected using Alexa Fluor 488-conjugated secondary antibodies and mean cellular fluorescence determined using the Intellicyt iQue flow cytometry platform. Mutated residues were identified as being critical to ADP2 or ADP13 epitope if they did not support the reactivity of the test Fabs but did support the reactivity of the reference Control Ab. This counter-screen strategy facilitates the exclusion of mutants that are locally misfolded or that have an expression defect. Binding of each test Fab to each mutant clone in the alanine scanning library was determined, in duplicate, by high-throughput flow cytometry. For each point, background fluorescence was subtracted from the raw data and antibody reactivity normalized to WT ADAM8.

To identify primary critical clones/residues, a threshold of Control Ab binding >70% of WT and test antibody binding <20% of WT binding was applied. Residues that did not meet the latter requirement but that still demonstrated substantially reduced test Fab binding and proximity to critical residues were identified as secondary important residues of the epitope. Lastly, the positions of the ADP2 and ADP13 critical and secondary binding residues were mapped on an ADAM8 crystal structure model that is based on the structure of vascular apoptosis-inducing protein-1 (PDB ID #2ERP, Takeda et al., *EMBO J.* 25:2388-2396, 2006).

Figure 2:
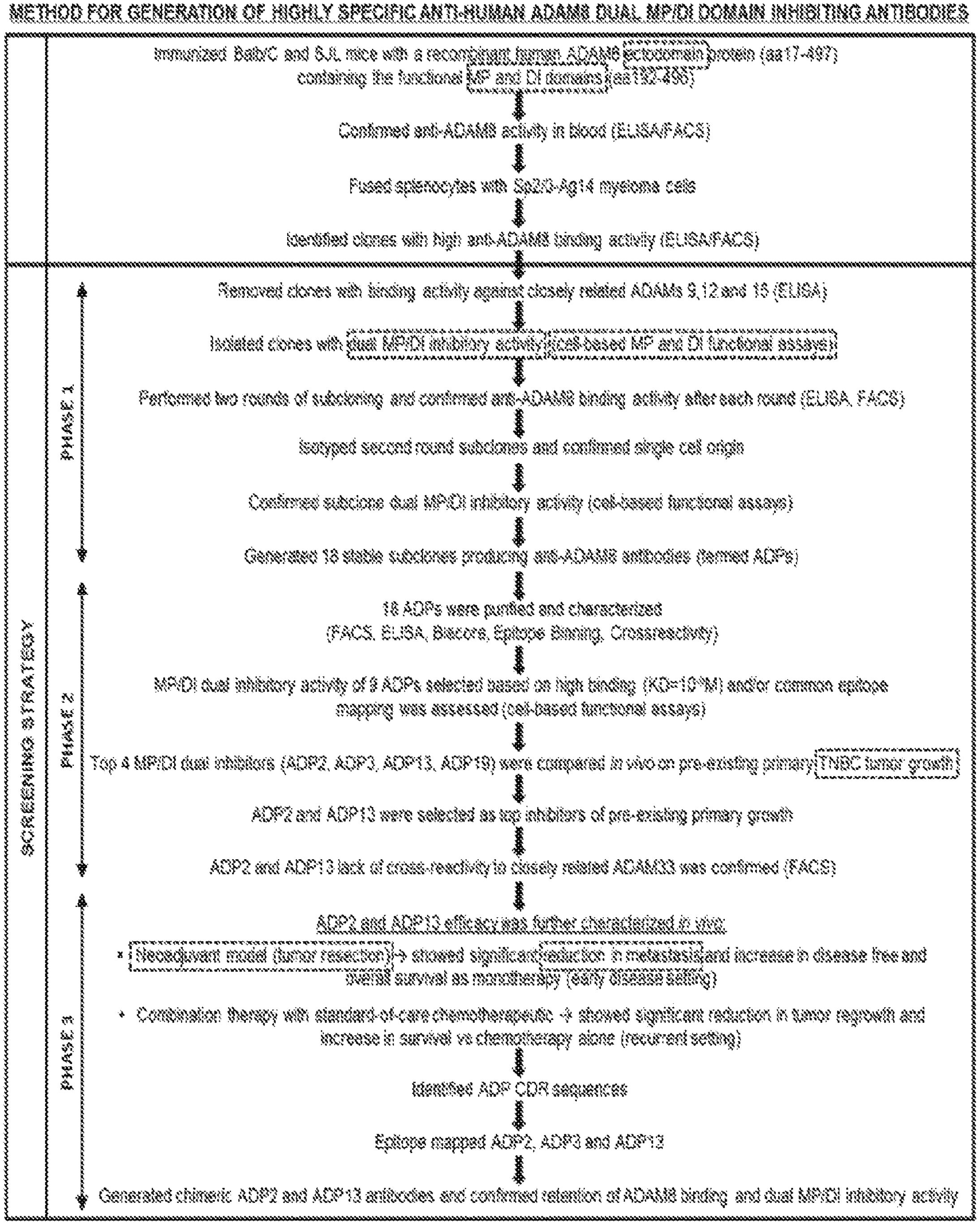
FIG. 2 is a diagram showing the steps used to generate highly specific human ADAM8 dual MP and DI domain inhibitory mouse monoclonal ADP antibodies and to select ADP2 and ADP13 as lead candidate therapeutics. Anti-ADAM8 antibodies were generated using the standard hybridoma method (indicated in top black box) followed by a complex novel screening strategy (bottom black box). The three phases of screening, performed to isolated antibodies with the desired functional characteristics, are indicated. Dotted boxes show specific methods and features described in U.S. Patent Publication No. 2016/0130365 as necessary for the generation of a successful Triple-Negative Breast Cancer (TNBC) therapeutic antibody.

Example 16. Preparation and Isolation of Highly Specific Anti-ADAM8 Dual MP/DI Inhibitory Antibodies Hybridoma Method of Antibody Preparation Highly specific, mouse monoclonal antibodies (mAbs) were prepared against human ADAM8 using a traditional hybridoma method combined with a unique three-phase screening approach (as outlined in FIG. 2). To make the anti-ADAM8 hybridomas, purified recombinant human ADAM8 ectodomain protein (aa17-497) (rHuADAM8), containing biologically active MP and DI domains as present on the outside of cancer cells, was injected into Balb/c and SJL mice, in order to give the broadest range of immune response. Anti-ADAM8 activity was confirmed in the blood of injected mice by ELISA [binding to rHuADAM8] and by FACS (binding to HEK293 cells ectopically expressing native human ADAM8). Following fusion of mouse splenocytes to Sp2/0-Ag14 myeloma cells, supernatants from the resulting hybridoma cells were screened by ELISA and FACS and clones expressing antibodies with high anti-ADAM8 binding activity identified (FIG. 2).

Example 17. Multi-Phase Screening Strategy: Overview of Phases 1-3

Phase 1

In Phase 1 of the screening strategy, hybridoma clones making antibodies cross-reacting with human ADAM8, ADAM12, and ADAM15 proteins, which have high homology with ADAM8, were identified by ELISA using recombinant ADAM proteins. Since high specificity for ADAM8 is critical for patient treatment, clones showing cross-reactivity to any of the related ADAM8 proteins were excluded from further consideration. Hybridoma supernatants were next tested in cell-based assays. Clones demonstrating dual antagonist MP and DI activity were identified and subcloned in two rounds by serial dilution. Retention of high ADAM8 binding was confirmed in ELISA and FACS experiments following each round of subcloning. Second round (final) subclones were isotyped to confirm single clone origin and dual MP/DI activity was confirmed in cell-based functional assays. Eighteen stable subclones were generated that produce dual antagonist antibodies (termed ADPs). ADPs are of either the IgG1, IgG2b, or IgG2c subclass and contain the more common κ light chain (FIG. 3).

Phase 2

In Phase 2 of the screening procedure, purified ADPs were extensively characterized as outlined in FIG. 2. Specificity and binding activity of the antibodies to native ADAM8 was first characterized using FACS analysis with HEK293 cells, which normally do not express ADAM8, but that were transfected with either a full-length human ADAM8 expression vector or an empty vector (EV) DNA. FACS analysis, using an antibody dose-response curve, demonstrated all 18 of the ADPs have the ability to bind to ADAM8 specifically (FIG. 4). As negative and positive controls normal mouse IgG (mIgG) and a test bleed sample from a mouse injected with rHuADAM8 were used, which confirmed the specificity of the binding. An ELISA assay confirmed effective binding of purified ADPs to rHuADAM8 (FIG. 5). A Biacore binding kinetics assay was performed on each of the 18 mAbs. The association rate constant ($k_a$) and dissociation rate constant ($k_d$) indicate that the ADPs bind ADAM8 with low equilibrium dissociation constants ($K_D$) [$1.3\times10^{-9}$ M and $7.23\times10^{-8}$ M] (FIG. 5).

For epitope binning of these mAbs, a competition analysis was performed to determine whether they bind to overlapping or to distinct regions of the ADAM8 protein. Specifically, binding of an ADP to rHuADAM8 was challenged with excess of a second "competitor" ADP ($ADP_C$). Values for percentage of competition were calculated as follows: ($1\text{-}OD_{450}$ $ADP_C/OD_{450}$ control mIgG) % (FIG. 6). Thus, a higher extent of cross-competition for ADAM8 indicates a greater epitope similarity or identity.

Figure 7:
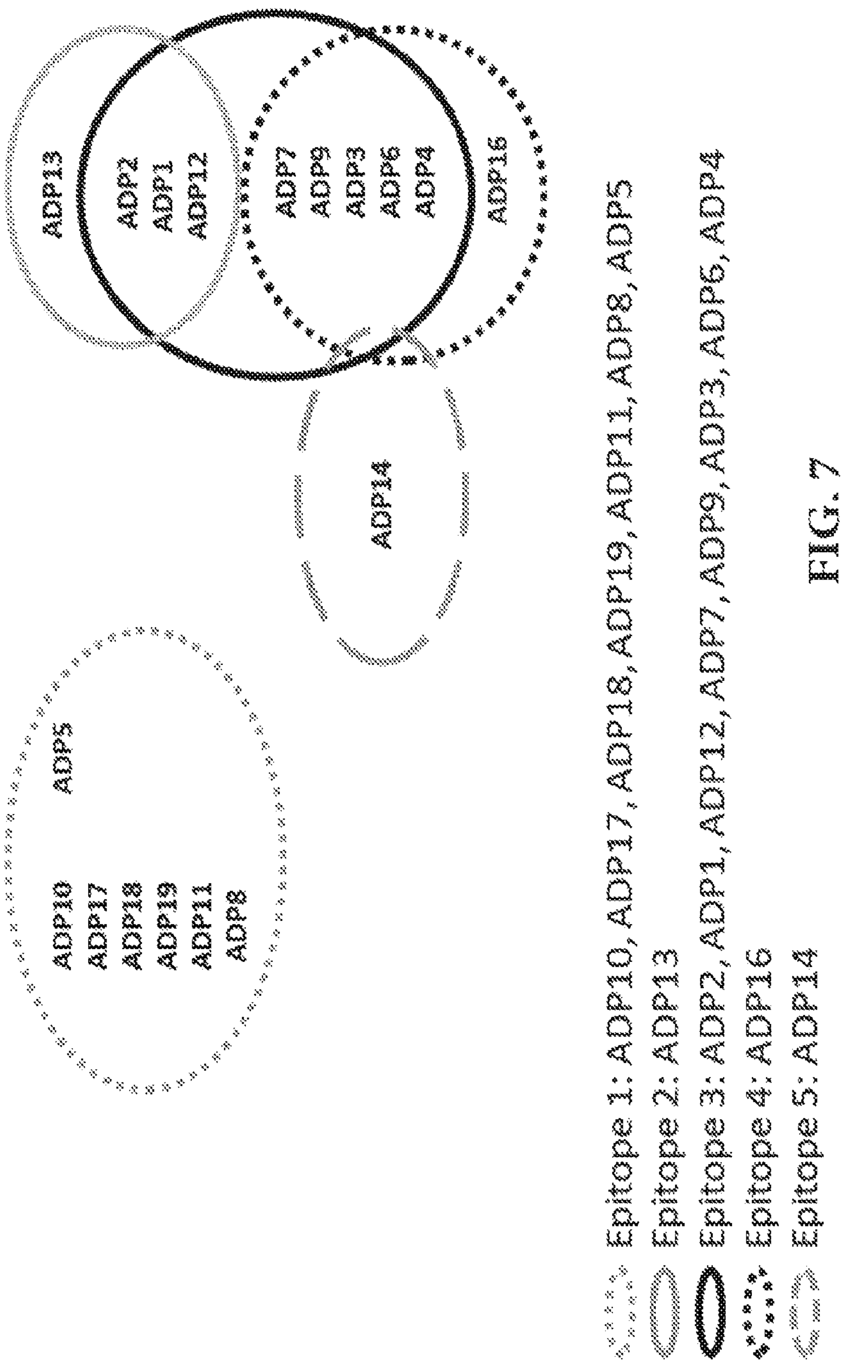
FIG. 7 is a diagram showing how the 18 ADPs can be separated into 5 epitope groups based on the epitope binning analysis in FIG. 6, four of which partially overlap.
Figure 9:
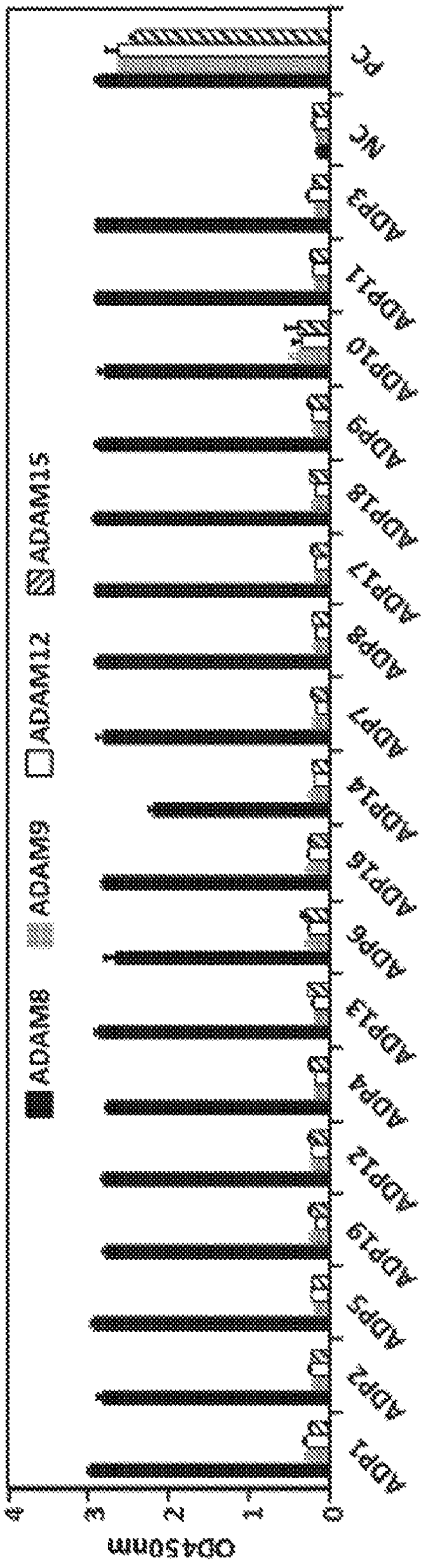
FIG. 9 is a bar graph representation of the results presented in FIG. 8, demonstrating ADPs bind ADAM8 specifically. That is, all ADP antibodies bind to ADAM8, but not to related ADAM proteins ADAM9, ADAM12 or ADAM15 in ELISA assays performed with recombinant ADAM proteins. Normal mouse IgG was used as a NC and indicates the level of general non-specific binding. A test bleed sample from a rHuADAM8 injected mouse was used as a PC.

Using a cross-competition level of equal to or greater than 75% (marked in black, FIG. 6), the ADPs could be epitope binned into 5 groups, of which 4 were partially overlapping as indicated by their respective extents of competition (FIG. 7). The lack of cross-reactivity of each of the ADPs to closely related recombinant ADAM8, ADAM12 and ADP15 protein in ELISA assays (FIG. 8) confirms the specificity of ADP binding to ADAM8, which is shown in bar graph form in FIG. 9.

Nine ADPs with high ADAM8 binding activity (KD=$1.3\times10^{-9}$ to $8.3\times10^{-8}$) and/or in the more abundant epitope groups (Epitopes 1, 2 and 3) were selected for further characterization. The MP and DI inhibitory activities of these ADPs were compared to the dual antagonist MAB1031 antibody (R&D Systems) (used in U.S. Patent Publication No. 2016/0130365) in cell-based assays (FIG. 10). The top four antibodies were then compared for their ability to inhibit pre-existing TNBC primary growth in mice. ADP2 and ADP13 were identified as lead tumor inhibitors. ADP3 and ADP19 showed incrementally lower activity under the tested conditions.

Phase 3

In Phase 3, the efficacy of antibodies ADP2 and ADP13 was further characterized in vivo in neoadjuvant and chemotherapy combinatorial mouse models (FIG. 2). Amino acid sequence analysis was performed to determine the distinctiveness of each antibody in terms of CDR sequences and binding epitope mapped for ADP2, ADP13, and ADP3. Finally, chimeric ADP2 and ADP13 antibodies were constructed and their ADAM8 binding and dual inhibitory activity tested.

Example 18. Phase 2: MP Inhibitory Activity

Figure 11:
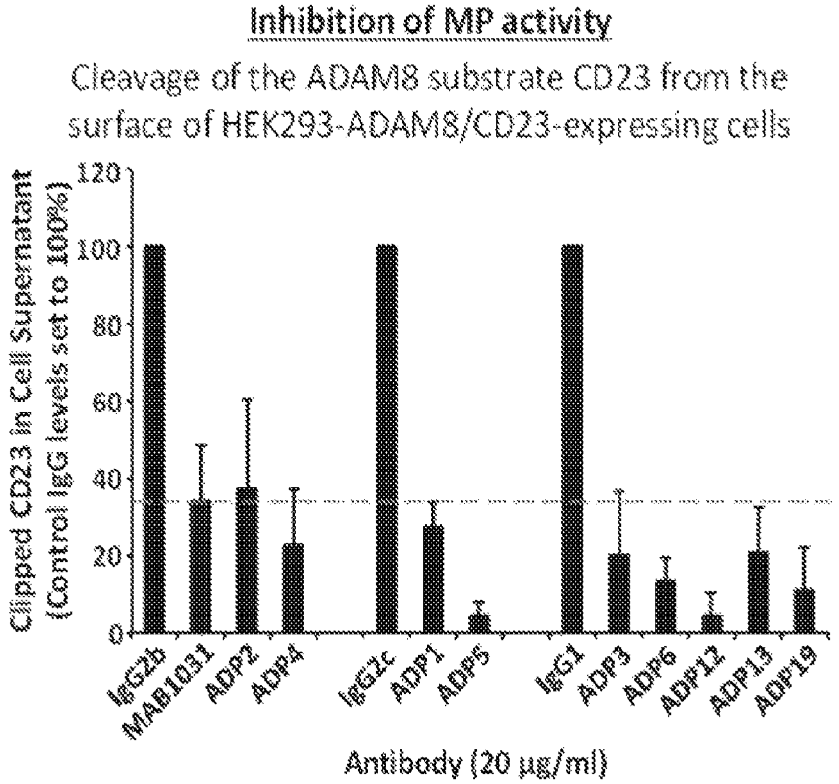
FIG. 11 is a bar graph representation of the results seen in FIG. 10 showing the MP inhibitory activity of ADP antibodies in CD23 cleavage cell-based functional assays vs their isotype-matched control IgGs. Values are Mean±S.D. from 3 independent experiments. Dashed line represents the level of activity seen with the prototype MAB1031.

To rank the ADPs that have the highest binding affinity and belong to the more common epitopes (i.e., Epitopes 1, 2, and 3, FIG. 7), we selected 9 candidates for functional cell-based assays. MP activity was assessed first using a CD23 cleavage assay. CD23 is a well-known target of ADAM8 MP activity (Fourie et al., *J Biol Chem,* 278(33): 30469-30477, 2003). ADAM8 digestion results in the release specifically of a 29 kDa CD23 fragment into the media from the surface of HEK293 cells transiently expressing a C-terminal HA-tagged CD23 and full-length ADAM8 protein that can be detected using Western blot analysis (Romagnoli et al., *EMBO Mol Med,* 6(2): 278-294, 2014; Srinivasan et al., *J Biol Chem,* 289(48): 33676-22688, 2014). Addition of an ADP antibody that inhibits the ADAM8 MP activity causes a reduction in release of cell-associated CD23 (Romagnoli et al., *EMBO Mol Med,* 6(2): 278-294, 2014; Srinivasan et al., *J Biol Chem,* 289(48): 33676-22688, 2014) (FIG. 10 and FIG. 11). All 9 of the ADP antibodies tested inhibited MP-mediated release of the 29 kDa CD23 band to an equal extent or better than the MAB1031 antibody. Thus, all 9 of the tested ADPs have potent anti-MP activity.

Example 19. Phase 2: DI Inhibitory Activity

Two assays were employed to rank the 9 candidate ADPs for their DI antagonist activity. Since active ADAM8 DI domain binds to and modifies β1-integrin on the surface of cells (Romagnoli et al., *EMBO Mol Med,* 6(2): 278-294, 2014), the first assay tested the effects of addition of an ADP on binding of CHO cells expressing α9β1 integrin to rHuADAM8. Six of the ADPs were either equal to or more effective than MAB1031 at inhibiting cell binding and therefore DI activity, with ADP2 and ADP13 showing the most robust inhibition (FIG. 10 and FIG. 12A). ADP5 and ADP6 displayed somewhat reduced activity compared to MAB1031, while ADP4 showed minimal DI inhibitory activity in this assay.

Figure 12B:
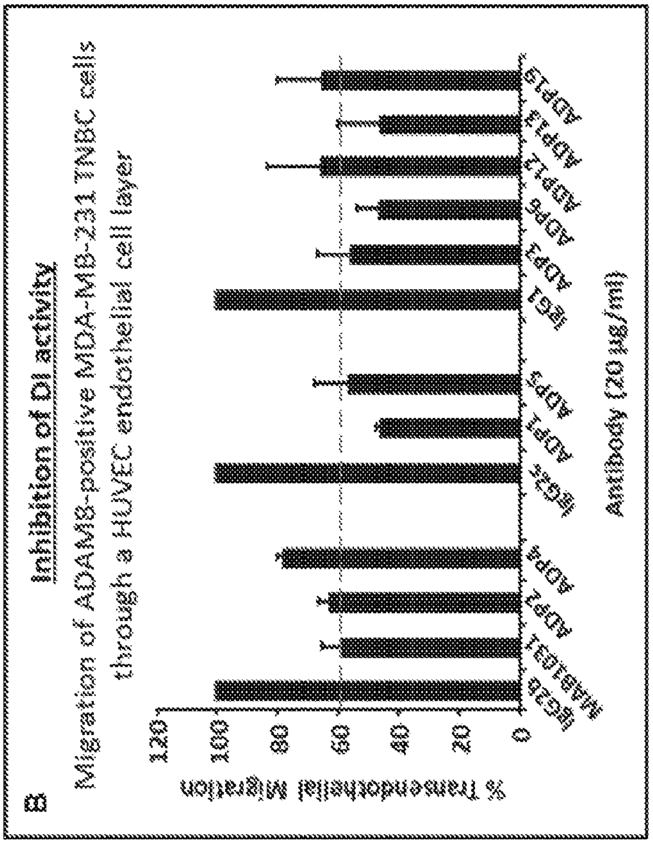
FIG. 12B is a bar graph representation of the results shown in FIG. 10 of the DI inhibitory activity of ADP antibodies in assays measuring TEM. Mean±S.D. from 3 independent experiments is given. Dashed line represents the level of activity seen with MAB1031.
Figure 12A:
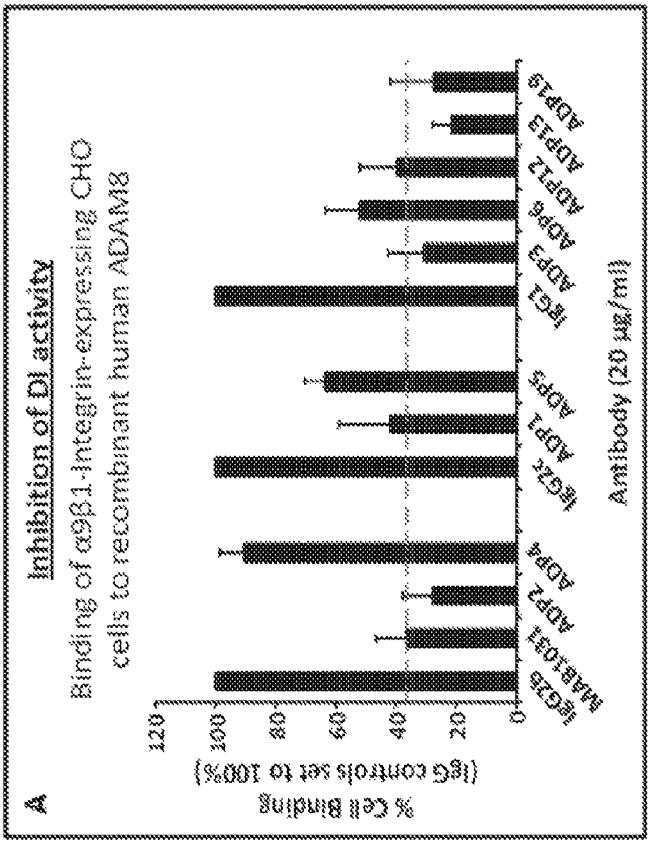
FIG. 12A is a bar graph representation of the results shown in FIG. 10 of the DI inhibitory activity of ADP antibodies in assays measuring α9β1 integrin binding to ADAM8. Mean±S.D. from 3 independent experiments is given. Dashed line represents the level of activity seen with MAB1031.

To further assess the ability of the ADPs to inhibit DI activity, they were next tested in transendothelial migration (TEM) assays (FIG. 10 and FIG. 12B). The modification of β1-integrin by the DI domain of ADAM8 is essential for the ability of a cell to bind to and move through an endothelial layer as mimicked in vitro by human umbilical vein endothelial cells (HUVEC). All ADPs, except ADP4, showed a level of inhibition of TEM that was comparable to or more effective than MAB1031. While ADP4 reduced TNBC cell migration across the endothelial layer to a measurable extent, it was only modestly effective.

Thus, eight of the tested 9 ADPs (all κ Light chain, IgGs) had potent dual antagonist activity comparable to or better than MAB1031 with respect to either MP, DI or both domains. ADP2, ADP3, ADP13, and ADP19 were selected for in vivo testing in an orthotopic MFP mouse model with pre-existing tumors based on high KD values [ADP2, $K_D$=3.3×$10^{-9}$; ADP3, $K_D$=1.8×$10^{-8}$; ADP13, $K_D$=1.3×$10^{-9}$; ADP19, $K_D$=9.1×$10^{-9}$] and significant dual inhibitory activity in cell-based assays.

Figure 13:
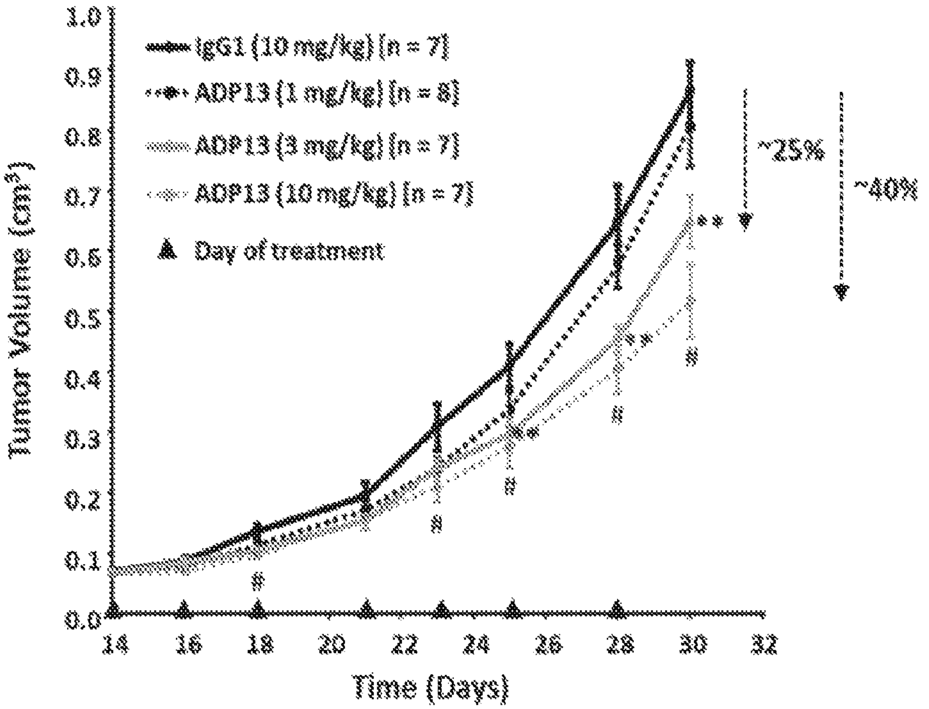
FIG. 13 is a graphic representation of the ability of ADP13 to inhibit growth of pre-existing ADAM8-positive MDA-MB-231 TNBC cell line-derived primary orthotopic tumors in a dose-dependent manner when compared to its isotype-matched control IgG1. Tumor volume (Mean±S.E.M.) over time is presented. n=number of animals/group. **, P-value <0.05 for IgG1 (10 mg/kg) vs ADP13 (3 mg/kg); #, P-value <0.05 for IgG1 (10 mg/kg) vs ADP13 (10 mg/kg) using a Student's t-test. Treatment with 10 mg/kg ADP13 resulted in a significant 40% reduction in pre-existing primary tumor growth. A higher dose of 30 mg/kg ADP13 did not provide any additional benefit (not shown).
Figure 14A:
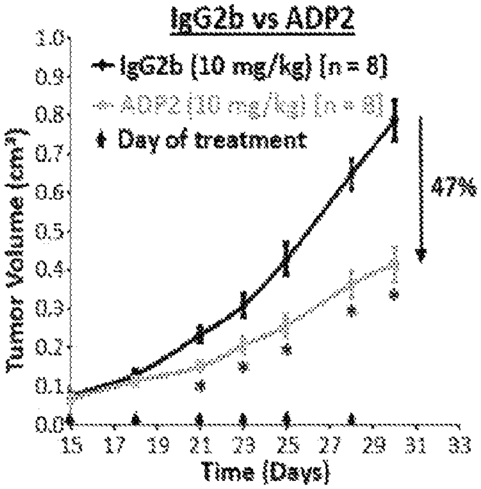
FIG. 14A is a graphic representation showing the single dose in vivo comparison of the ability of ADP2 to inhibit pre-existing MDA-MB-231 cell line-derived TNBC orthotopic tumor growth in mice, which identified ADP2 as a lead inhibitory antibody. Tumor volume (mean±S.E.M. for ADP2 vs its matched control) over time is shown. n=number of animals/group. *P-value <0.05 using a Student's t-test. Treatment with ADP2 resulted in significant reductions in tumor volume of 47%.
Figure 14B:
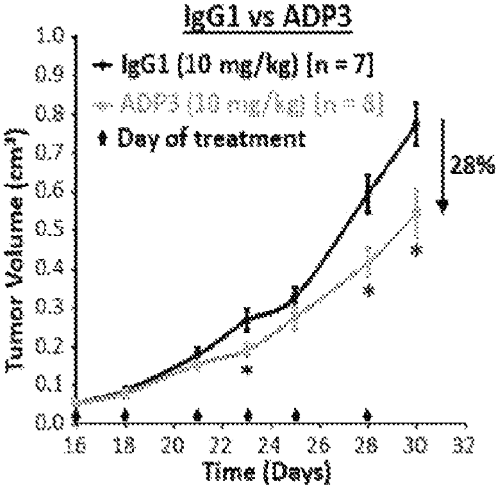
FIG. 14B is a graphic representation showing the single dose in vivo comparison of the ability of ADP3 to inhibit pre-existing MDA-MB-231 cell line-derived TNBC orthotopic tumor growth in mice. Tumor volume (mean±S.E.M. for ADP3 vs its matched control) over time is shown. n=number of animals/group. *P-value <0.05 using a Student's t-test. Treatment with ADP3 resulted in significant reductions in tumor volume of 28%.
Figure 14C:
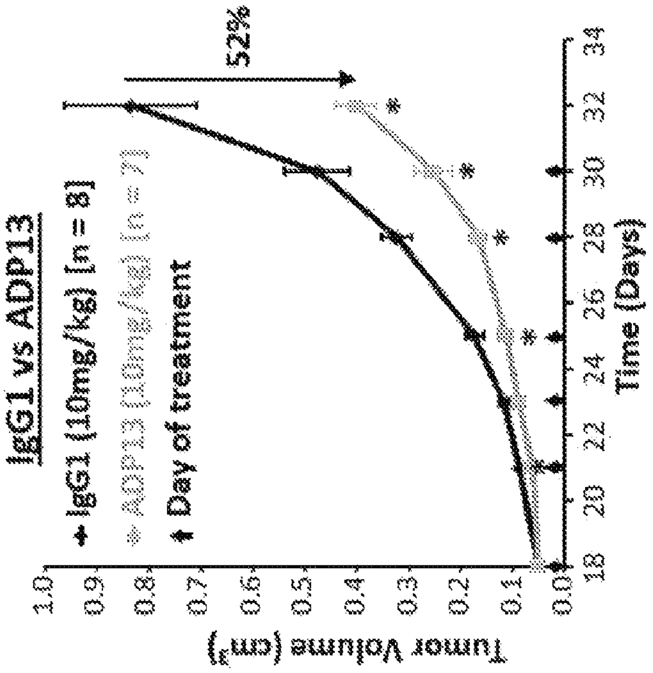
FIG. 14C is a graphic representation showing the single dose in vivo comparison of the ability of ADP13 to inhibit pre-existing MDA-MB-231 cell line-derived TNBC orthotopic tumor growth in mice, which identified ADP13 as a lead inhibitory antibody. Tumor volume (mean±S.E.M. for ADP13 vs its matched control) over time is shown. n=number of animals/group. *P-value <0.05 using a Student's t-test. Treatment with ADP13 resulted in significant reductions in tumor volume of 52%.
Figure 14D:
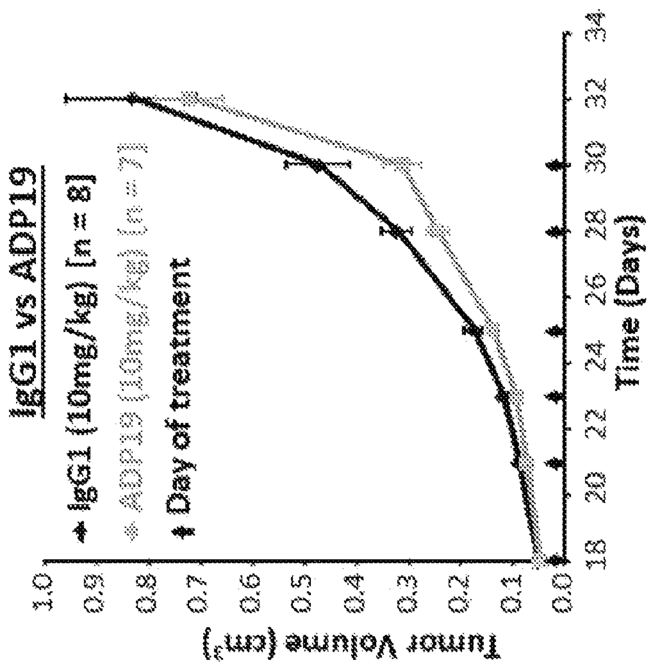
FIG. 14D is a graphic representation showing the single dose in vivo comparison of the ability of ADP19 to inhibit pre-existing MDA-MB-231 cell line-derived TNBC orthotopic tumor growth in mice. Tumor volume (mean±S.E.M. for ADP19 vs its matched control) over time is shown. n=number of animals/group.

Example 20. Phase 2: Growth Inhibitory Activity on Pre-Existing Orthotopic TNBC Tumors in Mice An optimal ADP treatment dose was first determined using ADP13 as the test antibody. Female NOD/SCID mice were implanted with luciferase-labeled MDA-MB-231 (MDA-MB-231-luc) TNBC cells in the fourth inguinal MFP. Once tumors reached ~50-75 $mm^3$, mice were treated with 1, 3 or 10 mg/kg ADP13 vs 10 mg/kg control IgG1. Tumor size was measured using calipers 3×/week. Tumor volume was calculated as (Length×Width$^2$)/2. Mice were sacrificed when tumor growth in the control group approached the 1 $cm^3$ limit of the IACUC protocol. ADP13 inhibited tumor growth in a dose-dependent manner such that 10 mg/kg was the maximum effective dose (FIG. 13); further escalation to 30 mg/kg had no additional effect. Thus, a 10 mg/kg mAb dose was chosen for the efficacy comparison of the 4 selected ADPs.

Figure 15:
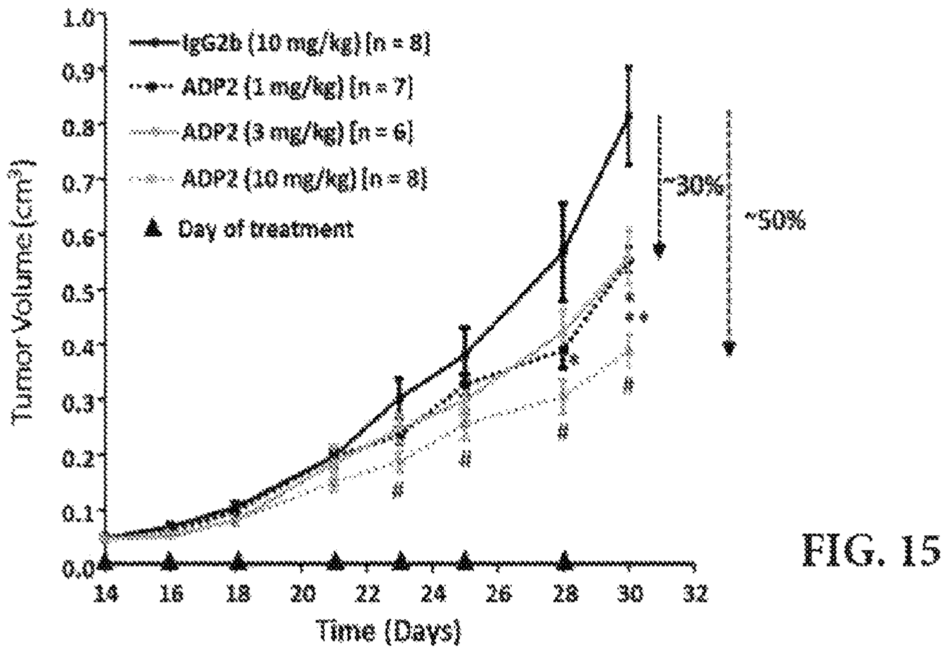
FIG. 15 is a graphic representation of the ability of ADP2 to inhibit pre-existing MDA-MB-231 TNBC cell line-derived primary orthotopic tumor growth in a dose-dependent manner when compared to its isotype-matched control IgG2b. Tumor volume (Mean±S.E.M.) over time is presented. n=number of animals/group. *, P-value <0.05 for IgG2b (10 mg/kg) vs ADP2 (1 mg/kg); **, P-value <0.05 for IgG2b (10 mg/kg) vs ADP2 (3 mg/kg); #, P-value <0.05 for IgG2b (10 mg/kg) vs ADP2 (10 mg/kg) using a Student's t-test. Treatment with 10 mg/kg ADP2 resulted in a significant 50% reduction in pre-existing primary tumor growth. A higher dose of 30 mg/kg ADP2 did not provide any additional benefit (not shown).

A single-dose (10 mg/kg) comparison of the ability of ADP2, ADP3, ADP13, and ADP19 to inhibit tumor growth was carried out. As controls, their isotype-matched control IgGs were used. Tumor Growth Inhibition (TGI) was: 47% for ADP2 (P=0.0001), 28% with ADP3 (P=0.0155), and 52% with ADP13 (P=0.0089). ADP19 showed no tumor growth inhibition under the tested conditions (FIGS. 14A-D). A dose-response curve up to 30 mg/kg was next performed with ADP2 vs IgG2B and 10 mg/kg was again the optimal inhibitory dose (TGI=50%, P=0.0004) (FIG. 15).

Figure 16A:
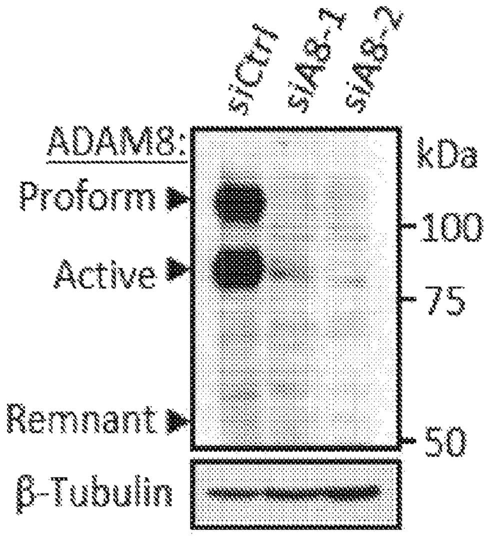
FIG. 16A is an image of a Western blot showing effective knockdown of ADAM8 protein expression in SUM149 TNBC cells treated with ADAM8-specific siRNAs vs a scrambled control siRNA (siCtrl). Position of marker proteins and ADAM8 forms are indicated. siA8-1: siADAM8 RNA-1 (SEQ ID NO: 101); siA8-2: siADAM8 RNA-2 (SEQ ID NO: 102).
Figure 16B:
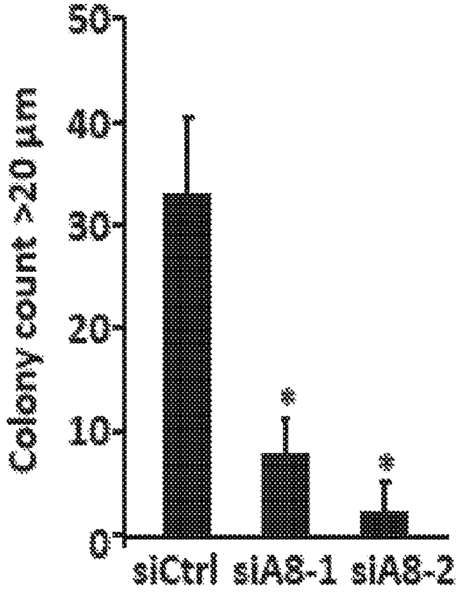
FIG. 16B is a bar graph showing inhibition of anchorage independent growth in an agarose colony formation assay of SUM149 cells transfected with siA8-1 and siA8-2 vs siCtrl. Bar graph is representative of two independent experiments with similar results. siA8-1: siADAM8 RNA-1 (SEQ ID NO: 101); siA8-2: siADAM8 RNA-2 (SEQ ID NO: 102); *, P-value <0.05 by Student's t-test.
Figure 16C:
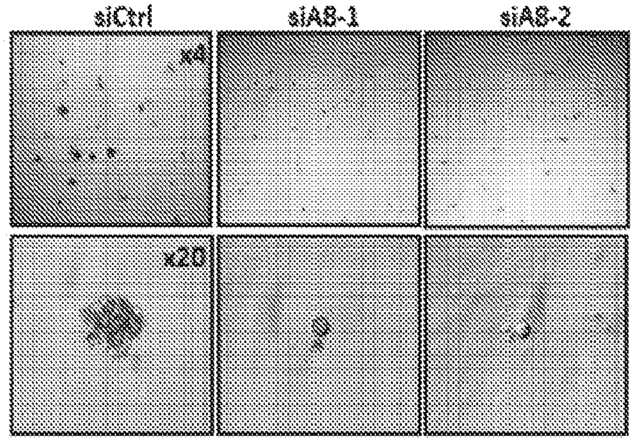
FIG. 16C is a set of images showing invasion of SUM149 cells transfected with siA8-1 and siA8-2 vs siCtrl through Matrigel.
Figure 16D:
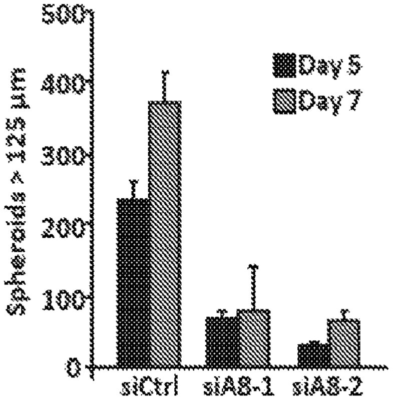
FIG. 16D is a bar graph showing formation of spheroids by SUM149 cells transfected with siA8-1 and siA8-2 vs siCtrl grown in suspension for 5 or 7 days. Bar graph is representative of two independent experiments with similar results. siA8-1: siADAM8 RNA-1 (SEQ ID NO: 101); siA8-2: siADAM8 RNA-2 (SEQ ID NO: 102).
Figure 17A:
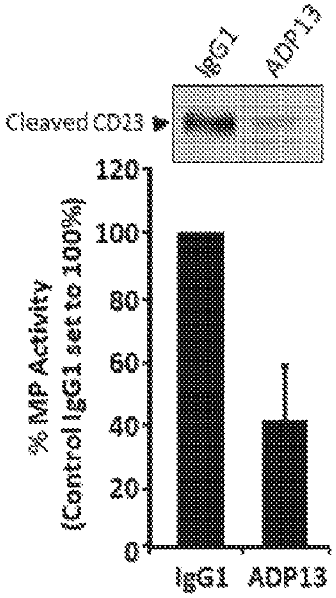
FIG. 17A is an image of a Western blot showing cleavage of CD23 in the presence of ADP13 or control isotype matched IgG1 (top panel) in the cell supernatant of SUM149 cells co-expressing CD23 and ADAM8. Bottom panel is a bar graph showing band intensity quantified. Bar graph and image are representative of two independent experiments in each case.
Figure 17B:
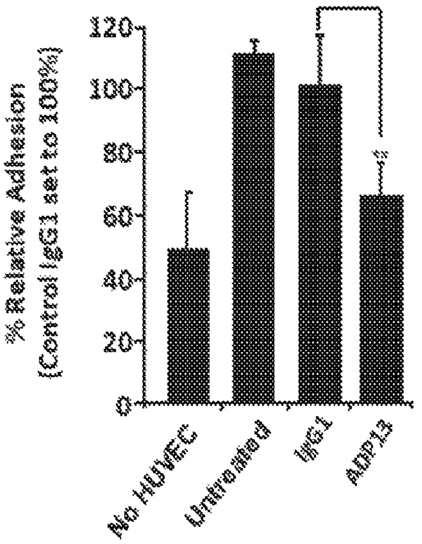
FIG. 17B is a bar graph showing DI activity using a SUM149 cancer cell-to-HUVEC endothelial cell adhesion assay. Percent relative adhesion of SUM149 cells in the absence of HUVEC cells or in the presence of HUVEC cells and either ADP13, control isotype matched IgG1 or no treatment (untreated) were assessed. Bar graph is representative of two independent experiments. **, P-value <0.05 by Student's t-test.
Figure 18:
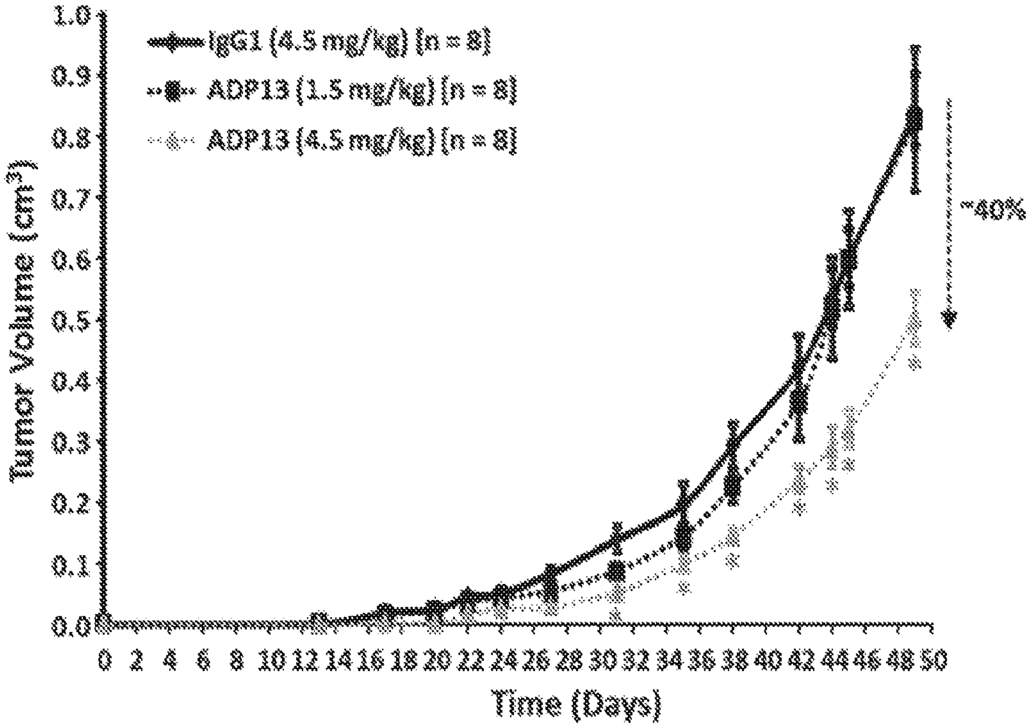
FIG. 18 is a graph showing tumor volume ($cm^3$; Mean±S.E.M.) over time (in days) of SUM149 primary orthotopic tumors implanted in the female NOD/SCID mice (n=number of animals/group). Mice were treated with the indicated doses (1.5 mg/kg, 4.5 mg/kg) of ADP13 or control IgG1 in intraperitoneal (i.p.) injection 2×/week from the time of implantation. *, P-value <0.05 by Student's t-test.
Figure 19:
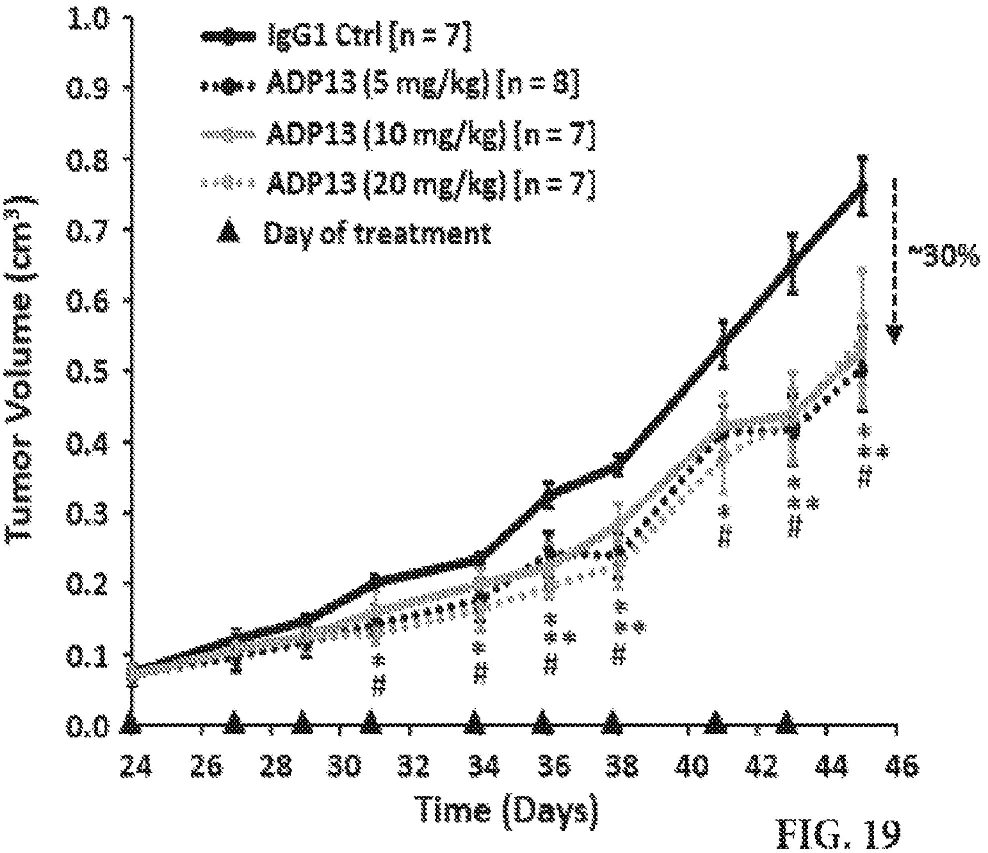
FIG. 19 is a graph showing tumor volume ($cm^3$; Mean±S.E.M.) over time (in days) of SUM149 primary orthotopic tumors implanted in the female NOD/SCID mice (n=number of animals/group). Mice with 50-75 $mm^3$ tumors were treated with the indicated doses (5 mg/kg, 10 mg/kg, 20 mg/kg) of ADP13 or control IgG1 in i.p. injection 3×/week (n=number of animals/group). *, P-value <0.05 for IgG1 Control (Ctrl) vs ADP13 (5 mg/kg); **, P-value <0.05 for IgG1 Ctrl vs ADP13 (10 mg/kg); #, P-value <0.05 for IgG1 Ctrl vs ADP13 (20 mg/kg) using a Student's t-test.

Example 21. Phase 2: ADP13 Inhibits Growth of Tumors Derived from a Second TNBC Line To test whether the inhibition of ADAM8 activity can reduce growth of a second ADAM8-driven TNBC cell line, the SUM149 line was selected. SUM149 TNBC cells are representative of the highly aggressive inflammatory breast cancer (IBC) subtype. SUM149 cells express a very high level of ADAM8. Knockdown of ADAM8 using siRNA technology (FIG. 16A) demonstrated that this protein mediates the ability of SUM149 cells to grow in an anchorage independent fashion in agarose (FIG. 16B), to invade through Matrigel (FIG. 16C) and to form spheroids in suspension culture (FIG. 16D). Treatment with ADP13 inhibited the MP and DI activities of ADAM8 in SUM149 cells, as judged by reduced cleavage of co-expressed CD23 (FIG. 17A) and decreased ability to bind to a monolayer of endothelial cells (FIG. 17B), respectively. Notably, treatment of mice with 4.5 mg/kg ADP13 initiated at the time of SUM149 cell implantation into the MFP led to significant inhibition of tumor growth (TGI=40%, P=0.0004) (FIG. 18). Treatment of pre-existing SUM149 cell-derived TNBC tumors also significantly reduced growth, i.e., treatment with 5 mg/kg ADP13 results in TGI of 30% (P=0.0307) (FIG. 19). Thus, ADP treatment reduces growth of a second ADAM8-positive TNBC cell line, although, not-surprisingly to a reduced degree given its highly aggressive IBC phenotype.

Example 22. Phase 2: Lack of Cross-Reactivity to Closely Related ADAM33 Protein The specificity of the ADP2 and ADP13 antibodies for ADAM8 was further tested with analysis of their binding to ADAM33, another closely related ADAM protein (Takeda, Toxins, 8(5). pii: E155, 2016). Both ADP2 and ADP13 failed to bind to HEK293 cells that were transfected to express ADAM33, termed HEK293-A33 cells, thus further confirming the specificity of these antibodies for ADAM8 (FIGS. 20A-B).

These studies demonstrate that the anti-ADAM8 MP/DI dual antagonist ADP2 and ADP13 mAbs are highly specific and display an ability to inhibit the growth of tumors derived from aggressive TNBC cells. Thus, ADP2 and ADP13 were identified as lead antibodies.

Example 23. Phase 3: Dual Antagonist ADP2 and ADP13 Antibodies Inhibit Metastases of Pre-Existing Orthotopic TNBC Tumors and Improve Survival in a Neoadjuvant Model To test whether ADP antibodies could decrease metastasis and improve outcome, a neoadjuvant protocol was performed, as is currently done in patients to better assess tumor response to therapy. MDA-MB-231-luc cells, which preferentially metastasize to the bone, were used. Once tumors reached 50-75 $mm^3$, mice were treated with ADP2, ADP13 or their control IgGs, as described above. Tumors (~200 $mm^3$) were then surgically removed and the mAb treatment continued for 12 weeks. The resulting Kaplan-Meier (KM) curves indicate ADP2 and ADP13 increase disease-free and overall survival of mice when the primary tumor has been surgically removed (FIGS. 21A-D).

Metastases are responsible for 90% of all breast cancer deaths (World Health Organization, WHO). Thus, mice from the above survival experiment were assessed for metastases to the bone. Imaging of dissected organs was performed when mice were sacrificed either due to the presence of a large recurrent tumor or at the end of the experiment. Treatment with either ADP2 or ADP13 resulted in a robust reduction in bone metastasis with respect to both their frequency and size (FIGS. 22A-D).

Thus, these studies indicated anti-ADAM8 antagonist ADP2 and ADP13 mAbs inhibited the dissemination of tumors derived from aggressive TNBC cells and improved outcome for the tumor-bearing mice.

Example 24. Phase 3: Pharmacokinetic Profiles of ADP2 and ADP13 in NOD/SCID Mice Indicate Administration of a Bolus Initial Dose Leads to a More Constant Steady-State Antibody Level Pharmacokinetic (PK) analysis was performed to elucidate the levels of ADP2 or ADP13 in the blood over time in antibody treated NOD/SCID mice. Following a single i.p. injection with either ADP2 (FIGS. 23A-C) or ADP13 (FIGS. 24A-C), plasma concentrations of antibody were determined over a 21-day time course (n=3 mice per time point) using an ELISA assay that detects anti-ADAM8 mouse antibodies.

Based on the PK curve for ADP2, the maximum plasma concentration of the antibody over the dosing (Cmax) was ~1270 nM at 2 hours (FIG. 23C). The concentration of ADP2 was stable between 4 and 8 hours, but started to decrease thereafter, such that, the antibody was fully eliminated by 21 days. The plasma concentration curve was biphasic (FIG. 25A). Thus, a conservative "non-compartmental" approach was used to calculate the PK parameters: the area under curve (AUC) was 127996 nM·hr/mL and the clearance rate was 0.1537 mL/min (FIG. 25B). Thus, the decay pattern of ADP2 was bi-exponential and nonlinear.

This pattern fits a two-compartment model composed of a distribution phase [alpha(α)-phase] followed by an elimination phase [beta(β)-phase]. The elimination half-life (T½) calculated using the formula (Ln2/Ke) is ~6.2 days. Similar findings were made for ADP13. The $C_{max}$ (~795 nM) was reached at 2 hours (FIG. 24C). The concentration of ADP13 was stable for 8 hours, followed by a rapid decrease to ~398 nM after 24 hours. Thus, it appeared that once ADP13 equilibrated between the different body compartments and the plasma after 2 days (~529 nM), a linear decline was observed until 21 days. For ADP13, the AUC was 168444 nM·hr/mL, the clearance rate was 0.1 mL/min and a T½ of ~10.2 days was calculated (FIGS. 25C and 25D). These PK profiles were used to determine a modified treatment regimen that would achieve a more constant steady-state ADP2 or ADP13 antibody concentration in the mice: a loading bolus dose of 20 mg/kg followed by 3×/week maintenance doses of 10 mg/kg. The effectiveness of this new regimen was confirmed in a second series of mouse studies (FIGS. 26A-C), and thus has been used in subsequent preclinical testing.

Example 25. Phase 3: ADP-Mediated Inhibition of ADAM8 Enhances NPAC-Mediated TNBC Tumor Growth Inhibition in a Tumor Regrowth Model Recurrence and metastatic dissemination occur frequently in TNBC patients treated with the current chemotherapy options (Dent et al., *Clin Cancer Res,* 13(15): 4429-4434, 2007; Pogoda et al., *Med Oncol,* 30: 388-395, 2013). Here the hypothesis that addition of ADP2 or ADP13 to a current Standard-of-Care (SoC) chemotherapy for TNBC will either enhance tumor killing, tumor growth inhibition or inhibit life-threatening metastases, thereby improving outcome was tested. SoC chemotherapies for metastatic TNBC include taxols, which are mitotic inhibitors that lead to tumor killing. NPAC was selected as it is more stable and more effectively taken up by the cancer cell than unmodified paclitaxel (PAC) and has demonstrated greater efficacy in clinical trials compared to paclitaxel or docetaxel (Gradishar et al., *J Clin Oncol,* 23(31): 7794-7803, 2005; Gradishar et al., *J Clin Oncol,* 27(22): 3611-3619, 2009).

NOD/SCID mice bearing well-established, rapidly growing MDA-MB-231-luc tumors were divided into 4 treatment groups: a) isotype-matched control IgG+Saline, b) ADP2 or ADP13+Saline, c) isotype-matched control IgG+NPAC and d) Combinatorial regimen of ADP2 or ADP13+NPAC. To treat with NPAC, mice were given one cycle of 5 consecutive i.v. treatments of 10 mg/kg NPAC (dissolved in saline), rested for one week and then given a second cycle (FIG. 27 and FIG. 30); alternatively, an equivalent volume of vehicle saline was administered. ADP or control IgGs were given starting with a loading dose of 20 mg/kg initiated concurrently with the first chemotherapy cycle, followed by maintenance doses of 10 mg/kg given 3×/week throughout the time course. The endpoint for evaluation of Tumor Growth Inhibition (TGI, percent reduction in mean tumor volume) was an average tumor volume approaching 1 $cm^3$ in the appropriate control group (IgG+NPAC vs ADP+NPAC and IgG+Saline vs ADP+Saline). NPAC treatment led to dramatic disease regression such that tumors were barely palpable by Day 55-62 in both IgG+NPAC and ADP+NPAC groups (FIG. 27 and FIG. 30). However, over time tumors regrew. Strikingly, tumor regrowth in the combinatorial groups with ADP2 or ADP13+NPAC was profoundly inhibited compared to animals treated with IgG+NPAC [ADP2: TGI=82%, P-value=0.027; ADP13: TGI=70%, P-value=0.044).

Furthermore, both the frequency and extent of metastases to the bone was decreased with the combinatorial regimen (FIGS. 28A-D and FIGS. 31A-D). Consistently, a significant survival benefit was seen with ADP2 or ADP13+NPAC vs IgG2b or IgG1+NPAC (FIGS. 29A-B and FIGS. 32A-B). As monotherapies, ADP2 (TGI=38%, P-value=0.011) and ADP13 (TGI=22%, P-value=0.06) led to a significant and modest benefit in primary TGI, respectively, under these more advanced disease conditions (larger primary tumor size at start of treatment). Thus, the combinatorial regimen of ADP2 or ADP13 and NPAC worked synergistically to reduce tumor regrowth and dissemination, and to improve survival vs NPAC or ADP treatment alone.

These studies demonstrated that the anti-ADAM8 MP/DI dual antagonist ADP2 and ADP13 mAbs were highly active against TNBC tumors both as monotherapies and in combination with SoC chemotherapy.

Example 26. The CDR Sequence of ADP H and L Chain V-Regions

The Heavy (H) and Light (L) chain Variable (V) regions of ADP1, ADP2, ADP3, ADP4, ADP12, ADP13, ADP17 and ADP19 were subcloned and sequenced. The three complementarity-determining regions (CDRs) of the light and heavy chains and the germline genes were identified. With the exception of CDR L2 and CDR H1 of ADP2 and ADP13, which bear some similarity to each other, the other CDRs of the light and heavy chains of ADP2, ADP3 and ADP13 were quite different, indicating these were distinct antibodies. Notably CDR H3 of ADP13 was longer than its counterparts in ADP2 or ADP3. Moreover, the similarities in H and L chain CDRs amongst the 8 sequenced ADPs are consistent with their epitope binning (FIG. 7).

Example 27. Epitope Mapping ADP-ADAM8 Interactions Using FACS Analysis and Hydrogen Deuterium Exchange (HDX) Mass Spectrometry To begin to map the epitope of ADAM8 that interacts with ADP antibodies to inhibit tumor formation in vivo, ADP2, ADP13 and ADP3 were selected for analysis. FACS was performed using HEK293 cells expressing either full-length ADAM8, which includes both the MP and DI domains, or the remnant form, which lacks the MP domain but still contains the DI domain (FIGS. 1A-B and FIGS. 33A-D). The ability of ADP2, ADP3, and ADP13 to bind to both the expressed full-length and remnant forms of ADAM8 suggested that the epitopes for these antibodies were contained within the DI domain.

HDX mass spectrometry of recombinant human ADAM8 was next used to identify the ADP2, ADP3, and ADP13 epitopes at the peptide level. For this analysis, ADAM8 was incubated with deuterium oxide for 60 s, 600 s, or 3600 s in either the absence or presence of ADP2, ADP3 or ADP13 and then subjected to pepsin/protease XIII digestion. The effects of antibody binding on the amount of deuterium in the resulting peptides was determined using liquid chromatography-mass spectrometry (LC-MS) (FIG. 34). ADAM8 showed specific reduction in deuterium uptake at the following sequences within the DI domain going from the amino to carboxy termini:

```
ADP3:
                                        (SEQ ID NO: 88)
DCGPPEDCRNRCCNSTTCQ (aa423-441)

ADP2:
                                        (SEQ ID NO: 86)
CCNSTTCQLAEGAQCAHGTCCQECK (aa434-458) and

ADP13:
                                        (SEQ ID NO: 87)
LAEGAQCAHGTCCQECKVKPAGELCRPKKDMCDLEEFCDGRHPECPEDAF
(aa442-491).
```

The three antibodies bound to sequences, which were partially overlapping (FIG. 34 and FIG. 35). The overlapping regions between (i) ADP3 and ADP2 and (ii) between ADP2 and ADP13 are indicated above by a dashed line, and a solid line, respectively. In their entirety the sequences bound by these three antibodies define SEQ ID NO: 1.

These findings were consistent with the binning described in FIG. 6, which showed no significant epitope overlap between ADP3 and ADP13, whereas the epitopes for (i) ADP3 and ADP2 and (ii) ADP2 and ADP13 substantially overlapped (~90%). Together these results indicate that ADP13, ADP2 and ADP3, define a family of ADPs, with dual MP/DI inhibitory activity that bind to SEQ ID NO: 1 within the DI domain and display significant in vivo functionality.

Competition binning analysis indicated that, within the panel of antibodies, this family includes Epitope 2 antibody ADP13, and Epitope 3 antibodies ADP2, ADP3, ADP1, ADP12, ADP4, ADP6, ADP7 and ADP9 (FIG. 7). The KD for ADP2 was 3.34E-09. The KD for ADP13 was 1.3E-09. The KD for ADP3 was 1.83E-08.

These findings showed that binding to the DI region inhibited the activities of both the MP and DI domains required for tumor growth and metastasis. ADP binding to the DI region likely disrupted the ability of ADAM8 to interact with integrins and other ECM components via multiple mechanisms.

For ADP13, whose site overlaps with the integrin binding site (DMCD) and the consensus $Ca^{2+}$ binding site III (aa473-489 (CDLEEFCDGRHPECPED (SEQ ID NO: 103)), inhibition of DI activity may result via direct competition with integrins and other ECM components for interaction with ADAM8 (FIG. 34). For antibodies within the Epitope 3 group, additional mechanisms may be involved. These mechanisms include: 1) altering/destroying the tight structural constraints of the C-shaped DI/CRD structure; 2) reducing structural stability by preventing binding of the required $Ca^{2+}$ at sites II and III; 3) blocking access to the integrin binding motif.

Notably, binding to the DI region has profound inhibitory effects on MP activity. This inhibition may also occur via several potential mechanisms. ADP binding at the DI domain may: 1) prevent substrate access to the MP domain or the HVR of the CRD domain; 2) change the orientation of the MP domain relative to the DI/CDR regions by disturbing the sequence linking the MP and DI domains; 3) change the configuration of the MP domain active site; 4) reduce MP function by preventing binding of the required $Ca^{2+}$ at site I; 5) disrupt the tight structural constraints of the C-shaped DI/CRD structure, which would impact the HVR loops at the end of the CRD domain that are critical for substrate recognition by the ADAM8 metalloproteinase activity.

Example 28. Mouse V-Region/Human IgG1 Constant (C)-Region Chimeras are Functional Vectors expressing chimeric ADP2 and ADP13 proteins with their $V_L$ and $V_H$ regions linked to the C region of human IgG1, a commonly used Fc region in therapeutic antibodies, were prepared. The chimeric proteins have been termed chADP2-IgG1 and chADP13-IgG1. A mutation had to be introduced into ADP13 $V_L$ chain to avoid the creation of a new site of glycosylation. This change made the $V_L$ more germline. Chimeric proteins were synthesized in CHO cells, purified and characterized for binding to ADAM8 and for dual MP and DI domain antagonist activity. The ability of chADP2-IgG1 and chADP13-IgG1 to bind to ADAM8 was confirmed using both ELISA assays with recombinant protein (FIG. 36A) and FACS analysis of HEK293 cells stably expressing full-length ADAM8 vs control empty vector (EV) DNA (FIGS. 36B-C). Functionally, in cell-based assays, the two chimeras inhibited the MP and DI activities equal to or better than mouse ADP2 and ADP13 (FIGS. 37A-D).

Example 29. Epitope Mapping Interactions of ADP2 and ADP13 with ADAM8 Via Shotgun Mutagenesis Shotgun mutagenesis paired with high-throughput flow cytometry was next used to identify specific amino acid residues that mediate the interaction of ADP2 and ADP13 with ADAM8. Both the MP and DI domains were assessed to confirm the data obtained by HDX mass spectrometry. For this analysis, high-throughput, site-directed mutagenesis was used to generate a library of human ADAM8 expression constructs with single alanine mutations introduced into each amino acid residue between 192 to 497 (covering the MP and DI domains) except when alanine was the original amino acid—in which case it was mutated to serine. Following transfection into HEK293 cells and subcloning, the library was screened by high-throughput flow cytometry under high stringency (HS) conditions using antigen-binding fragments (Fabs) of ADP2 and ADP13, or a positive control ADAM8 antibody (Control Ab). One amino acid in ADP2 (E444) and four amino acids (G445, Q447, K458, and R482) in ADP13 reached the threshold guidelines for critical binding residues (i.e., control antibody binding >70% of WT and test antibody binding <20% of WT binding) (FIG. 38). Mutations in these amino acid positions resulted in a significant reduction of ADP2 and ADP13 Fab binding, respectively but no reduction of control antibody binding. Three amino acids in ADP2 (R431, G445, and K458) and two amino acids in ADP13 (V459 and A462) are residues of secondary importance, i.e., that did not reach the <20% of WT binding criterion for critical residues, but still led to a substantial reduction in ADP2 and ADP13 Fab binding activity (FIG. 38). Mutations in these amino acid positions resulted in a significant reduction of ADP2 and ADP13 Fab binding, but no reduction of control antibody binding. This change in binding in combination with their proximity to critical residues indicates that they are part of the antibody epitope. The positions of the ADP2 and ADP13 critical and secondary binding residues are indicated in an ADAM8 crystal structure model that is based on the structure of vascular apoptosis-inducing protein-1 (PDB ID #2ERP, Takeda et al. EMBO J. 25, 2388-2396, 2006) (FIG. 39A and FIG. 39B, respectively).

Overall, there is tremendous concordance between the amino acid residues identified by shotgun mutagenesis and HDX mass spectrometry, i.e., all of the critical amino acid residues mapped by mutagenesis fall within the peptide regions of ADP2 and ADP13 mapped by HDX mass spectrometry, and only the ADAM8 R431 amino acid of secondary importance for ADP2 binding maps three amino acids upstream, thus extending the region mediating binding to ADP2 to RNRCCNSTTCQLAEGAQCAHGTCCQECK (aa431-458) (SEQ ID NO: 104).

These findings demonstrate that antibodies binding within SEQ ID NO: 1 of the DI domain function to inhibit both the MP and DI activities of ADAM8.

Example 30. Overview of Approach Used to Identify ADP2 as a Lead Diagnostic Antibody for IHC-Based Detection of ADAM8 and to Generate a Breast Control Cell Line Microarray (CCM) Scoring System To identify diagnostic antibodies for use in IHC-based detection of ADAM8-positive tumors, the multistage strategy outlined in FIG. 40 was performed. Briefly, the ADP panel of antibodies was first screened using FACS analysis of fixed cells with ectopic (i.e., exogenous) ADAM8 expression. ADPs with good binding activity under fixed conditions were then tested in IHC with formalin-fixed paraffin-embedded (FFPE) pellets of cells with both exogenous ADAM8 expression (HEK293-ADAM8 cells) and endogenous ADAM8 expression (untransformed breast and breast cancer cells), and the staining conditions for the RUO ADAM8 LS-B4068 antibody, previously used in our studies of patient biopsies (Romagnoli et al., EMBO Mol Med, 6(2):278-294, 2014). The breast cancer studies led us to determine that the LS-B4068 conditions were not appropriate for use with the ADP panel of antibodies. ADP-specific IHC staining conditions were then identified. Using these newly optimized conditions, multiple ADPs were found capable of detecting ADAM8 in IHC. ADP2 was selected as lead diagnostic antibody and ADP17 as a backup. Furthermore, by comparing Western blotting for active ADAM8 protein levels with IHC staining of FFPE breast cell pellets, a control cell line microarray (CCM) with low, medium and high ADAM8 levels was established for an IHC 1+, 2+, 3+ scoring system. Finally, ADP2 IHC staining and the CCM scoring system were validated using TNBC patient-derived xenograft (PDX) samples.

Example 31. Identification of ADP Candidate Diagnostic Antibodies Using FACS Analysis of Fixed HEK293-ADAM8 Cells To determine whether the antibodies within the ADP panel were able to detect ADAM8 under fixed conditions, a critical requirement of all IHC antibodies, 12 antibodies were selected, based on high binding affinity (ELISA and Biacore) and production, for screening in FACS analysis of fixed 2D cultured HEK293-ADAM8 (HEK-A8-2D) cells. As controls, 2D grown HEK293-Empty Vector cells (HEK-EV-2D) that did not express ADAM8 and isotype-matched control IgGs were used. Mouse IgG2b (anti-*Manduca sexta* ecdysone clone 10F1, Developmental Studies Hybridoma Bank, U. Iowa City) was the isotype matched control IgG for ADP2 and ADP4, while mouse IgG1 (anti-BrdU clone G3G4, Developmental Studies Hybridoma Bank, U. Iowa City) was the isotype matched control IgG for ADP3, ADP6, ADP7, ADP9, ADP10, ADP11, ADP13, ADP17, ADP18 and ADP19. Additionally, unfixed samples of these cells were used to confirm the FACS activity of these antibodies under native conditions, thus establishing if activity under fixed conditions is retained, improved or lost.

Briefly, HEK293-ADAM8 and HEK293-EV cells were trypsinized and single cell suspensions generated by passing cells through a syringe with a 21-gauge 1.5-inch needle. For unfixed samples, three hundred thousand cells per sample were resuspended in 50 μL FACS Buffer (1% BSA, 0.1% sodium azide in PBS) and exposed to 2 μg primary ADP or IgG control for 30 min on ice. After incubation, cells were washed twice in FACS buffer and then exposed to 1.25 μg of secondary antibody Alexa Fluor 488 donkey anti-mouse IgG (H+L) (Life Technologies, A-21202) for 30 minutes on ice. Cells were finally washed 3 times with FACS buffer, resuspended in 400 μL of fresh buffer and analyzed by flow cytometry using a BD FACSCalibur. Analysis of fixed cells was performed as above except, after a single cell suspension of cells was generated, samples containing three hundred thousand cells were resuspended in 50 μL of 4% paraformaldehyde and incubated on ice for 20 min before proceeding to primary antibody staining.

Example 32. Generation of Breast Specific Control Cell Line Microarray (CCM) and ADAM8 Scoring System A CCM containing breast cell lines was created with a gradient of endogenous ADAM8 levels and the HEK293-ADAM8 and HEK293-EV cells, as positive and negative controls, respectively, for use in optimization of ADP IHC conditions and as an ADAM8 IHC scoring system for evaluation of tissue samples. Briefly, to select appropriate lines for the CCM, ADAM8 protein levels were assessed in untransformed MCF-10A breast epithelial cells, and TNBC SUM149, MDA-MB-231 and MDA-MB-231-LUC cells using Western blotting. Cultures were grown either under 2D or 3D conditions for 48 hours. Whole cell extracts (WCE) were prepared and subjected to Western blotting for ADAM8. Briefly, WCE were prepared using Radioimmunoprecipitation assay buffer (RIPA, 50 mM Tris pH 7.6, 150 mM NaCl, 1% NP40, 0.1% SDS, 5 mM EDTA, 1% Sodium Sarkosyl) supplemented with Halt Protease and Phosphatase Inhibitor Single-Use Cocktail (1:100, Thermo Fisher Scientific, 78442), 0.5 M EDTA (1:100) and 1 M 1,10-Phenanthroline (1:100, Sigma, 131377) to inhibit the autocatalytic activity of ADAM8. Samples (30 μg) were subjected to Western blotting for ADAM8 with the LS-B4068 anti-ADAM8 antibody (LifeSpan BioSciences). Sample blotting with a β-actin antibody (Sigma) was used as a control for loading. A Precision Plus Protein Dual Color Standard (Biorad, #1610374) was used as a protein size marker.

Based on protein expression data from this Western blotting analysis, MCF10A-2D, MDA-MB-231-2D, MDA-MB-231-3D, HEK293-Empty Vector-2D and HEK293-ADAM8-2D were selected as appropriate cells with a broad range of ADAM8 levels. Next, the CCM was established. Briefly, for 2D cultured cells, confluent 100-mm plates were dissociated using Accutase (Gibco/StemPro A1110501) and subcultured at dilutions of 1:3 (MCF10A-2D), 1:2 (MDA-MB-231-2D) and 1:5 (HEK293-ADAM8-2D and HEK293-EV-2D) onto tissue culture treated 100-mm plates and grown to confluency (48-72 hours). For 3D culture, confluent 100-mm plates of 2D grown MDA-MB-231 cells were dissociated with Accutase and the entire single cell suspension per plate transferred to a 100-mm low attachment plate (Corning, 3262) for 48 hours to induce ADAM8 levels. Cultures of $30\times10^6$-$50\times10^6$ cells for each of these five lines were then collected by dissociation with Accutase and/or centrifugation and washed with 1×PBS. Cells were then resuspended in formalin, pelleted for 5 minutes at 1,000 rpm and allowed to fix overnight at 4° C. Pellets were washed once with 70% ethanol, without disrupting the pellet, centrifuged at 1,000 rpm for 5 minutes, to ensure a compact pellet is formed, and then paraffin-embedded together in a single block to create the microarray. Finally, sections (4-5 μM) were cut from this block onto slides for IHC analysis.

For quantification of the levels of active ADAM8 in the CCM breast cell lines, Western blot analyses of protein extracts were performed with LS-B4068 as above, except extracts from each of the five cell lines were loaded at various concentrations (2-120 μg) to ensure that blots displayed bands with levels within the linear range. Gels were quantified using densitometry and compared to staining from ADP2 IHC analyses of the CCM slides. Experiments were repeated with a second anti-ADAM8 antibody (LS-C20181, LifeSpan BioSciences) to confirm results. MCF10A-2D, MDA-MB-231-2D and MDA-MB-231-3D displayed a stepwise ~5-7-fold increase in relative active ADAM8 levels in Western blotting, and commensurately, a low, medium and high percent cell culture staining positivity in IHC and were thus defined as having a simple 1+, 2+ and 3+ ADAM8 IHC staining score. This scoring system was used to evaluate IHC results of TNBC PDX samples. PDX staining scores were determined by direct visual comparison to the scores established for the breast lines within the CCM.

Example 33. Method for IHC Analysis

The CCM, tissue microarrays (TMAs), and single section slides of formalin fixed paraffin embedded (FFPE) cell lines and TNBC patient derived xenograft (PDX) samples were analyzed by IHC in a Ventana BenchMark ULTRA automated clinical diagnostic slide stainer at the Tufts Medical Center Histopathology Laboratory, on a fee-for-service basis.

Staining Conditions for LS-B4068 ADAM8 Antibody

For IHC analysis with LS-B4068 (LifeSpan BioSciences), following the standard automated deparaffinization protocol (medium temperature 72° C.), slides were subjected to Heat-Induced Epitope Retrieval (HIER) using the Ventana standard Cell Conditioning (CC)1 Tris-EDTA-based basic buffer for 64 minutes. This incubation can disrupt the covalent bonds formed by formalin in tissue. Removing these bonds allows renaturation of protein molecules and increases antibody accessibility thereby improving binding and signal to noise ratio. Slides were then incubated with primary antibody LS-B4068, or its isotype matched control rabbit polyclonal IgG (Abcam, ab37415) at dilutions of 1:50 to 1:20,000 for 32 minutes. For detection, a Ventana iVIEW DAB kit (760-091) was used. This kit uses biotin-bound secondary antibodies and HRP-tagged streptavidin. The interaction of these reagents at the site of primary antibody binding promotes the conversion of hydrogen peroxide substrate and the 3,3'-diaminobenzidine tetrahydro-chloride (DAB) chromogen into a brown precipitate that can be easily observed using light microscopy. Immunostained slides were counterstained with hematoxylin for visualization of cell nuclei. ADP antibodies were initially used in IHC with these conditions before optimal conditions for their use were identified.

Staining Conditions for ADP Antibodies

As ADPs were found to detect only exogenously expressed ADAM8 in HEK293 cells and not endogenous protein in breast cells under LS-B4068 IHC staining conditions, a variety of parameters were modified to identify ideal conditions for use of the ADP antibodies in IHC. First, the antigen retrieval method was modified to HIER with CC2 citrate-based acidic buffer instead of the CC1 Tris-EDTA-based basic buffer. This resulted in even less staining and thus more focus was placed on the CC1 buffer and trying to optimize staining conditions with it. Next, the time of retrieval with CC1 was varied from the standard 64 minutes of incubation to a shorter (20 minute) and a longer (98 minute) period. This led to the discovery that shorter incubation is better and the realization that HIER conditioning even with CC1 in fact inhibits ADP staining. Thus, IHC was performed without epitope retrieval. This improved staining but the relative extent of staining of HEK293-ADAM8-2D vs MDA-MB-231-2D and MDA-MB-231-3D cells was still much lower than expected based on Western blot analysis. To try to improve the accessibility of the ADAM8 protein to antibody staining, a Proteolytic-Induced Epitope Retrieval (PIER) method with Protease 2 (P2), an alkaline endopeptidase of the serine protease family, was used. A further improvement of ADAM8 staining was seen following 4 minutes of this PIER protocol, but the relative staining in the breast cancer vs HEK293-ADAM8-2D cells still appeared weaker than expected.

To enhance the level of staining, an amplification step was added using the Ventana Amplification Kit (760-080), which relies on anti-mouse IgG heavy and light chains and mouse anti-rabbit IgG heavy chains that bind to the primary antibody on the tissue, increasing the total number of antibodies bound at the site of antigen to amplify the signal. A robust increase in staining was observed (FIG. 46), such that ADAM8 detection levels in the breast vs HEK293-ADAM8-2D cells appeared consistent with the Western blot analysis (FIG. 44). Thus, PIER method with P2 plus an amplification step was identified as the optimal protocol for use of ADP antibodies in IHC-based detection of ADAM8.

ADPs were tested at dilutions which ranged from 1:50 to 1:120,000. Isotype matched controls were mouse IgG1 (Abcam, ab18443) and IgG2b (ab18428 and ab18457, Abcam). To identify ADAM8-positive samples, two TMAs containing a total of 30 TNBC PDX samples were assessed using either LS-B4068 or ADP2, at a dilution of 1:100 and with the appropriate optimal staining conditions for each antibody. Three samples with substantial staining were identified: PDX 5998, PDX 3561, and PDX 4849.

To validate ADP2 staining in tissues and the CCM as a scoring system, two sets of single section slides for each of these 3 TNBC PDX tumors (4 consecutively cut slides/PDX/set) together with CCM slides were subjected on different days to IHC using ADP2 at dilutions of 1:50, 1:100 and 1:500 vs the isotype-matched control IgG2b at a 1:50 dilution. PDX samples were scored as described above.

Example 34. Screening of ADP Panel by FACS for Identification of Diagnostic Candidates that Detect Fixed ADAM8

FACS was used first to screen the panel of ADP antibodies to test their ability to detect exogenously expressed ADAM8 on the surface of fixed HEK293-ADAM8 cells that had been grown as adherent cultures on tissue culture treated plates (2D) (FIGS. 41A-C). As controls, HEK293-Empty Vector cells that did not express ADAM8 and isotype-matched control IgGs were used. Additionally, unfixed samples of these cells were used to demonstrate the FACS activity of these antibodies under native conditions. HEK293-ADAM8 and HEK293-Empty Vector cells cultured on tissue culture plates (2D) are abbreviated as HEK-A8-2D and HEK-EV-2D, respectively in FIGS. 40-51. Five ADPs (ADP2, ADP3, ADP4, ADP13, and ADP17) were found to detect ADAM8 exceptionally well in FACS analysis of fixed HEK293-ADAM8 vs HEK293-Empty Vector cells and selected for further testing in IHC.

Example 35. Testing of ADP Antibodies in IHC with Research Use Only (RUO) LS-B4068 Antibody Staining Conditions Conditions optimized for the RUO LS-B4068 anti-ADAM8 IHC antibody (LifeSpan BioSciences), described in Example 33 (Romagnoli et al., *EMBO Mol Med,* 6(2):278-294, 2014), and slides cut from FFPE pellets of HEK293-Empty Vector-2D and HEK293-ADAM8-2D cells were used. IHC analysis was performed in a Ventana BenchMark ULTRA automated clinical diagnostic slide stainer. Following the standard automated deparaffinization protocol (medium temperature 72° C.), slides were subjected to Heat-Induced Epitope Retrieval (HIER) using the Ventana standard Cell Conditioning (CC)1 Tris-EDTA-based basic buffer for 64 minutes.

Slides were then incubated with primary antibodies (ADPs, LS-B4068, or their appropriate control IgGs) at dilutions of 1:50 to 1:20,000 for 32 minutes. For detection, a Ventana iVIEW DAB kit (760-091) was used. This kit employed biotin-bound secondary antibodies and HRP-tagged streptavidin. The interaction of these reagents at the site of primary antibody binding promoted the conversion of hydrogen peroxide substrate and the 3,3'-diaminobenzidine tetrahydro-chloride (DAB) chromogen into a brown precipitate that could be easily observed using light microscopy. Immunostained slides were counterstained with hematoxylin.

ADP2 and ADP17 demonstrated strong ADAM8 staining, which was dose-dependent in a range from 1:50 to 1:1,000 (FIG. 42). ADP13 also displayed dose-dependent HEK293-ADAM8-2D positive staining, but the background was substantially higher (FIG. 42); whereas, ADP3 and ADP4 had no activity in IHC with HEK293-ADAM8-2D cells (data not shown). No staining was observed with the ADAM8-negative HEK293-Empty Vector-2D cells. Importantly, analysis of ADP2 and ADP17 vs LS-B4068 revealed comparable staining of HEK293-ADAM8-2D cells (FIG. 43).

Example 36. Selection of Cell Lines for Generation of Breast CCM

To extend IHC studies to analysis of endogenous ADAM8 levels, first a variety of cell lines were assessed for ADAM8 protein expression using Western blotting. Untransformed MCF-10A had very low ADAM8 levels compared to SUM149 or MDA-MB-231 TNBC cells grown in 2D (Romagnoli et al., *EMBO Mol Med,* 6(2):278-294, 2014). Moreover, growth of TNBC MDA-MB-231 cells in suspension culture (3D), e.g., in low attachment plates, resulted in a substantial induction in the overall level of ADAM8 and specifically the amount of active form (Romagnoli et al., *EMBO Mol Med,* 6(2):278-294, 2014). To compare the levels of ADAM8 in the various breast epithelial and cancer cell lines, Western blotting with the LS-B4068 anti-ADAM8 antibody was performed. Cultures were grown either under 2D or 3D conditions for 48 hours. Whole cell extracts were prepared (Romagnoli et al., *EMBO Mol Med,* 6(2):278-294, 2014) and subjected to Western blotting for ADAM8 (FIG. 44).

A gradient of ADAM8 expression was observed. MCF10A-2D breast epithelial cells express barely detectable ADAM8 levels, which were visible only when very long film exposures were performed (data not shown), whereas, SUM149-2D and MDA-MB-231-2D cells express moderate levels. Growth in 3D of MDA-MB-231 cells and of its more aggressive derivative MDA-MB-231-LUC induces extremely high endogenous ADAM8 levels, which are comparable to those seen in HEK293-ADAM8-2D cells, with exogenous ADAM8 expression (FIG. 44). Based on this protein expression data, MCF10A-2D, MDA-MB-231-2D, MDA-MB-231-3D, HEK293-Empty Vector-2D and HEK293-ADAM8-2D were selected to create a breast CCM with a gradient of low, medium and high ADAM8 levels for further ADP IHC optimization and assessment of their use in an early ADAM8 scoring system. Cells were grown in 2D or 3D conditions, fixed in formalin and paraffin-embedded in a single block to create a microarray containing these five samples. The block was sectioned onto slides which were then subjected to IHC.

Example 37. IHC Conditions for the RUO LS-B4068 ADAM8 Antibody are Inappropriate for ADP Recognition of Endogenous ADAM8 in the CCM CCM slides were subjected to IHC analysis under the conditions optimized for the LS-B4068 antibody with LS-B4068, ADP2 and ADP17 vs their respective control isotype matched IgGs (FIG. 45).

ADP2 and ADP17 detected ADAM8 only in HEK293-ADAM8-2D but not in MDA-MB-231-2D or MDA-MB-231-3D cells (FIG. 45); whereas, LS-B4068 detected ADAM8 in all three. As expected, neither antibody displayed staining in control HEK293-Empty Vector-2D or in the MCF10A-2D cells. These findings indicated that the conditions identified for LS-B4068 are not optimal for IHC use of ADPs, which more likely recognize ADAM8 in its native configuration.

Example 38. Established IHC Conditions for Detection of Endogeneous ADAM8 by ADP Antibodies As ADPs were found to detect only exogenously expressed ADAM8 in HEK293 cells and not endogenous protein in breast cells under LS-B4068 IHC staining conditions, a variety of parameters were modified to identify ideal conditions for use of the ADP antibodies in IHC as detailed in Example 33. ADP2 was used as the prototype antibody for the ADP panel in these studies. Optimal conditions were established using Proteolytic-Induced Epitope Retrieval (PIER) treatment with Protease 2 (P2), an alkaline endopeptidase of the serine protease family, followed by an amplification step using the Ventana Amplification Kit (760-080). This step, which relies on anti-mouse IgG heavy and light chains and mouse anti-rabbit IgG heavy chains that bind to the primary antibody on the tissue, increase the total number of antibodies bound at the site of antigen to amplify the signal. Using this protocol, a robust increase in staining was observed (FIG. 46), such that ADAM8 detection levels in the breast vs HEK293-ADAM8-2D cells appeared consistent with the Western blot analysis (FIG. 44). Thus, PIER method with P2 plus an amplification step was identified as the optimal protocol for use of ADP antibodies in IHC-based detection of ADAM8.

Example 39. Selection of ADP2 as Lead Diagnostic Antibody

Using the newly optimized ADP-specific IHC conditions, the ADP panel of antibodies was then re-assessed for their activity in IHC, focusing on the original 5 top binders identified in FACS and an additional 4 antibodies. ADP2, ADP13 and ADP17 showed comparable staining (FIGS. 47A, 47B and 48). ADP2 displayed the highest signal to background ratio, followed by ADP17 and then ADP13. ADP12 and ADP18 demonstrated substantial staining of ADAM8, but this was below the levels seen with ADP2; while, staining with ADP3, ADP4, ADP9 and ADP19 was barely detectable. Notably, only very poor staining was seen with LS-B4068 under the conditions optimized for ADP staining (FIG. 48). Thus, ADP2 was selected as the lead diagnostic antibody and ADP17 as a backup.

Example 40. Establishment of CCM Scoring System

To quantify the levels of active ADAM8 in the CCM breast cell lines, Western blot analyses were performed of protein extracts that were loaded at various concentrations to ensure that levels were within the linear range. Gels were quantified using densitometry and compared to staining from ADP2 IHC analyses of CCM slides. Relative levels of active ADAM8 were determined by densitometry of multiple Western blot images. The means are presented relative to the MCF-10A-2D cell line, which was set to 1.0 (FIG. 49).

MCF10A-2D, MDA-MB-231-2D and MDA-MB-231-3D cells displayed a stepwise ~5-7-fold increase in relative active ADAM8 levels in Western blotting, and commensurately, a low, medium and high percent cell culture staining positivity in IHC and were thus defined as having a simple 1+, 2+ and 3+ ADAM8 IHC staining score, respectively (FIG. 49). Based on the findings of all of these studies, MCF-10A-2D, MDA-MB-231-2D, and MDA-MB-231-3D were determined to be appropriate cells with a gradient of ADAM8 levels for a breast focused CCM scoring system to be used for evaluation of IHC stained tissue samples. HEK293-ADAM8-2D and HEK293-Empty Vector-2D were included in the CCM as positive and negative controls of staining.

Example 41. Validation of ADP2 Staining and CCM

To examine the range and linearity of ADP2 ADAM8 staining using the CCM, dilutions of ADP2 ranging from 1:50 to 1:120,000 were used (FIG. 50). A low level of ADAM8 was detected at 1:50 dilution in MCF10A-2D cells, which displayed a low level of ADAM8 in longer exposure of Western blots. This staining decreased with dilution to 1:5,000 where very little staining was observed; no staining was detected with further dilution to 1:20,000. With MDA-MB-231-2D, and MDA-MB-231-3D, which express an increasing gradient of ADAM8 levels (FIGS. 44 and 46), staining was detected up to 1:20,000 and 1:80,000, respectively (FIG. 50). Staining with HEK293-ADAM8-2D cells was still visible although greatly reduced even after a 1:120,000 dilution. No staining was observed in HEK293-Empty Vector-2D cells even at the highest dose of ADP2, consistent with lack of ADAM8 expression in the parental HEK293 cells (Romagnoli et al., *EMBO Mol Med,* 6(2): 278-294, 2014). Thus, dose-dependent ADAM8 staining was observed in all of the lines examined, with ADP2 being able to detect both very low and high levels of its target protein, demonstrating that this antibody had an excellent range and linearity of staining, appropriate for a diagnostic antibody and the analysis of patient samples with a wide range of protein levels.

As a critical test of ADP2 binding specificity, a competition assay was performed using increasing doses of the purified recombinant human ADAM8 (rhADAM8) protein (AA17-497, ACRO Biosystems AD8-H5223) that was the immunogen for generation of the ADP antibodies in mice. ADP2 was incubated overnight at 4° C. in the absence or presence of 1×, 10× or 100× molar equivalents of rhADAM8 and used in IHC of HEK293-ADAM8-2D and MDA-MB-231-3D cells (FIG. 51). A dose-dependent decrease in staining of both lines was seen with addition of rhADAM8. Competition using a rhADAM8 (AA1-497) from a second source (R&D Systems, 1031-AD) and HEK293-ADAM8-2D demonstrated a similar dose-dependent decrease in staining (data not shown). These data confirm the specificity of the ADP2 staining for ADAM8.

Patient-Derived Xenograft (PDX) samples were maintained in mice and displayed a stable phenotype across multiple transplant generations, as judged by histologic, transcriptomic, proteomic and genomic analyses (Zhang et al., *Cancer Res,* 73(15):4885-4897, 2013; Zhang et al., *Curr Protoc Mouse Biol,* 3(1):21-29, 2013). In order to further validate the IHC conditions and the CCM, two sets of TMAs with 30 TNBC PDX samples total were assessed using either LS-B4068 or ADP2, at a dilution of 1:100 and with the appropriate optimal staining conditions for each antibody. ADP2 staining demonstrated superior detection of ADAM8 in PDX samples vs LS-B4068 (data not shown). Three samples with substantial staining were selected for further dose-response and reproducibility analysis: PDX 5998, PDX 3561, and PDX 4849. Next, two sets of single section slides for each of these three TNBC PDX tumors (four consecutively cut slides/PDX/set) were subjected on different days to IHC using ADP2 at dilutions of 1:50, 1:100 and 1:500 vs the isotype-matched control IgG2b at 1:50. All three PDX samples displayed strong staining at the 1:50 dilution of ADP2 (FIG. 52). Decreased staining was seen at the 1:100 and 1:500 dilutions, whereas the isotype control was negative. Thus, the 1:50 dilution of ADP2 was selected as optimal for analysis of tissues.

Comparable staining was seen of the two sets performed on different days for each PDX sample, demonstrating the reproducibility of the assay (FIGS. 53A-C). Importantly, the PDX samples had IHC scores between 2+ and 3+, which were within the range of the breast lines of the CCM, confirming appropriate cells have been selected for scoring of tumor samples (FIG. 54).

At present, there are no marketed diagnostics for ADAM8-positive cancers. Commercially available RUO IHC antibodies which have been used in publications to define ADAM8 levels in different cancers cannot be used in clinical diagnostics as they lack the necessary characterization (e.g., demonstration of target specificity—no IHC recombinant ADAM8 competition studies or cross-reactivity studies against related ADAM family proteins). In addition, many of them, including LS-B4068 used in the preliminary assessment of ADAM8 in breast cancer samples, are polyclonal rabbit antibodies, which are difficult to reproduce long-term from rabbit to rabbit. One such antibody in particular, the MilliporeSigma rabbit anti-ADAM8 antibody (HPA064637) has been widely used by the Human Protein Atlas to characterize ADAM8 expression in normal human tissues (proteinatlas.org website). Of note, in addition to being a rabbit antibody, it was raised against a peptide within the ADAM8 prodomain, and therefore detects only inactive protein.

Taken together these observations demonstrate that ADAM8 clinical diagnostic-grade antibodies must be developed specifically for patient biopsy characterization and informed treatment against active ADAM8 and that having any antibody that simply binds this target, without extensive biological, specificity and manufacturing considerations, is not sufficient. In addition to being highly specific, and demonstrating excellent IHC staining range, linearity and reproducibility, ADP2 has the advantage of being a mouse monoclonal antibody, that is, it can be reliably supplied long term and it was also raised against functionally active forms of ADAM8.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. Section headings and any descriptions of materials, methods, and examples are illustrative only and not intended to be limiting.

What is claimed is:

1. A protein that inhibits both the metalloprotease activity and disintegrin activity of human ADAM8, wherein the protein comprises an antigen-binding domain comprising:

(a) heavy chain variable domain CDRs of GFSFPDYY (SEQ ID NO: 2), IRDSANGYTT (SEQ ID NO: 3), and ARYSRYYGMDY (SEQ ID NO: 4), and light chain variable domain CDRs of QTVNYD (SEQ ID NO: 5), FAS (SEQ ID NO: 6), and QQDYSAPWT (SEQ ID NO: 7);

(b) heavy chain variable domain CDRs of GYTFTDYY (SEQ ID NO: 12), ISPNIGGA (SEQ ID NO: 13), and TRGGSSYPYFYAMDY (SEQ ID NO: 14), and light chain variable domain CDRs of QSLLYSSNQKKY (SEQ ID NO: 15), WAS (SEQ ID NO: 16), and QQFYSYPYT (SEQ ID NO: 17);

(c) heavy chain variable domain CDRs of GFTFSDAW (SEQ ID NO: 22), IRGKVNNLAT (SEQ ID NO: 23), and LGRYDATYAMDY (SEQ ID NO: 24), and light chain variable domain CDRs of QSLVHSDGNTY (SEQ ID NO: 25), KLS (SEQ ID NO: 26), and SQSTHVPWT (SEQ ID NO: 27);

(d) heavy chain variable domain CDRs of GFSFTDYY (SEQ ID NO: 32), IRDSANGYTA (SEQ ID NO: 33), and ARYSRYYAMDY (SEQ ID NO: 34), and light chain variable domain CDRs of QSVNYD (SEQ ID NO: 35), FAS (SEQ ID NO: 36), and QQDYSSPWT (SEQ ID NO: 37);

(e) heavy chain variable domain CDRs of GYTFTDYN (SEQ ID NO: 42), INPNNGGT (SEQ ID NO: 43), and ARKRGLGQAWLAY (SEQ ID NO: 44), and light chain variable domain CDRs of QSLLYSGNQKNY (SEQ ID NO: 45), GAS (SEQ ID NO: 46), and QNDHSYPLT (SEQ ID NO: 47); or (f) heavy chain variable domain CDRs of GFTFSYAW (SEQ ID NO: 52), IRSKANNYAT (SEQ ID NO: 53), and MGRYDAAYGMDY (SEQ ID NO: 54), and light chain variable domain CDRs of QSLVHSNGITY (SEQ ID NO: 55), KVS (SEQ ID NO: 56), and SQSTHVPWT (SEQ ID NO: 57).

2. The protein of claim 1, wherein the protein is an antibody that is an IgG antibody.

3. The protein of claim 1, wherein the antigen-binding domain comprises:

(A) a light chain variable domain sequence of:

```
                                                 (SEQ ID NO: 8)
SIVMTQTPKILLVSAGDRVTITCKASQTVNYDVAWYQQKPGQSPKPVIY

FASNRYTGVPDRFTGSGFGTDFTFTISTVQAEDLAVYFCQQDYSAPWTF

GGGTKLEIK.
```

and heavy chain variable domain sequence of:

```
                                                (SEQ ID NO: 10)
EVKLVESGGGLVQPGGSLSLSCAASGFSFPDYYMSWVRQPPGKALEWLG

FIRDSANGYTTEYIASVKGRFTFSRDNSQSILYLQMNALRAEDSATYYC

ARYSRYYGMDYWGQGTSVTVSS.
```

(B) a light chain variable domain sequence of:

```
                                                (SEQ ID NO: 18)
DIVMSQSPSSLAVSVGEKVTMSCKSSQSLLYSSNQKKYLAWYQQKPGQS

PKLLIYWASTRESGVPDRFTGSGSGTDFTLTISSVKAEDLAVYYCQQFY

SYPYTFGGGTKLEINR.
```

and a heavy chain variable domain sequence of:

```
                                                (SEQ ID NO: 20)
EVQLQQSGPEMVKPGTSVKISCKASGYTFTDYYINWVKQSHGKSLEWIG

DISPNIGGATYNPKFKGKAILTVDKSARTAYMELRSLTSEDSAVYCCTR

GGSSYPYFYAMDYWGQGTSVTVSS.
```

(C) a light chain variable domain sequence of:

```
                                                (SEQ ID NO: 28)
DVVMTQTPLSLPVSLGDQASISCRSSQSLVHSDGNTYLHWYLQKPGQSP

KLLIYKLSNRFSGVPDRFSGSGSGTDFTLKISRVEAEDLGVYFCSQSTH

VPWTFGGGTKLEIK.
```

and a heavy chain variable domain sequence of:

```
                                                (SEQ ID NO: 30)
EVKLEESGGGLVQPGGSMKLSCAASGFTFSDAWMDWVRQSPEKGLEWVA

EIRGKVNNLATYYVESVKGRFTISRDDSKSSVYLQMNSLRAEDTGIYYC

LGRYDATYAMDYWGQGTSVTVSS.
```

(D) a light chain variable domain sequence of:

```
                                                (SEQ ID NO: 38)
FIVMTQTPKILLVSAGDRITITCKASQSVNYDVAWYQQKPGQSPKPVIY

FASNRYTGVPDRFTGSGFGTDFTFTISTVQAEDLAVYFCQQDYSSPWTF

GGGTKLEIK.
```

and a heavy chain variable domain sequence of:

(SEQ ID NO: 40)
EVKLVESGGGLVQPGGSLSLSCETSGFSFTDYYMIWVRQPPGKALEWLGF

IRDSANGYTAEYIASVKGRFTFSRDNSQSILYLQMNALRAEDSATYYCAR

YSRYYAMDYWGQGTSVTVAP.

(E) a light chain variable domain sequence of:

(SEQ ID NO: 48)
DIVMTQSPSSRSVSAGEKVTMSCKSSQSLLYSGNQKNYLAWYQQKPGQPP

KLLIYGASTRESGVPDRFTGSGSGTDFTLTISSVQAEDLAVYYCQNDHSY

PLTFGAGTKLELK.

and a heavy chain variable domain sequence of:

(SEQ ID NO: 50)
EVQLQQSGPELVKPGASVKIPCKASGYTFTDYNMDWVKQSHGKSLDWIGD

INPNNGGTIYNQKFKGKATLTVDKSSSTAYMELRSLTSEDTAVYYCARKR

GLGQAWLAYWGQGTLVTVSA.

or (F) a light chain variable domain sequence of:

(SEQ ID NO: 58)
DVVMTQTPLSLPVSLGYQASISCRSSQSLVHSNGITYLHWYLQKPGQSPK

WYKVSNRFSGVPDRFSGSGSGTDFTLKISRVEAEDLGVYFCSQSTHVPWT

FGGGTKLEIK.

and a heavy chain variable domain sequence of:

(SEQ ID NO: 60)
EVKLEESGGGLVQPGGSMKLSCAASGFTFSYAWMDWVRQSPEKGLEWVAE

IRSKANNYATYYAESVKGRFTISRNDSKSSVYLQMNSLRIEDTGIYYCMG

RYDAAYGMDYWGQGTSVTVSS.

4. The protein of claim 1, wherein the protein further comprises a conjugated toxin or therapeutic agent.

5. A nucleic acid encoding a protein of claim 1.

6. A mammalian cell comprising a nucleic acid of claim 5.

7. A method of producing a protein that comprises:

(a) culturing a mammalian cell of claim 6 in a liquid culture medium under conditions sufficient to produce the protein; and (b) recovering the protein from the mammalian cell or the liquid culture medium.

8. A pharmaceutical composition comprising a therapeutically effective amount of any of a protein of claim 1.

9. A method for inhibiting migration and/or invasion of an ADAM8 expressing cell in a subject, the method comprising administering to the subject a therapeutically effective amount of a protein of claim 1.

10. A method of decreasing the risk of developing a metastasis or developing an additional metastasis over a period of time in a subject identified as having an ADAM8-associated cancer, the method comprising administering to the subject a therapeutically effective amount of a protein of claim 1.

11. A method of inhibiting the growth of a solid tumor in a subject identified as having an ADAM8-associated cancer, the method comprising administering to the subject a therapeutically effective amount of a protein of claim 1.

12. A method of inhibiting the growth or proliferation of a hematological cancer in a subject identified as having an ADAM8-associated cancer, the method comprising administering to the subject a therapeutically effective amount of a protein of claim 1.

13. A method of killing an ADAM8-associated cancer cell in a subject, the method comprising administering to the subject a therapeutically effective amount of a protein of claim 1.

14. A method of treating an ADAM8-associated cancer in a subject, the method comprising administering to a subject identified as having an ADAM8-associated cancer a therapeutically effective amount of a protein of claim 1.

15. A method of diagnosing an ADAM8-associated cancer in a subject, the method comprising:

(a) contacting a biological sample from the subject with a protein of claim 1;

(b) determining a level of the protein specifically bound to the biological sample; and (c) identifying the subject as having an ADAM8-associated cancer if the level of the protein specifically bound to the biological sample is elevated as compared to a control level.

16. A method of determining the efficacy of treatment of an ADAM8-associated cancer in a subject, the method comprising:

(a) contacting a first biological sample obtained from a subject having an ADAM8-associated cancer at first time point with a protein of claim 1;

(b) determining a first level of the protein specifically bound to the first biological sample;

(c) contacting a second biological sample obtained from the same subject at a second time point with the protein, wherein the subject has been administered a treatment against an ADAM8-associated cancer between the first and second time points;

(d) determining a second level of the protein specifically bound to the second biological sample; and (e) determining the treatment as being effective in a subject having a decreased second level as compared to the first level, or determining the treatment as not being effective in a subject having about the same or an increased second level as compared to the first level.

17. A kit comprising a protein of claim 1.

18. The method of claim 14, wherein the method further comprises administering to the subject a therapeutically effective amount of: a chemotherapeutic agent, a targeted therapy, or an immunotherapy.

19. The method of claim 18, wherein the chemotherapeutic agent is an antimetabolite, a plant alkaloid, a microtubule inhibitor, an anthracycline, a taxol, a platinum agent, or an alkylating agent.

20. The method of claim 18, wherein the targeted therapy is an angiogenesis or a kinase inhibitor, or a hormone modulator.

21. The method of claim 18, wherein the immunotherapy is a chimeric antigen receptor (CAR) T-cell therapy or an inhibitor of PD-1, PD-L1, CTLA-4, LAG-3, CD70, CD80, ICOS, TIGIT, or IDO.

22. The method of claim 15, wherein an elevated level of ADAM8 in the biological sample indicates that the subject has a poorer prognosis.

23. The protein of claim 1, wherein the antigen-binding domain comprises heavy chain variable domain CDRs of GFSFPDYY (SEQ ID NO: 2), IRDSANGYTT (SEQ ID NO: 3), and ARYSRYYGMDY (SEQ ID NO: 4), and light chain variable domain CDRs of QTVNYD (SEQ ID NO: 5), FAS (SEQ ID NO: 6), and QQDYSAPWT (SEQ ID NO: 7).

24. The protein of claim 1, wherein the antigen-binding domain comprises heavy chain variable domain CDRs of GYTFTDYY (SEQ ID NO: 12), ISPNIGGA (SEQ ID NO: 13), and TRGGSSYPYFYAMDY (SEQ ID NO: 14), and light chain variable domain CDRs of QSLLYSSNQKKY (SEQ ID NO: 15), WAS (SEQ ID NO: 16), and QQFYSYPYT (SEQ ID NO: 17).

25. The protein of claim 1, wherein the antigen-binding domain comprises heavy chain variable domain CDRs of GFTFSDAW (SEQ ID NO: 22), IRGKVNNLAT (SEQ ID NO: 23), and LGRYDATYAMDY (SEQ ID NO: 24), and light chain variable domain CDRs of QSLVHSDGNTY (SEQ ID NO: 25), KLS (SEQ ID NO: 26), and SQSTHVPWT (SEQ ID NO: 27).

26. The protein of claim 1, wherein the antigen-binding domain comprises heavy chain variable domain CDRs of GFSFTDYY (SEQ ID NO: 32), IRDSANGYTA (SEQ ID NO: 33), and ARYSRYYAMDY (SEQ ID NO: 34), and light chain variable domain CDRs of QSVNYD (SEQ ID NO: 35), FAS (SEQ ID NO: 36), and QQDYSSPWT (SEQ ID NO: 37).

27. The protein of claim 1, wherein the antigen-binding domain comprises heavy chain variable domain CDRs of GYTFTDYN (SEQ ID NO: 42), INPNNGGT (SEQ ID NO: 43), and ARKRGLGQAWLAY (SEQ ID NO: 44), and light chain variable domain CDRs of QSLLYSGNQKNY (SEQ ID NO: 45), GAS (SEQ ID NO: 46), and QNDHSYPLT (SEQ ID NO: 47).

28. The protein of claim 1, wherein the antigen-binding domain comprises heavy chain variable domain CDRs of GFTFSYAW (SEQ ID NO: 52), IRSKANNYAT (SEQ ID NO: 53), and MGRYDAAYGMDY (SEQ ID NO: 54), and light chain variable domain CDRs of QSLVHSNGITY (SEQ ID NO: 55), KVS (SEQ ID NO: 56), and SQSTHVPWT (SEQ ID NO: 57).

* * * * *

SEQUENCE LISTING

```
<160> NUMBER OF SEQ ID NOS: 104

<210> SEQ ID NO 1
<211> LENGTH: 69
<212> TYPE: PRT
<213> ORGANISM: Homo sapiens

<400> SEQUENCE: 1

Asp Cys Gly Pro Pro Glu Asp Cys Arg Asn Arg Cys Cys Asn Ser Thr
1               5                   10                  15

Thr Cys Gln Leu Ala Glu Gly Ala Gln Cys Ala His Gly Thr Cys Cys
            20                  25                  30

Gln Glu Cys Lys Val Lys Pro Ala Gly Glu Leu Cys Arg Pro Lys Lys
        35                  40                  45

Asp Met Cys Asp Leu Glu Glu Phe Cys Asp Gly Arg His Pro Glu Cys
    50                  55                  60

Pro Glu Asp Ala Phe
65


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Ser Phe Pro Asp Tyr Tyr
1               5


<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 3

Ile Arg Asp Ser Ala Asn Gly Tyr Thr Thr
1 5 10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Ala Arg Tyr Ser Arg Tyr Tyr Gly Met Asp Tyr
1 5 10

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Gln Thr Val Asn Tyr Asp
1 5

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Phe Ala Ser
1

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Gln Gln Asp Tyr Ser Ala Pro Trp Thr
1 5

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Ser Ile Val Met Thr Gln Thr Pro Lys Ile Leu Leu Val Ser Ala Gly
1 5 10 15

Asp Arg Val Thr Ile Thr Cys Lys Ala Ser Gln Thr Val Asn Tyr Asp
20 25 30

Val Ala Trp Tyr Gln Gln Lys Pro Gly Gln Ser Pro Lys Pro Val Ile

```
        35                  40                  45

Tyr Phe Ala Ser Asn Arg Tyr Thr Gly Val Pro Asp Arg Phe Thr Gly
    50                  55                  60

Ser Gly Phe Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ala Pro Trp
                85                  90                  95

Thr Phe Gly Gly Gly Thr Lys Leu Glu Ile Lys
            100                 105


<210> SEQ ID NO 9
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

agtattgtga tgacccagac tcccaaaatc ctgcttgtgt cagcaggaga cagggttacc      60

ataacctgca aggccagtca gactgtgaat tatgatgtag cttggtacca acagaagcca     120

gggcagtctc ctaaaccggt gatatacttt gcatccaatc gctacactgg ggtccctgat     180

cgcttcactg gcagtggatt tgggacggat ttcactttca ccatcagcac tgtgcaggct     240

gaagacctgg cagtttattt ctgtcagcag gattatagtg ctccgtggac gttcggtgga     300

ggcaccaagc tggaaatcaa a                                               321


<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Ser Phe Pro Asp Tyr
            20                  25                  30

Tyr Met Ser Trp Val Arg Gln Pro Pro Gly Lys Ala Leu Glu Trp Leu
        35                  40                  45

Gly Phe Ile Arg Asp Ser Ala Asn Gly Tyr Thr Thr Glu Tyr Ile Ala
    50                  55                  60

Ser Val Lys Gly Arg Phe Thr Phe Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Tyr Ser Arg Tyr Tyr Gly Met Asp Tyr Trp Gly Gln
            100                 105                 110

Gly Thr Ser Val Thr Val Ser Ser
        115                 120


<210> SEQ ID NO 11
<211> LENGTH: 360
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 11
gaggtgaagc tggtggagtc tggaggaggc ttggtacagc ctgggggttc tctgagtctc 60
tcctgtgcag cttctggatt ctccttccct gattactaca tgagctgggt ccgccagcct 120
ccagggaagg cacttgagtg gttgggtttt attagagaca gtgctaatgg ttacacaaca 180
gagtacattg catctgtcaa gggtcggttc accttctcca gagataattc ccaaagcatc 240
ctctatcttc aaatgaatgc cctgagagct gaggacagtg ccacttatta ctgtgcaaga 300
tatagccgat actatggtat ggactattgg ggtcaaggaa cctcagtcac cgtctcctca 360

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gly Tyr Thr Phe Thr Asp Tyr Tyr
1 5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Ile Ser Pro Asn Ile Gly Gly Ala
1 5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Thr Arg Gly Gly Ser Ser Tyr Pro Tyr Phe Tyr Ala Met Asp Tyr
1 5 10 15

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Gln Ser Leu Leu Tyr Ser Ser Asn Gln Lys Lys Tyr
1 5 10

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Trp Ala Ser
1

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Gln Gln Phe Tyr Ser Tyr Pro Tyr Thr
1 5

<210> SEQ ID NO 18
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Lys Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Phe Tyr Ser Tyr Pro Tyr Thr Phe Gly Gly Gly Thr Lys Leu Glu Ile
100 105 110

Asn Arg

<210> SEQ ID NO 19
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
gacattgtga tgtcacagtc tccatcctcc ctagctgtgt cagttggaga gaaggttact 60
atgagctgca agtccagtca gagcctttta tatagtagca atcaaaagaa gtacttggcc 120
tggtaccagc agaaaccagg gcagtctcct aaattgttga tttactgggc atccactagg 180
gaatctgggg tccctgatcg cttcacaggc agtggatctg ggacagattt cactctcacc 240
atcagcagtg tgaaggctga agacctggca gtttattact gtcagcaatt ttatagctat 300
ccgtacacgt tcggaggggg gaccaagctg gaaataaacc gg 342

-continued

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

```
Glu Val Gln Leu Gln Gln Ser Gly Pro Glu Met Val Lys Pro Gly Thr
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Ser His Gly Lys Ser Leu Glu Trp Ile
        35                  40                  45

Gly Asp Ile Ser Pro Asn Ile Gly Gly Ala Thr Tyr Asn Pro Lys Phe
    50                  55                  60

Lys Gly Lys Ala Ile Leu Thr Val Asp Lys Ser Ala Arg Thr Ala Tyr
65                  70                  75                  80

Met Glu Leu Arg Ser Leu Thr Ser Glu Asp Ser Ala Val Tyr Cys Cys
                85                  90                  95

Thr Arg Gly Gly Ser Ser Tyr Pro Tyr Phe Tyr Ala Met Asp Tyr Trp
            100                 105                 110

Gly Gln Gly Thr Ser Val Thr Val Ser Ser
        115                 120
```

<210> SEQ ID NO 21
<211> LENGTH: 366
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21

```
gaggtccagc tgcaacaatc tggacctgaa atggtgaagc ctgggacttc agtgaagata     60

tcgtgtaagg cttctggata cacgttcact gactactaca taaactgggt gaagcagagc    120

catggaaaga gccttgagtg gattggagat attagtccta acattggtgg tgcgacctac    180

aacccgaagt tcaagggcaa ggccatattg actgtagaca agtccgccag aacagcctac    240

atggagctcc gcagcctgac atctgaggac tctgcagtct attgctgtac aagaggcggt    300

agtagctacc cctatttcta tgctatggac tactggggtc aaggaacctc agtcaccgtc    360

tcctca                                                               366
```

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

```
Gly Phe Thr Phe Ser Asp Ala Trp
1               5
```

<210> SEQ ID NO 23
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 23

Ile Arg Gly Lys Val Asn Asn Leu Ala Thr
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Gly Arg Tyr Asp Ala Thr Tyr Ala Met Asp Tyr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Leu Val His Ser Asp Gly Asn Thr Tyr
1               5                   10

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Leu Ser
1

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gln Ser Thr His Val Pro Trp Thr
1               5

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser

```
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Leu Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 29
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
gatgttgtga tgacccaaac tccactctcc ctgcctgtca gtcttggaga tcaagcctcc     60

atctcttgca gatctagtca gagccttgta cacagtgatg gaaacaccta tttacattgg    120

tacctgcaga agccaggcca gtctccaaag ctcctgatct acaaactttc caaccgattt    180

tctggggtcc cagacaggtt cagtggcagt ggatcaggga cagatttcac actcaagatc    240

agcagagtgg aggctgagga tctgggagtt tatttctgct ctcaaagtac acatgttccg    300

tggacgttcg gagggggac caagctggaa ataaaa                                336
```

<210> SEQ ID NO 30
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Gly Lys Val Asn Asn Leu Ala Thr Tyr Tyr Val Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Leu Gly Arg Tyr Asp Ala Thr Tyr Ala Met Asp Tyr Trp Gly
            100                 105                 110

Gln Gly Thr Ser Val Thr Val Ser Ser
        115                 120
```

<210> SEQ ID NO 31
<211> LENGTH: 363
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 31

gaagtgaagc ttgaggagtc tggaggaggc ttggtgcaac ctggaggatc catgaaactc      60

tcttgtgctg cctctggatt cacttttagt gacgcctgga tggactgggt ccgccagtct     120

ccagagaagg gacttgagtg ggttgctgaa attagaggca aagttaataa tcttgcaacg     180

tactatgttg agtctgtgaa agggaggttc accatctcaa gagatgattc caaaagtagt     240

gtctacctgc aaatgaacag cttaagagct gaagacactg gcatttatta ctgtttgggg     300

aggtacgacg cgacatatgc tatggactac tggggtcaag gaacctcagt caccgtctcc     360

tca                                                                   363


<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Phe Ser Phe Thr Asp Tyr Tyr
1               5


<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Arg Asp Ser Ala Asn Gly Tyr Thr Ala
1               5                   10


<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Arg Tyr Ser Arg Tyr Tyr Ala Met Asp Tyr
1               5                   10


<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ser Val Asn Tyr Asp
1               5


<210> SEQ ID NO 36
```

<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Phe Ala Ser
1

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gln Gln Asp Tyr Ser Ser Pro Trp Thr
1 5

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Phe Ile Val Met Thr Gln Thr Pro Lys Ile Leu Leu Val Ser Ala Gly
1 5 10 15

Asp Arg Ile Thr Ile Thr Cys Lys Ala Ser Gln Ser Val Asn Tyr Asp
20 25 30

Val Ala Trp Tyr Gln Gln Lys Pro Gly Gln Ser Pro Lys Pro Val Ile
35 40 45

Tyr Phe Ala Ser Asn Arg Tyr Thr Gly Val Pro Asp Arg Phe Thr Gly
50 55 60

Ser Gly Phe Gly Thr Asp Phe Thr Phe Thr Ile Ser Thr Val Gln Ala
65 70 75 80

Glu Asp Leu Ala Val Tyr Phe Cys Gln Gln Asp Tyr Ser Ser Pro Trp
85 90 95

Thr Phe Gly Gly Gly Thr Lys Leu Glu Ile Lys
100 105

<210> SEQ ID NO 39
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39
tttattgtga tgacccagac tcccaaaatc ctgcttgtat cagcaggaga caggatcacc 60
ataacctgca aggccagtca gagtgtgaat tatgatgtcg cttggtacca acagaagcca 120
gggcagtctc ctaaaccggt gatatacttt gcatccaatc gctacactgg agtccctgat 180
cgcttcactg gcagtggatt tgggacggat ttcactttca ccatcagcac tgtgcaggct 240
gaagacctgg cagtttattt ctgtcagcag gattatagct ctccgtggac gttcggtgga 300
ggcaccaagc tggaaatcaa a 321

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Glu Val Lys Leu Val Glu Ser Gly Gly Gly Leu Val Gln Pro Gly Gly
1 5 10 15

Ser Leu Ser Leu Ser Cys Glu Thr Ser Gly Phe Ser Phe Thr Asp Tyr
20 25 30

Tyr Met Ile Trp Val Arg Gln Pro Pro Gly Lys Ala Leu Glu Trp Leu
35 40 45

Gly Phe Ile Arg Asp Ser Ala Asn Gly Tyr Thr Ala Glu Tyr Ile Ala
50 55 60

Ser Val Lys Gly Arg Phe Thr Phe Ser Arg Asp Asn Ser Gln Ser Ile
65 70 75 80

Leu Tyr Leu Gln Met Asn Ala Leu Arg Ala Glu Asp Ser Ala Thr Tyr
85 90 95

Tyr Cys Ala Arg Tyr Ser Arg Tyr Tyr Ala Met Asp Tyr Trp Gly Gln
100 105 110

Gly Thr Ser Val Thr Val Ala Pro
115 120

<210> SEQ ID NO 41
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41
gaggtgaagc tggtggagtc tggaggaggc ttggtacagc ctggggggttc tctgagtctc 60 tcctgtgaaa cttctggatt ctccttcact gattactata tgatctgggt ccgccagcct 120
ccagggaagg cacttgagtg gttgggtttt atcagagaca gtgctaatgg ttacacagca 180
gagtacattg catctgtgaa gggtcggttc accttctcca gagataattc ccaaagcatc 240
ctctatcttc aaatgaatgc cctgagagct gaggacagtg ccacttatta ctgtgcaaga 300
tatagccgat actatgctat ggactattgg ggtcagggaa cctcagtcac cgtcgcccca 360

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Gly Tyr Thr Phe Thr Asp Tyr Asn
1 5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Ile Asn Pro Asn Asn Gly Gly Thr
1 5

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Ala Arg Lys Arg Gly Leu Gly Gln Ala Trp Leu Ala Tyr
1 5 10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Gln Ser Leu Leu Tyr Ser Gly Asn Gln Lys Asn Tyr
1 5 10

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Gly Ala Ser
1

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Gln Asn Asp His Ser Tyr Pro Leu Thr
1 5

<210> SEQ ID NO 48
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 48

Asp Ile Val Met Thr Gln Ser Pro Ser Ser Arg Ser Val Ser Ala Gly
1 5 10 15

-continued

```
Glu Lys Val Thr Met Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Leu
            100                 105                 110

Lys


<210> SEQ ID NO 49
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

gacattgtga tgacacagtc tccatcctcc cggagtgtgt cagcaggaga gaaggtcact      60

atgagctgca agtccagcca gagtctgtta tacagtggaa atcaaaagaa ctacttggcc     120

tggtaccagc agaaaccagg gcagcctcct aaactgttga tctacggggc atccactagg     180

gaatctgggg tccctgatcg cttcacaggc agtggatctg gaaccgattt cactcttacc     240

atcagcagtg tgcaggctga agacctggca gtttattact gtcagaatga tcatagttat     300

ccgctcacgt tcggtgctgg gaccaagctg gagctgaaa                            339


<210> SEQ ID NO 50
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Asp Trp Ile
        35                  40                  45

Gly Asp Ile Asn Pro Asn Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Lys Arg Gly Leu Gly Gln Ala Trp Leu Ala Tyr Trp Gly Gln
            100                 105                 110

Gly Thr Leu Val Thr Val Ser Ala
        115                 120
```

-continued

<210> SEQ ID NO 51
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
gaggtccagc tgcaacagtc tggacctgag ctggtgaagc ctggggcttc agtgaagata 60
ccctgcaagg cttctggata cacattcact gactacaaca tggactgggt gaagcagagc 120
catggaaaga gccttgactg gattggagat attaatccaa acaatggtgg tactatctac 180
aaccagaagt tcaagggcaa ggccacattg actgtagaca agtcctccag cacagcctac 240
atggagctcc gcagcctgac atctgaggac actgcagtct attactgtgc aagaaagaga 300
ggcctgggac aggcctggtt agcttactgg ggccaaggga ctctggtcac tgtctctgca 360

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Gly Phe Thr Phe Ser Tyr Ala Trp
1 5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Ile Arg Ser Lys Ala Asn Asn Tyr Ala Thr
1 5 10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Met Gly Arg Tyr Asp Ala Ala Tyr Gly Met Asp Tyr
1 5 10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Gln Ser Leu Val His Ser Asn Gly Ile Thr Tyr
1 5 10

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Lys Val Ser
1

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Ser Gln Ser Thr His Val Pro Trp Thr
1 5

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

Asp Val Val Met Thr Gln Thr Pro Leu Ser Leu Pro Val Ser Leu Gly
1 5 10 15

Tyr Gln Ala Ser Ile Ser Cys Arg Ser Ser Gln Ser Leu Val His Ser
20 25 30

Asn Gly Ile Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Trp Thr Phe Gly Gly Gly Thr Lys Leu Glu Ile Lys
100 105 110

<210> SEQ ID NO 59
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59
gatgttgtga tgacccaaac tccactctcc ctgcctgtca gtcttggata tcaagcctcc 60
atctcttgca gatctagtca gagccttgtt cacagcaatg gaatcaccta tttacattgg 120
tacctgcaga agccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tatttctgct ctcaaagtac acatgttccg 300

```
tggacgttcg gtggaggcac caagctggaa atcaaa                            336


<210> SEQ ID NO 60
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Tyr Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn Tyr Ala Thr Tyr Tyr Ala Glu
    50                  55                  60

Ser Val Lys Gly Arg Phe Thr Ile Ser Arg Asn Asp Ser Lys Ser Ser
65                  70                  75                  80

Val Tyr Leu Gln Met Asn Ser Leu Arg Ile Glu Asp Thr Gly Ile Tyr
                85                  90                  95

Tyr Cys Met Gly Arg Tyr Asp Ala Ala Tyr Gly Met Asp Tyr Trp Gly
            100                 105                 110

Gln Gly Thr Ser Val Thr Val Ser Ser
        115                 120


<210> SEQ ID NO 61
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

gaagtgaagc ttgaggagtc tggaggaggc ttggtgcaac ctggaggatc catgaaactc     60

tcttgtgctg cctctggatt cacttttagt tacgcctgga tggactgggt ccgccagtct    120

cccgagaagg gacttgagtg ggttgctgaa attagaagca aagctaataa ttatgcaaca    180

tactatgctg agtctgtgaa agggaggttc accatctcaa gaaatgattc caaaagtagt    240

gtctacctac aaatgaacag cttgagaatt gaagacactg gcatttatta ctgtatgggg    300

aggtacgacg cggcctatgg tatggactac tggggtcaag gaacctcagt caccgtctcc    360

tca                                                                  363


<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Phe Thr Phe Ser Asp Ala Trp
1               5


<210> SEQ ID NO 63
```

<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Arg Asn Lys Ala Asn Ser His Ala Thr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Arg Asp Gly Gly Tyr Tyr Ala Trp Phe Ala Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ser Ile Val His Ser Asp Gly Asn Thr Tyr
1               5                   10

<210> SEQ ID NO 66
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Val Ser
1

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe His Gly Ser His Ile Pro Leu Thr
1               5

<210> SEQ ID NO 68
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Gly Ala Leu Leu Thr Gln Thr Pro Leu Ser Leu Pro Val Ser Leu Gly
1               5                   10                  15

Asp Gln Val Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe His Gly
                85                  90                  95

Ser His Ile Pro Leu Thr Phe Gly Ala Gly Thr Lys Leu Glu Leu Lys
            100                 105                 110


<210> SEQ ID NO 69
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

ggtgctttgc tgacccaaac tccactctcc ctgcctgtca gtcttggaga tcaagtctcc      60

atctcttgca ggtctagtca gagcattgta catagtgatg gaaacaccta tttagaatgg     120

tacctgcaga agccaggcca gtctccaaag ctcctgattt acagagtttc caaccgattt     180

tctggggtcc cagacaggtt cagtggcagt ggatcaggga cagacttcac actcaagatc     240

agcagagtgg aggctgagga tctgggaatt tattactgct ttcacggttc acatattccg     300

ctcacgttcg gtgctgggac caagctggag ctgaaa                               336


<210> SEQ ID NO 70
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Lys Phe Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Asn Ser His Ala Thr Tyr Tyr Ala Glu
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Ala Glu Asp Thr Gly Ile Tyr
                85                  90                  95

Tyr Cys Thr Arg Asp Gly Gly Tyr Tyr Ala Trp Phe Ala Tyr Trp Gly
            100                 105                 110

Gln Gly Thr Leu Val Thr Val Ser Ala
        115                 120
```

<210> SEQ ID NO 71
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
gaagtgaagt ttgaggagtc tggaggaggc ttggtgcaac ctggaggatc catgaaactc 60
tcttgtgctg cctctggatt cacttttagt gacgcctgga tggactgggt ccgccagtct 120
ccagagaagg ggcttgagtg ggttgctgaa attagaaaca aagctaatag tcatgcaaca 180
tactatgctg agtctgtgaa agggaggttc accatctcaa gagatgattc caaaagtact 240
gtctacctgc aaatgaacag cttaagagct gaagacactg gcatttatta ctgtaccagg 300
gatggtggtt actacgcctg gtttgcttac tggggccaag ggactctggt cactgtctct 360
gca 363

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Gly Phe Thr Phe Ser Asp Ala Trp
1 5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Ile Arg Asn Lys Ala Asn Asn His Ala Thr
1 5 10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Thr Arg Asp Gly Gly Tyr Tyr Ala Trp Phe Ala Tyr
1 5 10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Gln Ser Ile Val His Ser Asp Gly Asn Thr Tyr 1 5 10

<210> SEQ ID NO 76
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Lys Val Ser
1

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Phe His Gly Ser His Ile Pro Leu Thr
1 5

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

Gly Val Leu Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asp Gly Asn Thr Tyr Leu Glu Trp Tyr Leu Gln Lys Pro Gly Gln Ser
35 40 45

Pro Lys Leu Leu Leu Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe His Gly
85 90 95

Ser His Ile Pro Leu Thr Phe Gly Ala Gly Thr Lys Leu Glu Leu Lys
100 105 110

<210> SEQ ID NO 79
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79
ggtgttttga tgacccaaac tccactctcc ctgcctgtca gtcttggaga tcaagcctcc 60
atctcttgca ggtctagtca gagcattgta catagtgatg gaaacaccta tttagaatgg 120
tacctgcaga agccaggcca gtctccaaag ctcctgctct acaaagtttc caaccgattt 180

-continued tctggggtcc cagacaggtt cagtggcagt ggatcaggga cagatttcac actcaagatc 240
agcagagtgg aggctgagga tctgggagtt tattactgct ttcatggttc acatattccg 300
ctcacgttcg gtgctgggac caagctggag ctgaaa 336

<210> SEQ ID NO 80
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

Glu Val Lys Phe Glu Glu Ser Gly Gly Gly Leu Val Gln Pro Gly Gly
1 5 10 15

Ser Met Lys Leu Ser Cys Ala Ala Ser Gly Phe Thr Phe Ser Asp Ala
20 25 30

Trp Met Asp Trp Val Arg Gln Ser Pro Glu Lys Gly Leu Glu Trp Val
35 40 45

Ala Glu Ile Arg Asn Lys Ala Asn Asn His Ala Thr Tyr Tyr Ala Glu
50 55 60

Ser Val Lys Gly Arg Phe Thr Ile Ser Arg Asp Asp Ser Lys Ser Ser
65 70 75 80

Val Tyr Leu Gln Met Asn Ser Leu Arg Ala Glu Asp Thr Gly Ile Tyr
85 90 95

Tyr Cys Thr Arg Asp Gly Gly Tyr Tyr Ala Trp Phe Ala Tyr Trp Gly
100 105 110

Gln Gly Thr Leu Val Thr Val Ser Ala
115 120

<210> SEQ ID NO 81
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 81
gaagtgaagt ttgaggagtc tggaggaggc ttggtgcaac ctggaggatc catgaaactc 60
tcttgtgctg cctctggatt cacttttagt gacgcctgga tggactgggt ccgccagtct 120
ccagagaagg ggcttgagtg ggttgctgaa attagaaaca aagctaataa tcatgcaaca 180
tactatgctg agtctgtgaa agggaggttc accatctcaa gagatgattc caaaagtagt 240
gtctacctgc aaatgaacag tttaagagct gaagacactg gcatttatta ctgtaccagg 300
gatggtggtt actacgcctg gtttgcttac tggggccaag ggactctggt cactgtctct 360
gca 363

<210> SEQ ID NO 82
<211> LENGTH: 449
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

Glu Val Lys Leu Val Glu Ser Gly Gly Gly Leu Val Gln Pro Gly Gly
1 5 10 15

-continued

```
Ser Leu Ser Leu Ser Cys Ala Ala Ser Gly Phe Ser Phe Pro Asp Tyr
            20                  25                  30

Tyr Met Ser Trp Val Arg Gln Pro Pro Gly Lys Ala Leu Glu Trp Leu
        35                  40                  45

Gly Phe Ile Arg Asp Ser Ala Asn Gly Tyr Thr Thr Glu Tyr Ile Ala
    50                  55                  60

Ser Val Lys Gly Arg Phe Thr Phe Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Tyr Ser Arg Tyr Tyr Gly Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

-continued

Glu Ala Leu His Asn His Tyr Thr Gln Lys Ser Leu Ser Leu Ser Pro
        435                 440                 445

Gly

<210> SEQ ID NO 83
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ser Ile Val Met Thr Gln Thr Pro Lys Ile Leu Leu Val Ser Ala Gly
1               5                   10                  15

Asp Arg Val Thr Ile Thr Cys Lys Ala Ser Gln Thr Val Asn Tyr Asp
            20                  25                  30

Val Ala Trp Tyr Gln Gln Lys Pro Gly Gln Ser Pro Lys Pro Val Ile
        35                  40                  45

Tyr Phe Ala Ser Asn Arg Tyr Thr Gly Val Pro Asp Arg Phe Thr Gly
    50                  55                  60

Ser Gly Phe Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ala Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Gln Gln Ser Gly Pro Glu Met Val Lys Pro Gly Thr
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Ser His Gly Lys Ser Leu Glu Trp Ile
        35                  40                  45

Gly Asp Ile Ser Pro Asn Ile Gly Gly Ala Thr Tyr Asn Pro Lys Phe

-continued

```
    50                  55                  60

Lys Gly Lys Ala Ile Leu Thr Val Asp Lys Ser Ala Arg Thr Ala Tyr
65                  70                  75                  80

Met Glu Leu Arg Ser Leu Thr Ser Glu Asp Ser Ala Val Tyr Cys Cys
                85                  90                  95

Thr Arg Gly Gly Ser Ser Tyr Pro Tyr Phe Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

<210> SEQ ID NO 85

-continued

<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Lys Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Phe Tyr Ser Tyr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 86
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

```
Cys Cys Asn Ser Thr Thr Cys Gln Leu Ala Glu Gly Ala Gln Cys Ala
1               5                   10                  15

His Gly Thr Cys Cys Gln Glu Cys Lys
            20                  25
```

<210> SEQ ID NO 87
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

-continued

Leu Ala Glu Gly Ala Gln Cys Ala His Gly Thr Cys Cys Gln Glu Cys
1 5 10 15

Lys Val Lys Pro Ala Gly Glu Leu Cys Arg Pro Lys Lys Asp Met Cys
20 25 30

Asp Leu Glu Glu Phe Cys Asp Gly Arg His Pro Glu Cys Pro Glu Asp
35 40 45

Ala Phe
50

<210> SEQ ID NO 88
<211> LENGTH: 19
<212> TYPE: PRT
<213> ORGANISM: Homo sapiens

<400> SEQUENCE: 88

Asp Cys Gly Pro Pro Glu Asp Cys Arg Asn Arg Cys Cys Asn Ser Thr
1 5 10 15

Thr Cys Gln

<210> SEQ ID NO 89
<211> LENGTH: 9
<212> TYPE: PRT
<213> ORGANISM: Homo sapiens

<400> SEQUENCE: 89

Cys Arg Pro Lys Lys Asp Met Cys Asp
1 5

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid

<400> SEQUENCE: 90

His Glu Xaa Xaa His Xaa Xaa Gly Xaa Xaa His
1 5 10

<210> SEQ ID NO 91
<211> LENGTH: 824
<212> TYPE: PRT
<213> ORGANISM: Homo sapiens

<400> SEQUENCE: 91

Met Arg Gly Leu Gly Leu Trp Leu Leu Gly Ala Met Met Leu Pro Ala
1 5 10 15

Ile Ala Pro Ser Arg Pro Trp Ala Leu Met Glu Gln Tyr Glu Val Val
20 25 30

Leu Pro Trp Arg Leu Pro Gly Pro Arg Val Arg Arg Ala Leu Pro Ser
35 40 45

-continued

```
His Leu Gly Leu His Pro Glu Arg Val Ser Tyr Val Leu Gly Ala Thr
    50                  55                  60

Gly His Asn Phe Thr Leu His Leu Arg Lys Asn Arg Asp Leu Leu Gly
65                  70                  75                  80

Ser Gly Tyr Thr Glu Thr Tyr Thr Ala Ala Asn Gly Ser Glu Val Thr
                85                  90                  95

Glu Gln Pro Arg Gly Gln Asp His Cys Phe Tyr Gln Gly His Val Glu
            100                 105                 110

Gly Tyr Pro Asp Ser Ala Ala Ser Leu Ser Thr Cys Ala Gly Leu Arg
        115                 120                 125

Gly Phe Phe Gln Val Gly Ser Asp Leu His Leu Ile Glu Pro Leu Asp
    130                 135                 140

Glu Gly Gly Glu Gly Gly Arg His Ala Val Tyr Gln Ala Glu His Leu
145                 150                 155                 160

Leu Gln Thr Ala Gly Thr Cys Gly Val Ser Asp Asp Ser Leu Gly Ser
                165                 170                 175

Leu Leu Gly Pro Arg Thr Ala Ala Val Phe Arg Pro Arg Pro Gly Asp
            180                 185                 190

Ser Leu Pro Ser Arg Glu Thr Arg Tyr Val Glu Leu Tyr Val Val Val
        195                 200                 205

Asp Asn Ala Glu Phe Gln Met Leu Gly Ser Glu Ala Ala Val Arg His
    210                 215                 220

Arg Val Leu Glu Val Val Asn His Val Asp Lys Leu Tyr Gln Lys Leu
225                 230                 235                 240

Asn Phe Arg Val Val Leu Val Gly Leu Glu Ile Trp Asn Ser Gln Asp
                245                 250                 255

Arg Phe His Val Ser Pro Asp Pro Ser Val Thr Leu Glu Asn Leu Leu
            260                 265                 270

Thr Trp Gln Ala Arg Gln Arg Thr Arg Arg His Leu His Asp Asn Val
        275                 280                 285

Gln Leu Ile Thr Gly Val Asp Phe Thr Gly Thr Thr Val Gly Phe Ala
    290                 295                 300

Arg Val Ser Ala Met Cys Ser His Ser Ser Gly Ala Val Asn Gln Asp
305                 310                 315                 320

His Ser Lys Asn Pro Val Gly Val Ala Cys Thr Met Ala His Glu Met
                325                 330                 335

Gly His Asn Leu Gly Met Asp His Asp Glu Asn Val Gln Gly Cys Arg
            340                 345                 350

Cys Gln Glu Arg Phe Glu Ala Gly Arg Cys Ile Met Ala Gly Ser Ile
        355                 360                 365

Gly Ser Ser Phe Pro Arg Met Phe Ser Asp Cys Ser Gln Ala Tyr Leu
    370                 375                 380

Glu Ser Phe Leu Glu Arg Pro Gln Ser Val Cys Leu Ala Asn Ala Pro
385                 390                 395                 400

Asp Leu Ser His Leu Val Gly Gly Pro Val Cys Gly Asn Leu Phe Val
                405                 410                 415

Glu Arg Gly Glu Gln Cys Asp Cys Gly Pro Pro Glu Asp Cys Arg Asn
            420                 425                 430

Arg Cys Cys Asn Ser Thr Thr Cys Gln Leu Ala Glu Gly Ala Gln Cys
        435                 440                 445

Ala His Gly Thr Cys Cys Gln Glu Cys Lys Val Lys Pro Ala Gly Glu
    450                 455                 460

Leu Cys Arg Pro Lys Lys Asp Met Cys Asp Leu Glu Glu Phe Cys Asp
```

-continued

```
465                 470                 475                 480

Gly Arg His Pro Glu Cys Pro Glu Asp Ala Phe Gln Glu Asn Gly Thr
                485                 490                 495

Pro Cys Ser Gly Gly Tyr Cys Tyr Asn Gly Ala Cys Pro Thr Leu Ala
            500                 505                 510

Gln Gln Cys Gln Ala Phe Trp Gly Pro Gly Gly Gln Ala Ala Glu Glu
        515                 520                 525

Ser Cys Phe Ser Tyr Asp Ile Leu Pro Gly Cys Lys Ala Ser Arg Tyr
    530                 535                 540

Arg Ala Asp Met Cys Gly Val Leu Gln Cys Lys Gly Gly Gln Gln Pro
545                 550                 555                 560

Leu Gly Arg Ala Ile Cys Ile Val Asp Val Cys His Ala Leu Thr Thr
                565                 570                 575

Glu Asp Gly Thr Ala Tyr Glu Pro Val Pro Glu Gly Thr Arg Cys Gly
            580                 585                 590

Pro Glu Lys Val Cys Trp Lys Gly Arg Cys Gln Asp Leu His Val Tyr
        595                 600                 605

Arg Ser Ser Asn Cys Ser Ala Gln Cys His Asn His Gly Val Cys Asn
    610                 615                 620

His Lys Gln Glu Cys His Cys His Ala Gly Trp Ala Pro Pro His Cys
625                 630                 635                 640

Ala Lys Leu Leu Thr Glu Val His Ala Ala Ser Gly Ser Leu Pro Val
                645                 650                 655

Phe Val Val Val Val Leu Val Leu Leu Ala Val Val Leu Val Thr Leu
            660                 665                 670

Ala Gly Ile Ile Val Tyr Arg Lys Ala Arg Ser Arg Ile Leu Ser Arg
        675                 680                 685

Asn Val Ala Pro Lys Thr Thr Met Gly Arg Ser Asn Pro Leu Phe His
    690                 695                 700

Gln Ala Ala Ser Arg Val Pro Ala Lys Gly Gly Ala Pro Ala Pro Ser
705                 710                 715                 720

Arg Gly Pro Gln Glu Leu Val Pro Thr Thr His Pro Gly Gln Pro Ala
                725                 730                 735

Arg His Pro Ala Ser Ser Val Ala Leu Lys Arg Pro Pro Pro Ala Pro
            740                 745                 750

Pro Val Thr Val Ser Ser Pro Pro Phe Pro Val Pro Val Tyr Thr Arg
        755                 760                 765

Gln Ala Pro Lys Gln Val Ile Lys Pro Thr Phe Ala Pro Pro Val Pro
    770                 775                 780

Pro Val Lys Pro Gly Ala Gly Ala Ala Asn Pro Gly Pro Ala Glu Gly
785                 790                 795                 800

Ala Val Gly Pro Lys Val Ala Leu Lys Pro Pro Ile Gln Arg Lys Gln
                805                 810                 815

Gly Ala Gly Ala Pro Thr Ala Pro
            820


<210> SEQ ID NO 92
<211> LENGTH: 2475
<212> TYPE: DNA
<213> ORGANISM: Homo sapiens

<400> SEQUENCE: 92

atgcgcggcc tcgggctctg gctgctgggc gcgatgatgc tgcctgcgat tgcccccagc      60

cggccctggg ccctcatgga gcagtatgag gtcgtgttgc cgtggcgtct gccaggcccc     120
```

-continued

```
cgagtccgcc gagctctgcc ctcccacttg ggcctgcacc cagagagggt gagctacgtc    180
cttggggcca cagggcacaa cttcaccctc cacctgcgga agaacaggga cctgctgggc    240
tccggctaca cagagaccta tacggctgcc aatggctccg aggtgacgga gcagcctcgc    300
gggcaggacc actgcttcta ccagggccac gtagaggggt acccggactc agccgccagc    360
ctcagcacct gtgccggcct caggggtttc ttccaggtgg ggtcagacct gcacctgatc    420
gagcccctgg atgaaggtgg cgagggcgga cggcacgccg tgtaccaggc tgagcacctg    480
ctgcagacgg ccgggacctg cggggtcagc gacgacagcc tgggcagcct cctgggaccc    540
cggacggcag ccgtcttcag gcctcggccc ggggactctc tgccatcccg agagacccgc    600
tacgtggagc tgtatgtggt cgtggacaat gcagagttcc agatgctggg gagcgaagca    660
gccgtgcgtc atcgggtgct ggaggtggtg aatcacgtgg acaagctata tcagaaactc    720
aacttccgtg tggtcctggt gggcctggag atttggaata gtcaggacag gttccacgtc    780
agccccgacc ccagtgtcac actggagaac ctcctgacct ggcaggcacg gcaacggaca    840
cggcggcacc tgcatgacaa cgtacagctc atcacgggtg tcgacttcac cgggactacc    900
gtggggtttg ccagggtgtc cgccatgtgc tcccacagct caggggctgt gaaccaggac    960
cacagcaaga accccgtggg cgtggcctgt accatggccc atgagatggg ccacaacctg   1020
ggcatggacc atgatgagaa cgtccagggc tgccgctgcc aggaacgctt cgaggccggc   1080
cgctgcatca tggcgggcag cattggctcc agtttcccca ggatgttcag tgactgcagc   1140
caggcctacc tggagagctt tttggagcgg ccgcagtcgg tgtgcctcgc caacgcccct   1200
gacctcagcc acctggtggg cggcccccgtg tgtgggaacc tgtttgtgga gcgtggggag   1260
cagtgcgact gcggcccccc cgaggactgc cggaaccgct gctgcaactc taccacctgc   1320
cagctggctg aggggggccca gtgtgcgcac ggtacctgct gccaggagtg caaggtgaag   1380
ccggctggtg agctgtgccg tcccaagaag gacatgtgtg acctcgagga gttctgtgac   1440
ggccggcacc ctgagtgccc ggaagacgcc ttccaggaga acggcacgcc ctgctccggg   1500
ggctactgct acaacggggc ctgtcccaca ctggcccagc agtgccaggc cttctggggg   1560
ccaggtgggc aggctgccga ggagtcctgc ttctcctatg acatcctacc aggctgcaag   1620
gccagccggt acagggctga catgtgtggc gttctgcagt gcaagggtgg gcagcagccc   1680
ctggggcgtg ccatctgcat cgtggatgtg tgccacgcgc tcaccacaga ggatggcact   1740
gcgtatgaac cagtgcccga gggcacccgg tgtggaccag agaaggtttg ctggaaagga   1800
cgttgccagg acttacacgt ttacagatcc agcaactgct ctgcccagtg ccacaaccat   1860
ggggtgtgca accacaagca ggagtgccac tgccacgcgg gctgggcccc gccccactgc   1920
gcgaagctgc tgactgaggt gcacgcagcg tccgggagcc tccccgtctt cgtggtggtg   1980
gttctggtgc tcctggcagt tgtgctggtc accctggcag gcatcatcgt ctaccgcaaa   2040
gcccggagcc gcatcctgag caggaacgtg gctcccaaga ccacaatggg gcgctccaac   2100
cccctgttcc accaggctgc cagccgcgtg ccggccaagg gcggggctcc agccccatcc   2160
aggggccccc aagagctggt ccccaccacc cacccgggcc agcccgcccg acacccggcc   2220
tcctcggtgg ctctgaagag gccgcccct gctcctccgg tcactgtgtc cagcccaccc   2280
ttcccagttc ctgtctacac ccggcaggca ccaaagcagg tcatcaagcc aacgttcgca   2340
cccccagtgc cccccagtcaa acccggggct ggtgcggcca accctggtcc agctgagggt   2400
gctgttggcc caaaggttgc cctgaagccc cccatccaga ggaagcaagg agccggagct   2460
```

```
cccacagcac cctag                                                  2475


<210> SEQ ID NO 93
<211> LENGTH: 742
<212> TYPE: PRT
<213> ORGANISM: Homo sapiens

<400> SEQUENCE: 93

Met Arg Gly Leu Gly Leu Trp Leu Leu Gly Ala Met Met Leu Pro Ala
1               5                   10                  15

Ile Ala Pro Ser Arg Pro Trp Ala Leu Met Glu Gln Tyr Glu Val Val
            20                  25                  30

Leu Pro Trp Arg Leu Pro Gly Pro Arg Val Arg Arg Ala Leu Pro Ser
        35                  40                  45

His Leu Gly Leu His Pro Glu Arg Val Ser Tyr Val Leu Gly Ala Thr
    50                  55                  60

Gly His Asn Phe Thr Leu His Leu Arg Lys Asn Arg Asp Leu Leu Gly
65                  70                  75                  80

Ser Gly Tyr Thr Glu Thr Tyr Thr Ala Ala Asn Gly Ser Glu Val Thr
                85                  90                  95

Glu Gln Pro Arg Gly Gln Asp His Cys Phe Tyr Gln Gly His Val Glu
            100                 105                 110

Gly Tyr Pro Asp Ser Ala Ala Ser Leu Ser Thr Cys Ala Gly Leu Arg
        115                 120                 125

Gly Phe Phe Gln Val Gly Ser Asp Leu His Leu Ile Glu Pro Leu Asp
    130                 135                 140

Glu Gly Gly Glu Gly Gly Arg His Ala Val Tyr Gln Ala Glu His Leu
145                 150                 155                 160

Leu Gln Thr Ala Gly Thr Cys Gly Val Ser Asp Asp Ser Leu Gly Ser
                165                 170                 175

Leu Leu Gly Pro Arg Thr Ala Ala Val Phe Arg Pro Arg Pro Gly Asp
            180                 185                 190

Ser Leu Pro Ser Arg Glu Thr Arg Tyr Val Glu Leu Tyr Val Val Val
        195                 200                 205

Asp Asn Ala Glu Phe Gln Met Leu Gly Ser Glu Ala Ala Val Arg His
    210                 215                 220

Arg Val Leu Glu Val Val Asn His Val Asp Lys Leu Tyr Gln Lys Leu
225                 230                 235                 240

Asn Phe Arg Val Val Leu Val Gly Leu Glu Ile Trp Asn Ser Gln Asp
                245                 250                 255

Arg Phe His Val Ser Pro Asp Pro Ser Val Thr Leu Glu Asn Leu Leu
            260                 265                 270

Thr Trp Gln Ala Arg Gln Arg Thr Arg Arg His Leu His Asp Asn Val
        275                 280                 285

Gln Leu Ile Thr Gly Val Asp Phe Thr Gly Thr Thr Val Gly Phe Ala
    290                 295                 300

Arg Val Ser Ala Met Cys Ser His Ser Ser Gly Ala Val Asn Gln Asp
305                 310                 315                 320

His Ser Lys Asn Pro Val Gly Val Ala Cys Thr Met Ala His Glu Met
                325                 330                 335

Gly His Asn Leu Gly Met Asp His Asp Glu Asn Val Gln Gly Cys Arg
            340                 345                 350

Cys Gln Glu Arg Phe Glu Ala Gly Arg Cys Ile Met Ala Gly Ser Ile
        355                 360                 365
```

-continued

```
Gly Ser Ser Phe Pro Arg Met Phe Ser Asp Cys Ser Gln Ala Tyr Leu
    370                 375                 380

Glu Ser Phe Leu Glu Arg Pro Gln Ser Val Cys Leu Ala Asn Ala Pro
385                 390                 395                 400

Asp Leu Ser His Leu Val Gly Gly Pro Val Cys Gly Asn Leu Phe Val
                405                 410                 415

Glu Arg Gly Glu Gln Cys Asp Cys Gly Pro Pro Glu Asp Cys Arg Asn
            420                 425                 430

Arg Cys Cys Asn Ser Thr Thr Cys Gln Leu Ala Glu Gly Ala Gln Cys
        435                 440                 445

Ala His Gly Thr Cys Cys Gln Glu Cys Lys Val Lys Pro Ala Gly Glu
    450                 455                 460

Leu Cys Arg Pro Lys Lys Asp Met Cys Asp Leu Glu Glu Phe Cys Asp
465                 470                 475                 480

Gly Arg His Pro Glu Cys Pro Glu Asp Ala Phe Gln Glu Asn Gly Thr
                485                 490                 495

Pro Cys Ser Gly Gly Tyr Cys Tyr Asn Gly Ala Cys Pro Thr Leu Ala
            500                 505                 510

Gln Gln Cys Gln Ala Phe Trp Gly Pro Gly Gly Gln Ala Ala Glu Glu
        515                 520                 525

Ser Cys Phe Ser Tyr Asp Ile Leu Pro Gly Cys Lys Ala Ser Arg Tyr
    530                 535                 540

Arg Ala Asp Met Cys Gly Val Leu Gln Cys Lys Gly Gly Gln Gln Pro
545                 550                 555                 560

Leu Gly Arg Ala Ile Cys Ile Val Asp Val Cys His Ala Leu Thr Thr
                565                 570                 575

Glu Asp Gly Thr Ala Tyr Glu Pro Val Pro Glu Gly Thr Arg Cys Gly
            580                 585                 590

Pro Glu Lys Val Cys Trp Lys Gly Arg Cys Gln Asp Leu His Val Tyr
        595                 600                 605

Arg Ser Ser Asn Cys Ser Ala Gln Cys His Asn His Gly Val Cys Asn
    610                 615                 620

His Lys Gln Glu Cys His Cys His Ala Gly Trp Ala Pro Pro His Cys
625                 630                 635                 640

Ala Lys Leu Leu Thr Glu Val His Ala Gly Cys Gln Pro Arg Ala Gly
                645                 650                 655

Gln Gly Arg Gly Ser Ser Pro Ile Gln Gly Pro Pro Arg Ala Gly Pro
            660                 665                 670

His His Pro Pro Gly Pro Ala Arg Pro Thr Pro Gly Leu Leu Gly Gly
        675                 680                 685

Ser Glu Glu Ala Ala Pro Cys Ser Ser Gly His Cys Val Gln Pro Thr
    690                 695                 700

Leu Pro Ser Ser Cys Leu His Pro Ala Gly Thr Lys Ala Gly His Gln
705                 710                 715                 720

Ala Asn Val Arg Thr Pro Ser Ala Pro Ser Gln Thr Arg Gly Trp Cys
                725                 730                 735

Gly Gln Pro Trp Ser Ser
            740
```

<210> SEQ ID NO 94
<211> LENGTH: 2229
<212> TYPE: DNA
<213> ORGANISM: Homo sapiens

<400> SEQUENCE: 94

```
atgcgcggcc tcgggctctg gctgctgggc gcgatgatgc tgcctgcgat tgcccccagc     60
cggccctggg ccctcatgga gcagtatgag gtcgtgttgc cgtggcgtct gccaggcccc    120
cgagtccgcc gagctctgcc ctcccacttg ggcctgcacc cagagagggt gagctacgtc    180
cttggggcca cagggcacaa cttcaccctc cacctgcgga agaacaggga cctgctgggc    240
tccggctaca cagagaccta tacggctgcc aatggctccg aggtgacgga gcagcctcgc    300
gggcaggacc actgcttcta ccagggccac gtagaggggt acccggactc agccgccagc    360
ctcagcacct gtgccggcct caggggtttc ttccaggtgg ggtcagacct gcacctgatc    420
gagcccctgg atgaaggtgg cgagggcgga cggcacgccg tgtaccaggc tgagcacctg    480
ctgcagacgg ccgggacctg cggggtcagc gacgacagcc tgggcagcct cctgggaccc    540
cggacggcag ccgtcttcag gcctcggccc ggggactctc tgccatcccg agagacccgc    600
tacgtggagc tgtatgtggt cgtggacaat gcagagttcc agatgctggg gagcgaagca    660
gccgtgcgtc atcgggtgct ggaggtggtg aatcacgtgg acaagctata tcagaaactc    720
aacttccgtg tggtcctggt gggcctggag atttggaata gtcaggacag gttccacgtc    780
agccccgacc ccagtgtcac actggagaac ctcctgacct ggcaggcacg gcaacggaca    840
cggcggcacc tgcatgacaa cgtacagctc atcacgggtg tcgacttcac cgggactacc    900
gtggggtttg ccagggtgtc cgccatgtgc tcccacagct caggggctgt gaaccaggac    960
cacagcaaga accccgtggg cgtggcctgt accatggccc atgagatggg ccacaacctg   1020
ggcatggacc atgatgagaa cgtccagggc tgccgctgcc aggaacgctt cgaggccggc   1080
cgctgcatca tggcgggcag cattggctcc agtttcccca ggatgttcag tgactgcagc   1140
caggcctacc tggagagctt tttggagcgg ccgcagtcgg tgtgcctcgc caacgcccct   1200
gacctcagcc acctggtggg cggccccgtg tgtgggaacc tgtttgtgga gcgtggggag   1260
cagtgcgact gcggcccccc cgaggactgc cggaaccgct gctgcaactc taccacctgc   1320
cagctggctg agggggccca gtgtgcgcac ggtacctgct gccaggagtg caaggtgaag   1380
ccggctggtg agctgtgccg tcccaagaag gacatgtgtg acctcgagga gttctgtgac   1440
ggccggcacc ctgagtgccc ggaagacgcc ttccaggaga acggcacgcc ctgctccggg   1500
ggctactgct acaacggggc ctgtcccaca ctggcccagc agtgccaggc cttctggggg   1560
ccaggtgggc aggctgccga ggagtcctgc ttctcctatg acatcctacc aggctgcaag   1620
gccagccggt acagggctga catgtgtggc gttctgcagt gcaagggtgg gcagcagccc   1680
ctggggcgtg ccatctgcat cgtggatgtg tgccacgcgc tcaccacaga ggatggcact   1740
gcgtatgaac cagtgcccga gggcacccgg tgtggaccag agaaggtttg ctggaaagga   1800
cgttgccagg acttacacgt ttacagatcc agcaactgct ctgcccagtg ccacaaccat   1860
ggggtgtgca accacaagca ggagtgccac tgccacgcgg gctgggcccc gccccactgc   1920
gcgaagctgc tgactgaggt gcacgcaggc tgccagccgc gtgccggcca agggcggggc   1980
tccagcccca tccaggggcc cccaagagct ggtccccacc acccacccgg gccagcccgc   2040
ccgacacccg gcctcctcgg tggctctgaa gaggccgccc cctgctcctc cggtcactgt   2100
gtccagccca cccttcccag ttcctgtcta cacccggcag gcaccaaagc aggtcatcaa   2160
gccaacgttc gcacccccag tgcccccagt caaacccggg gctggtgcgg ccaaccctgg   2220
tccagctga                                                           2229
```

<210> SEQ ID NO 95

<211> LENGTH: 733
<212> TYPE: PRT
<213> ORGANISM: Homo sapiens

<400> SEQUENCE: 95

```
Met Arg Gly Leu Gly Leu Trp Leu Leu Gly Ala Met Met Leu Pro Gly
1               5                   10                  15

Pro Ala Pro Arg Glu Gly Glu Leu Arg Pro Trp Gly His Arg Ala Gln
            20                  25                  30

Leu His Pro Pro Pro Ala Glu Glu Gln Gly Pro Ala Gly Leu Arg Leu
        35                  40                  45

His Arg Asp Leu Tyr Gly Cys Gln Trp Leu Arg Gly Asp Gly Ala Ala
    50                  55                  60

Ser Arg Ala Gly Pro Leu Leu Leu Pro Gly Pro Arg Arg Gly Val Pro
65                  70                  75                  80

Gly Leu Ser Arg Gln Pro Gln His Leu Cys Arg Pro Gln Val Gly Ser
                85                  90                  95

Asp Leu His Leu Ile Glu Pro Leu Asp Glu Gly Gly Glu Gly Gly Arg
            100                 105                 110

His Ala Val Tyr Gln Ala Glu His Leu Leu Gln Thr Ala Gly Thr Cys
        115                 120                 125

Gly Val Ser Asp Asp Ser Leu Gly Ser Leu Leu Gly Pro Arg Thr Ala
    130                 135                 140

Ala Val Phe Arg Pro Arg Pro Gly Asp Ser Leu Pro Ser Arg Glu Thr
145                 150                 155                 160

Arg Tyr Val Glu Leu Tyr Val Val Val Asp Asn Ala Glu Phe Gln Met
                165                 170                 175

Leu Gly Ser Glu Ala Ala Val Arg His Arg Val Leu Glu Val Val Asn
            180                 185                 190

His Val Asp Lys Leu Tyr Gln Lys Leu Asn Phe Arg Val Val Leu Val
        195                 200                 205

Gly Leu Glu Ile Trp Asn Ser Gln Asp Arg Phe His Val Ser Pro Asp
    210                 215                 220

Pro Ser Val Thr Leu Glu Asn Leu Leu Thr Trp Gln Ala Arg Gln Arg
225                 230                 235                 240

Thr Arg Arg His Leu His Asp Asn Val Gln Leu Ile Thr Gly Val Asp
                245                 250                 255

Phe Thr Gly Thr Thr Val Gly Phe Ala Arg Val Ser Ala Met Cys Ser
            260                 265                 270

His Ser Ser Gly Ala Val Asn Gln Asp His Ser Lys Asn Pro Val Gly
        275                 280                 285

Val Ala Cys Thr Met Ala His Glu Met Gly His Asn Leu Gly Met Asp
    290                 295                 300

His Asp Glu Asn Val Gln Gly Cys Arg Cys Gln Glu Arg Phe Glu Ala
305                 310                 315                 320

Gly Arg Cys Ile Met Ala Gly Ser Ile Gly Ser Ser Phe Pro Arg Met
                325                 330                 335

Phe Ser Asp Cys Ser Gln Ala Tyr Leu Glu Ser Phe Leu Glu Arg Pro
            340                 345                 350

Gln Ser Val Cys Leu Ala Asn Ala Pro Asp Leu Ser His Leu Val Gly
        355                 360                 365

Gly Pro Val Cys Gly Asn Leu Phe Val Glu Arg Gly Glu Gln Cys Asp
    370                 375                 380

Cys Gly Pro Pro Glu Asp Cys Arg Asn Arg Cys Cys Asn Ser Thr Thr
```

-continued

```
385                 390                 395                 400

Cys Gln Leu Ala Glu Gly Ala Gln Cys Ala His Gly Thr Cys Cys Gln
                405                 410                 415

Glu Cys Lys Val Lys Pro Ala Gly Glu Leu Cys Arg Pro Lys Lys Asp
            420                 425                 430

Met Cys Asp Leu Glu Glu Phe Cys Asp Gly Arg His Pro Glu Cys Pro
        435                 440                 445

Glu Asp Ala Phe Gln Glu Asn Gly Thr Pro Cys Ser Gly Gly Tyr Cys
    450                 455                 460

Tyr Asn Gly Ala Cys Pro Thr Leu Ala Gln Gln Cys Gln Ala Phe Trp
465                 470                 475                 480

Gly Pro Gly Gly Gln Ala Ala Glu Glu Ser Cys Phe Ser Tyr Asp Ile
                485                 490                 495

Leu Pro Gly Cys Lys Ala Ser Arg Tyr Arg Ala Asp Met Cys Gly Val
            500                 505                 510

Leu Gln Cys Lys Gly Gly Gln Gln Pro Leu Gly Arg Ala Ile Cys Ile
        515                 520                 525

Val Asp Val Cys His Ala Leu Thr Thr Glu Asp Gly Thr Ala Tyr Glu
    530                 535                 540

Pro Val Pro Glu Gly Thr Arg Cys Gly Pro Glu Lys Val Cys Asn His
545                 550                 555                 560

Lys Gln Glu Cys His Cys His Ala Gly Trp Ala Pro Pro His Cys Ala
                565                 570                 575

Lys Leu Leu Thr Glu Val His Ala Ala Ser Gly Ser Leu Pro Val Phe
            580                 585                 590

Val Val Val Val Leu Val Leu Leu Ala Val Val Leu Val Thr Leu Ala
        595                 600                 605

Gly Ile Ile Val Tyr Arg Lys Ala Arg Ser Arg Ile Leu Ser Arg Asn
    610                 615                 620

Val Ala Pro Lys Thr Thr Met Gly Arg Ser Asn Pro Leu Phe His Gln
625                 630                 635                 640

Ala Ala Ser Arg Val Pro Ala Lys Gly Gly Ala Pro Ala Pro Ser Arg
                645                 650                 655

Gly Pro Gln Glu Leu Val Pro Thr Thr His Pro Gly Gln Pro Ala Arg
            660                 665                 670

His Pro Ala Ser Ser Val Ala Leu Lys Arg Pro Pro Pro Ala Pro Pro
        675                 680                 685

Val Thr Val Ser Ser Pro Pro Phe Pro Val Pro Val Tyr Thr Arg Gln
    690                 695                 700

Ala Pro Lys Gln Gly Ala Val Gly Pro Lys Val Ala Leu Lys Pro Pro
705                 710                 715                 720

Ile Gln Arg Lys Gln Gly Ala Gly Ala Pro Thr Ala Pro
                725                 730


<210> SEQ ID NO 96
<211> LENGTH: 2202
<212> TYPE: DNA
<213> ORGANISM: Homo sapiens

<400> SEQUENCE: 96

atgcgcggcc tcgggctctg gctgctgggc gcgatgatgc tgcctgggcc tgcacccaga      60

gagggtgagc tacgtccttg gggccacagg gcacaacttc accctccacc tgcggaagaa     120

cagggacctg ctgggctccg gctacacaga gacctatacg gctgccaatg gctccgaggt     180
```

-continued

```
gacggagcag cctcgcgggc aggaccactg cttctaccag ggccacgtag aggggtaccc    240
ggactcagcc gccagcctca gcacctgtgc cggcctcagg tggggtcaga cctgcacctg    300
atcgagcccc tggatgaagg tggcgagggc ggacggcacg ccgtgtacca ggctgagcac    360
ctgctgcaga cggccgggac ctgcggggtc agcgacgaca gcctgggcag cctcctggga    420
ccccggacgg cagccgtctt caggcctcgg cccggggact ctctgccatc ccgagagacc    480
cgctacgtgg agctgtatgt ggtcgtggac aatgcagagt tccagatgct ggggagcgaa    540
gcagccgtgc gtcatcgggt gctggaggtg gtgaatcacg tggacaagct atatcagaaa    600
ctcaacttcc gtgtggtcct ggtgggcctg gagatttgga atagtcagga caggttccac    660
gtcagccccg accccagtgt cacactggag aacctcctga cctggcaggc acggcaacgg    720
acacggcggc acctgcatga caacgtacag ctcatcacgg gtgtcgactt caccgggact    780
accgtggggt ttgccagggt gtccgccatg tgctcccaca gctcaggggc tgtgaaccag    840
gaccacagca agaaccccgt gggcgtggcc tgtaccatgg cccatgagat gggccacaac    900
ctgggcatgg accatgatga gaacgtccag ggctgccgct gccaggaacg cttcgaggcc    960
ggccgctgca tcatggcggg cagcattggc tccagtttcc ccaggatgtt cagtgactgc   1020
agccaggcct acctggagag ctttttggag cggccgcagt cggtgtgcct cgccaacgcc   1080
cctgacctca gccacctggt gggcggcccc gtgtgtggga acctgtttgt ggagcgtggg   1140
gagcagtgcg actgcggccc ccccgaggac tgccggaacc gctgctgcaa ctctaccacc   1200
tgccagctgg ctgagggggc ccagtgtgcg cacggtacct gctgccagga gtgcaaggtg   1260
aagccggctg gtgagctgtg ccgtcccaag aaggacatgt gtgacctcga ggagttctgt   1320
gacggccggc accctgagtg cccggaagac gccttccagg agaacggcac gccctgctcc   1380
gggggctact gctacaacgg ggcctgtccc acactggccc agcagtgcca ggccttctgg   1440
gggccaggtg ggcaggctgc cgaggagtcc tgcttctcct atgacatcct accaggctgc   1500
aaggccagcc ggtacagggc tgacatgtgt ggcgttctgc agtgcaaggg tgggcagcag   1560
cccctggggc gtgccatctg catcgtggat gtgtgccacg cgctcaccac agaggatggc   1620
actgcgtatg aaccagtgcc cgagggcacc cggtgtggac cagagaaggt gtgcaaccac   1680
aagcaggagt gccactgcca cgcgggctgg gccccgcccc actgcgcgaa gctgctgact   1740
gaggtgcacg cagcgtccgg gagcctcccc gtcttcgtgg tggtggttct ggtgctcctg   1800
gcagttgtgc tggtcaccct ggcaggcatc atcgtctacc gcaaagcccg gagccgcatc   1860
ctgagcagga acgtggctcc caagaccaca atggggcgct ccaacccccct gttccaccag   1920
gctgccagcc gcgtgccggc caagggcggg gctccagccc catccagggg cccccaagag   1980
ctggtcccca ccacccaccc gggccagccc gcccgacacc cggcctcctc ggtggctctg   2040
aagaggccgc cccctgctcc tccggtcact gtgtccagcc caccccttccc agttcctgtc   2100
tacacccggc aggcaccaaa gcagggtgct gttggcccaa aggttgccct gaagcccccc   2160
atccagagga agcaaggagc cggagctccc acagcaccct ag                      2202
```

<210> SEQ ID NO 97
<211> LENGTH: 826
<212> TYPE: PRT
<213> ORGANISM: Mus sp.

<400> SEQUENCE: 97

```
Met Leu Gly Leu Trp Leu Leu Ser Val Leu Trp Thr Pro Ala Val Ala
1               5                   10                  15
```

-continued

```
Pro Gly Pro Pro Leu Pro His Val Lys Gln Tyr Glu Val Val Trp Pro
            20                  25                  30

Arg Arg Leu Ala Ala Ser Arg Ser Arg Arg Ala Leu Pro Ser His Trp
        35                  40                  45

Gly Gln Tyr Pro Glu Ser Leu Ser Tyr Ala Leu Gly Thr Ser Gly His
    50                  55                  60

Val Phe Thr Leu His Leu Arg Lys Asn Arg Asp Leu Leu Gly Ser Ser
65                  70                  75                  80

Tyr Thr Glu Thr Tyr Ser Ala Ala Asn Gly Ser Glu Val Thr Glu Gln
                85                  90                  95

Leu Gln Glu Gln Asp His Cys Leu Tyr Gln Gly His Val Glu Gly Tyr
            100                 105                 110

Glu Gly Ser Ala Ala Ser Ile Ser Thr Cys Ala Gly Leu Arg Gly Phe
        115                 120                 125

Phe Arg Val Gly Ser Thr Val His Leu Ile Glu Pro Leu Asp Ala Asp
    130                 135                 140

Glu Glu Gly Gln His Ala Met Tyr Gln Ala Lys His Leu Gln Gln Lys
145                 150                 155                 160

Ala Gly Thr Cys Gly Val Lys Asp Thr Asn Leu Asn Asp Leu Gly Pro
                165                 170                 175

Arg Ala Leu Glu Ile Tyr Arg Ala Gln Pro Arg Asn Trp Leu Ile Pro
            180                 185                 190

Arg Glu Thr Arg Tyr Val Glu Leu Tyr Val Val Ala Asp Ser Gln Glu
        195                 200                 205

Phe Gln Lys Leu Gly Ser Arg Glu Ala Val Arg Gln Arg Val Leu Glu
    210                 215                 220

Val Val Asn His Val Asp Lys Leu Tyr Gln Glu Leu Ser Phe Arg Val
225                 230                 235                 240

Val Leu Val Gly Leu Glu Ile Trp Asn Lys Asp Lys Phe Tyr Ile Ser
                245                 250                 255

Arg Tyr Ala Asn Val Thr Leu Glu Asn Phe Leu Ser Trp Arg Glu Gln
            260                 265                 270

Asn Leu Gln Gly Gln His Pro His Asp Asn Val Gln Leu Ile Thr Gly
        275                 280                 285

Val Asp Phe Ile Gly Ser Thr Val Gly Leu Ala Lys Val Ser Ala Leu
    290                 295                 300

Cys Ser Arg His Ser Gly Ala Val Asn Gln Asp His Ser Lys Asn Ser
305                 310                 315                 320

Ile Gly Val Ala Ser Thr Met Ala His Glu Leu Gly His Asn Leu Gly
                325                 330                 335

Met Ser His Asp Glu Asp Ile Pro Gly Cys Tyr Cys Pro Glu Pro Arg
            340                 345                 350

Glu Gly Gly Gly Cys Ile Met Thr Glu Ser Ile Gly Ser Lys Phe Pro
        355                 360                 365

Arg Ile Phe Ser Arg Cys Ser Lys Ile Asp Leu Glu Ser Phe Val Thr
    370                 375                 380

Lys Pro Gln Thr Gly Cys Leu Thr Asn Val Pro Asp Val Asn Arg Phe
385                 390                 395                 400

Val Gly Gly Pro Val Cys Gly Asn Leu Phe Val Glu His Gly Glu Gln
                405                 410                 415

Cys Asp Cys Gly Thr Pro Gln Asp Cys Gln Asn Pro Cys Cys Asn Ala
            420                 425                 430

Thr Thr Cys Gln Leu Val Lys Gly Ala Glu Cys Ala Ser Gly Thr Cys
```

-continued

```
        435                 440                 445

Cys His Glu Cys Lys Val Lys Pro Ala Gly Glu Val Cys Arg Leu Ser
    450                 455                 460

Lys Asp Lys Cys Asp Leu Glu Glu Phe Cys Asp Gly Arg Lys Pro Thr
465                 470                 475                 480

Cys Pro Glu Asp Ala Phe Gln Gln Asn Gly Thr Pro Cys Pro Gly Gly
                485                 490                 495

Tyr Cys Phe Asp Gly Ser Cys Pro Thr Leu Ala Gln Gln Cys Arg Asp
            500                 505                 510

Leu Trp Gly Pro Gly Ala Arg Val Ala Ala Asp Ser Cys Tyr Thr Phe
        515                 520                 525

Ser Ile Pro Pro Gly Cys Asn Gly Arg Met Tyr Ser Gly Arg Ile Asn
    530                 535                 540

Arg Cys Gly Ala Leu Tyr Cys Glu Gly Gly Gln Lys Pro Leu Glu Arg
545                 550                 555                 560

Ser Phe Cys Thr Phe Ser Ser Asn His Gly Val Cys His Ala Leu Gly
                565                 570                 575

Thr Gly Ser Asn Ile Asp Thr Phe Glu Leu Val Leu Gln Gly Thr Lys
            580                 585                 590

Cys Glu Glu Gly Lys Val Cys Met Asp Gly Ser Cys Gln Asp Leu Arg
        595                 600                 605

Val Tyr Arg Ser Glu Asn Cys Ser Ala Lys Cys Asn Asn His Gly Val
    610                 615                 620

Cys Asn His Lys Arg Glu Cys His Cys His Lys Gly Trp Ala Pro Pro
625                 630                 635                 640

Asn Cys Val Gln Arg Leu Ala Asp Val Ser Asp Glu Gln Ala Ala Ser
                645                 650                 655

Thr Ser Leu Pro Val Ser Val Val Val Val Leu Val Ile Leu Val Ala
            660                 665                 670

Ala Met Val Ile Val Ala Gly Ile Val Ile Tyr Arg Lys Ala Pro Arg
        675                 680                 685

Gln Ile Gln Arg Arg Ser Val Ala Pro Lys Pro Ile Ser Gly Leu Ser
    690                 695                 700

Asn Pro Leu Phe Tyr Thr Arg Asp Ser Ser Leu Pro Ala Lys Asn Arg
705                 710                 715                 720

Pro Pro Asp Pro Ser Glu Thr Val Ser Thr Asn Gln Pro Pro Arg Pro
                725                 730                 735

Ile Val Lys Pro Lys Arg Pro Pro Pro Ala Pro Pro Gly Ala Val Ser
            740                 745                 750

Ser Ser Pro Leu Pro Val Pro Val Tyr Ala Pro Lys Ile Pro Asn Gln
        755                 760                 765

Phe Arg Pro Asp Pro Pro Thr Lys Pro Leu Pro Glu Leu Lys Pro Lys
    770                 775                 780

Gln Val Lys Pro Thr Phe Ala Pro Pro Thr Pro Pro Val Lys Pro Gly
785                 790                 795                 800

Thr Gly Gly Thr Val Pro Gly Ala Thr Gln Gly Ala Gly Glu Pro Lys
                805                 810                 815

Val Ala Leu Lys Val Pro Ile Gln Lys Arg
            820                 825
```

<210> SEQ ID NO 98
<211> LENGTH: 2481
<212> TYPE: DNA
<213> ORGANISM: Mus sp.

-continued

<400> SEQUENCE: 98
atgcttggcc tctggctgct cagcgtctta tggacaccag cagtagcccc tggacctcct 60
ttgccccatg tgaaacagta tgaagtggtt tggcctcggc gcctagctgc atcccgctcc 120
cgcagagccc tgccctccca ctggggccag tacccagaga gtctgagcta tgctcttggg 180
accagcgggc acgttttcac cctgcacctt cgaaagaaca gggacctgct gggctcaagc 240
tacacagaga cctactcagc tgccaatggc tctgaggtga cagagcaact gcaggagcag 300
gaccattgcc tctaccaagg ccatgtggaa gggtacgagg gctcagctgc cagtattagc 360
acctgtgctg gcctcagggg ctttttccga gttgggtcca ctgtccactt gattgagcct 420
ctggatgctg atgaagaggg gcaacatgcg atgtatcagg caaagcatct gcaacagaag 480
gctgggacct gtggggtcaa agataccaac ctgaatgacc tagggcctcg ggcattagaa 540
atatacaggg ctcagccacg gaactggctg atacccagag aaacccgcta tgtggagttg 600
tatgtggttg cagacagcca agagttccag aagttgggga gcagagaggc cgtgcgccag 660
cgagtgctgg aggttgtaaa ccacgtggac aagctttatc aggaactcag ttttcgagtt 720
gtcctggtgg gcctggagat ctggaacaag gacaaattct acatcagccg ctatgccaac 780
gtgacactgg agaacttctt gtcctggagg gaacagaact tgcaagggca gcacccacat 840
gacaacgtgc aacttatcac gggggttgat ttcattggga gcactgttgg actggctaag 900
gtgtctgccc tgtgttcccg tcactccgga gctgtgaatc aggaccactc caagaactcc 960
attggtgtag cctccaccat ggcccatgag ctgggccaca acctgggcat gagccatgat 1020
gaggacattc caggatgcta ctgtcctgaa ccacgggagg gtggtggctg catcatgacc 1080
gaaagcatcg gctccaagtt ccccaggata ttcagcaggt gtagcaagat tgacctagag 1140
tcattcgtga caaaacccca gacaggctgc ctgaccaatg ttccagatgt caaccggttc 1200
gtgggtggcc ctgtgtgtgg aaacctgttt gtggagcatg gagagcagtg tgactgtggc 1260
acacctcagg actgtcaaaa cccctgctgc aatgccacca cttgccagct ggtcaagggg 1320
gcagagtgtg ccagtggtac ctgttgtcat gaatgcaagg tgaagccagc tggagaggtg 1380
tgtcgtctca gtaaggacaa atgtgacctg gaggagttct gtgatggccg gaagccaaca 1440
tgtcccgaag atgccttcca acagaatggc actccctgcc cagggggcta ctgctttgat 1500
gggagctgtc ccaccctggc acagcagtgc cgggatctgt gggggccagg tgctcgggta 1560
gcagccgact cctgctatac ctttagcatc cctccgggct gcaatgggag gatgtactct 1620
ggcaggatca accggtgtgg agcgctgtac tgtgagggag gccagaagcc ccttgaacgc 1680
tccttctgca ctttctcctc caaccatgga gtctgccatg ctcttggcac aggcagcaac 1740
attgacacct ttgagctggt attgcagggc accaagtgcg aggagggaaa ggtttgcatg 1800
gatggaagct gccaggacct ccgtgtatac agatctgaaa actgctctgc taaatgcaac 1860
aaccatgggg tatgcaacca caagagggag tgccactgtc acaagggctg ggcaccaccc 1920
aactgtgtac agcggctggc agatgtatca gatgaacaag cagcgtctac gagcctccca 1980
gtcagtgtgg ttgtggtctt ggtgatcctg gtggctgcga tggtcatcgt ggcaggcatc 2040
gtcatctacc gaaaggctcc gagacaaatc cagaggagga gtgtggcacc caagcctatc 2100
tcggggctct ccaacccccct attctacaca agggacagca gcctgccagc taagaacagg 2160
cctccagacc cttctgagac agtttctacc aaccagcccc caagacccat agtgaaacca 2220
aagaggcctc cccctgcacc tccaggtgct gtgtccagtt caccactccc agttcctgtt 2280

```
tatgccccaa agataccaaa tcagtttaga cctgatcctc ccaccaagcc cctcccagag   2340

ctgaaaccca agcaggtcaa gccaaccttt gcacccccga caccaccagt caagcccggg   2400

actggaggga cggtgcctgg agcaactcag ggagctggtg agccaaaggt tgctctgaag   2460

gtccccatcc agaagaggtg a                                              2481


<210> SEQ ID NO 99
<211> LENGTH: 825
<212> TYPE: PRT
<213> ORGANISM: Mus sp.

<400> SEQUENCE: 99

Met Leu Gly Leu Trp Leu Leu Ser Val Leu Trp Thr Pro Val Ala Pro
1               5                   10                  15

Gly Pro Pro Leu Pro His Val Lys Gln Tyr Glu Val Val Trp Pro Arg
            20                  25                  30

Arg Leu Ala Ala Ser Arg Ser Arg Arg Ala Leu Pro Ser His Trp Gly
        35                  40                  45

Gln Tyr Pro Glu Ser Leu Ser Tyr Ala Leu Gly Thr Ser Gly His Val
    50                  55                  60

Phe Thr Leu His Leu Arg Lys Asn Arg Asp Leu Leu Gly Ser Ser Tyr
65                  70                  75                  80

Thr Glu Thr Tyr Ser Ala Ala Asn Gly Ser Glu Val Thr Glu Gln Leu
                85                  90                  95

Gln Glu Gln Asp His Cys Leu Tyr Gln Gly His Val Glu Gly Tyr Glu
            100                 105                 110

Gly Ser Ala Ala Ser Ile Ser Thr Cys Ala Gly Leu Arg Gly Phe Phe
        115                 120                 125

Arg Val Gly Ser Thr Val His Leu Ile Glu Pro Leu Asp Ala Asp Glu
    130                 135                 140

Glu Gly Gln His Ala Met Tyr Gln Ala Lys His Leu Gln Gln Lys Ala
145                 150                 155                 160

Gly Thr Cys Gly Val Lys Asp Thr Asn Leu Asn Asp Leu Gly Pro Arg
                165                 170                 175

Ala Leu Glu Ile Tyr Arg Ala Gln Pro Arg Asn Trp Leu Ile Pro Arg
            180                 185                 190

Glu Thr Arg Tyr Val Glu Leu Tyr Val Val Ala Asp Ser Gln Glu Phe
        195                 200                 205

Gln Lys Leu Gly Ser Arg Glu Ala Val Arg Gln Arg Val Leu Glu Val
    210                 215                 220

Val Asn His Val Asp Lys Leu Tyr Gln Glu Leu Ser Phe Arg Val Val
225                 230                 235                 240

Leu Val Gly Leu Glu Ile Trp Asn Lys Asp Lys Phe Tyr Ile Ser Arg
                245                 250                 255

Tyr Ala Asn Val Thr Leu Glu Asn Phe Leu Ser Trp Arg Glu Gln Asn
            260                 265                 270

Leu Gln Gly Gln His Pro His Asp Asn Val Gln Leu Ile Thr Gly Val
        275                 280                 285

Asp Phe Ile Gly Ser Thr Val Gly Leu Ala Lys Val Ser Ala Leu Cys
    290                 295                 300

Ser Arg His Ser Gly Ala Val Asn Gln Asp His Ser Lys Asn Ser Ile
305                 310                 315                 320

Gly Val Ala Ser Thr Met Ala His Glu Leu Gly His Asn Leu Gly Met
                325                 330                 335
```

-continued

```
Ser His Asp Glu Asp Ile Pro Gly Cys Tyr Cys Pro Glu Pro Arg Glu
            340                 345                 350

Gly Gly Gly Cys Ile Met Thr Glu Ser Ile Gly Ser Lys Phe Pro Arg
        355                 360                 365

Ile Phe Ser Arg Cys Ser Lys Ile Asp Leu Glu Ser Phe Val Thr Lys
    370                 375                 380

Pro Gln Thr Gly Cys Leu Thr Asn Val Pro Asp Val Asn Arg Phe Val
385                 390                 395                 400

Gly Gly Pro Val Cys Gly Asn Leu Phe Val Glu His Gly Glu Gln Cys
                405                 410                 415

Asp Cys Gly Thr Pro Gln Asp Cys Gln Asn Pro Cys Cys Asn Ala Thr
            420                 425                 430

Thr Cys Gln Leu Val Lys Gly Ala Glu Cys Ala Ser Gly Thr Cys Cys
        435                 440                 445

His Glu Cys Lys Val Lys Pro Ala Gly Glu Val Cys Arg Leu Ser Lys
    450                 455                 460

Asp Lys Cys Asp Leu Glu Glu Phe Cys Asp Gly Arg Lys Pro Thr Cys
465                 470                 475                 480

Pro Glu Asp Ala Phe Gln Gln Asn Gly Thr Pro Cys Pro Gly Gly Tyr
                485                 490                 495

Cys Phe Asp Gly Ser Cys Pro Thr Leu Ala Gln Gln Cys Arg Asp Leu
            500                 505                 510

Trp Gly Pro Gly Ala Arg Val Ala Ala Asp Ser Cys Tyr Thr Phe Ser
        515                 520                 525

Ile Pro Pro Gly Cys Asn Gly Arg Met Tyr Ser Gly Arg Ile Asn Arg
    530                 535                 540

Cys Gly Ala Leu Tyr Cys Glu Gly Gly Gln Lys Pro Leu Glu Arg Ser
545                 550                 555                 560

Phe Cys Thr Phe Ser Ser Asn His Gly Val Cys His Ala Leu Gly Thr
                565                 570                 575

Gly Ser Asn Ile Asp Thr Phe Glu Leu Val Leu Gln Gly Thr Lys Cys
            580                 585                 590

Glu Glu Gly Lys Val Cys Met Asp Gly Ser Cys Gln Asp Leu Arg Val
        595                 600                 605

Tyr Arg Ser Glu Asn Cys Ser Ala Lys Cys Asn Asn His Gly Val Cys
    610                 615                 620

Asn His Lys Arg Glu Cys His Cys His Lys Gly Trp Ala Pro Pro Asn
625                 630                 635                 640

Cys Val Gln Arg Leu Ala Asp Val Ser Asp Glu Gln Ala Ala Ser Thr
                645                 650                 655

Ser Leu Pro Val Ser Val Val Val Val Leu Val Ile Leu Val Ala Ala
            660                 665                 670

Met Val Ile Val Ala Gly Ile Val Ile Tyr Arg Lys Ala Pro Arg Gln
        675                 680                 685

Ile Gln Arg Arg Ser Val Ala Pro Lys Pro Ile Ser Gly Leu Ser Asn
    690                 695                 700

Pro Leu Phe Tyr Thr Arg Asp Ser Ser Leu Pro Ala Lys Asn Arg Pro
705                 710                 715                 720

Pro Asp Pro Ser Glu Thr Val Ser Thr Asn Gln Pro Pro Arg Pro Ile
                725                 730                 735

Val Lys Pro Lys Arg Pro Pro Pro Ala Pro Pro Gly Ala Val Ser Ser
            740                 745                 750

Ser Pro Leu Pro Val Pro Val Tyr Ala Pro Lys Ile Pro Asn Gln Phe
```

```
        755                 760                 765

Arg Pro Asp Pro Pro Thr Lys Pro Leu Pro Glu Leu Lys Pro Lys Gln
    770                 775                 780

Val Lys Pro Thr Phe Ala Pro Pro Thr Pro Pro Val Lys Pro Gly Thr
785                 790                 795                 800

Gly Gly Thr Val Pro Gly Ala Thr Gln Gly Ala Gly Glu Pro Lys Val
                805                 810                 815

Ala Leu Lys Val Pro Ile Gln Lys Arg
            820                 825


<210> SEQ ID NO 100
<211> LENGTH: 2478
<212> TYPE: DNA
<213> ORGANISM: Mus sp.

<400> SEQUENCE: 100

atgcttggcc tctggctgct cagcgtctta tggacaccag tagcccctgg acctcctttg     60

ccccatgtga aacagtatga agtggtttgg cctcggcgcc tagctgcatc ccgctcccgc    120

agagccctgc cctcccactg gggccagtac ccagagagtc tgagctatgc tcttgggacc    180

agcgggcacg ttttcaccct gcaccttcga aagaacaggg acctgctggg ctcaagctac    240

acagagacct actcagctgc caatggctct gaggtgacag agcaactgca ggagcaggac    300

cattgcctct accaaggcca tgtggaaggg tacgagggct cagctgccag tattagcacc    360

tgtgctggcc tcaggggctt tttccgagtt gggtccactg tccacttgat tgagcctctg    420

gatgctgatg aagaggggca acatgcgatg tatcaggcaa agcatctgca acagaaggct    480

gggacctgtg gggtcaaaga taccaacctg aatgacctag ggcctcgggc attagaaata    540

tacagggctc agccacggaa ctggctgata cccagagaaa cccgctatgt ggagttgtat    600

gtggttgcag acagccaaga gttccagaag ttggggagca gagaggccgt gcgccagcga    660

gtgctggagg ttgtaaacca cgtggacaag ctttatcagg aactcagttt tcgagttgtc    720

ctggtgggcc tggagatctg gaacaaggac aaattctaca tcagccgcta tgccaacgtg    780

acactggaga acttcttgtc ctggagggaa cagaacttgc aagggcagca cccacatgac    840

aacgtgcaac ttatcacggg ggttgatttc attgggagca ctgttggact ggctaaggtg    900

tctgccctgt gttcccgtca ctccggagct gtgaatcagg accactccaa gaactccatt    960

ggtgtagcct ccaccatggc ccatgagctg ggccacaacc tgggcatgag ccatgatgag   1020

gacattccag gatgctactg tcctgaacca cgggagggtg gtggctgcat catgaccgaa   1080

agcatcggct ccaagttccc caggatattc agcaggtgta gcaagattga cctagagtca   1140

ttcgtgacaa aaccccagac aggctgcctg accaatgttc cagatgtcaa ccggttcgtg   1200

ggtggccctg tgtgtggaaa cctgtttgtg gagcatggag agcagtgtga ctgtggcaca   1260

cctcaggact gtcaaaaccc ctgctgcaat gccaccactt gccagctggt caagggggca   1320

gagtgtgcca gtggtacctg ttgtcatgaa tgcaaggtga agccagctgg agaggtgtgt   1380

cgtctcagta aggacaaatg tgacctggag gagttctgtg atggccggaa gccaacatgt   1440

cccgaagatg ccttccaaca gaatggcact ccctgcccag gggctactgc ctttgatggg   1500
```

-continued

```
agctgtccca ccctggcaca gcagtgccgg gatctgtggg ggccaggtgc tcgggtagca   1560

gccgactcct gctatacctt tagcatccct ccgggctgca atgggaggat gtactctggc   1620

aggatcaacc ggtgtggagc gctgtactgt gagggaggcc agaagcccct tgaacgctcc   1680

ttctgcactt tctcctccaa ccatggagtc tgccatgctc ttggcacagg cagcaacatt   1740

gacacctttg agctggtatt gcagggcacc aagtgcgagg agggaaaggt ttgcatggat   1800

ggaagctgcc aggacctccg tgtatacaga tctgaaaact gctctgctaa atgcaacaac   1860

catggggtat gcaaccacaa gagggagtgc cactgtcaca agggctgggc accacccaac   1920

tgtgtacagc ggctggcaga tgtatcagat gaacaagcag cgtctacgag cctcccagtc   1980

agtgtggttg tggtcttggt gatcctggtg gctgcgatgg tcatcgtggc aggcatcgtc   2040

atctaccgaa aggctccgag acaaatccag aggaggagtg tggcacccaa gcctatctcg   2100

gggctctcca accccctatt ctacacaagg gacagcagcc tgccagctaa gaacaggcct   2160

ccagaccctt ctgagacagt ttctaccaac cagcccccaa gacccatagt gaaaccaaag   2220

aggcctcccc ctgcacctcc aggtgctgtg tccagttcac cactcccagt tcctgtttat   2280

gccccaaaga taccaaatca gtttagacct gatcctccca ccaagcccct cccagagctg   2340

aaacccaagc aggtcaagcc aacctttgca cccccgacac caccagtcaa gcccgggact   2400

ggagggacgg tgcctggagc aactcaggga gctggtgagc caaaggttgc tctgaaggtc   2460

cccatccaga agaggtga                                                 2478
```

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101

```
cggcacctgc atgacaacgt a                                               21
```

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102

```
ctgcgcgaag ctgctgactg a                                               21
```

<210> SEQ ID NO 103
<211> LENGTH: 17
<212> TYPE: PRT
<213> ORGANISM: Homo sapiens

<400> SEQUENCE: 103

```
Cys Asp Leu Glu Glu Phe Cys Asp Gly Arg His Pro Glu Cys Pro Glu
1               5                   10                  15

Asp
```

<210> SEQ ID NO 104
<211> LENGTH: 28
<212> TYPE: PRT
<213> ORGANISM: Artificial Sequence
<220> FEATURE:

-continued

```
<223> OTHER INFORMATION: Synthetic oligonucleotide

<400> SEQUENCE: 104

Arg Asn Arg Cys Cys Asn Ser Thr Thr Cys Gln Leu Ala Glu Gly Ala
1               5                   10                  15

Gln Cys Ala His Gly Thr Cys Cys Gln Glu Cys Lys
            20                  25
```